(12) United States Patent
Bonutti

(10) Patent No.: US 6,635,073 B2
(45) Date of Patent: Oct. 21, 2003

(54) METHOD OF SECURING BODY TISSUE

(76) Inventor: Peter M. Bonutti, 15167 N. Cardinal Dr., Effingham, IL (US) 62401

( * ) Notice: Subject to any disclaimer, the term of this patent is extended or adjusted under 35 U.S.C. 154(b) by 272 days.

(21) Appl. No.: 09/789,621

(22) Filed: Feb. 21, 2001

(65) Prior Publication Data

US 2001/0041916 A1 Nov. 15, 2001

Related U.S. Application Data

(63) Continuation-in-part of application No. 09/556,458, filed on May 3, 2000.

(51) Int. Cl.[7] ............................................. A61B 17/04
(52) U.S. Cl. ....................................... 606/232; 606/216
(58) Field of Search .................................. 606/232, 216

(56) References Cited

U.S. PATENT DOCUMENTS

| | | | | |
|---|---|---|---|---|
| 3,825,010 A | * | 7/1974 | McDonald | 604/173 |
| 4,235,238 A | | 11/1980 | Ogiu et al. | 606/232 |
| 4,448,194 A | | 5/1984 | DiGiovanni et al. | |
| 4,526,173 A | * | 7/1985 | Sheehan | 606/216 |
| 4,669,473 A | | 6/1987 | Richards et al. | |
| 4,832,026 A | * | 5/1989 | Jones | 606/216 |
| 4,841,960 A | * | 6/1989 | Garner | 606/216 |
| 4,924,866 A | * | 5/1990 | Yoon | 606/216 |
| 5,085,661 A | | 2/1992 | Moss | |
| 5,158,566 A | * | 10/1992 | Pianetti | 606/216 |
| 5,179,964 A | * | 1/1993 | Cook | 128/898 |
| 5,236,438 A | * | 8/1993 | Wilk | 411/455 |
| 5,324,308 A | | 6/1994 | Pierce | 606/232 |
| 5,372,146 A | | 12/1994 | Branch | |
| 5,464,426 A | | 11/1995 | Bonutti | |
| 5,591,206 A | * | 1/1997 | Moufarrege | 606/153 |
| 5,593,425 A | | 1/1997 | Bonutti et al. | 606/232 |
| 5,718,717 A | | 2/1998 | Bonutti | 606/232 |
| 5,948,002 A | | 9/1999 | Bonutti | 606/232 |
| 6,056,772 A | | 5/2000 | Bonutti | 606/232 |
| 6,059,817 A | | 5/2000 | Bonutti et al. | 606/232 |
| 6,063,095 A | | 5/2000 | Wang et al. | 606/232 |
| 6,077,292 A | | 6/2000 | Bonutti | 606/232 |
| 6,102,850 A | | 8/2000 | Wang et al. | |
| 6,264,675 B1 | * | 7/2001 | Brotz | 606/216 |

* cited by examiner

Primary Examiner—Gary Jackson
(74) Attorney, Agent, or Firm—Fleit, Kain, Gibbons, Gutman & Bongini; Paul D. Bianco; Martin Fleit

(57) ABSTRACT

To secure a first body tissue with a second body tissue, a first anchor is moved along a first path through the first body tissue into the second body tissue. A second anchor is moved along a second path through the first body tissue into the second body tissue. A suture extending between the anchors may be tightened by moving the second anchor along a path which extends transverse to the path of the first anchor. The suture which extends between the anchors may have free ends which are connected with a suture retainer. The free ends of the suture may be interconnected either before or after the anchors are moved along the first and second paths. Alternatively, the suture may be a continuous loop which extends between the two anchors. A guide assembly may be provided to guide movement of the anchors along the two paths. The paths along which the anchors move may intersect so that the anchors may be interconnected at the intersection between the two paths.

208 Claims, 15 Drawing Sheets

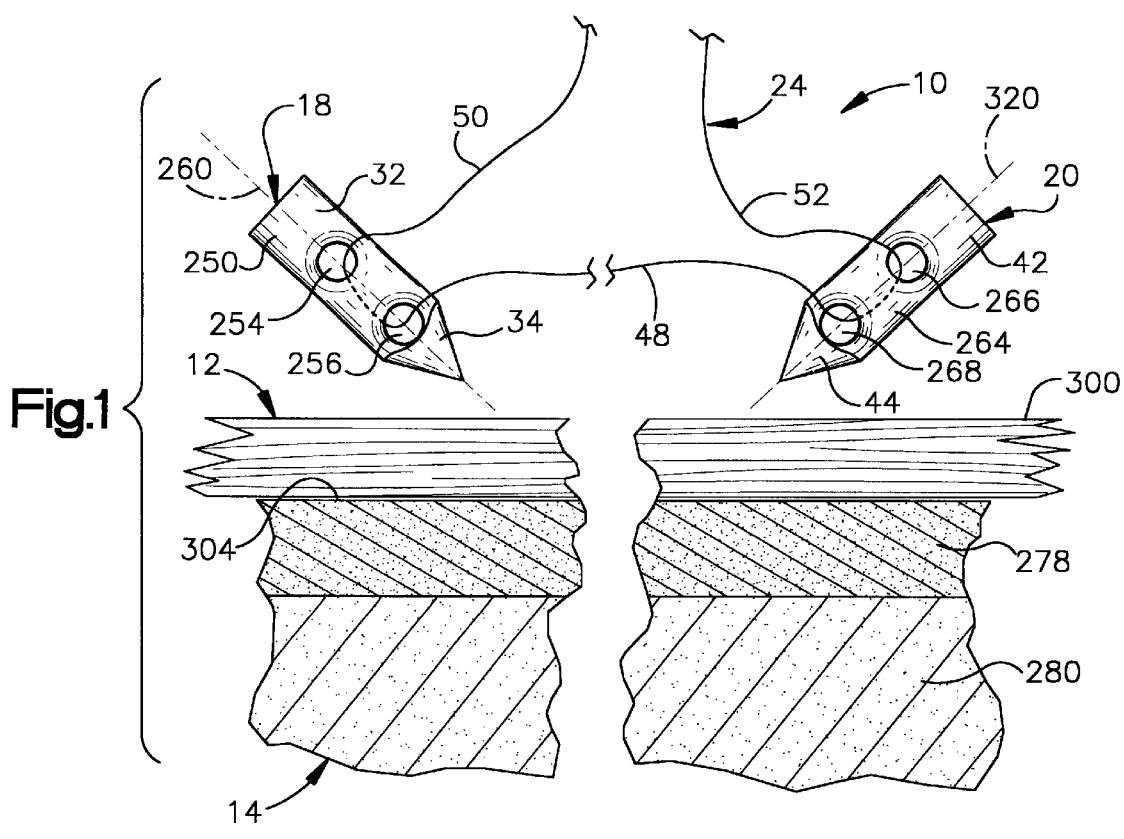
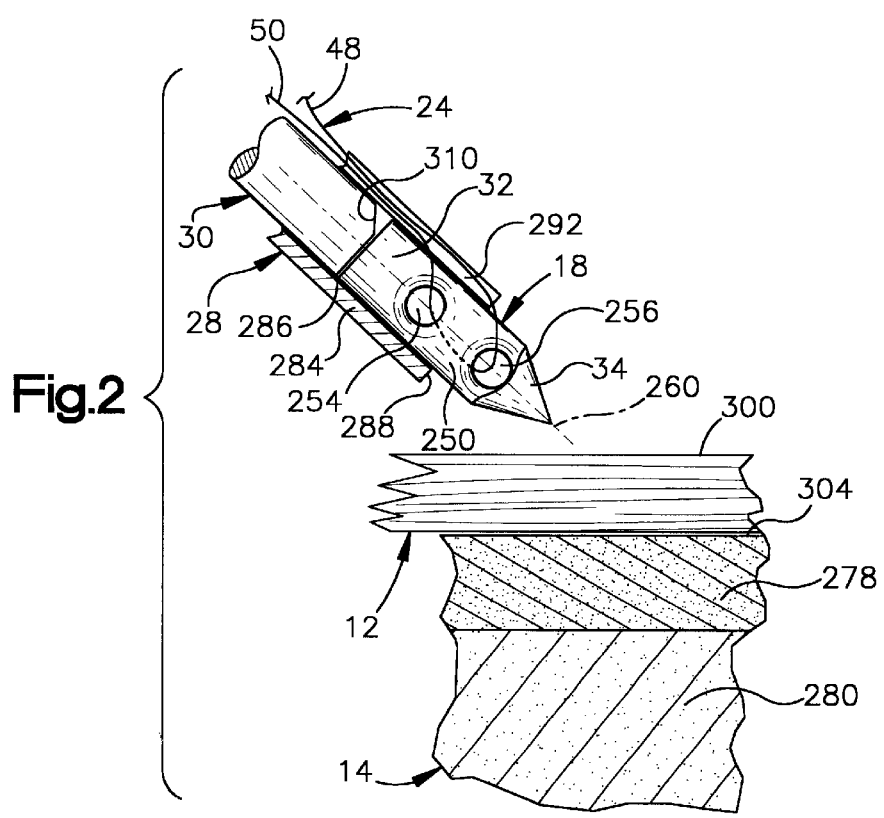

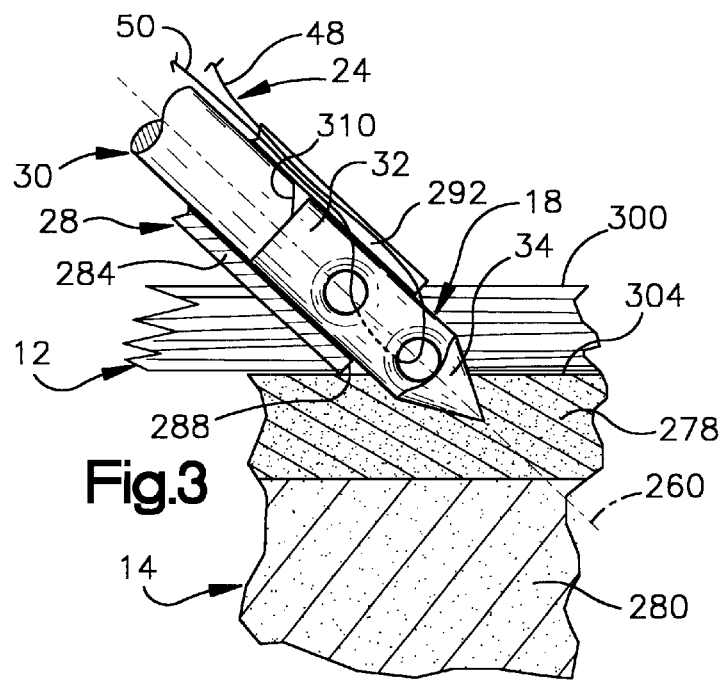
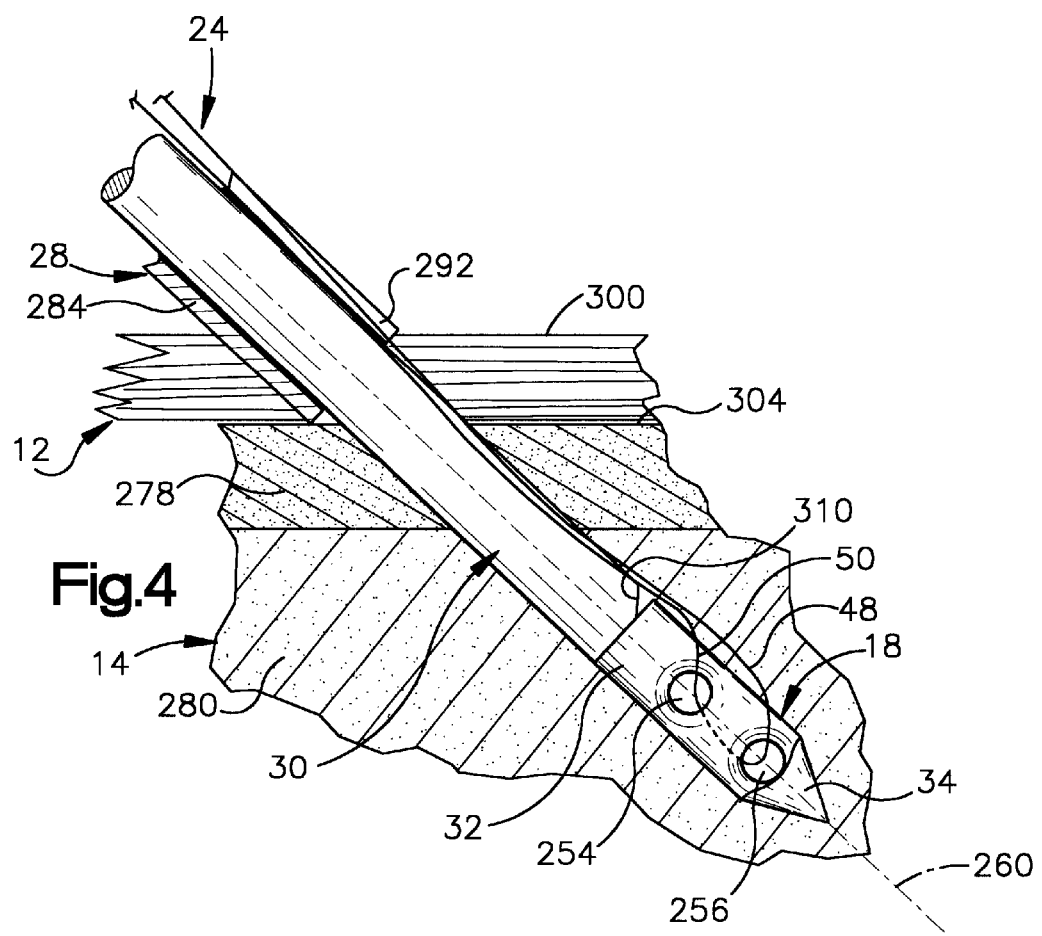

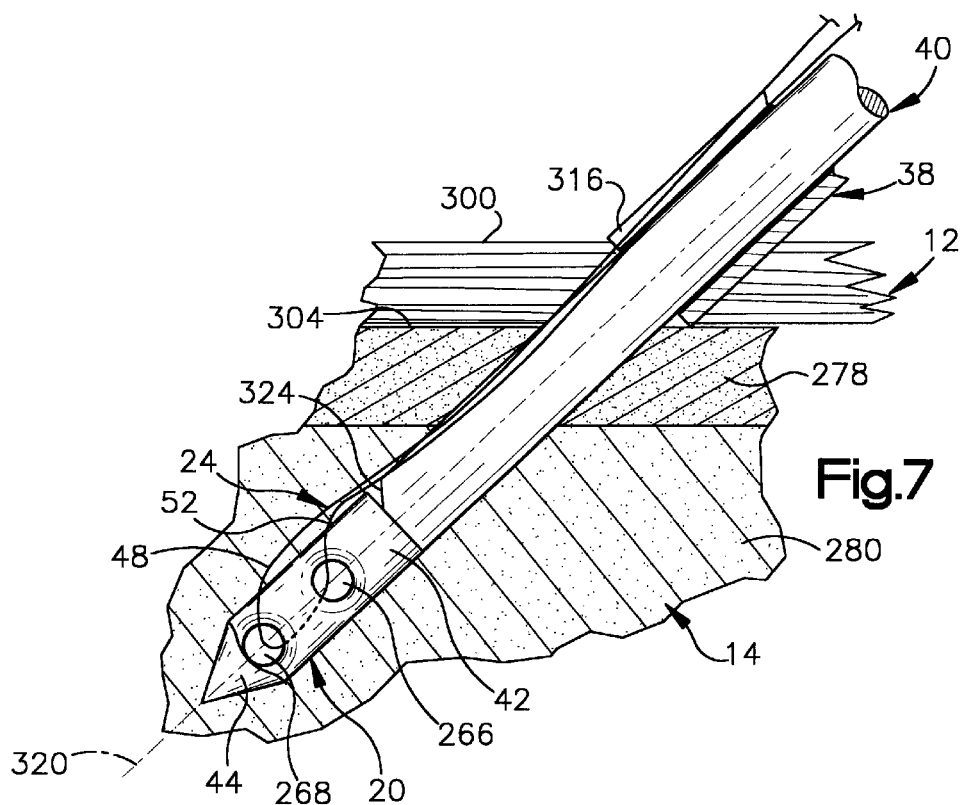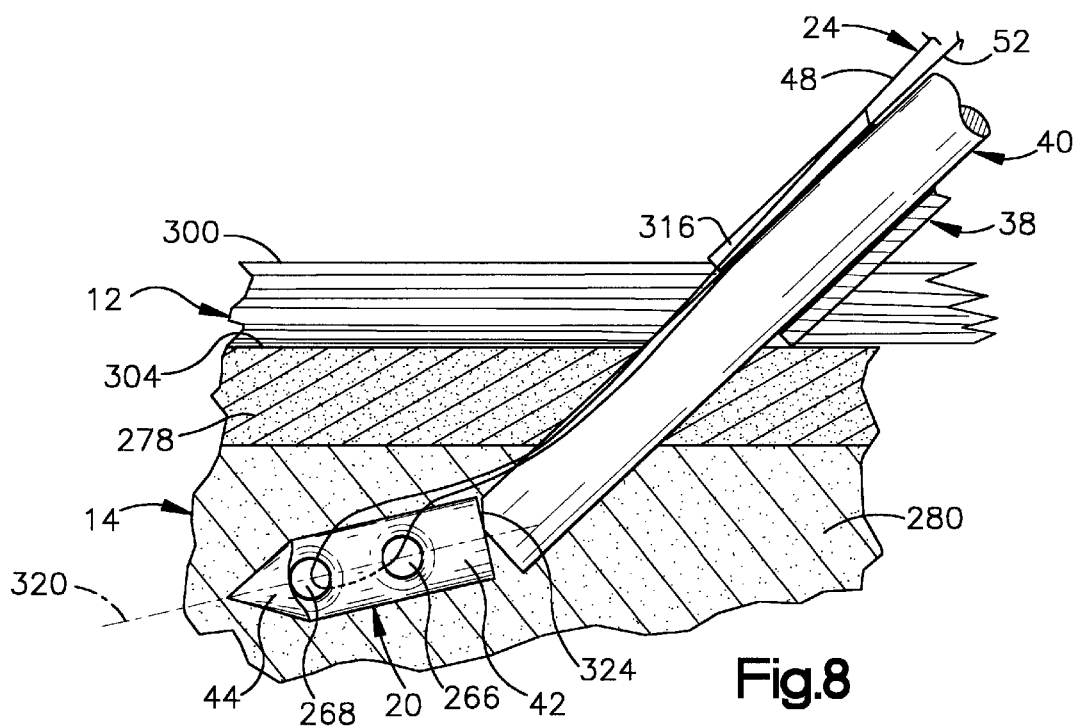

US 6,635,073 B2

METHOD OF SECURING BODY TISSUE

RELATED APPLICATION

This application is a continuation-in-part of U.S. patent application Ser. No. 09/556,458, filed May 3, 2000 by Peter M. Bonutti and entitled "Method and Apparatus for Securing Tissue". The benefit of the earlier filing date of the aforementioned application Ser. No. 09/556,458 is hereby claimed for all subject matter common to this application and the aforementioned application.

BACKGROUND OF THE INVENTION

The present invention relates to a method of securing tissue in a body of a patient. The method may be utilized to secure soft body tissues, hard body tissues, or to secure both soft and hard body tissues.

Many different devices have previously been utilized to secure body tissues. Many of these devices have utilized anchors which engage either soft body tissue or hard body tissue to hold a suture in a desired location relative to the body tissue. Various methods and devices for use in positioning anchors relative to either soft or hard body tissues are disclosed in U.S. Pat. Nos. 5,403,348; 5,464,426; 5,534,012; 5,593,425; 5,718,717; and 5,948,002. The devices and methods disclosed in these patents have been generally satisfactory in securing either soft, hard, or hard and soft body tissues. Other devices and methods for securing body tissues are disclosed in U.S. Pat. Nos. 4,235,238; 4,448,194; 4,669,473; 5,085,661; and 5,372,146.

SUMMARY OF THE INVENTION

The present invention relates to a new and improved method of securing a first body tissue with a second body tissue. The first body tissue may be a soft body tissue and the second body may be a hard body tissue. Alternatively, the first and second body tissues may both be soft body tissues. It is also contemplated that both the first and second body tissues could be hard body tissues.

When the first and second body tissues are to be interconnected, a first anchor is moved into the second body tissue. If desired, the first anchor could be moved into and through the second body tissue. A second anchor is also moved into the second body tissue. If desired, the second anchor could be moved into and through the second body tissue. The first body tissue may be pressed against or otherwise secured with the second body tissue under the influence of force transmitted from the suture to the first body tissue.

The suture which extends between the anchors may be tensioned by moving at least one of the anchors into the body tissue along a path which extends transverse to a path along which the other anchor is moved into the body tissue. The paths along which the anchors move into the body tissue may extend toward each other. The transverse paths of movement of the anchors into the body tissue promotes gripping of body tissue with the anchors and suture and promotes tensioning of the suture as the anchors move into the body tissue. Although it is believed that it may be desired to move the anchors into the body tissue along transverse paths, it is contemplated that the anchors could be moved into the body tissue along parallel paths if desired.

A desired tension may be established in the suture by moving the anchors into the body tissue. Alternatively, a desired tension may be established in the suture by applying force to portions of the suture and then interconnecting the portions of the suture. A retainer or a knot may be utilized to interconnect portions of the suture.

Regardless of how the tension is established in the suture, it may be desired to establish a predetermined tension in the suture. This may be done by determining the tension in the suture as the anchors are moved into the body tissue. Alternatively, the tension in the suture may be determined during movement of a retainer relative to portions of the suture prior to gripping of the suture with the retainer.

The suture may be a continuous loop which extends between the two anchors. The tension in the loop may be determined as one or more of the anchors are moved into the body tissue. Alternatively, the suture may be formed by a pair of separate portions which are tensioned after the anchors are moved into the body tissue.

One or more guides may be utilized to facilitate positioning of the anchors for movement along paths disposed in a desired spatial relationship with the body tissue. The guides may have tubular guide surfaces with central axes which extend transverse to each other.

Leading end portions of the anchors may be utilized to initiate the formation of openings in the first and/or second body tissue. The leading end portion of each of the anchors may be utilized to pierce soft body tissue, a hard outer layers of bone, and/or cancellous bone as the anchor is moved into the body tissue. If either or both of the anchors are associated with body tissue which is bone, one or more of the anchors may be supported in a spaced apart relationship with a hard outer layer of bone by cancellous bone which is enclosed by the hard outer layer of bone. If desired, passages for the anchors may be formed with a drill or similar tool.

The anchors may advantageously be interconnected while they are disposed in the body tissue. When this is done, the anchors may be moved along transverse paths which intersect in the body tissue. The anchors may be interconnected at the intersection between the two paths.

There are a plurality of embodiments of the invention. Each embodiment of the invention has one or more features which may be advantageously utilized with one or more of the other embodiments of the invention. It is contemplated that the various features of the embodiments of the invention may be utilized separately or combined in any one of many different combinations.

BRIEF DESCRIPTION OF THE DRAWINGS

The foregoing and other features of the invention will become more apparent upon a consideration of the following description taken in connection with the accompanying drawings wherein:

FIG. 1 is a fragmentary schematic illustration depicting the relationship between a plurality of anchors and body tissue prior to movement of the anchors into the body tissue;

FIG. 2 is a fragmentary schematic illustration depicting the manner in which one of the anchors of FIG. 1 is positioned relative to body tissue prior to initiation of formation of an opening in body tissue with a leading end portion of the anchor;

FIG. 3 is a fragmentary schematic view illustrating the manner in which the anchor of FIG. 2 is moved through first body tissue into second body tissue;

FIG. 4 is a fragmentary schematic illustration illustrating the manner in which the anchor of FIG. 3 is moved deeper into the second body tissue;

Figure 5:
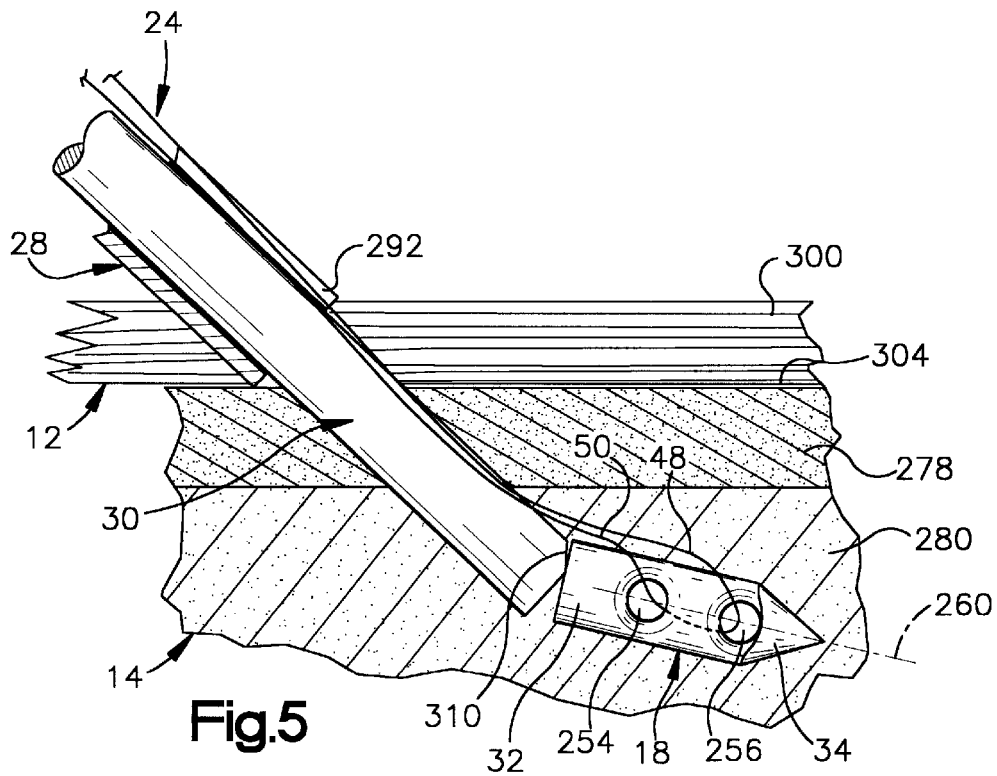
FIG. 5 is a fragmentary schematic illustration depicting the manner in which the orientation of the anchor of FIG. 4 is changed relative to the body tissue after the anchor has been moved to a desired depth in the body tissue.
Figure 6:
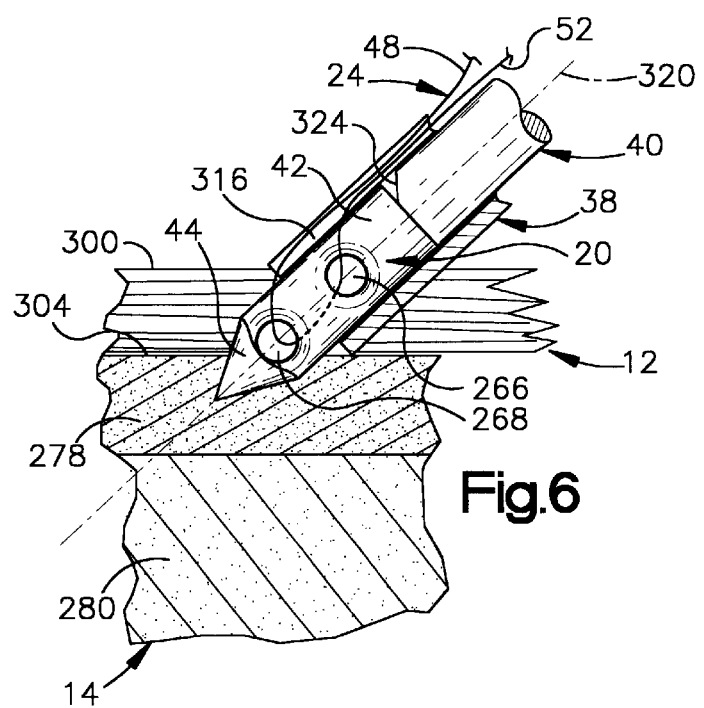
Figure 9:
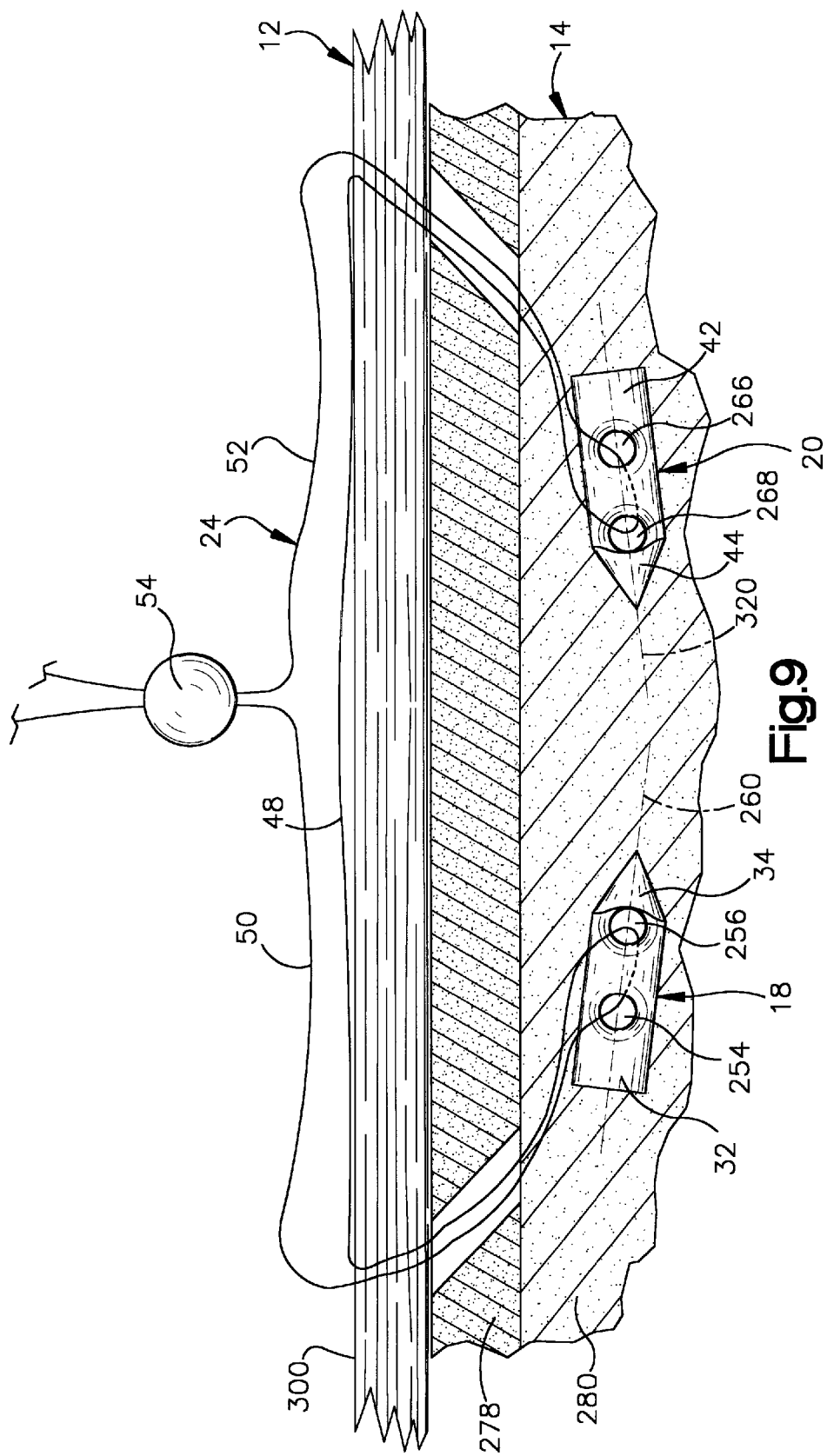
Figure 10:
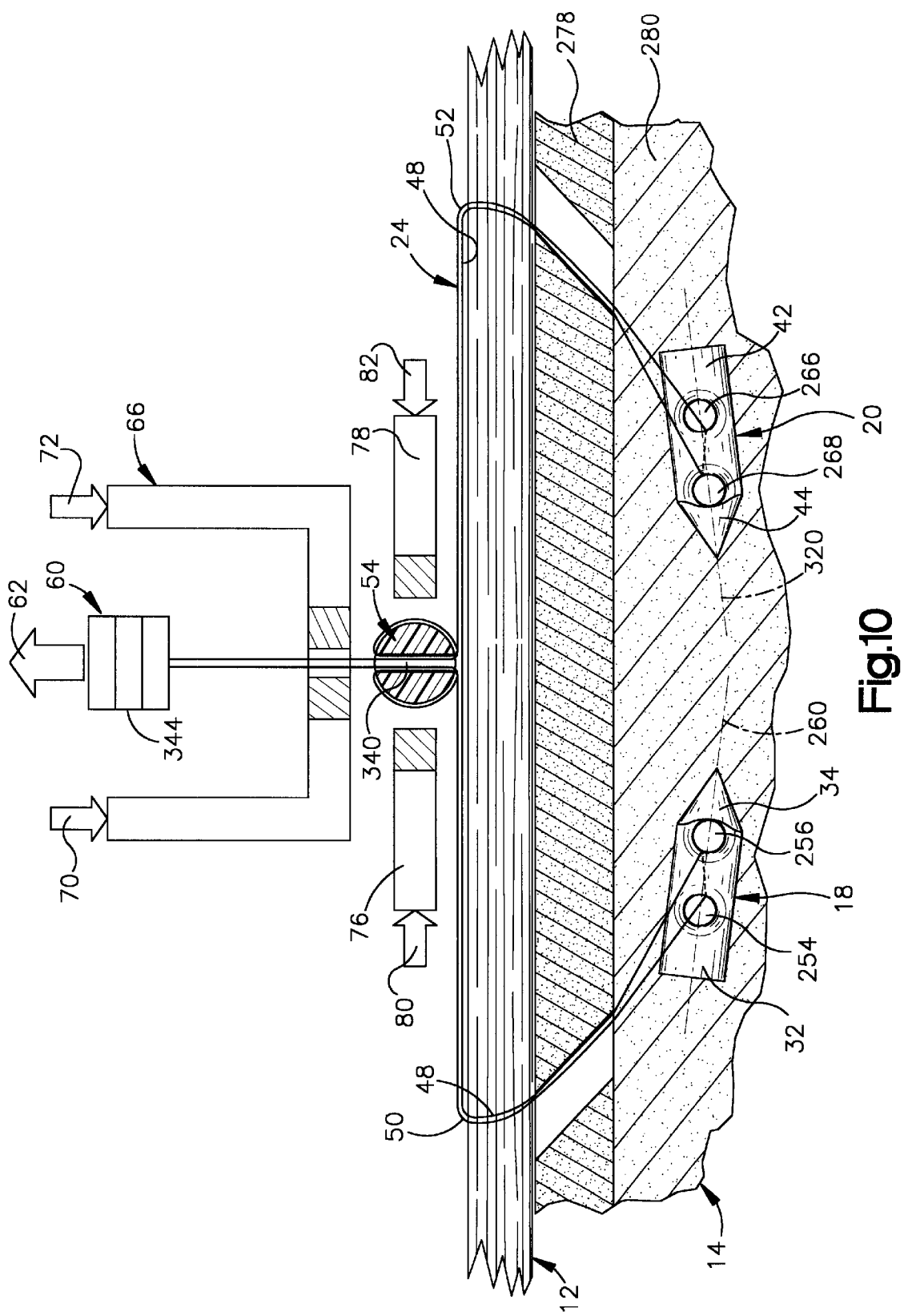
Figure 11:
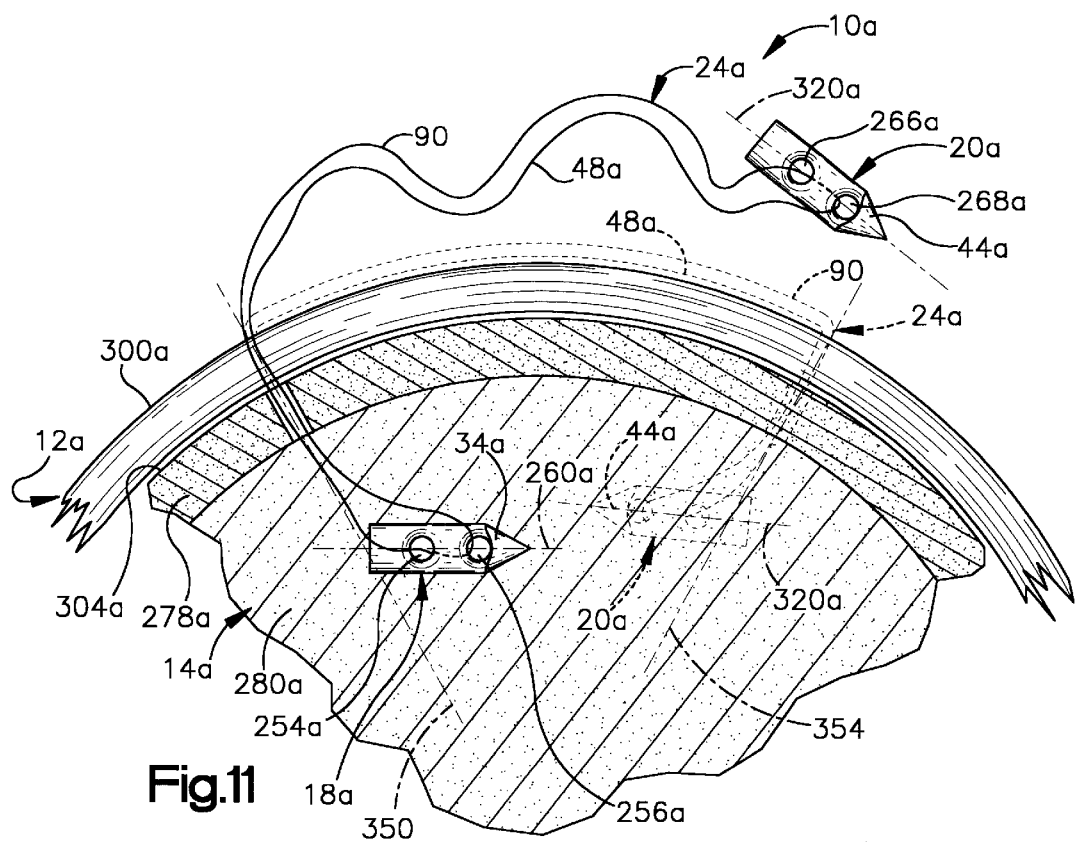
Figure 12:
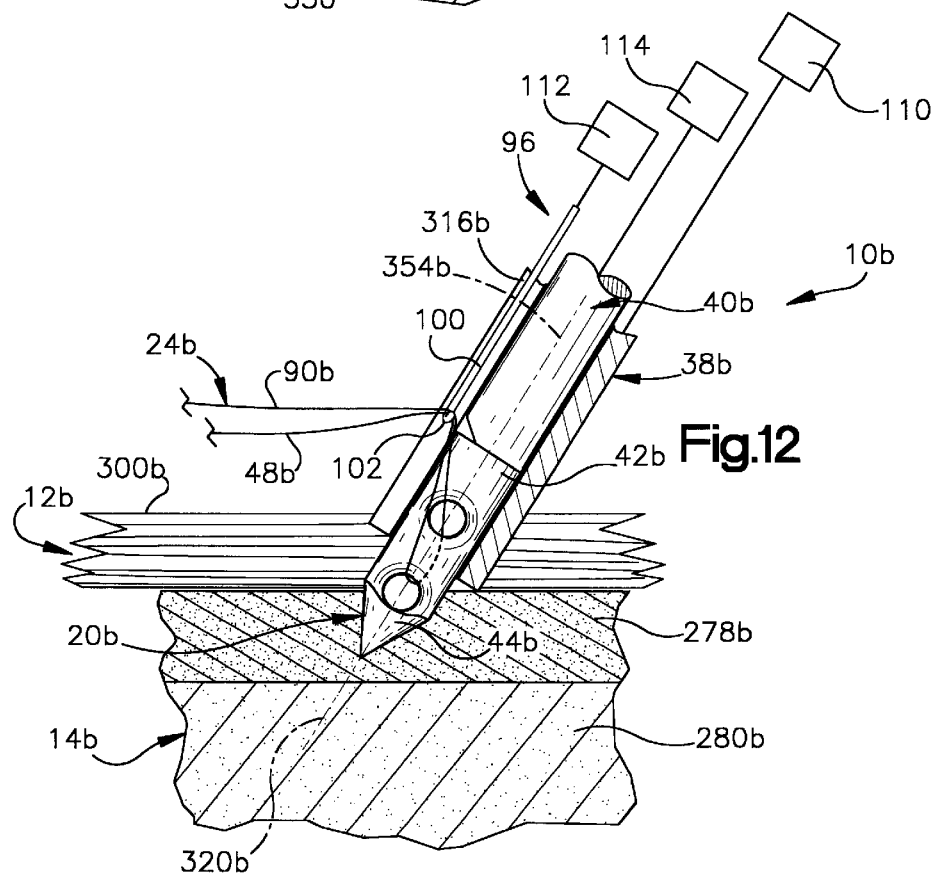
Figure 13:
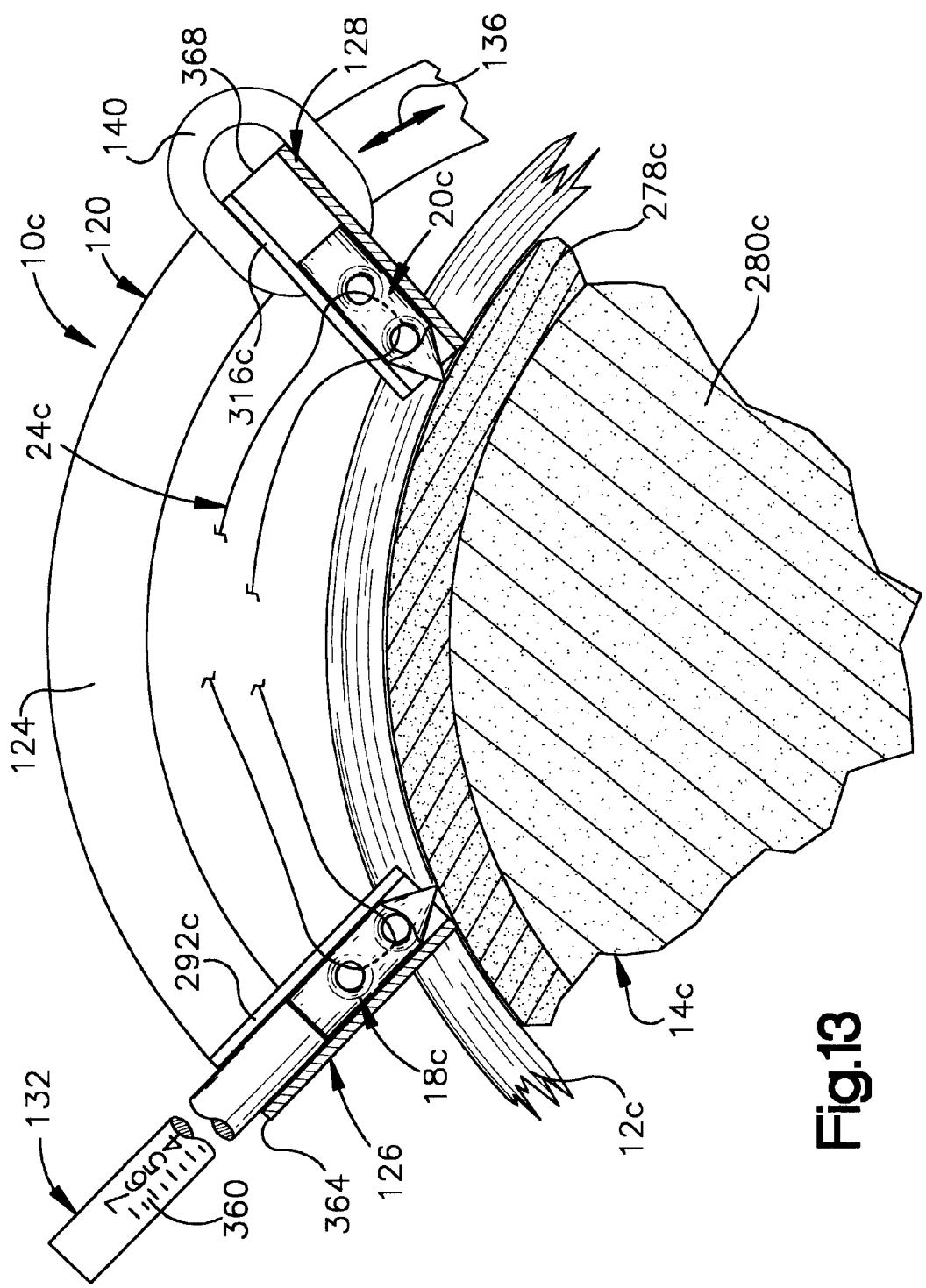
Figure 14:
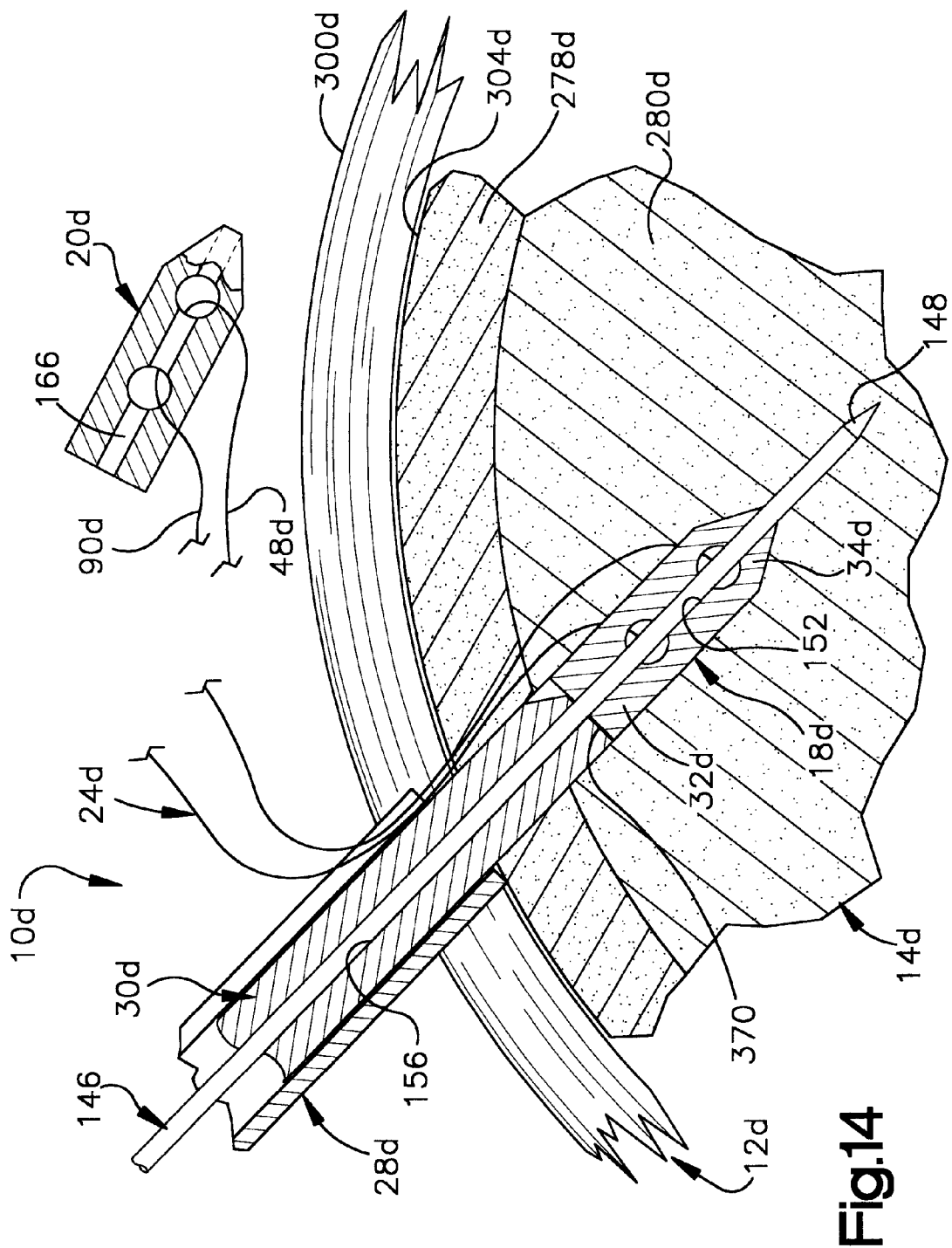
Figure 15:
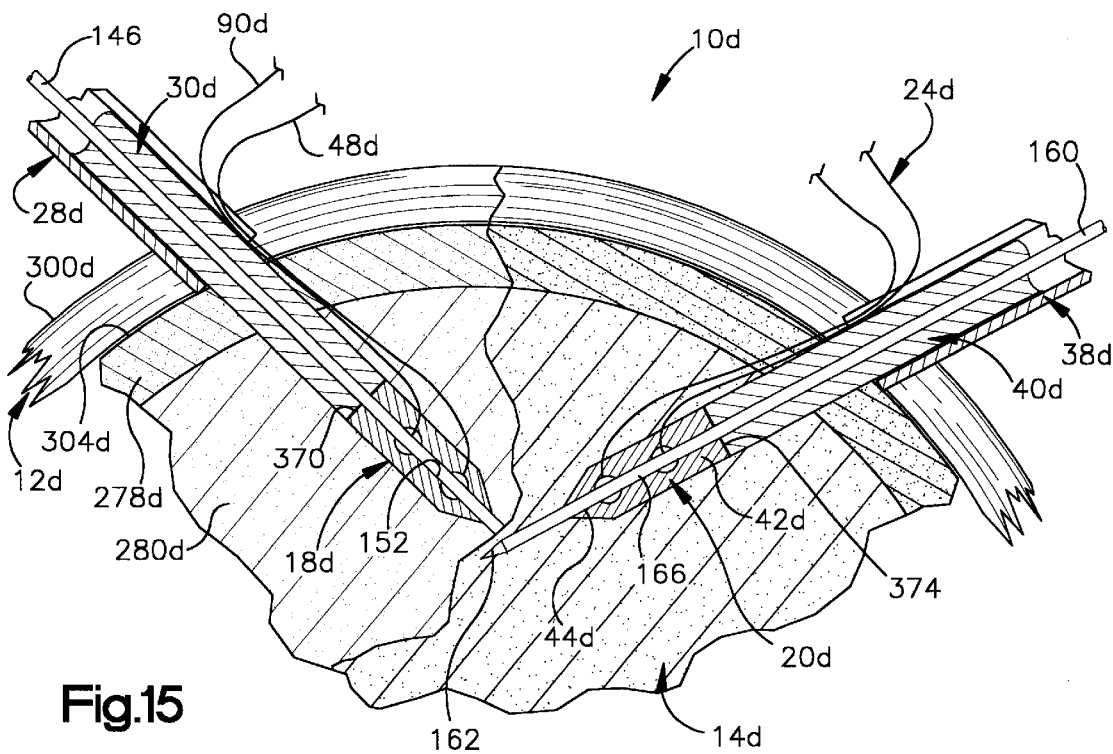
Figure 16:
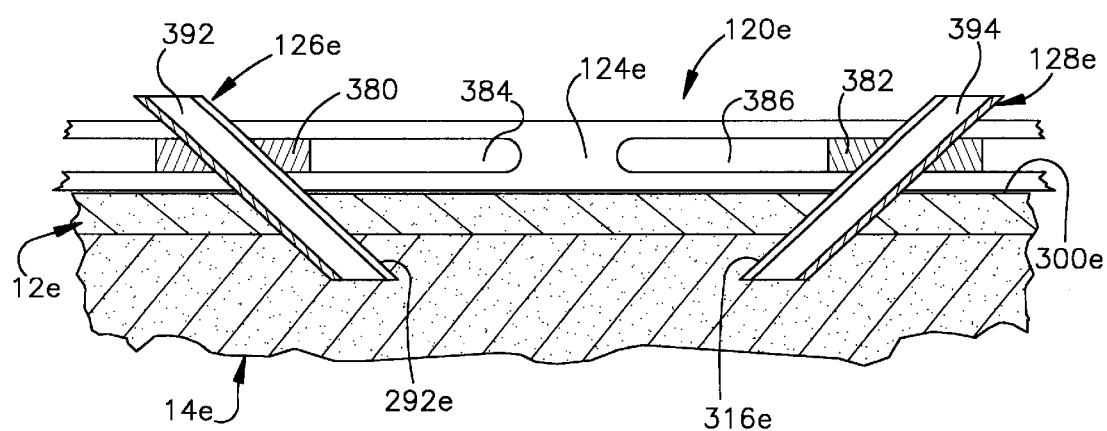
Figure 17:
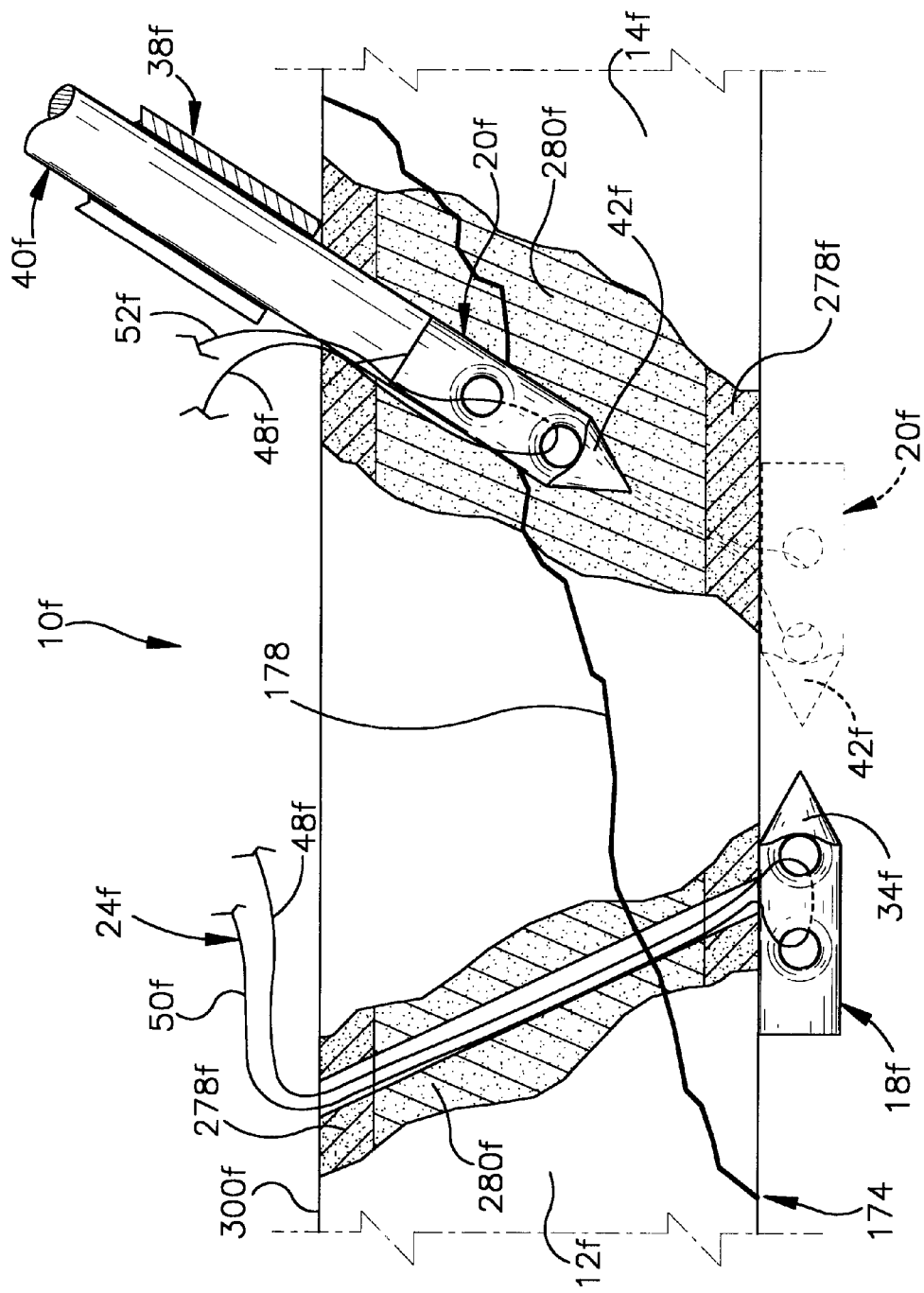
Figure 18:
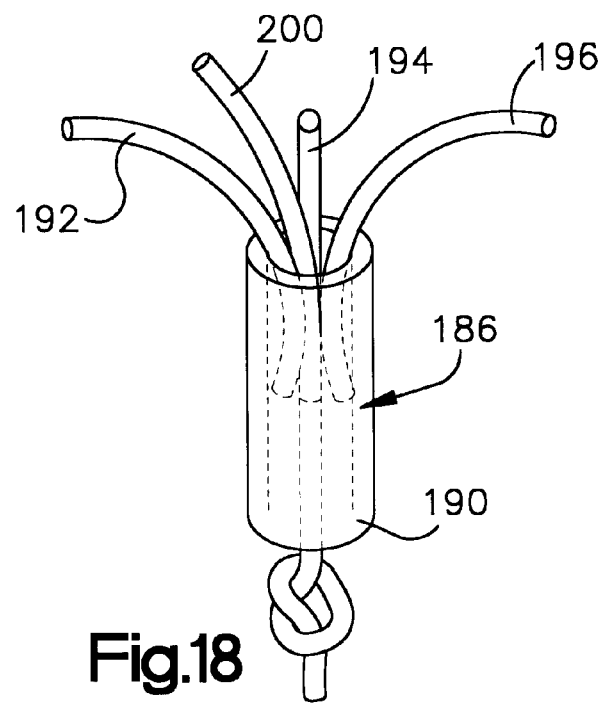
Figure 19:
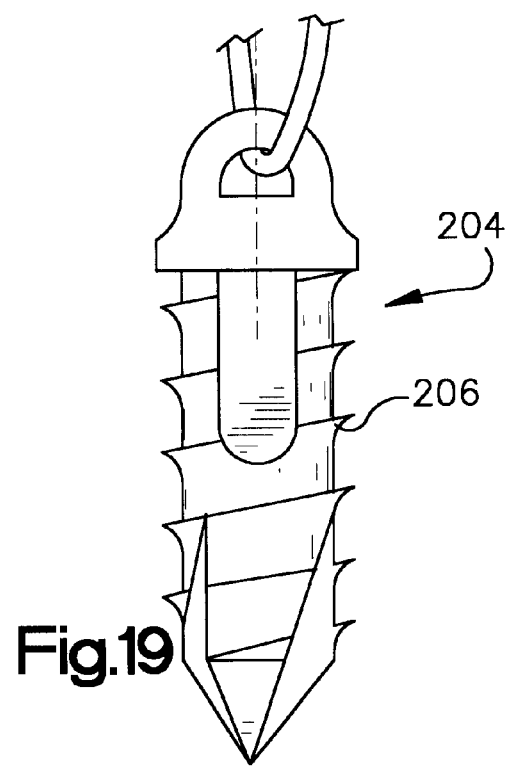
Figure 20:
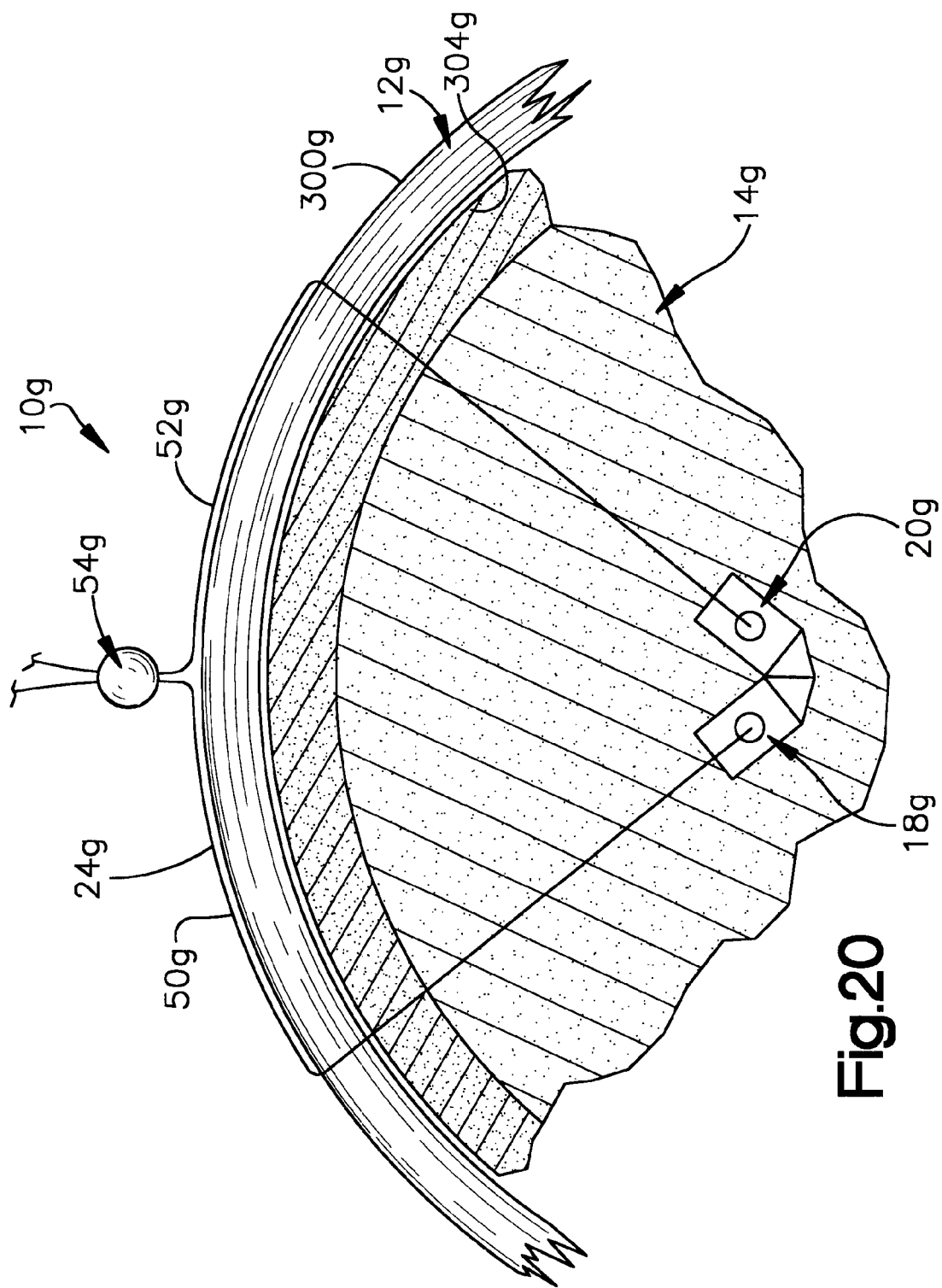
Figure 21:
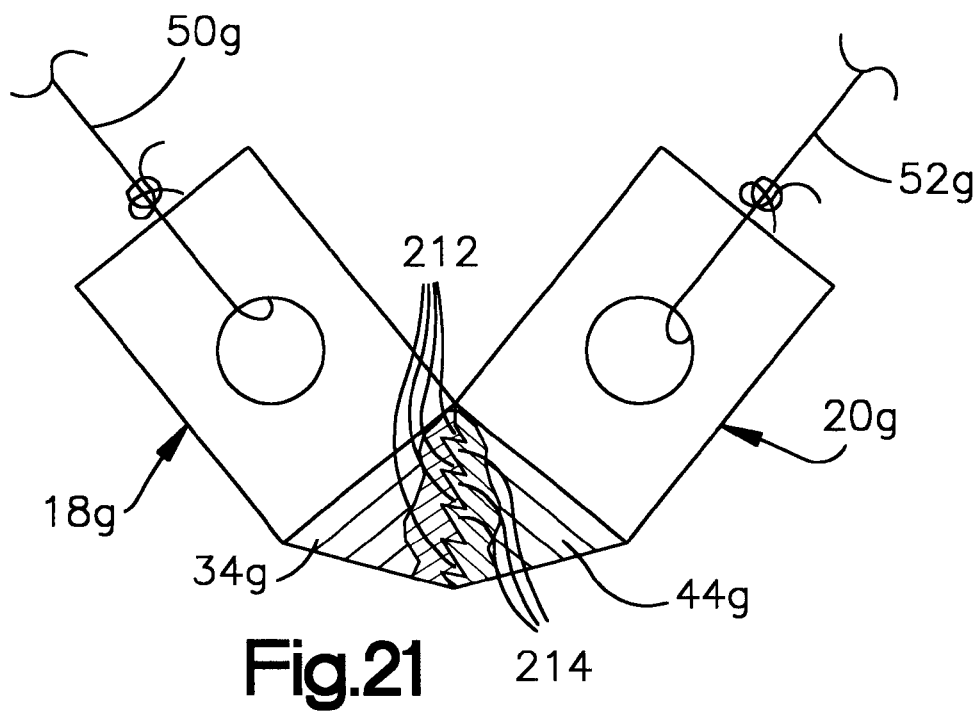
Figure 22:
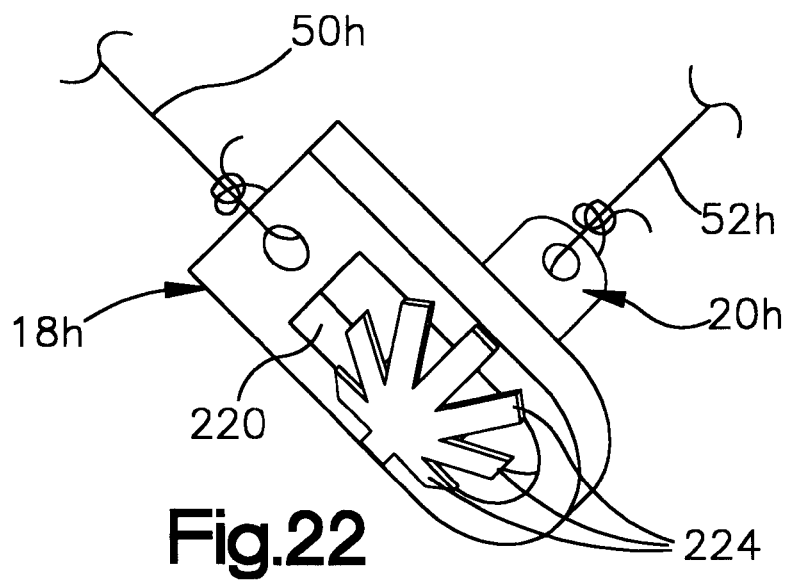
Figure 23:
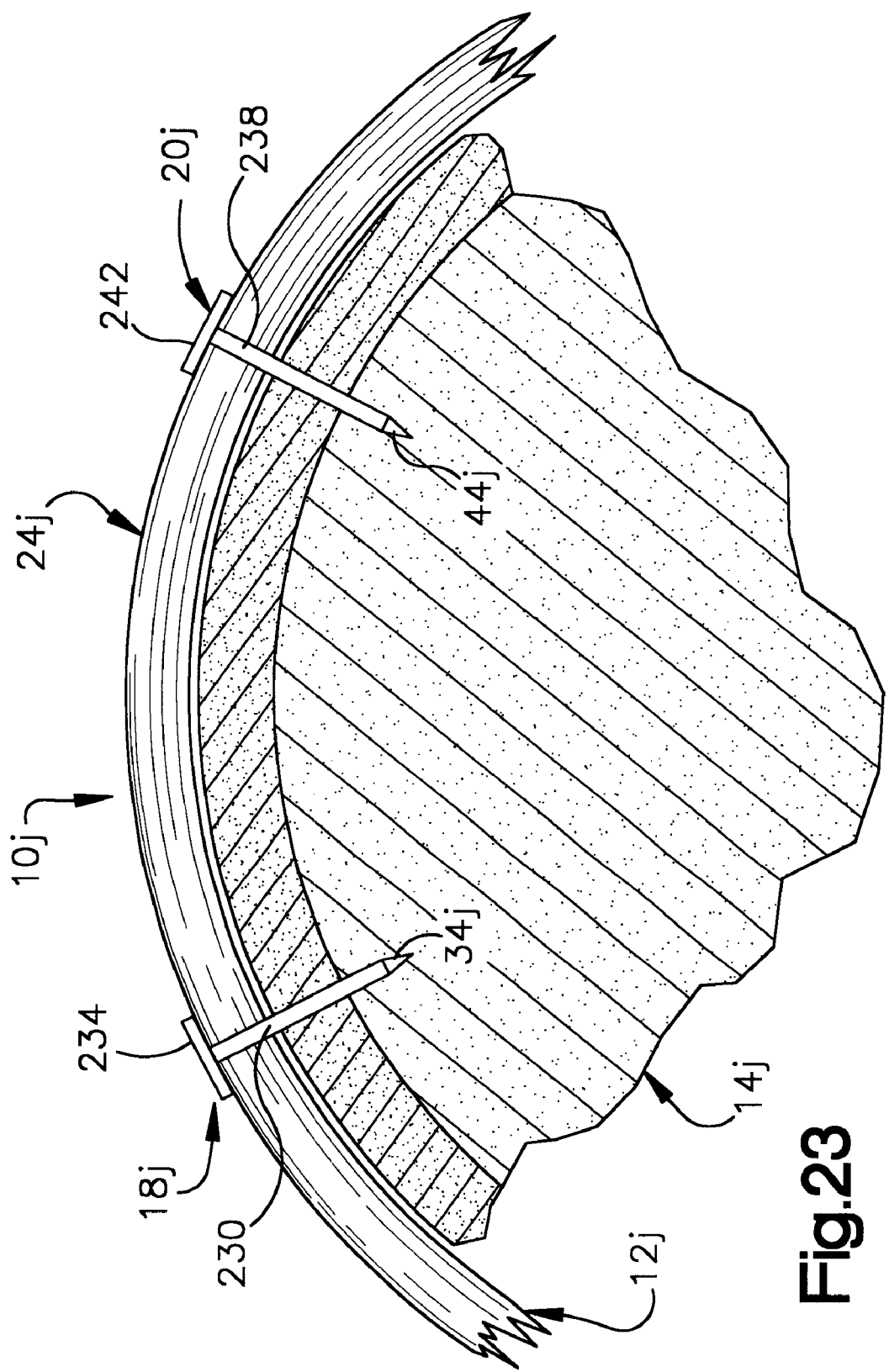

FIG. 6 is a schematic fragmentary illustration, generally similar to FIG. 3, illustrating the manner in which a second one of the anchors of FIG. 1 is moved through first body tissue into second body tissue;

FIG. 7 is a fragmentary schematic illustration, generally similar to FIG. 4, depicting the manner in which the anchor of FIG. 6 is moved deeper into the body tissue;

FIG. 8 is fragmentary schematic illustration, generally similar to FIG. 5, depicting the manner in which the orientation of the anchor of FIG. 7 is changed after the anchor has been moved to a desired depth in the body tissue;

FIG. 9 is a fragmentary schematic illustration depicting the relationship between the anchors of FIG. 1 and a suture extending between the anchors after the anchors have been moved into the body tissue;

FIG. 10 is schematic illustration, generally similar to FIG. 9, depicting the manner in which the suture extending between the anchors is tensioned with a predetermined force and in which a retainer is deformed to grip portions of the suture;

FIG. 11 is a fragmentary schematic illustration, generally similar to FIGS. 1 and 9, depicting the manner in which a pair of anchors interconnected by a continuous loop of suture are positioned relative to body tissue and the loop is tensioned during positioning of the anchors relative to the body tissue;

FIG. 12 is a fragmentary schematic illustration, generally similar to FIG. 6, illustrating the relationship between an anchor of FIG. 11 and an apparatus which is utilized to effect movement of the anchor into body tissue and to measure tension in the continuous loop of suture extending between the anchors of FIG. 11;

FIG. 13 is a schematic illustration, generally similar to FIG. 11, illustrating the manner in which a guide assembly is utilized to position anchors relative to body tissue;

FIG. 14 is a schematic illustration depicting the manner in which a thin elongated member is utilized to guide movement of an anchor into body tissue;

FIG. 15 is a fragmentary schematic illustration depicting the manner in which a second thin elongated member is utilized to guide movement of a second one of the anchors of FIG. 14 into the body tissue;

FIG. 16 is a fragmentary schematic illustration, similar to FIG. 13, of another embodiment of a guide assembly which is utilized to position anchors relative to body tissue and depicting the manner in which tubular guide members extend through first body tissue into second body tissue;

FIG. 17 is a fragmentary schematic illustration depicting the manner in which anchors are utilized to repair a fracture in a bone;

FIG. 18 is a schematic illustration of another embodiment of the anchor;

FIG. 19 is an illustration of still another embodiment of the anchor;

FIG. 20 is a fragmentary schematic illustration, generally similar to FIG. 9, illustrating the manner in which anchors are interconnected at an intersection between transverse paths along which the anchors are moved into body tissue;

FIG. 21 is an enlarged fragmentary view of a portion of FIG. 20 and illustrating how the anchors are interconnected at the intersection of the paths along which the anchors are moved into in the body tissue;

FIG. 22 is a fragmentary schematic illustration, generally similar to FIG. 21, illustrating the manner in which another embodiment of the anchors are interconnected at the intersection between the paths along which the anchors are moved into the body tissue; and FIG. 23 is a fragmentary sectional view, generally similar to FIG. 12, illustrating the manner in which another embodiment of the anchors may be utilized to secure body tissues.

DESCRIPTION OF SPECIFIC PREFERRED EMBODIMENTS OF THE INVENTION

General Description

An apparatus 10 (FIG. 1) is used to secure first human body tissue 12 with second human body tissue 14. In the illustration of FIG. 1, the first body tissue 12 is soft body tissue and the second body tissue 14 is hard body tissue. However, it should be understood that both the first body tissue 12 and the second body tissue 14 could be soft body tissue if desired. Alternatively, both the first body tissue 12 and the second body tissue 14 could be hard body tissue.

The apparatus 10 includes a plurality of suture anchors 18 and 20. Although only two suture anchors 18 and 20 have been illustrated in FIG. 1, it should be understood that a greater number of suture anchors could be provided if desired. For example, it is contemplated that three anchors could be provided if desired.

The apparatus 10 also includes a suture 24 which extends between the suture anchors 18 and 20. Although the illustrated suture 24 is integrally formed as one piece and extends between the anchors 18 and 20, it is contemplated that the suture 24 could be formed by a plurality of separate portions each of which is connected with one of the anchors. Thus, a first segment of a suture could be connected with the left suture anchor 18 and a second segment of a suture could be connected with the right suture anchor 20.

When the first and second body tissues 12 and 14 are to be interconnected, the suture anchors 18 and 20 are moved through the first body tissue 12 into the second body tissue 14. If desired, the suture anchors 18 and 20 could be moved into and through the second body tissue 14.

When the anchor 18 is to be moved into the body tissue 12, the anchor may be positioned in an inserter 28 and pressed against the body tissue 12 by a pusher member 30 (FIG. 2). A trailing end portion 32 of the anchor 18 is positioned in the inserter 28 and is engaged by the pusher member 30. A pointed leading end portion 34 of the anchor 18 extends from the inserter 28.

In the embodiment illustrated in FIG. 2, the inserter 28 has a tubular configuration and the pusher member 30 is telescopically inserted into the inserter. However, if desired, the inserter 28 could have a different configuration and could be constructed in such a manner as to perform the function of the pusher member 30. For example, the inserter 28 could be constructed could be a solid rod with a gripper at one end of the rod. This inserter would grip and apply axial force against a trailing end portion 32 of the anchor 18.

When the anchor 18 is to be moved into the body tissue 12, the leading end portion 34 of the anchor 18 initiates the formation of an opening in the body tissue 12. Force applied against the trailing end portion 32 of the anchor 18 by the pusher member 30 causes the anchor to pierce the body tissue 12. As the anchor 18 moves through the body tissue 12, the leading end portion 34 of the anchor moves into engagement with the body tissue 14.

The leading end portion 34 of the anchor 18 initiates the formation of an opening in the body tissue 14. Force applied against the trailing end portion 32 of the anchor 18 by the pusher member 30 moves the leading end portion of the anchor into the body tissue 14 (FIG. 3). Continued axial movement of the pusher member 30 relative to the inserter 28 moves the anchor 18 deeper into the body tissue 14 (FIG. 4). As the anchor 18 moves into the body tissue 14, the leading end portion 34 of the anchor pierces the body tissue. The anchor 18 may be moved along a linear or nonlinear path in the body tissues 12 and 14.

In the embodiment of the invention illustrated in FIGS. 1–10, the anchor 18 is utilized to form its own passage in the body tissues 12 and 14. However, a drill or other tool could be utilized to form a passage for the anchor 18 in either the body tissue 12 or 14 or in both of the body tissues.

Once the anchor 18 has moved into the body tissue 14, the anchor may be toggled from the orientation shown in FIG. 4 to the orientation shown in FIG. 5 relative to the body tissue 14. Changing the orientation of the anchor 18 relative to the body tissue 14 increases the ability of the anchor to withstand pull out force applied against the anchor by the suture 24.

The anchor 20 (FIG. 1) is inserted into the body tissue in the same manner as previously described in conjunction with the anchor 18. Thus, the anchor 20 is positioned in an inserter 38 (FIG. 6) and is engaged by a pusher member 40. The pusher member 40 engages a trailing end portion 42 of the anchor 20.

The pusher member 40 presses a pointed leading end portion 44 of the anchor 20 against the body tissue 12 to initiate the formation of an opening in the body tissue. The anchor 20 then moves through the body tissue 12 and moves into engagement with the body tissue 14. The continued application of force against the trailing end portion 42 of the anchor 20 by the pusher member 40 causes the leading end portion 44 of the anchor to initiate the formation of an opening in the body tissue 14.

As the anchor 20 moves deeper into the body tissue 14, the anchor pierces the body tissue in the manner illustrated in FIG. 7. The anchor 20 may be moved along a linear or nonlinear path in the body tissue 14.

Once the anchor 20 has moved into the body tissue 14, the orientation of the anchor relative to the body tissue is changed with a toggling action. Thus, the orientation of the anchor 20 is changed from the orientation illustrated in FIG. 7 to the orientation illustrated in FIG. 8. Changing the orientation of the anchor 20 relative to the body tissue increases the ability of the anchor to withstand pull out forces transmitted through the suture 24.

Once both anchors 18 and 20 have moved through the body tissue 12 into the body tissue 14, the pusher members 30 and 40 (FIGS. 4, 5, 7, and 8) are withdrawn from the body tissue. It is contemplated that the anchors 18 and 20 may be either sequentially moved into the body tissue 12 and 14 or simultaneously moved into the body tissue 12 and 14. If the anchors 18 and 20 are sequentially moved into the body tissue 12 and 14, the same inserter and pusher member may be utilized to move both of the anchors into the body tissue. If the anchors 18 and 20 are simultaneously moved into the body tissue 12 and 14, separate inserters 28 and 38 and pusher members 30 and 40 may be used to move the anchors into the body tissue. If desired, the inserters 28 and 38 and pusher members 30 and 40 may be interconnected and form portions of an inserter assembly.

Although it is believed that it will be desired to pivot the anchors 18 and 20 from the orientations illustrated in FIGS. 4 and 7 to the orientations shown in FIGS. 5 and 8, the anchors 18 and 20 may be left in the orientations shown in FIGS. 4 and 7 if desired. It is believed that pivoting the anchors 18 and 20 to the orientations shown in FIGS. 5 and 8 will enable the anchors to remain stationary relative to the body tissue 14 when relatively large tension forces are transmitted to the anchors through the suture 24.

The suture 24 (FIG. 9) is integrally formed as one piece and includes a connector portion 48 which extends between the two anchors 18 and 20. In addition, the suture 24 includes a leg portion 50 which extends from the anchor 18. The suture 24 also includes a leg portion 52 which extends from the anchor 20. A suture retainer (crimp) 54 is utilized to interconnect the leg portions 50 and 52 of the suture 24. Alternatively, the leg portions 50 and 52 may be tied together in a knot to interconnect the leg portions. If desired, the leg portions 50 and 52 could be bonded together by the application of ultrasonic vibratory energy directly to the leg portions.

When the leg portions 50 and 52 of the suture 24 are to be interconnected with the retainer 54, the suture 24 may be tensioned with a force application assembly 60 (FIG. 10). The force application assembly 60 applies a predetermined force, indicated schematically by an arrow 62 in FIG. 10, to the leg portions 50 and 52 of the suture 24. The predetermined force 62 has a magnitude which is a function of the size and strength of the suture 24.

The suture retainer 54 is pressed against the body tissue 12 by a force application member 66. Forces, indicated schematically at 70 and 72 in FIG. 10, are transmitted through the force application member 66 to the suture retainer 54 to press the suture retainer against the body tissue 12. The magnitude of the forces indicated by the arrows 70 and 72 and applied to the suture retainer 54 by the force application member 66, are a function of the size and strength of the suture 24.

While the suture 24 is being tensioned under the influence of force 62 and while the suture retainer 54 is being pressed against the body tissue 12 under the influence of forces 70 and 72, the suture retainer 54 is plastically deformed to firmly grip the suture 24. To plastically deform the suture retainer 54, a pair of force application members 76 and 78 are pressed against opposite sides of the suture retainer 54. The force with which the force application members 76 and 78 are pressed against the suture retainer 54 is indicated schematically by arrows 80 and 82 in FIG. 10. The force applied against the suture retainer 54 by the force application members 76 and 78 plastically deforms the material of the suture retainer while the suture retainer is being pressed against the body tissue 12 by the force application member 66 and while the suture is being tensioned by the force application assembly 60.

In the embodiment of the invention illustrated in FIGS. 1–10, the anchors 18 and 20 are embedded in the body tissue 14 (FIG. 10). However, the anchors 18 and 20 could be moved through the body tissue 14 if desired. This would result in the anchors 18 and 20 engaging an outer surface of the body tissue 14.

When the body tissue 12 and 14 are both soft body tissues, it is contemplated that the body tissues could be placed in apposition. Once the soft body tissues 12 and 14 have been approximated, the anchors 18 and 20 would be moved through the body tissue 12 into the body tissue 14. If desired, the anchors 18 and 20 could be moved through the body tissue 14.

In the embodiment of the invention illustrated in FIGS. 1–10, the body tissue 12 is secured with the body tissue 14 by the suture 24. In this embodiment, the suture 24 extends through the body tissue 12 and presses the body tissue 12 against the body tissue 14. However, the body tissue 12 could be secured with the body tissue 14 in a different manner. For example, the suture 24 could extend around the body tissue 12 without extending through the body tissue 12. The body tissue 12 could be spaced from the body tissue 14 and secured with the body tissue 14 by a portion of the suture extending between the body tissue 12 and the body tissue 14.

In the embodiment of the invention illustrated in FIGS. 1–10, the suture 24 has leg portions 50 and 52 which extend from the suture anchors 18 and 20 and a connector portion 48 which extends between the suture anchors. In the embodiment of the invention illustrated in FIG. 11, the suture is formed as a continuous loop which extends between the two anchors. Since the embodiment of the invention illustrated in FIG. 11 is generally similar to the embodiment of the invention illustrated in FIGS. 1–10, similar numerals will be utilized to designate similar components, the suffix letter "a" being associated with the numerals of FIG. 11 to avoid confusion.

An apparatus 10a (FIG. 11) for use in securing first body tissue 12a with second body tissue 14a includes a plurality of suture anchors 18a and 20a. A suture 24a extends between the anchors 18a and 20a. Although the suture 24a has been illustrated in FIG. 11 as extending between only two anchors 18a and 20a, a greater number of anchors could be provided if desired.

The suture 24a is forms a continuous flexible loop. Thus, the suture 24a includes a first connector portion 48a which extends between the suture anchors 18a and 20a and a second connector portion 90 which extends between the suture anchors. The connector portions 48a and 90 are interconnected by bonding their ends together under the influence of ultrasonic vibratory energy. However, the connector portions 48a and 90 could be integrally formed as one piece. The connector portions 48a and 90 do not have free ends. The connector portions 48a and 90 may be interconnected by a device, such as the retainer 54 of FIG. 9, or a knot.

Since the suture 24a is a continuous closed loop without free ends, the suture 24a is tensioned whenever the anchors 18a and 20a are moved into the body tissue 14a. The anchor 18a is moved through the body tissue 12a into the body tissue 14a in the same manner as previously described in conjunction with the embodiment of the invention illustrated in FIGS. 1–10. The anchor 20a is then moved through the body tissue 12a into the body tissue 14a.

As the anchor 20a moves into the body tissue 14a, the anchor 20a moves from the position illustrated in solid lines in FIG. 11 to the position illustrated in dashed lines in FIG. 11. As the anchor 20a moves into the body tissue 14a, the connector portions 48a and 90 of the suture 24a are both tensioned. The magnitude of the tension force in the continuous loop which is formed by the suture 24a will be a function of magnitude of the force which is utilized to move the suture anchors 18a and 20a into the body tissue 14a.

The anchors 18a and 20a may be moved either sequentially or simultaneously into the body tissue 14a. Thus, the anchor 18a may be moved through the body tissue 12a into the body tissue 14a in the manner illustrated in solid lines in FIG. 11. The anchor 20a may then be moved through the tissue 12a into the tissue 14a to the position illustrated in dashed lines in FIG. 11. Alternatively, the anchors 18a and 20a may both be simultaneously moved through the body tissue 12a and into the body tissue 14a. The anchors 18a and 20a may be moved along either linear or nonlinear paths in the body tissues 12a and 14a.

It is contemplated that an inserter, corresponding to the inserter 18 of FIGS. 2–5, and a pusher member, corresponding to the pusher member 30 of FIGS. 2–5, will be utilized to position the anchor 18a in the body tissue 14a (FIG. 11). Similarly, an inserter, corresponding to the inserter 38 of FIGS. 6–8, and a pusher member, corresponding to the pusher member 40 of FIGS. 6–8, will be utilized to position the anchor 20a in the body tissue 14a (FIG. 11).

In the embodiment of the invention illustrated in FIG. 11, only two anchors 18a and 20a are connected with the continuous loop formed by the suture 24a. However, a greater number of anchors, for example three, could be connected with the loop formed by the suture 24a. Upon insertion of the last anchor of the plurality of anchors, the loop formed by the suture 24a would probably slide in passages in at least one of the other anchors and the suture would be tensioned.

In the embodiment of the invention illustrated in FIG. 12, an apparatus is provided to measure tension in a suture which forms a continuous closed loop. Since the embodiment of the invention illustrated in FIG. 12 is generally similar to the embodiment of the invention illustrated in FIGS. 1–11, similar numerals will be utilized to designate similar components, the suffix letter "b" being associated with the numerals of FIG. 12 to avoid confusion.

An anchor 20b is positioned in an inserter 28b and moved into body tissue under the influence of force applied against a trailing end portion 42b of the anchor 20b by a pusher member 40b. A tension measuring assembly 96 is provided in association with the inserter 38b. The tension measuring assembly 96 includes a force transmitting member 100 having an end portion 102 which engages connector portions 48b and 90b of a suture 24b. Although only a single anchor 20b is illustrated in FIG. 12, it should be understood that the suture 24b forms a continuous loop connected with a second anchor, corresponding to the anchor 18a of FIG. 11.

As the anchor 20b moves into the body tissue 14b, the suture 24b applies force against the end portion 102 of the force transmitting member 100. A force measuring device 112 is connected with the force transmitting member 100. The force measuring device 112 measures the tension force in the continuous closed loop formed by the suture 24b. The force measuring device 112 may be a load cell or other transducer.

During movement of the anchor 20b into the body tissue 14b, the inserter 38b is pressed against the body tissue 14b by a remote inserter drive assembly 110 (FIG. 12). While the inserter 38b is held stationary and pressed against the body tissue 14b, a pusher member drive assembly 114 moves the pusher member 40b and anchor 20b into the body tissue 14b in the manner previously described in conjunction with the embodiment of the invention illustrated in FIGS. 1–10. The anchor 20b may be moved along either a linear path or a nonlinear path into the body tissue 14b.

The force measuring assembly 96 is illustrated in FIG. 12 in association with a suture 24b which is formed as a continuous loop. However, the force measuring assembly 96 could be utilized with a suture having free end portions. Thus, the force measuring assembly 96 could be used with the suture 24 of FIGS. 1–10 if desired. If this was done, the connector portion 48 of the suture 24 would engage the end portion 102 of the force transmitting member 100. If desired, the leg portion 52 of the suture 24 could also engage the end portion 102 of the force transmitting member 100.

If desired, the force measuring device 112, pusher member drive assembly 114, and inserter drive assembly 110 may be formed as part of a robotic tool which is associated with a console that gives a three dimensional view of an operating table in an operating room of a hospital. Controls at the console provide tactile feedback to a surgeon operating the controls. The controls effect operation of the drive assemblies 110 and 114 to move the anchor 20b into the body tissue 14b.

The robotic tool may include apparatus to move an anchor corresponding to the anchors 18 or 18a of FIGS. 1 and 11 into the body tissue 12b and 14b. Thus, the robotic tool also includes a second inserter drive assembly, having the same construction as the inserter drive assembly 110 of FIG. 12, to position an inserter, corresponding to the inserter 28 of FIG. 2, relative to the body tissue 12b and 14b. The robotic tool also includes a second pusher member drive assembly, having the same construction as the pusher member drive assembly 114 of FIG. 12, to position a pusher member, corresponding to the pusher member 40 of FIG. 2, relative to the body tissue 12b and 14b.

The robotic tool may be operated to effect simultaneous movement of two anchors, that is, an anchor corresponding to the anchor 18 (FIG. 1) and an anchor corresponding to the anchor 20b (FIG. 12), into the body tissues 12b and 14b. As the anchors 18 and 20b moves into the body tissue 14b, the continuous loop formed by the suture 24b is tensioned. The force transmitting member 100 transmits a force which is a function of the tension in the suture 24b to the force measuring device 112. When the force measuring device 112 detects that the desired tension is present in the suture 24b, operation of the pusher member drive assemblies is interrupted with the anchors 18 and 20b in a desired position relative to the body tissue 14b.

In the embodiment of the invention illustrated in FIG. 13, a guide assembly is utilized to position a suture anchor relative to the body tissue. Since the embodiment of the invention illustrated in FIG. 13 is generally similar to the embodiments of the invention illustrated in FIGS. 1–12, similar numerals will be utilized to designate similar components, the suffix letter "c" being associated with the numerals of FIG. 13 to avoid confusion.

A guide assembly 120 is utilized in association with an apparatus 10c. The apparatus 10c includes a plurality of suture anchors 18c and 20c. Although only two anchors 18c and 20c have been illustrated, a greater number of anchors could be utilized if desired.

A suture 24c extends from the suture anchors 18c and 20c. In the embodiment of the invention illustrated in FIG. 13, the suture 24c is a continuous loop, in the same manner as the suture 24a of FIG. 11. However, the suture 24c could have free ends and leg portions corresponding to the leg portions 50 and 52 of the suture 24 of FIG. 1.

The guide assembly 120 includes a base 124 which positions guides 126 and 128 relative to body tissue 12c and 14c. The guides 126 and 128 have a tubular configuration. Although only two guides 126 and 128 have been provided for only two anchors 18c and 20c, a greater number of guides could be provided for a greater number of anchors.

The anchors 18c and 20c are positioned in the guides 126 and 128 in the same manner as in which they are positioned in the inserters 28 and 38 of the embodiment of the invention illustrated in FIGS. 2–8. A pusher member 132 is utilized to apply force against the anchors 18c and 20c to move the anchors relative to the guides 126 and 128 and into the body tissue 12c and 14c.

The guide 128 is movable along the base 124 to enable the distance between locations where the anchors 18c and 20c move into the body tissue 12c and 14c to be adjusted. The manner in which the guide 128 is moved along the base 124 is indicated schematically by arrows 136 in FIG. 13. A suitable retainer 140 is provided to connect the guide 128 with the base 124 in a desired position relative to the guide 126.

If the anchors 18c and 20c are to be moved along nonlinear paths in the body tissue 14c, the guides 126 and 128 could have a nonlinear configuration. For example, the guides 126 and 128 could be formed with an arcuate configuration. If this was done, the pusher member 132 would be formed with an arcuate configuration corresponding to the arcuate configuration of the guides 126 and 128.

In the embodiments of the invention illustrated in FIGS. 1–13, the anchors have pointed leading end portions which initiate the formation of openings in the body tissue. In the embodiment of the invention illustrated in FIGS. 14 and 15, thin elongated members are provided to initiate the formation of openings in the body tissue. The thin elongated members are also be utilized to guide movement of the anchors into the body tissue. Since the embodiment of the invention illustrated in FIGS. 14 and 15 is generally similar to the embodiments of the invention illustrated in FIGS. 1–13, similar numerals will be utilized to designate similar components, the suffix letter "d" being associated with the numerals of FIGS. 14 and 15 to avoid confusion.

An apparatus 10d includes a plurality of anchors 18d and 20d which are interconnected by a suture 24d. The suture 24d is formed as a continuous flexible loop, in the same manner as is illustrated in FIG. 11. However, the suture 24d could have legs with free end portions, in the manner illustrated in FIG. 1.

A tubular inserter 28d (FIG. 14) cooperates with a pusher member 30d during movement of the anchor 18d into body tissue. Similarly, a tubular inserter 38d (FIG. 15) cooperates with a pusher member 40d during movement of the anchor into body tissue.

When the anchor 18d (FIG. 14) is to be positioned relative to body tissue, a thin elongated member 146 is utilized to initiate formation of an opening in the body tissue 12d and 14d. The thin elongated member 146 may be a cylindrical rod similar to a K-wire. The thin elongated member 146 has a pointed end portion 148.

When the anchor 18d is to be moved along a linear path in the body tissue 14b, the thin elongated member 146 will have the linear configuration illustrated in FIG. 14. When the anchor 18d is to be moved along an arcuate path, the thin elongated member 146 will have an arcuate configuration.

When the thin elongated member 146 (FIG. 14) is to be moved into the body tissue 12d and 14d, the thin elongated member 146 is positioned in a desired orientation relative to the body tissue. The thin elongated member is then forced axially into the body tissue 12d and 14d. As the thin elongated member 146 moves into the body tissue 12d, the pointed end portion 148 of the thin elongated member initiates the formation of an opening in the body tissue 12d. As the thin elongated member 146 moves through the body tissue 12d, the pointed end portion 148 engages the body tissue 14d and initiates the formation of an opening the body tissue 14d.

Once the thin elongated member 146 has initiated the formation of an opening in the body tissue 14d, the thin elongated member is moved through the hard outer layer 278d of bone into the cancellous bone 280d. The thin elongated member 146 is moved to a desired depth in the cancellous bone 280d. The depth to which the elongated member 146 is moved into the cancellous bone 280d is somewhat greater than a depth to which the anchor 18d is to be moved into the cancellous bone.

Once the thin elongated member 146 ahs been moved to the desired depth in the cancellous bone 280d, the anchor 18d is telescopically positioned relative to the stationary thin elongated member 146. When this is done, the thin elongated member 146 will extend through a cylindrical passage 152 in the anchor 18d. The pusher member 30d is then positioned in a telescopic relationship with the stationary thin elongated member 146. When this is done, the thin elongated member 146 will extend through a cylindrical passage 156 in the pusher member 30d and the through passage 152 in the anchor 18d. The cylindrical inserter 28d extends around the pusher member 30d and a trailing end portion 32d of the anchor 18d.

The pusher member 30d (FIG. 14) is pressed axially against the trailing end portion of the anchor 18d to slide the pusher member and the anchor along the stationary thin elongated member 146. As the anchor 18d slides along the stationary thin elongated member 146, a pointed leading end portion 34d of the anchor 18d pierces the body tissue 12d and the body tissue 14d. When the anchor 18d has been moved to a desired position relative to the body tissue 14d, movement of the anchor along the thin elongated member is interrupted (FIG. 14).

The anchor 20d (FIG. 15) is positioned relative to the body tissue in the same manner as the anchor 18d. When the anchor 20d is to be positioned relative to the body tissue 12d and 14d, a second thin elongated member 160 (FIG. 15) is positioned in a desired orientation relative to the body tissue 12d and 14d. A pointed end portion 162 of the thin elongated member 160 is then forced into the body tissue. The thin elongated member 160 may have a linear configuration or nonlinear configuration.

The anchor 20d is then telescopically positioned on the stationary thin elongated member 160. When this is done, the thin elongated member 160 will extend through a cylindrical passage 166 (FIG. 15) in the anchor 20d. The anchor 20d is moved along the thin elongated member 160 until a pointed leading end portion 44d of the anchor 20d engages the body tissue 12d. A pusher member 40d is then telescopically moved along the thin elongated member into engagement with a trailing end portion 42d of the anchor 20d. The pusher member 40d then applies force against the trailing end portion 42d of the anchor 20d to move the anchor into the body tissue to the position shown in FIG. 15.

Once the anchors 18d and 20d have been positioned in the body tissue 14d, the thin elongated members 146 and 160 are withdrawn from the anchors and from the body tissue. The anchors 18d and 20d may then be pivoted or toggled relative to each other to change their orientation relative to the body tissue. Alternatively, the anchors 18d and 20d may be left in the orientation illustrated in FIG. 15.

In the embodiment of the invention illustrated in FIG. 13, a guide assembly 120 is utilized to position the guides 126 and 128 relative to the body tissue. A second embodiment of the guide assembly is illustrated in FIG. 16. Since the embodiment of the guide assembly illustrated in FIG. 16 is generally similar to the embodiment of the guide assembly illustrated in FIG. 13, similar numerals will be utilized to designate similar components, the suffix letter "e" being associated with the numerals FIG. 16 to avoid confusion.

A guide assembly 120e includes a base 124e. Tubular cylindrical guides 126e and 128e are provided on the base 124e. The guides 126e and 128e are utilized to guide movement of anchors, corresponding to the anchors 18c and 20c of FIG. 13. The guides 126e and 128e may have either a linear or a nonlinear configuration depending upon the configuration of the paths along which the anchors are to be moved in the boy tissue 12d and 14d. When more than two anchors are to be positioned relative to the body tissues 12e and 14e, a corresponding number of guides would be provided.

In the embodiment of the invention illustrated in FIG. 16, the guides 126e and 128e penetrate both the body tissue 12e and the body tissue 14e. The body tissue 14e is soft body tissue which is easily penetrated by the guides 126e and 128e. Alternatively, the body tissue 14e could be hard body tissue which requires the application of a relatively large force against the guides 126e and 128e to cause them to penetrate the body tissue. The guides 126e and 128e have slots 292e and 316e to receive portions of a suture.

In the embodiment of the invention illustrated in FIGS. 1–10, the suture anchors 18 and 20 are utilized to connect soft body tissue 12 with hard body tissue 14. In the embodiment of the invention illustrated in FIG. 17, the anchors are utilized to connect hard body tissue with hard body tissue. Since the embodiment of the guide assembly illustrated in FIG. 17 is generally similar to the embodiment of the invention illustrated in FIGS. 1–16, similar numerals will be utilized to designate similar components, the suffix letter "f" being associated with the numerals of FIG. 17 to avoid confusion.

First body tissue 12f (FIG. 17) is connected with second body tissue 14f with anchors 18f and 20f. A suture 24f extends between the anchors 18f and 20f. The body tissue 12f and 14f are portions of a bone 174. A fracture 178 extends across the bone 174.

The anchors 18f and 20f (FIG. 17) are moved from one side of the bone 174 to the opposite side of the bone to interconnect the body tissue 12f and 14f with the suture 24f. An inserter 38f and pusher member 40f may be utilized to move the anchors 18f and 20f through the bone 12f and 14f. The pusher member 40f is effective to apply sufficient force against the anchors 18f and 20f to enable them to initiate the formation of openings in the body tissue 12f and 14f and to enable them to be moved from one side of the bone 174 to the opposite side of the bone.

If desired, passages could be drilled through the bone 174 prior to movement of the anchors 18f and 20f through the bone. If thin elongated members, corresponding to the thin elongated members 146 and 160 (FIG. 15) are to be used to guide the anchors 18f and 20f (FIG. 17), the drilled passages would have a relatively small diameter. If the anchors 18f and 20f are to be moved through the bone 174 without thin elongated members, the drilled passages would have a larger diameter.

In the embodiment of the invention illustrated in FIGS. 1–17, the anchors 18 and 20 all have the same general construction. However, it is contemplated that the anchors could have a construction similar to the construction of an anchor 186 illustrated in FIG. 18. The anchor 186 includes a body 190 from which a plurality of barbs 192, 194 and 196 extend. The anchor 186 is connected with a portion of a suture 200. The anchor 186 has a known construction and is merely illustrative of any one of many different types of anchors which may have projections, corresponding to barbs 192, 194 and 196, which engage body tissue. The projections may have a configuration which is substantially different than the configurations of the barbs 192, 194 and 196.

It should be understood that the anchor could have a construction which is different than the construction of the anchors 18, 20 and 186. For example, the anchor could have a construction similar to the construction of an anchor 204 (FIG. 19). The anchor 204 has a threaded portion 206 which engages body tissue.

In the embodiments of the invention illustrated in FIGS. 1–19, the various anchors are connected with the body tissue in a spaced apart relationship. In the embodiment of the invention illustrated in FIGS. 20 and 21, the anchors are interconnected while they are in the body tissue. Since the embodiment of the invention illustrated in FIGS. 20 and 21 is generally similar to the embodiments of the invention illustrated in FIGS. 1–19, similar numerals will be utilized to designate similar components, the suffix letter "g" being associated with the numerals of FIG. 20 to avoid confusion.

An apparatus 10g (FIG. 20) is utilized to secure body tissue 12g to body tissue 14g. The apparatus 10g includes an anchor 18g and an anchor 20g. A suture 24g extends between the anchors 18g and 20g.

The suture 24g includes a first leg portion 50g which extends from the suture 18g and a second leg portion 52g which extends from the anchor 20g. The two leg portions 50g and 52g of the suture 24g are interconnected by a retainer 54g. In the embodiment of the invention illustrated in FIG. 20, the leg portions 50g and 52g of the suture 24g are two separate pieces of suture. However, the leg portions 50g and 52g may be formed as one piece.

The anchor 18g and the anchor 20g engage each other in the body tissue 14g. Portions of the anchors 18g and 20g cooperate to interconnect the anchors and hold them against movement relative to each other. Thus, the anchor 18g has projections 212 (FIG. 21) which engage projections 214 on the anchor 20g.

The projections 212 and 214 (FIG. 21) on the anchors 18g and 20g intermesh in such a manner as to prevent the anchors from being moved relative to each other under the influence of tension in the leg portions 50g and 52g of the suture 24g. Although specific projections 212 and 214 have been illustrated in FIG. 21, it is contemplated that the projections 212 and 214 could have a different configuration if desired.

In the embodiment of the invention illustrated in FIGS. 20 and 21, the anchors 18g and 20g are interconnected by engagement of projections 212 and 214 on the anchors. In the embodiment of the invention illustrated in FIG. 22, the anchors are interconnected by moving a portion of one anchor into an opening in the other anchor. Since the embodiment of the invention illustrated in FIG. 22 is generally similar to the embodiment of the invention illustrated in FIGS. 20 and 21, similar numerals will be utilized to designate similar components, the suffix letter "h" being associated with the numerals of FIG. 22 to avoid confusion.

An anchor 18h and an anchor 20h are connected with a suture 24h. The suture 24h includes a leg portion 50h which is connected to and extends from the anchor 18h. The suture 24h also includes a leg portion 52h which is connected to and extends from the anchor 20h. The leg portions 50h and 52h may be interconnected by a retainer, corresponding to the retainer 54g of FIG. 20. Alternatively, the leg portions 50h and 52h may be integrally formed as one piece.

In accordance with a feature of this embodiment of the invention, the anchor 18h is provided with an opening 220 (FIG. 22) through which a portion of the anchor 20h extends. The anchor 20h has retainers 224 which move through the opening 220 and engage the anchor 18h when the anchors 18h and 20h are disposed in body tissue 14h. Engagement of the retainers 224 with the anchor 18h interconnects the anchors 18h and 20h.

In the embodiments of the invention illustrated in FIGS. 1–15, the anchors are enclosed by the body tissue 14. In the embodiment of the invention illustrated in FIG. 23, the anchor is partially disposed outside of body tissue 12 and 14. Since the embodiment of the invention illustrated in FIG. 23 is generally similar to the embodiments of the invention illustrated in FIGS. 1–22, similar numerals will be utilized to designate similar components, the suffix letter "j" being associated with the numerals of FIG. 23 to avoid confusion.

An apparatus 10j (FIG. 23) includes a plurality of anchors. The plurality of anchors includes the anchor 18j and an anchor 20j. A suture 24j extends between the anchors 18j and 20j. A greater number of anchors could be provided if desired.

The anchor 18j has a shank portion 230 which extends through body tissue 12j into body tissue 14j. If desired, the shank portion 230 of the anchor 18j could extend through the body tissue 14j. A head end portion 234 of the anchor 230 is pressed against the body tissue 12j and presses the body tissue 12j against the body tissue 14j.

Similarly, the anchor 20j includes a shank portion 238 which extends through the body tissue 12j into the body tissue 14j. If desired, the shank portion 238 of the anchor 20j could extend through the body tissue 14j. The anchor 20j has a head end portion 242 which is pressed against the body tissue 12j.

The suture 24j extends around the shank portions 230 and 238 of the anchors 18j and 20j. The suture 24j engages the shank portions 230 and 238 of the anchors 18j and 20j at a location immediately beneath (as viewed in FIG. 23) the head end portions 234 and 242 of the anchors 18j and 20j.

The suture 24j is formed as a continuous loop. The loop extends around the shank portions 230 and 238 of the anchors 18j and 20j. The continuous loop formed by the suture 24j is generally similar to the loop formed by the suture 24a of FIG. 11. However, if desired, the suture 24j (FIG. 23) could be a single strand which extends between the two anchors 18j and 20j. Alternatively, the suture 24j could be formed with two leg portions, corresponding to the leg portions 50 and 52 (FIG. 9) of the suture 24. If the suture 24j (FIG. 23) is formed with a pair of leg portions, the leg portions could be interconnected with a retainer, similar to the retainer 54 of FIG. 9.

Embodiment of FIGS. 1–10

In the embodiment of the invention illustrated in FIGS. 1–10, the apparatus 10 (FIG. 1) includes a plurality of anchors which are interconnected by a suture 24. Although only two anchors 18 and 20 have been illustrated in FIG. 1, it should be understood that a greater number of anchors could be connected with the suture 24. In the embodiment of the invention illustrated in FIG. 1, the anchors 18 and 20 both have the same construction. However, it is contemplated that the anchor 18 could have a construction which is different than a construction of the anchor 20.

The anchor 18 includes a body portion 250 from which the pointed leading end portion 34 extends. The specific anchor 18 illustrated in FIG. 1 has a cylindrical body portion 250 and a generally conical pointed leading end portion 34 which are disposed in a coaxial relationship.

Although the pointed leading end portion 34 of the anchor 18 (FIG. 1) has a conical configuration, the pointed leading end portion could have a different configuration if desired. For example the pointed leading end portion 34 could be wedge-shaped. Alternatively, the pointed leading end portion 34 could have a pyramidal configuration and be formed by the intersection three, four, or more surfaces. The surfaces could be flat or concave in configuration.

The anchor 18 is provided with a pair of passages 254 and 256 through which the suture 24 extends. The passages 254 and 256 have a cylindrical configuration and extend diametrically through the cylindrical body portion 250. Central axes of the passages 254 and 256 extend parallel to each other and intersect a central axis 260 of the anchor. The central axes of the passages 254 and 256 extend perpendicular to the central axis 260 of the anchor 18.

In the illustrated embodiment of the anchor 18, two passages 254 and 256 extend diametrically through the body portion 250 of the anchor. However, it is contemplated that only a single passage may be provided through the anchor. This single passage could be skewed at an acute angle to the central axis 260 of the anchor 18. Alternatively, the passage could extend axially through the anchor.

The anchor 20 (FIG. 1) is identical to the anchor 18. The anchor 20 has a cylindrical body portion 264 through which passages 266 and 268 extend. The anchor 20 has a conical end portion 44 which is coaxial with the cylindrical body portion 264.

The anchors 18 and 20 maybe formed of many different materials. However, the anchors 18 and 20 are formed of bone, specifically, hard compact bone (cortical bone). The bone from which the anchors 18 and 20 are formed may be autogenic bone or allogenic bone. Alternatively, the anchors may be formed of xenogenic bone.

The anchors 18 and 20 may be formed of bone obtained from many different sources. However, it is believed that it may be preferred to form the anchors 18 and 20 of freeze dried bone which has been obtained from a human cadaver. The bone may be harvested under clean conditions and treated to achieve sterility. Of course, the bone forming the anchors 18 and 20 could be obtained in any one of many different ways under any one of many different conditions.

Although the anchors 18 and 20 are formed of bone, the anchors 18 and 20 may be formed of other materials if desired. The anchors 18 and 20 may be formed of biodegradable or non-biodegradable materials. For example, the anchors 18 and 20 may be formed of polycaperlactone. Alternatively, the anchors 18 and 20 may be formed of metal, such as titanium or stainless steel. If desired, the anchors 18 and 20 could be formed of biodegradable or bioerodible copolymers. It is believed that it may be desired to form the anchors 18 and 20 of bone or polymeric materials in order to minimize any possibility of interference with imaging systems such as magnetic resonance imaging systems.

The anchors 18 and 20 have the same construction as disclosed in co-pending U.S. patent application Ser. No. 09/556,458 filed May 3, 2000 by Peter M. Bonutti and entitled "Method and Apparatus for Securing Tissue". However, it should be understood that the anchors 18 and 20 may be constructed with a different configuration if desired. For example, the anchors 18 and 20 may have a construction of any one of the anchors disclosed in U.S. Pat. Nos. 5,527,343 or 5,534,012. The disclosure in the aforementioned U.S. patent application Ser. No. 09/556,458 and the aforementioned U.S. Pat. Nos. 5,527,343 and 5,534,012 are hereby incorporated herein in their entirety by this reference thereto.

It is contemplated that the anchors 18 and 20 will be used in situations where the anchors are exposed to body fluids. In such a situation, the anchors 18 and 20 may be formed of a material which absorbs body fluids and expands. The anchors 18 and 20 may be formed of a polymeric material which absorbs body liquid. The polymeric material may be hydrophilic. The polymeric material may be cellulose, petroylglutamic acid, high purity carboxymethylcellulose, a collagen, or polylactide. Of course, the anchors 18 and 20 could be formed of other materials which absorb body liquid.

When the anchors 18 and 20 are to absorb body liquid and expand, it is contemplated that the anchors may be constructed in accordance with the disclosure in U.S. Pat. No. 5,718,717 issued Feb. 17, 1998 to Peter M. Bonutti and entitled "Suture Anchor". The disclosure in the aforementioned U.S. Pat. No. 5,718,717 is hereby incorporated herein in its entirety by this reference thereto.

The suture 24 (FIG. 1) extends from the anchors 18 and 20. The suture 24 extends through the passages 254 and 256 in the anchor 18. Similarly, the suture 24 extends through the passages 266 and 268 in the anchor 20.

The suture 24 is freely movable relative to the anchors 18 and 20. By being freely movable relative in the anchor passages 254, 256, 266 and 268, the length of the suture between the anchors 18 and 20 can be varied to accommodate positioning of the anchors at different locations in a patient's body. Thus, by pulling on the leg portions 50 and 52 of the suture 24, the length of the connector portion 48 (FIG. 1) of the suture 24 extending between the anchors can be shortened to accommodate positioning of the anchors in the body tissue 14 at the locations which are relatively close together. Similarly, the anchors 18 and 20 can be pulled apart to lengthen the connector portion 48 of the suture 24 to accommodate positioning of the anchors 18 and 20 in the body tissue 14 at locations which are spaced a substantial distance apart.

Once the anchors 18 and 20 have been positioned in body tissue, in the manner illustrated in FIG. 9, force applied to the leg portions 50 and 52 is effective to tension the connector portion 48 of the suture 24. Any excess material in the connector portion 48 of the suture 24 will be pulled into the leg portions 50 and 52 as the leg portions and connector portion are tensioned. This results in the leg portions 50 and 52 and connector portion 48 of the suture 24 being tensioned with substantially the same force by the force application assembly 60 (FIG. 10) prior to gripping of the leg portions 50 and 52 of the suture 24 with the suture retainer 54.

Since the suture 24 is movable relative to the anchors 18 and 20, the tension in the connector portion 48 (FIG. 9) of the suture 24 can be increased after the anchors 18 and 20 have been positioned in the body tissue 14. Thus, once the anchors 18 and 20 have been moved to the positions illustrated in FIG. 9, pulling on the leg portions 50 and 52 of the suture 24 causes the suture to slide in the passages 254 and 256 in the anchor 18 and to slide in the passages 266 and 268 in the anchor 20. As the suture 24 moves in the passages 254, 256, 266 and 268 in the anchors 18 and 20, the length of the connector portion 48 of the suture 24 decreases. At the same time the length of the leg portions 50 and 52 increase.

Pulling on the leg portions 50 and 52 of the flexible suture 24 increases the tension in the leg portions. This increase in tension is transmitted from the leg portions 50 and 52 of the suture 24 through the passages 254, 256, 266 and 268 in the anchors 18 and 20 to the connector portion 48 of the suture. Therefore, pulling on the leg portions 50 and 52 of the suture 24 eliminates any extra length in the connector portion 48 of the suture and effects a corresponding increase in the combined lengths of the leg portions of the suture. As this occurs, tension in the connector portion 48 of the suture 24 increases to equal tension in the leg portions 50 and 52 of the suture.

The suture 24 may be formed of a plastic material which is a biopolymer. Thus, the suture 24 may be formed of polyglycolide which is commercially available under the trademark DEXON. Polyglycolide is a crystalline material that melts about 225° Celsius. Although the suture 24 is a monofilament suture having a continuous outer side surface, it is contemplated that the suture could be formed in a different manner. For example, the suture 24 could be a cable having an interlaced structure formed by a plurality of filaments or strands which have been twisted, braided, twined, and/or threaded together. If desired, the suture 24 and anchors 18 and 20 could be formed of the same polymeric material.

It is contemplated that the suture 24 may be formed of a polyglycolide-based copolymer which is commercially available under the trademark VICRYL. The suture 24 may have a multifilament construction which is similar to the construction of the suture disclosed in U.S. Pat. No. 5,928,267. The disclosure in the aforementioned U.S. Pat. No. 5,928,267 is hereby incorporated herein by this reference thereto.

The strength of the suture 24 will vary as a function of the size of the suture. It is contemplated that the specific strength of a particular suture size will vary depending upon the material from which the suture is constructed and whether the suture has a monofilament or multifilament construction. By consulting a chart, a surgeon can select a suture 24 of a size and strength suitable for a particular use. Thus, a relatively large size suture 24 having substantial strength may be selected when body tissue is to be connected with a bone or when portions of a bone are to be interconnected by the suture. On the other hand, a relatively small size suture 24 having a relatively small strength may be selected when delicate body tissue, such as stomach tissue or intestinal tissue, and/or mucosa are to be interconnected with the suture.

Once a suture of a size and strength suitable for retaining specific body tissue has been selected, the suture is threaded through the passages 254 and 256 in the anchor 18 through the passages 266 and 268 in the anchor 20. By moving the anchors 18 and 20 away from each other, the length of the connector section 48 can be increased. Alternatively, by tensioning the leg portions 50 and 52 (FIG. 1) of the suture 24, the length of the connector portion 48 can be decreased.

In the embodiment of the invention illustrated in FIGS. 1–10, the suture 24 and anchors 18 and 20 are formed of different materials. Thus, the anchors 18 and 20 are formed of bone while the suture 24 is a monofilament of polymeric material. However, it is contemplated that both the suture 24 and the anchors 18 and 20 could be formed of similar materials. For example, the suture 24 and anchors 18 and 20 could both be formed of polymers or copolymers which are biodegradable or bioerodible. Even when the anchors 18 and 20 are formed of metal, it may be desirable to form the suture 24 of a biodegradable polymeric material.

The anchors 18 and 20 could have many different constructions. For example, the anchors 18 and 20 could be constructed in the manner illustrated in FIGS. 18–23 herein. Alternatively, the anchors 18 and 20 have any of the constructions disclosed in U.S. Pat. Nos. 5,403,348 and 5,989,282. If desired, the anchors 18 and 20 could have different constructions. The disclosures in the aforementioned U.S. Pat. Nos. 5,403,348 and 5,989,282 are hereby incorporated herein in their entirety by this reference thereto.

After the anchors 18 and 20 have been connected with the suture 24, in the manner illustrated in FIG. 1, the anchors and suture are used to connect body tissue 12 with the body tissue 14. In the specific embodiment of the invention illustrated in FIGS. 1–10, the body tissue 12 is soft body tissue and the body tissue 14 is hard body tissue. The soft body tissue 12 may be a tendon or a ligament. The body tissue 14 is a bone having a hard (cortical) outer layer 278 and relatively soft cancellous bone 280 which is enclosed by the relatively hard outer layer 278.

It should be understood that many different kinds of soft tissue can be connected with bone at many different locations in a patient's body. For example, the anchors 18 and 20 and suture 24 could be used to secure a meniscus to a bone in a knee joint of a patient. Alternatively, the suture 24 and anchors 18 and 20 could be used to secure the rotator cuff in a shoulder of a patient. The soft tissue 12 may be mucosa. The soft tissue 12 may be musculofascial tissue. It should be understood that the foregoing specific locations for use of the apparatus 10 in the body of a patient have been set forth herein merely as examples and it is contemplated that the apparatus 10 may be used at any desired location in the body of a patient.

In the embodiment of the invention illustrated in FIGS. 1–10, the body tissue 12 is pressed against the body tissue 14 by force transmitted from the suture 24 to the body tissue 12. However, the body tissue 12 could be spaced from the body tissue 14. For example, the suture 24 could extend at least part way around the body tissue 12 with the body tissue 12 spaced from the body tissue 14. The body tissue 12 could be soft body tissue which has a range of movement, relative to the body tissue 14, limited by the suture 24. The body tissue 14 could be either hard body tissue (bone) or soft body tissue. Alternatively, the anchor 18 could be disposed in one bone and the anchor 20 disposed in another bone. If this was done, the suture 24 could be utilized to limit the range of movement between the bones or to hold the bones in engagement with each other.

It is contemplated that the suture 24 and anchors 18 and 20 may be used in vascular tissue. For example, the anchors 18 and 20 could be used to connect the suture 24 with body tissue which forms a portion of a blood vessel. Body tissue forming two sections of a blood vessel may be placed in a side-by-side relationship and interconnected with the anchors 18 and 20 and the suture 24.

When the body tissue 12 is to be secured to the body tissue 14 with the apparatus 10, the anchor 18 is positioned in the inserter 28 (FIG. 2). The illustrated inserter 28 includes a cylindrical tubular outer member 284 which is connected with a suitable handle (not shown). The pusher member 30 has a generally cylindrical configuration and is received in a cylindrical passage 286 in the tubular outer member 284.

The cylindrical passage 286 extends between an entrance opening adjacent to the handle and a circular exit opening 288. The pusher member 30 extends along the passage 286 through the opening adjacent to the handle of the outer member 284. Although the illustrated inserter 28 and pusher member 30 have linear central axes, they could have nonlinear central axes if desired. For example, the inserter 28 and pusher member 30 could have arcuate central axes.

A slot 292 extends between the entrance opening adjacent to the handle of the inserter 28 and the exit opening 288. The slot 292 facilitates positioning the anchor 18 in the passage 286. This is because the anchor 18 is visible through the slot 292. In addition, the connector portion 48 and leg portion 50 of the suture 24 can be readily positioned in the slot 292.

The slot 292 has a straight longitudinal central axis which extends parallel to the longitudinal central axis of the passage 286 and to the longitudinal central axis of the tubular outer member 284. The connector portion 48 and leg portion 50 of the suture 24 extend along the slot 292 away from the opening 288 toward the opposite end portion of the tubular outer member 284. The slot 292 encloses the connector portion 48 and leg portion 50 of the suture 24 and protects the connector portion 48 and leg portion of the suture 24 against being snagged by objects in the environment around the inserter 28.

The passage 286 has a circular cross sectional configuration with a diameter which is slightly greater than the diameter of the body portion 250 of the anchor 18. Immediately adjacent to the exit opening 288, the passage 286 tapers inwardly to a cross sectional size which is somewhat smaller than the cross sectional size of the body portion 250 of the anchor 18. This enables the outer member 284 to firmly grip the trailing end portion 32 of the anchor 18.

The slot 292 has a uniform width throughout the length of the slot until the slot approaches the exit opening 288. Immediately ahead of the exit opening 288, the width of the slot 292 decreases to reduce the cross sectional size of the passage 286.

When the anchor 18 is to be positioned in the inserter 28, the anchor is inserted through the opening to the passage 286 adjacent to the handle with the end portion 34 of the anchor leading. The pusher member 30 is moved into the passage 286 and applies force against the trailing end portion 32 of the anchor 18 to move the anchor along the passage 286. At this time, the connector portion 48 and leg portion 50 of the suture 24 are disposed in the slot 292.

When the anchor 18 approaches the exit opening 288, the tapered leading end portion 34 of the anchor applies force against the outer member 284 to resiliently deflect the end portion of the outer member and expand the exit opening 288. At this time, the portion of the outer member 284 adjacent to the exit opening 288 resiliently grips the body portion 250 of the anchor to hold the anchor in the position illustrated in FIG. 2.

Although the inserter 28 may have many different constructions, the specific inserter 28 illustrated in FIG. 2 has the same construction as is disclosed in U.S. Pat. No. 5,948,002 issued Sep. 7, 1999 for "Apparatus and Method for Use in Positioning a Suture Anchor". It should be understood that the inserter 28 may have a construction which is similar to any one of the constructions illustrated in the aforementioned U.S. Pat. No. 5,948,002. It is also contemplated that the inserter 28 could have a construction which is similar to the construction of any one of many other known inserters. However, it is believed that it may be desired to use an inserter having the construction disclosure in the aforementioned U.S. Pat. No. 5,948,002 to facilitate handling and positioning of the anchor 18 relative to the body tissue 12 and 14. The disclosure in U.S. Pat. No. 5,948,002 is hereby incorporated herein by this reference thereto.

The anchor 18 is held in the inserter 28 with the leading end portion 34 of the anchor extending from the inserter. The pusher member 30 engages the trailing end portion 32 of the anchor 18 to block movement of the anchor along the passage 286 in a direction away from the exit opening 288.

The longitudinal central axis of the inserter 28 is then positioned in an orientation relative to the body tissue 12 corresponding to the orientation of a path along which the anchor is to be moved into the body tissue. Thus, if the anchor 18 is to be moved straight downward (as viewed in FIG. 2) into the body tissue 12 and into the body tissue 14, the inserter 28 would be positioned with its longitudinal central axis extending generally perpendicular to an outer surface 300 of the body tissue 12. However, in the embodiment of the invention illustrated in FIGS. 1–10, it is desired to move the anchor 18 into the body tissue 12 and 14 along a path which is skewed at an acute angle to the outer surface 30 of the body tissue 12.

In the specific instance illustrated in FIG. 2, the inserter 28 is positioned with its longitudinal axis extending at an angle of approximately 40° to the outer surface 300 of the body tissue 12. However, it is contemplated that the inserter 28 could be positioned with its longitudinal axis extending at an angle of between 30° and 90° to the outer surface 300 of the body tissue 12. The specific angle which is selected between the outer surface 300 of the body tissue 12 and the longitudinal central axis of the inserter 28 will depend upon the desired path of movement of the anchor 18 into the body tissue. It is believed that it may be desired to have the path of movement of the anchor 18 into the body tissue 12 and 14 at an angle of between 30° and 70° to the outer surface 300 of the body tissue.

It is believed that it will be desired to move the anchor 18 for a predetermined distance into the body tissue 14. It is also believed that it may be desired to limit the depth of movement of the anchor into the body tissue 14. In order to enable the anchor to be moved through a substantial distance into the body tissue 14 while minimizing the depth to which the anchor is moved into the body tissue, the path of movement of the anchor into the body tissue is skewed at an acute angle to the outer surface 300 of the body tissue 12. When the anchor 18 is to be moved along a path which is skewed relative to the outer surface 300, it is believed that it may be desired to move the anchor into the body tissue 12 and 14 at an angle of between 30° and 70° to the outer surface 300 of the body tissue.

Once a desired angle for the path of movement of the anchor 18 through the body tissue 12 and into the body tissue 14 has been selected, the inserter 28 and pusher member 30 are moved toward the outer surface 300 of the body tissue 12 with the anchor extending from the inserter, in the manner illustrated in FIG. 2. The pointed leading end portion 34 of the anchor 18 is moved into engagement with an imperforate area on the outer surface 300 of the body tissue 12. As the inserter 28 and pusher member 300 continue to move along their longitudinal central axes toward the body tissue 12, the pointed leading end portion 34 of the anchor 18 initiates the formation of an opening in the outer surface 300 of the body tissue 12.

Continued movement of the inserter 28 and pusher member 30 toward the body tissue 12 causes the anchor 18 to pierce body tissue 12. As the anchor 18 moves through the body tissue 12, the pointed leading end portion of the anchor moves into engagement with an imperforate area on an outer surface 304 of the hard outer layer 278 of the bone 14. It should be understood that the body tissue 12 could have a thickness which is greater than the thickness illustrated schematically in FIG. 2. It is contemplated that the body tissue 12 could have a thickness which is substantially greater than the axial extent of the anchor 18.

The pointed leading end portion 34 of the anchor 18 then initiates the formation of an opening in an imperforate area on the surface 304 on the hard outer layer 278 of the bone. Continued movement of the inserter 28 along its path of movement moves the leading end portion 34 of the anchor into the hard outer layer 278 of the bone, in the manner illustrated schematically in FIG. 3. As this occurs, the inserter 28 moves through the soft tissue 12 into abutting engagement with the outer surface 304 on the hard outer layer 278 of the bone 14.

The axial force applied against the inserter 28 is insufficient to cause the inserter to penetrate the hard outer layer 278 of the bone 14. Therefore, movement of the inserter 28 along its longitudinal central axis relative to the body tissue 12 and 14 is interrupted when the leading end portion of the inserter engages the outer surface 304 of the hard outer layer 278 of the bone 14. At this time, the leading end portion 34 of the anchor 18 will have initiated penetration of the outer layer 278 of the bone 14 (FIG. 3).

The movement of the inserter along the path of insertion of the anchor 18 into the body tissue 12 and 14 has been illustrated in FIG. 3 as being interrupted when the inserter engages outer surface 304 of the bone 14. However, it is contemplated that movement of the inserter 28 along the path of insertion of the anchor 18 could be interrupted when the inserter engages the outer surface 300 on the body tissue 12. If this was done, the inserter would be moved from the position illustrated in FIG. 2 along the path of movement of the anchor 18 into the body tissue 12 and 14 until the leading of the inserter engaged the outer surface 300 of the body tissue 12. At this time, the leading end portion 34 of the anchor 18 may or may not have moved into engagement with the bone 14. Whether or not the anchor has moved into engagement with the bone 14 when the inserter 28 engages the outer surface 300 of the body tissue 12 will depend upon the thickness of the body tissue 12, the angle of the path of movement of the anchor relative to the body tissue 12, and the distance which the anchor 18 extends from the inserter 28.

When the tissue 12 is soft tissue and the tissue 14 is bone or other hard body tissue, it is believed that it will be desirable to have the inserter move with the anchor 18 during initiation of penetration of the anchor into the hard body tissue. However, when the body tissue 14 is soft body tissue, it may not be desired to have the inserter hold the trailing end portion 32 of the anchor during initiation of penetration of the anchor into the body tissue 14.

It is contemplated that it may be desired to move the inserter 28 into the bone 14. Thus, the inserter 28 could be moved through the hard outer layer 278 of the bone 14 into the cancellous bone 280. This would have the advantage of enabling the inserter 28 to at least partially support the anchor 18 as the anchor moves through the hard outer layer 278 of the bone 14.

In the embodiment of the invention illustrated in FIGS. 1–10, the body tissue 14 is hard body tissue, that is, bone. It is believed that initiation of penetration of the anchor into the hard outer layer 278 of the bone 14 will be facilitated by having the anchor held in the inserter 28 as the pointed leading end portion 34 begins to move through the imperforate outer surface 304 of the outer layer 278. Therefore, it is believed that it may be desired to move the inserter 28 through the soft body tissue 12 into engagement with the outer surface 304 of the bone 14 during at least the initiation of formation of an opening in the hard outer layer 278 of the bone 14.

Once the inserter 28 has moved into engagement with the outer surface 304 of the bone 14 and movement of the inserter relative to the bone 14 is interrupted, the pusher member 30 is moved relative to the inserter 28 to apply force against the trailing end portion 32 of the anchor and to move the anchor further into the bone 14, in the manner illustrated in FIG. 4. Thus, the inserter 28 is held stationary relative to the body tissue 12 and 14 while the pusher member 30 is moved axially along the longitudinal central axis of the inserter 28. The pusher member is telescopically extended from the inserter 28 and moves the anchor 18 through the hard outer layer 278 of the bone 14 into the relatively soft cancellous bone 280 (FIG. 4).

As this occurs, the suture 24 moves along the slot 292 in the inserter 28. As the anchor 18 moves into the bone 14, the anchor pulls the suture 24 into the bone. This results in movement of the suture 24 along the slot 292 in the inserter 28. As the anchor 18 moves into the cancellous bone 280, the leading end portion 34 of the anchor pierces the cancellous bone.

The anchor 18 is moved into the body tissue 12 and 14 along an insertion path which is skewed at an acute angle to the outer surface 300 of the body tissue 12 and the outer surface 304 of the body tissue 14. Therefore, the distance which the anchor 18 is moved into the bone 14 tends to be maximized while the depth, as measured perpendicular to the outer surfaces 300 and 304 of the body tissue 12 and 14, of insertion of the anchor is minimized.

If the inserter 28 was positioned in engagement with the outer surface 304 of the bone 14 with the longitudinal central axis of the inserter extending perpendicular to the outer surface of the bone, and if the pusher member 300 was moved through the same distance relative to the inserter 28 from the retracted condition shown in FIG. 3 to the extended condition shown in FIG. 4, the anchor 18 would be moved further into the bone 14 as measured along a path extending perpendicular to the outer surface 304 of the bone. It is believed that in at least some locations in a patient's body, it will be desired to have the distance which the anchor is moved into the bone 14 maximized while at the same time minimizing the depth of penetration of the anchor. This may be due to the bone 14 being relatively thin, the particular configuration of the bone 14, or other causes.

In order to increase the resistance of the anchor to pull out under the influence of tension forces in the suture 24, the anchor is toggled or pivoted from the orientation illustrated in FIG. 4 to the orientation illustrated in FIG. 5. This results in the anchor being moved from a position in which a longitudinal central axis of the anchor is aligned with the longitudinal central axis of a path of movement of the anchor into the bone 14 (FIG. 4) to a position in which the longitudinal central axis of the anchor is skewed relative to the path of movement of the anchor into the bone 14 (FIG. 5).

Once the anchor 18 has been moved to the desired depth in the bone 14 (FIG. 4), toggling movement of the anchor is initiated by tensioning the connector portion 48 and leg portion 50 of the suture 24. A sloping or bevel surface 310 is provided on the leading end portion of the pusher member 30 to facilitate initiation of the pivotal movement of the anchor 18 relative to the pusher member 30. The force applied against the anchor 18 by the suture 24 pulls the anchor back or upward (as viewed in FIG. 4) toward the surface 310 on the pusher member 30. Therefore, the tension in the suture 24 tends to rotate the anchor 18 in a counterclockwise direction from the position illustrated in FIG. 4 to the position illustrated in FIG. 5 relative to the soft cancellous bone 280.

As the anchor 18 is pivoted, the upper (as viewed in FIG. 5) portion of the anchor deflects the soft cancellous bone tissue 280. The viscoelastic nature of the soft cancellous bone tissue 280 causes the tissue to tend to close behind the anchor as it is pivoted upward to the position shown in FIG. 5. The manner in which the anchor 18 is pivoted relative to the body tissue is similar to that disclosed in U.S. Pat. Nos. 5,948,002; 5,941,900; and 5,403,348.

Once the anchor 18 has been moved to the position illustrated in FIG. 5, the pusher member 30 is withdrawn from the body tissue 12 and 14. This results in the anchor 18 being supported in the body tissue 12 and 14 by the cancellous bone 280. The anchor 18 is spaced from the hard outer layer 278 of the bone 14. Therefore, tension forces in the suture 24 are transmitted from outer side surfaces of the anchor to the cancellous bone 280 while the anchor is maintained in a spaced apart relationship with the hard outer layer 278 of bone. The manner in which the anchor 18 is supported in the cancellous bone 280 in a spaced apart relationship with the hard outer layer 278 of bone is the same as is disclosed in U.S. Pat. No. 6,077,292.

Rotating the anchor 18 relative to the path of movement of the anchor into the body tissue 12 and 14 increases the resistance of the anchor to pull out forces transmitted through the suture 24 to the anchor. The anchor 18 could remain in the bone 14 in the orientation shown in FIG. 4 in which the longitudinal central axis of the anchor is coincident with the longitudinal central axis of the path along which the anchor moves into the bone. However, by toggling or pivoting the anchor from the position shown in FIG. 4 to the position shown in FIG. 5 the resistance of the anchor to pull out forces tends to be increased. Of course, if the anchor is to be subjected to only relatively small pull out forces, the anchor could be left in the position shown in FIG. 4 relative to the bone 14 without being pivoted to the orientation illustrated in FIG. 5.

In the embodiment of the invention illustrated in FIGS. 1–10, the anchor 18 is moved into the body tissue 12 and 14 from the initial position of FIG. 2 to the intermediate position of FIG. 4 along a linear path. However, the anchor 18 could be moved from the initial position (FIG. 2) to the intermediate position (FIG. 4) along a nonlinear path if desired. For example, the anchor 18 could be moved along an arcuate path from the initial position to the intermediate position.

When the anchor 18 is to be moved along an arcuate path from the initial position (FIG. 2) to the intermediate position (FIG. 4), the inserter 28 and pusher member 30 may be formed with an arcuate configuration. The arcuate configuration of the inserter 28 and pusher member 30 would be the same as the arcuate configuration of the path along which the anchor 18 is to be moved into the body tissue 12 and 14.

When the inserter 28 and pusher member 30 have a rigid construction, it is believed that it may be desired to form the passage 286 in the inserter and to form the pusher member 30 to have the same arc of curvature. This is done to facilitate movement of the pusher member 30 along the passage 286 in the inserter 28. However, it is contemplated that the inserter 28 and/or pusher member 30 could have a flexible construction if desired. For example, the inserter 28 and pusher member 30 could have a construction similar to the construction disclosed in U.S. Pat. No. 5,897,574. The disclosure in U.S. Pat. No. 5,897,574 is hereby included herein in its entirety by this reference thereto.

The anchor 20 is moved through the soft body tissue 12 into the hard body tissue 14 in the same manner as in which the anchor 18 is moved through the soft body tissue into the hard body tissue. Thus, the anchor 20 is positioned in an inserter 38 (FIG. 6) having the same construction as the inserter 28 of FIG. 3. A pusher member 40 (FIG. 6) is telescopically moved along the inserter 38 into engagement with the trailing end portion 42 of the anchor 20 in the same manner as previously described in conjunction with the anchor 18, pusher member 30 and inserter 28 of FIG. 3.

The leg portion 52 of the suture 24 and the connector portion 48 of the suture are at least partially received in a slot 316 in the inserter 38 in the same manner as in which the suture is received in the slot 292 in the inserter 28 of FIG. 3. The inserter 38 and pusher member 40 have the same construction and cooperate in the same manner as is disclosed in U.S. Pat. No. 5,948,002 and have the same construction and mode of operation as the inserter 28 and pusher member 30 of FIGS. 2–4.

When the anchor 20 is to be used in securing the body tissue 12 to the body tissue 14, the anchor 20 is positioned in the inserter 38 and the pusher member 40 is moved into engagement with the trailing end portion of the anchor. The leading end portion 44 of the anchor is then moved from a position spaced from the body tissue 12 to a position in which the leading end portion engages an imperforate area on the outer surface 300 of the body tissue 12. At this time, the inserter 38 and pusher member 40 are positioned in an angular orientation relative to the surface 300 of the body tissue 12 corresponding to the angle of the desired path of insertion of the anchor 20 into the body tissue 12 and 14.

In the specific situation illustrated in FIG. 6, the path of insertion of the anchor 20 into the body tissue 12 and 14 is skewed at an acute angle of approximately 40° relative to the surface 300 of the body tissue 12. It is contemplated that the path of insertion of the anchor 20 into the body tissue 12 and 14 may be located an at angle between 30° and 90° relative to the surface 300 of the body tissue 12. In order to reduce the depth of insertion of the anchor 20 into the bone 14, it is believed that it may be desired to have the path of movement of the anchor 20 into the body tissue 12 and 14 skewed at an acute angle of between 30° and 70° relative to the surface 300 of the body tissue 12.

When the inserter 38 and pusher member 40 have been positioned with their longitudinal central axes coincident with the longitudinal central axis of the desired path of movement of the anchor 20 into the body tissue 12 and 14, the pusher member 40 and inserter 38 are moved together toward the surface 300 of the body tissue 12. As this occurs, the pointed leading end portion 44 of the anchor 20 initiates the formation of an opening in the surface 300 of the body tissue 12.

The inserter 38, pusher member 40, and anchor 20 continue to move together relative to the body tissue 12 and 14 as the anchor pierces the body tissue 12. When the pointed leading end portion 44 of the anchor 20 engages an imperforate portion of the outer surface 304 of the bone 14, the leading end portion 44 of the anchor initiates formation of an opening in the outer surface 304 of the bone 14.

Continued movement of the inserter 38, pusher member 40 and anchor 20 together along the path of insertion of the anchor into the body tissue 12 and 14 results in the leading end portion 44 of the anchor moving into the hard outer layer 278 of the bone 14 in the manner illustrated in FIG. 6. As this occurs, the inserter 38 moves into engagement with the outer surface 304 of the bone 14. Movement of the inserter 38 relative to the bone 14 is interrupted with the inserter in engagement with the outer surface 304 of the bone, in the manner illustrated schematically in FIG. 6.

It may be desired to move the inserter 38 through the body tissue 12 into engagement with the bone 14, in the manner illustrated in FIG. 6. This results in the anchor 20 being supported by the inserter 38 as the anchor initially penetrates the hard outer layer 278 of the bone 14. The anchor 20, inserter 38 and pusher member 40 are moved together along the path of movement of the anchor into the body tissue 12 and 14 until the inserter 38 engages the surface 304 on the hard outer layer 278 of the bone. By the time the inserter 38 engages the surface 304 on the hard outer layer 278 of the bone 14, the leading end portion of the anchor has moved into the hard outer layer of the bone (FIG. 6).

When the inserter 38 moves into engagement with the outer surface 304 of the bone 14, movement of the inserter relative to the bone is interrupted. The pusher member 40 is then moved relative to inserter 38. Movement of the pusher member 40 relative to the inserter 38 applies force against the trailing end portion 42 of the anchor 20 and moves the anchor 20 into the bone 14. The anchor 20 is moved into the bone 14 through the hard outer layer 278 and into the cancellous bone 280 as the pusher member 40 is telescopically extended from the inserter 38 (FIG. 7). As the anchor 20 moves into the bone 14, the suture 24 moves along the slot 316 in the inserter 38.

Once the anchor 20 has been moved to the desired depth in the cancellous bone 280, the pusher member 40 and inserter 38 may be withdrawn from the body tissue 12 and 14 and the anchor left in the orientation illustrated in FIG. 7 relative to the body tissue. Thus, the anchor may remain in the cancellous bone 280 with a longitudinal central axis 320 of the anchor aligned with the central axis of the path of movement of the anchor into the body tissue 12 and 14. Alternatively, the orientation of the anchor relative to the path of movement of the anchor into the body tissue 12 and 14 may be changed to increase the resistance to the anchor to pull out forces transmitted through the suture 24.

When the orientation of the anchor 20 is to be changed relative to the bone 14 from the orientation illustrated in FIG. 7 to the orientation illustrated in FIG. 8, the suture 24 is tensioned. Tensioning the suture 24 tends to pivot the anchor 20 in a clockwise direction (as viewed in FIGS. 7 and 8) about a location where the trailing end portion 42 of the anchor engages the pusher member 40. The pusher member 40 has a bevel surface 324 which extends transversely to a longitudinal central axis of the pusher member 40. The bevel surface 324 facilitates pivotal movement of the anchor 20 relative to the pusher member 40.

When the anchor 20 has been pivoted to the orientation illustrated in FIG. 8, the pusher member 40 is telescopically moved back into the inserter 38. The inserter 38 and pusher member 40 are then withdrawn from the body tissue 12. When the anchor 20 is in the orientation shown in FIG. 8, the central axis 320 of the anchor extends transverse to the path of movement of the anchor into the bone 14. This increases the pull out force which is required to remove the anchor from the bone.

After the anchors 18 and 20 have been moved into the bone and toggled to the orientations illustrated in FIGS. 5 and 8, the anchors are pointed toward each other (FIG. 9). Thus, the leading end portion 34 of the anchor 18 points toward the anchor 20 and the leading end portion 44 of the anchor 20 points toward the anchor 18. At this time, the longitudinal central axis 260 of the anchor 18 extends generally parallel to the outer surface 300 of the body tissue 12 and to the outer surface 304 of the bone 14. Similarly, the central axis 320 of the anchor 20 extends parallel to the outer surface 300 of the body tissue 12 and to the outer surface 304 of the bone 14. At this time, both the anchors 18 and 20 are supported by the cancellous bone 280 in a spaced apart relationship with the hard outer layer 278 of the bone 14.

In FIG. 9, the central axes 260 and 320 of the anchors 18 and 20 are disposed in a plane which extends perpendicular to the outer surface 300 of the body tissue 12 and the outer surface 304 of the body tissue 14. However, it is contemplated that the axes 260 and 320 of the anchors 18 and 20 could be offset relative to each other. For example, one of the axes 260 or 320 could be offset from the other axis in a direction extending into the sheet on which the drawing of FIG. 9 is disposed. In addition, rather than being generally parallel to the outer surfaces 300 and 304 of the body tissue 12 and 14, the axes 260 and 320 of the anchors 18 and 20 could be skewed at a greater angle relative to the outer surfaces of the body tissue.

The paths of movement of the anchors 18 and 20 into the body tissue 12 and 14 have central axes disposed in a plane which extends perpendicular to the outer surfaces 300 and 304 of the body tissue 12 and 14. However, the path of movement of one of the anchors, for example, the anchor 18, into the body tissue 12 and 14 could have a central axis which is offset from the central axis of the path of movement of the other anchor into the body tissue.

Regardless of whether or not the central axes of the paths along which the anchors 18 and 20 move into the body tissue 12 and 14 are disposed in the same plane, it is believed that it may be desired to have the paths extend toward each other. Thus, the path along which the anchor 18 moves into the body tissue 12 and 14 extends toward the path along which the anchor 20 moves into the body tissue. Even though the central axes of the paths along which the anchors move into the body tissue are not disposed in a common plane, the anchor 18 moves toward the location where the anchor 20 enters the body tissue 12 and 14 as the anchor 18 is moved into the body tissue. Similarly, the anchor 20 moves toward locations where the anchor 18 moved into the body tissue 12 and 14 as the anchor 20 is moved into the body tissue.

By having the anchors 18 and 20 move along insertion paths which extend toward each other, even though central axes of the insertion paths may not be disposed in a common plane, the anchors approach each other as they move in the cancellous material of the bone 14. This results in the suture 24 being effective to press the body tissue 12 against the body tissue 14 with a clinching action. The clinching action with which the suture 24 presses the body tissue 12 against the bone 14 is similar to the clinching action which is obtained by the legs of a staple. This clinching action increases the force which is transmitted from the suture 24 to the body tissue 12 and increases the resistance of the anchors 18 and 20 to pull out under the influence of tension forces in the suture.

Although it is believed that it may be desired to move the anchors 18 and 20 toward each other along their insertion paths to decrease the distance between the anchors as they move into the body tissue 14, the anchors could be moved along insertion paths which are either parallel or diverge. For example, the insertion path of the anchor 18 into the body tissue 12 and 14 could extend parallel to the insertion path of the anchor 20 into the body tissue. If this was done, the insertion paths of the anchors 18 and 20 would have parallel central axes disposed in a plane extending perpendicular to the outer surfaces 300 and 304 of the body tissue 12 and 14.

Alternatively, it is contemplated that the anchors 18 and 20 could be moved into the body tissue 12 and 14 along diverging insertion paths. Thus, the anchor 18 could be moved along an insertion path which extends parallel to the illustrated insertion path of the anchor 20 in FIG. 7. Similarly, the anchor 20 could be moved along an insertion path which extends parallel to the insertion path of the anchor 18 in FIG. 4. It should be understood that the angular orientation of the insertion paths for the anchors 18 and 20 relative to each other will depend upon the specific environment in which the anchors are utilized.

In the embodiment of the invention illustrated in FIGS. 1–10, the anchor 20 is moved into the body tissue 12 and 14 from an initial position to the intermediate position of FIG. 7 along a linear path. However, the anchor 20 could be moved from the initial position to the intermediate position (FIG. 7) along a nonlinear path if desired. For example, the anchor 20 could be moved along an arcuate path from the initial position to the intermediate position.

When the anchor 20 is to be moved along an arcuate path from the initial position to the intermediate position, the inserter 38 and pusher member 40 may be formed with an arcuate configuration. The arcuate configuration of the inserter 38 and pusher member 40 would be the same as the arcuate configuration of the path along which the anchor 20 is to be moved into the body tissue 12 and 14.

When the inserter 38 and pusher member 40 have a rigid construction, it is believed that it may be desired to form the passage in the inserter and to form the pusher member 40 to have the same arc of curvature. This is done to facilitate movement of the pusher member 40 along the passage in the inserter 38. However, it is contemplated that the inserter 38 and/or pusher member 40 could have a flexible construction if desired. For example, the inserter 38 and pusher member 40 could have a construction similar to the construction disclosed in U.S. Pat. No. 5,897,574.

Once the anchors 18 and 20 have been moved to the position illustrated in FIG. 9, ends of the leg portions 50 and 52 of the suture are positioned in an opening in the retainer or crimp 54. While the leg portions 50 and 52 of the suture are tensioned at a location above the retainer 54, as viewed in FIG. 9, the retainer is moved downward toward the body tissue 12. As the retainer 54 is moved downward toward the body tissue 12, the tension in the connector portion 48, leg portion 50 and leg portion 52 of the suture is increased.

By initially providing the connector portion 48 of the suture with a length which is slightly less than the length illustrated in FIG. 9, the connector portion 48 of the suture 24 is tensioned as the anchor 20 is moved into the bone 14. This is because as the anchor 20 moves into the bone 14, the anchor pulls the suture 24 into the bone. If the connector portion of the suture 48 is shorter than is required when the anchors 18 and 20 have been moved to the positions illustrated in FIG. 9, the connector portion of the suture 48 is tensioned as the anchor 20 moves into the bone 14. This tensioning of the connector portion 48 of the suture 24 causes the suture to move relative to the anchor 20 in the passages 266 and 268. As this occurs, the length of the leg portion 52 of the suture 24 is decreased and the length of the connector portion 48 of the suture is increased.

After the anchors 18 and 20 have been positioned in the body tissue 14, the surgeon pulls on the free end of the leg portions 50 and 52 and moves the retainer 54 toward the body tissue 12. As this occurs, the leg portions 50 and 52 of the suture 24 are tensioned. Any excess material in the connector portion 48 of the suture 24 is pulled from the connector portion 48 by movement of the suture relative to the anchors 18 and 20 and a resulting increasing of the overall length of the leg portions 50 and 52. Since the suture 24 is movable in the passages 254, 256, 266 and 268 in the anchors 18 and 20, the same tension is present in the connector portion 48 and leg portions 50 and 52 of the suture 24.

When the retainer 54 has been moved downward into engagement with the outer surface 300 of the body tissue 12 and the desired tension is present in the connector portion 48 and leg portions 50 and 52 of the suture 24, the crimp is plastically deformed to grip the leg portions of the suture. Plastic deformation of the suture retainer results in cold flowing of the material of the suture retainer. If desired, energy, such as heat or vibrational energy, may be transmitted to the retainer 54 to facilitate plastic deformation of the material of the retainer under the influence of force applied against opposite sides of the retainer.

The retainer 54 may be plastically deformed in the same manner as disclosed in U.S. patent application Ser. No. 09/685,795 filed Oct. 10, 2000 by Peter M. Bonutti et al. and entitled "Method and Apparatus for Securing a Suture". The disclosure in the aforementioned application Ser. No. 09/685,795 is hereby incorporated herein in its entirety by this reference thereto.

It is contemplated that the suture retainer 54 could be plastically deformed in other ways if desired. For example, ultrasonic vibratory energy may be transmitted to the material of the suture retainer 54 to effect heating of at least some of the material of the suture retainer. The ultrasonic vibratory energy may be applied while the suture 54 is being tensioned with a predetermined force and while a predetermined force is being transmitted from the connector portion 48 and leg portions 50 and 52 of the suture 24 to the body tissue 12. It is contemplated that the suture retainer 54 may be deformed by the use of ultrasonic vibratory energy in the manner disclosed in U.S. patent application Ser. No. 09/524, 397 filed Mar. 13, 2000 by Peter M. Bonutti et al. and entitled "Method of Using Ultrasonic Vibration to Secure Body Tissue". The disclosure in the aforementioned application Ser. No. 09/524,397 is hereby incorporated herein in its entirety by this reference thereto.

In the embodiment of the invention illustrated in FIG. 9, the connector portion 48 and leg portions 50 and 52 of the suture 24 are pressed against the body tissue 12 by tension in the suture. If desired, a protective member, such as a pledget, may be positioned between the suture 24 and the body tissue 12. The protective member may be provided with openings through which the suture 24 extends into the body tissue 12. During tensioning of the suture 24, the retainer 54 may be moved into engagement with the protective member. The protective member may have the same construction as any of the protective members disclosed in U.S. Pat. No. 4,823,794.

It is believed that it may be desired to tension the suture 24 with a predetermined tension. It is also believed that it will be desired to transmit a predetermined force from the retainer 54 to the body tissue 12 during tensioning of the suture 24. This may be accomplished by utilizing the apparatus which is illustrated schematically in FIG. 10.

The apparatus includes of FIG. 10 the force application assembly 60 which applies an upwardly (as viewed in FIG. 10) directed force 62 to the leg portions 50 and 52 of the suture 24. Contemporaneously with the application of the predetermined tension force 62 to the leg portions 50 and 52 of the suture 24, the force application member 66 presses the suture retainer 54 downward toward the body tissue 12 with a predetermined force indicated by the arrows 70 and 72 in FIG. 10. While the predetermined tension force 62 is applied to the suture 24 and the predetermined forces 70 and 72 are applied to the retainer 54 by the force application member 66, the retainer is plastically deformed under the influence of forces 80 and 82 applied against opposite sides of the retainer by the force application members 76 and 78.

Although the leg portions 50 and 52 of the suture 24 could extend straight through the suture retainer 54, it is preferred to form a plurality of bends in the leg portions 50 and 52 of the suture 24. In the illustrated embodiment of the suture retainer 54, two bends are formed in the leg portion 50 of the suture 24 as it is wrapped around the suture retainer 54. Similarly, two bends are formed in the leg portion 52 of the suture 24 as it is wrapped around the suture retainer 54.

The suture retainer 54 has a spherical configuration. A cylindrical passage 340 extends through the center of the spherical suture retainer 54. If desired, the suture retainer 54 could have a different configuration. For example, the suture retainer 54 could have an oval or elliptical configuration. Although the passage 340 has a linear central axis, the passage could have a nonlinear central axis. If desired, a plurality of passages having the same or different configurations could be provided in the suture retainer 54. The suture retainer 54 could have any one of the constructions disclosed in the aforementioned U.S. patent applications Ser. Nos. 09/685,795 and 09/524,397.

After the leg portions 50 and 52 of the suture 24 have been inserted through the suture retainer 54, in the manner indicated schematically in FIG. 10, the suture retainer is moved along the leg sections 50 and 52 to tension the leg sections of the suture 24. The downward forces 70 and 72 are then applied against the suture retainer 54 by the force application member 66. This downward force results in the transmission of a predetermined force from the suture retainer to the body tissue 12 as the leg portions 50 and 52 of the suture 24 are tensioned with a predetermined tension force.

While the predetermined tension is maintained in the leg portions 50 and 52 and the connector portion 48 of the suture 24 and while the suture retainer 54 is being pressed downward against the body tissue 12 with a predetermined force, the force application members 76 and 78 are pressed against opposite sides of the suture retainer 54. The force applied against the suture retainer member 54 by the force application members 76 and 78 plastically deforms the material of the suture retainer. If desired, ultrasonic vibratory energy could be applied to the suture retainer 54 by either or both of the force application members 76 and 78.

The force applied against the material of the suture retainer 54 results in a collapsing of the passage 340. In addition, cold flowing of the material of the suture retainer results in a flow of the material around the leg portions 50 and 52 of the suture 24.

A transducer or load cell 344 is provided to measure the amount of force, indicated by the arrow 62, which is utilized to tension the leg portions 50 and 52 of the suture. While the predetermined tension force is applied to the leg portions 50 and 52 of the suture, the force application members 76 and 78 are applying clamping forces against opposite sides of the suture retainer. Upon disengagement of the force application members 76 and 78 from the suture retainer 54, the application of downward (as viewed in FIG. 10) force against the suture retainer 54 is also interrupted. The upward tensioning of the leg portions 50 and 52 of the suture 24 is also interrupted.

The suture retainer 54 may be formed of many different materials. However, it is believed that it will be preferred to form the suture retainer 54 of a biodegradable polymer. One biodegradable polymer which may be utilized is polycaperlactone. Alternatively, the suture retainer could be formed of polyethylene oxide terephthalate or polybutylene terephthalate. It is also contemplated that other biodegradable or bioerodible copolymers could be utilized if desired.

Although it is preferred to form the suture retainer 54 of a biodegradable material, the suture retainer could be formed of a material which is not biodegradable. For example, the suture retainer 54 could be formed of an acetyl resin such as "Delrin" (trademark). Alternatively, the suture retainer 54 could be formed of a para-dimethylamino-benzenediazo sodium sulfonated, such as "Dexon" (trademark). If desired, the suture retainer 54 may be formed of the same material as the suture 24. However, the suture retainer 54 could be formed of a material which is different than the material of the suture 24. The manner in which the suture retainer 54 cooperates with the suture 24 is the same as is disclosed in the aforementioned U.S. patent application Ser. No. 09/685, 795 filed Oct. 10, 2000 by Peter M. Bonutti et al. and entitled "Method and Apparatus for Securing a Suture.

In the embodiment of the invention illustrated in FIGS. 1–10, the suture 24 is tightened with a desired tension by pulling on the leg portions 50 and 52 of the suture. The tension is maintained in the suture 24 by the retainer 54. However, if desired, the suture 24 could be further tensioned by the application of heat to the suture. The application of heat to the polymeric material of the suture 24 causes the suture to shrink and increase the tension in the suture.

Rather than using the suture retainer 54 to interconnect the leg portions 50 and 52, the leg portions could be bonded to each other. This could be accomplished by the application of heat and/or ultrasonic vibratory energy to the leg portions. The application of heat and/or ultrasonic vibratory energy to the leg portions 50 and 52 causes them to weld together in the manner disclosed in the aforementioned U.S. patent application Ser. No. 09/524,397 filed Mar. 13, 2000 by Peter M. Bonutti et al. and entitled "Method of Using Ultrasonic Vibration to Secure Body Tissue".

Embodiment of FIG. 11

In the embodiment of FIG. 11, the anchors 18*a* and 20*a* are interconnected by a suture 24*a* which forms a continuous loop. By forming a continuous closed loop with the suture 24*a*, anchors 18*a* and 20*a* are interconnected when the anchors are moved into the body tissue 12*a* and 14*a*.

In the illustrated embodiment of the invention, the suture 24*a* is formed into a continuous flexible ring by the application of ultrasonic energy to end portions of the suture. This may be accomplished in the manner disclosed in the aforementioned U.S. patent application Ser. No. 09/524,397 filed Mar. 13, 2000. The continuous loop of the suture 24*a* may be closed to form a flexible ring by knotting together opposite ends of a length of suture. Alternatively, opposite ends of a length of suture material may be spliced or bonded together to form a continuous closed loop. If desired, a connector member formed of polymeric material could be utilized to interconnect opposite ends of a length of suture material to form the continuous closed loop.

The loop of the suture 24*a* forms a continuous flexible ring which extends through passages 254*a* and 256*a* in the suture anchor 18*a*. The continuous flexible ring formed by the suture 24*a* extends through passages 266*a* and 268*a* in the anchor 20*a*. The continuous loop or flexible ring formed by the suture 24*a* is freely movable in the passages 254*a* and 256*a* in the anchor 18*a* and in the passages 266*a* and 268*a* in the anchor 20*a*. This enables the length of the connector portion 48*a* and the connector portion 90 of the suture 24*a* to be varied as the suture anchors 18*a* and 20*a* are positioned relative to the body tissue 12*a* and 14*a*.

The anchor 18*a* has the same construction as the suture anchor 18 of FIGS. 1–10. Similarly, the anchor 20*a* has the same construction as the suture anchor 20 of FIGS. 1–10. Although the suture 24*a* forms a continuous closed loop between the suture anchors 18*a* and 20*a*, the suture 24*a* is formed of the same material as the suture 24 of FIGS. 1–10.

It should be understood that the anchors 18*a* and 20*a* may be formed with any of many known configurations, including the configurations illustrated in FIGS. 18 and 19 herein. It should also be understood that the anchors 18*a* and 20*a* maybe formed of any of many known materials, including the anchor materials mentioned herein in association with the embodiment of FIGS. 1–10. The suture 24*a* may be formed with any known suture constructions mentioned herein in association with the embodiment of FIGS. 1–10. The suture 24a may be formed of many known materials, including the suture materials mentioned herein in association with the embodiment of FIGS. 1–10.

The apparatus 10a of FIG. 11 is associated with body tissue 12a and 14a having arcuate outer surfaces 300a and 304a. In the illustration of FIG. 11, the body tissue 14a is hard body tissue, that is bone, while the body tissue 12a is soft body tissue, such as a tendon or ligament. However, it should be understood that both the body tissue 12a and the body tissue 14a could be soft body tissue.

If the body tissue 12a and 14a are both soft body tissue, the apparatus 10a would be utilized to connect the soft body tissue 12a with the soft body tissue 14a in a manner similar to the disclosure in U.S. Pat. No. 5,464,426 to Peter M. Bonutti for "Method of Closing Discontinuity in Tissue". In the event that both of the body tissues 12a and 14a are soft body tissue, the anchors 18a and 20a may be embedded in the soft tissue forming the soft tissue 14a in much the same manner as is illustrated in FIG. 11. However, it is also contemplated that the anchors 18a and 20a could be moved into and through the soft body tissue 12a and into and through the soft body tissue 14a.

In the illustration of FIG. 11, the body tissue 14a is bone having a hard outer layer 278a which encloses a relatively soft cancellous bone 280a. The body tissue 12a and 14a may be many different tissues in a patient's body. For example, the tissue 12a could be a meniscus and the tissue 14a could be a bone in a patient's leg. Alternatively, the tissue 12a could be a rotor (musculotendinous) cuff and the tissue 14a could be a bone in an upper portion of a patient's body. The body tissues 12a and 14a could be vascular tissue.

An inserter and pusher member corresponding to the inserter 28 and pusher member 30 of FIG. 2 are utilized to move the anchor 18a into and through the body tissue 12a and into the body tissue 14a. As the anchor 18a moves into the body tissue 12a, a pointed leading end portion 34a of the anchor 18a initiates the formation of an opening in an imperforate surface on the outer surface 300a of the body tissue 12a. As the anchor 18a moves into and through the soft body tissue 12a, the leading end portion 34a is utilized to pierce the body tissue 12a.

As the anchor 18a moves through the body tissue 12a, the leading end portion 34a of the anchor 12a moves into engagement with the outer surface 304a on the hard outer layer 278a of the bone 14a. The force applied against the anchor 18a by the pusher member causes the leading end portion 34a of the anchor 18a to initiate the formation of an opening at an imperforate area on the outer surface 304a of the hard outer layer 278a. As the anchor 18a is moved into the hard outer layer 278a, the leading end portion 34a of the anchor pierces the outer layer ahead of the pusher member. As the anchor 18a moves through the outer layer 278a, the leading end portion 34a of the anchor initiates the formation of an opening in the soft cancellous bone 280a. As the anchor 18a is pushed into the soft cancellous bone 280a by the pusher member, the leading end portion 34a of the anchor 18a deforms the soft cancellous bone.

The anchor 18a moves through the soft body tissue 12a and the hard outer layer 278a of the bone 14a into the soft cancellous bone 280a along an insertion path having a straight longitudinal central axis 350. However, the anchor 18a could be moved along a nonlinear path if desired. As the suture anchor 18a moves through the body tissue 12a into the body tissue 14a, a longitudinal central axis 260a of the anchor 18a is coincident with the longitudinal central axis 350 of the path along which the anchor moves into the body tissue.

Once the anchor 18a has been moved to a desired depth in the body tissue 14a, the pusher member 30 (FIG. 4) may be moved from the extended condition back to the retracted condition of FIG. 3. The inserter, corresponding to the inserter 28 of FIGS. 3 and 4, may then be withdrawn from the body tissue 12a.

Alternatively, the orientation of the anchor 18a may be changed from an orientation in which the longitudinal central axis 360a of the anchor 18a is aligned with the longitudinal central axis 350 of the path along which the anchor is inserted into the body tissue 12a and 14a to an orientation in which the central axis 260a of the anchor extends transverse to the longitudinal central axis 350 of the insertion path. It is believed that it may be desired to change the orientation of the anchor 18a relative to the insertion path in order to increase the resistance of the anchor to tension forces transmitted through the suture 24a to the anchor 18a.

In order to move the anchor 18a from an orientation in which the longitudinal central axis 260a of the anchor is aligned with the longitudinal central axis 350 of the insertion path to the orientation illustrated in FIG. 11, the suture 24a is tensioned. The tension forces initiate a toggling or pivoting action about the end portion of the pusher member which engages the anchor 18a. This toggling action occurs in the same manner as was previously discussed in conjunction with the embodiment of the invention illustrated in FIGS. 4 and 5.

Once the anchor 18a has been pivoted to the desired orientation relative to the body tissue 14a, the pusher member is telescopically withdrawn into the inserter and the inserter is removed from the soft body tissue 12. The viscoelastic nature of the body tissues 12a and 14a cause the passages formed by the anchor 18a to constrict as the pusher member and inserter are withdrawn from the body tissues 12a and 14a.

Once the anchor 18a has been positioned in the body tissue 14a, in the manner illustrated schematically in solid lines in FIG. 11, the anchor 20a is positioned in the body tissue 14a. To position the anchor 20a in the body tissue 14a, the anchor is moved from the position illustrated in solid lines in FIG. 11 along an insertion path having a central axis 354. The insertion path along which the anchor 20a is moved into the body tissue 12a and 14a may be either linear or nonlinear.

An inserter and pusher member, corresponding to the inserter 38 and pusher member 40 of FIGS. 6 and 7, are utilized to move the suture anchor 20a through the body tissue 12a and into the body tissue 14a in the same manner as previously described in conjunction with the embodiment of the invention illustrated in FIGS. 1–10. As the anchor 20a is moved along the insertion path by the pusher member, the longitudinal central axis 320a of the anchor is aligned with the longitudinal central axis 354 of the insertion path.

In the embodiment of the invention illustrated in FIG. 11, the anchors 18a and 20a are formed with pointed leading end portions 34a and 44a. The pointed end portions 34a and 44a enable the anchors 18a and 20a to form their own passages through the body tissues 12a and 14a. However, it is contemplated that the anchors 12a and 14a could be provided with blunt leading end portions. If this was done, passages for the anchors 12a and 14a could be formed in the body tissues by a suitable tool, such as a drill.

As the anchor 20a moves along the insertion path, the suture 24a is tensioned by movement of the anchor 20a. Thus, as the anchor 20a moves along the insertion path, the connector sections 48a and 90 of the suture are tensioned and pressed against the outer surface 300a of the body tissue 12a. The flexible suture 24a conforms to any irregularities in the outer surface 300a of the body tissue 12a and is effective to firmly press the body tissue 12a against the outer surface 304a on the bone 14a.

As the suture 24a moves from the initial loose condition, indicated schematically in solid lines in FIG. 11, to the tensioned condition, indicated schematically in dashed lines in FIG. 11, the suture may move in the passages 266a and 268a in the anchor 20a to enable the length of the connector sections 48a and 90 of the suture 24a to be adjusted. This shifting movement of the suture 24a relative to the anchor 20a results in the same tension forces being present in both connector sections 48a and 90 of the suture 24a.

As the anchor 20a is moved along the insertion path 354, the tension forces in both connector sections 48a and 90a of the suture increase. When a desired tension is present in both of the connector sections 48a and 90 of the suture 24a, movement of the suture anchor 20a along the insertion path is interrupted. Thus, as the anchor 20a is moved into the cancellous bone 280a, the suture 24a is pulled taut between the two anchors 18a and 20a. As the anchor 20a moves along the insertion path, the tension in the suture 24a increases and the force which is transmitted from the suture to the body tissue 12a increases. The increase in force transmitted to the body tissue 12a firmly presses the body tissue against the bone 14a.

In order to enhance the resistance of the anchor 20a to pull out forces applied to the anchor by the suture 24a, the anchor may be pivoted from an orientation in which the longitudinal central axis 320a of the anchor is aligned with the central axis 354 of the insertion path to an orientation in which the central axis of the anchor 20a extends transverse to the central axis of the insertion path. This toggling or pivotal movement of the anchor 20a is initiated by tension in the suture 24a as the anchor is moved along the insertion path by the pusher member. A bevel surface on the leading end portion of the pusher member promotes pivoting or toggling of the anchor relative to the pusher member.

During movement of the anchor 20a along the insertion path 354 by the pusher member, the suture 24a is pulled against the anchor 18a which was initially inserted into the body tissue 14a. As the suture 24a is pulled against the anchor 18a and the anchor 20a moves into the body tissue 14a, a toggling action is automatically initiated by the resulting tension in the suture 24a. This toggling action results in pivotal movement of the anchor 20a about a leading end portion of the pusher member. As the anchor 20a pivots relative to the leading end portion of the pusher member, the anchor moves from an orientation in which the longitudinal central axis 320a of the anchor is coincident with the longitudinal central axis 354 of the insertion path to the orientation illustrated schematically in dashed lines in FIG. 11. As the anchor 20a moves toward the position illustrated in dashed lines in FIG. 11, the central axis 320a of the anchor moves out of alignment with the central axis 354 of the insertion path.

In the embodiment of the invention illustrated in FIG. 11, the central axes 350 and 354 of the insertion paths for the anchors 18a and 20a are disposed in a plane which extends through a center of curvature of the outer surface 300a of the body tissue 12a and a center of curvature of the outer surface 304a of the body tissue 14a. The central axes 350 and 354 of the insertion paths along which the anchors 18a and 20a are moved into the body tissue 12a and 14a intersect at the center of curvature of the outer surface 300a of the body tissue 12a and the outer surface 304a of the body tissue 14a.

Although the central axes 350 and 354 of the insertion paths along which the anchors 18a and 20a are moved into the body tissue 12a and 14a are disposed in a single plane, it is contemplated that the central axes 350 and 354 of the insertion paths could be offset relative to each other. Thus, the central axis 354 could be offset from the central axis 350 in a direction extending into the sheet of the drawing of FIG. 11. Although the central axes 350 and 354 of the insertion paths intersect at the center of curvature of the outer surface 300a of the body tissue 12a and the outer surface 304a of the body tissue 14a, the angle of the axes 350 and 354 relative to the outer surfaces 300a and 304a of the body tissue 12a and 14a could be such that the axes 350 and 354 do not extend through the center of curvature of the surfaces 300a and 304a of the body tissue 12a and 14a.

In the embodiment of the invention illustrated schematically in FIG. 11, the central axes 350 and 354 of the insertion paths of the anchors 18a and 20a extend generally perpendicular to a tangent to the arcuate outer surface 300a of the body tissue 12a. It is contemplated that the central axes 350 and 354 of the insertion paths along which the anchors 18a and 20a are moved into the body tissue 12a and 14a could be skewed at an angle of between 30° and 90° relative to a tangent to the outer surface 300a of the body tissue 12a.

In the embodiment of the invention illustrated in FIG. 11, the anchor 18a is disposed deeper in the body tissue 14a than is the anchor 20a. Thus, the distance which the anchor 18a was moved along its insertion path from the outer surface 304a of the body tissue 14a was greater than the distance which the anchor 20a was moved along its insertion path from the outer surface of the body tissue 14a. It is contemplated that the anchors 18a and 20a could be moved to substantially the same depth in the body tissue 14a if desired. It is also contemplated that the anchor 20a could be moved deeper into the body tissue 14a than the anchor 18a.

The anchors 18a and 20a have been illustrated in FIG. 11 with their longitudinal central axes 260a and 320a extending transverse to each other. It is contemplated that the anchors 18a and 20a could be positioned in the body tissue 14a with their longitudinal central axes 260a and 320a disposed in a parallel relationship. In FIG. 11, the outer side surfaces 300a and 304a of the body tissue 12a and 14a have been illustrated as having an arcuate configuration. However, it is contemplated that the body tissues 12a and 14a could have outer surfaces which have an irregular arcuate configuration, or an irregular generally flat configuration, or a combination of irregular, arcuate and flat configurations. For example, the surface 304a could be disposed on the end of a bone and the central axes 350 and 354 of the insertion paths for the anchors 18a and 20a could be offset so as to extend through the sides of the bone.

It is contemplated that the apparatus 10a will be utilized in many different environments to secure body tissue. Thus, the apparatus 10a may be used to connect a meniscus with a bone in a knee joint of a patient. It is also contemplated that the apparatus 10a may be utilized to connect a rotator cuff with the bone in a shoulder of a patient. The apparatus 10a may be used to interconnect sections of blood vessels. The apparatus 10a may be used to secure mucosa. It should be understood that these are only specific examples of many different locations in a patient's body in which the apparatus 10a may be utilized to secure body tissues.

Although the apparatus 10a has been described in FIG. 11 in conjunction with the connection of soft body tissue 12a with bone 14a, it is contemplated that the apparatus 10a may be utilized to connect one portion of soft body tissue in a patient's body with another portion of the soft body tissue in a patient's body. For example, layers of soft tissue may be positioned in a side-by-side relationship and interconnected using the apparatus 10a. When relatively thin layers of soft tissue are placed in apposition, the anchors 18a and 20a may be moved through the both layers of tissue and disposed adjacent to a side of the tissue in a manner similar to that disclosed in the aforementioned U.S. Pat. No. 5,464,426. Alternatively, the anchors 18a and 20a may be moved through a relatively thin layer of soft body tissue into a relatively thick mass of soft body tissue. When this is done, it is believed that it may be desired to have the anchors embedded in the soft body tissue in the same manner as is illustrated schematically in FIG. 11.

In the foregoing description, the anchor 18a has been inserted into the body tissue 14a before the anchor 20a is inserted into the body tissue 14a. It should be understood that both anchors 18a and 20a could be inserted into the body tissue at the same time. Thus, a first pusher member and inserter, corresponding to the pusher member 30 and inserter 28 of FIG. 2 could be used to move the anchor 18a along a first insertion path into the body tissue 14a at the same time that a second inserter and pusher member, corresponding to the inserter and pusher member 38 and 40 of FIG. 6, are utilized to move the anchor 20a into the body tissue 14a. As this occurs, the rate of insertion of the anchors 18a and 20a could be coordinated so that they would be at the same depth in the body tissue 14a at the same time.

As the anchors 18a and 20a are moved together into the body tissue 14a, the suture 24a is pulled into the body tissue 14a by both of the anchors. This results in the suture 24a being tensioned between the two anchors as both of the anchors move relative to the body tissue 14a. Since both anchors 18a and 20a are being moved at the same time relative to the body tissue 14a, there will be relative movement between the suture 24a and both of the anchors to obtain the required length of suture in the connector portion 48a and 90. Adjusting of the lengths of the connector portions 48a and 90 of the suture 24a is accommodated by the fact that the suture can move in the passages 254a and 256a in the anchor 18a and in the passages 266a and 268a in the anchor 20a.

If desired, both anchors could be left in the body tissue 14a with their longitudinal central axes coincident with the longitudinal central axes of their paths of insertion. Thus, the anchor 18a could be left in the body tissue 14a with its central axis 260a coincident with the central axis 350 of the insertion path of the anchor 18a. Similarly, the anchor 20a could be left in the body tissue 14a with its central axis 320a coincident with the central axis 354 of the insertion path of the anchor 20a into the body tissue 14a. If it is desired to leave the anchors in the body tissue 14a with their central axes 260a and 320a coincident with the central axes 350 and 354 of their insertion paths, the beveled surfaces, corresponding to the surface 310 of FIG. 4 and the surface 324 of FIG. 7 on the pusher members could be omitted.

Since the central axes 350 and 354 of the insertion paths of the anchors 18a and 20a into the body tissue 14a extend transverse to each other, the anchors 18a and 20a move toward each other as they move along their insertion paths. Thus, as the anchor 18a is moved along the longitudinal central axis 350 of its insertion path into the body tissue 14a, the anchor 18a moves toward the axis 354 of the insertion path for the anchor 20a. Similarly, as the anchor 20a moves along the central axis 354 of its insertion path, the anchor 20a moves toward the insertion path for the anchor 18a. By moving the anchors 18a and 20a toward each other along their insertion paths, the suture 24a grips the body tissues 12a and 14a with a clinching action. This clinching action firmly presses the body tissue 12a against the body tissue 14a. If the anchors 18a and 20a are toggled or pivoted to the orientation indicated in solid lines for the anchor 18a and dashed lines for the anchor 20a in FIG. 11, the clinching action of the suture 24a against the body tissues 12a and 14a is increased. This clinching action tends to maximize the tension forces which can be transmitted through the suture 24a without pulling the anchors 18a and 20a out of the body tissue 14a.

The anchors 18a and 20a are supported in the cancellous bone 280a in a spaced apart relationship with the hard outer layer 278a of the bone 14a. Thus, the tension forces transmitted through the suture 24a are transmitted from the anchors 18a and 20a to the cancellous bone 280a.

In the embodiment of the invention illustrated in FIG. 8, the suture 24a extends through both the body tissue 12a and the body tissue 14a. Tension in the suture 24a presses the body tissue 12a against the body tissue 14a. However, the suture 24a could extend across the body tissue 12a and the anchors 18a and 20a moved into the body tissue 14a without passing through the body tissue. If this was done, the suture 24a would extend into the body tissue 14a at locations offset from opposite edges of the body tissue 12a. Alternatively, the body tissue 12a could be spaced from the body tissue 14a and an extension could extend from the continuous loop formed by the suture 24a to the body tissue 12a.

It is contemplated that it may be desired to increase the tension in the suture 24a after the anchors 18a and 20a have been positioned relative to the body tissues 12a and 14a. This may be done by contracting the suture 24a under the influence of heat. If the suture 24a is to be heated, it may be desired to position a protective member between the suture and the tissue 12a. The protective member may have any desired construction, including any of the constructions disclosed in U.S. Pat. No. 4,823,794.

Embodiment of FIG. 12

In the embodiment of the invention illustrated in FIG. 11, a force application assembly 60 is effective to apply tension force to the suture 24 and to determine when a predetermined tension force is present in the suture 24. In the embodiment of the invention illustrated in FIG. 12, a tension measuring device 106 is associated with the inserter 38b and pushrod 40b for a suture anchor 20b. The suture anchor 20b is connected with a second suture anchor (not shown) corresponding to the suture anchor 18a in FIG. 11, by a suture 24b. The suture 24b is formed as a continuous closed loop which extends between the suture anchor 20b and another suture anchor, corresponding to the suture anchor 18a of FIG. 11.

The suture anchor corresponding to the suture anchor 18a of FIG. 11 is moved into the body tissue 14b, to a position corresponding to the position illustrated in solid lines in FIG. 11. The suture anchor 20b is then moved through the body tissue 12b and into the body tissue 14b with an inserter 38b and pusher member 40b (FIG. 12). The suture anchor 20b is moved through the hard outer layer 278b of the bone forming the body tissue 14b into the relatively soft cancellous bone 280b. The anchor 20b is then pivoted or toggled to a position corresponding to the position illustrated in dashed lines in FIG. 11 for the suture anchor 20a.

As the anchor 20b is moved into the body tissue 14b, tension in the connector portions 48b and 90b of the suture 24b is measured by the force measuring device 106. When a predetermined tension is present in the connector portion 48b and 90b of the suture 24b, the output from the force measuring device 106 causes the pusher member drive assembly 114 to interrupt movement of the pusher member into the body tissue 14b. When this occurs, a longitudinal central axis 320b of the anchor 20b is coincident with a longitudinal central axis 354b of the path along which the anchor 20b is moved into the body tissues 12b and 14b. The connector portions 48b and 90b of the suture 24b extend through the slot 316b in the inserter 38b.

In the illustrated embodiment of the invention, the force transmitting member 100 of the tension measuring device 96 is disposed in the slot 316b in the side wall of the tubular inserter 38b. The connector portions 48b and 90b of the suture 24b extend across the end portion 102 of the force transmitting member 100. Although the force transmitting member 100 has been illustrated in FIG. 12 as being disposed in the slot 316b, it is contemplated that the force transmitting member 100 could be disposed outside of the slot adjacent to an outer side surface of the inserter 38b.

As the pusher member drive assembly 114 is operated to move the pusher member 40b axially relative to the stationary inserter 38b, the anchor 20b is moved from the position illustrated in FIG. 12 into the body tissue 14b. As the suture anchor 20b moves into the body tissue 14b, the suture 24b is pulled into the body tissue along with the suture anchor. As this occurs, a tension force is established in the connector portions 48b and 90b of the suture 24b.

The tension force in the connector portions 48b and 90b of the suture 24b results in the application of a downward (as viewed in FIG. 12) force against the end portion 102 of the force transmitting member 100 by the connector portions 48b and 90b of the suture 24b. This force is transmitted through the force transmitting member 100 to the force measuring device 112. The force measuring device 112 includes a piezoelectric cell. When the force measuring device 112 detects that a predetermined tension force is present in the connector portions 48b and 90b of the suture 24b, an output signal from the force measuring device is transmitted to a control apparatus, that is, a microprocessor, which interrupts operation of the pusher drive assembly 114.

At the time when operation of the pusher drive assembly 114 is interrupted, the tension force in the connector portions 48b and 90b of the suture 24b have initiated toggling or pivoting movement of the suture anchor 20b in the cancellous bone 280b. This toggling or pivotal action moves the central axis of the anchor 20b from an orientation in which it is aligned with the central axis 354b of the path along which the suture anchor 20b is moved into the body tissue 14b to an orientation in which the central axis 320b of the suture anchor 20b extends transverse to the central axis 354b of the path along which the suture anchor moves into the body tissue 14b. When the operation of the pusher drive assembly 114 is interrupted, the anchor 20b will have pivoted to a position corresponding to the position illustrated in dashed lines in FIG. 11 for the anchor 20a.

Although it is believed that it will be preferred to utilize a tension measuring device, corresponding to the tension measuring device 96, which is connected with the inserter 38b, it is contemplated that the tension measuring device could be separate from the inserter 38b. For example, the tension measuring device 96 could engage the connector portions 48b and 90b of the suture 24b at a location which is approximately midway between the anchor 20b and the another anchor connected with the suture 24b and corresponding to the anchor 18a of FIG. 11. If desired, a tension measuring device could be substituted for the force application assembly of FIG. 10.

It is contemplated that a protective member, such as a pledget, could be provided between the suture 24b and the body tissue 12b. The protective member provided between the suture 24b and the body tissue 12b may be formed of a biodegradable or bioerodible polymer or copolymer if desired. The protective member may have any one of the constructions disclosed in U.S. Pat. No. 4,823,794.

It is contemplated that a robotic apparatus may be 10 utilized to position suture anchors corresponding to the suture anchors 18 and 20 of FIGS. 1–10, the suture anchors 18a and 20a of FIG. 11, and the suture anchor 20b of FIG. 12 relative to body tissue. The inserters 28 (FIGS. 2–4), 38 (FIGS. 6 and 7), and 38b (FIG. 12) along with the pusher members 30 (FIGS. 2–4), 40 (FIGS. 6 and 7), and 40b (FIG. 12) are connected with articulate arms of the robotic apparatus. Devices for effecting relative movement between the inserter members and the pusher members, similar to the pusher member drive assembly 114 and inserter drive assembly 110 of FIG. 12, are connected with the articulate arms of the robotic apparatus.

Operation of the pusher member drive assembly 114 and the inserter drive assembly 110 is controlled by one or more computers in the robotic apparatus. The tension measuring device 96 is also be associated with an articulate arm of the robotic apparatus. The tension measuring device 96 is mounted on the articulate arm of the robotic apparatus in association with a slot, corresponding to the slot 316b of FIG. 12, in the inserter 38b. Alternatively, the tension measuring device 96 could be mounted on the articulate arm of the robotic apparatus in a spaced apart relationship with the inserter.

It is contemplated that the robotic apparatus will be utilized to position anchors, corresponding to the anchors 18 and 20 of FIGS. 1–10, the anchors 18a and 20a of FIG. 11, and the anchor 18b of FIG. 12 relative to body tissue at many different locations in a patient's body. The body tissue may be hard body tissue, soft body tissue, or a combination of hard and soft body tissue. If desired, a drill or similar tool could be associated with an articulate arm of the robotic apparatus to assist in the formation of an opening in the body tissue. The drill would form an opening extending through the hard outer layer 278b into the cancellous bone 280b. The opening formed by the drill could have a cross sectional area which is smaller than the cross sectional area of the anchor 20b.

The robotic apparatus may have any one of many different constructions. It is contemplated that the robotic apparatus may have a construction similar to the construction illustrated in U.S. Pat. Nos. 6,063,095 and 6,102,850. The disclosures in the aforementioned U.S. Pat. Nos. 6,063,095 and 6,102,850 are hereby incorporated herein in their entirety by this reference thereto.

Embodiment of FIG. 13

In the embodiments of the invention illustrated in FIGS. 1–12, the suture anchors 18, 20, 18a, 20a, and 20b are either positioned manually relative to body tissue or positioned relative to the body tissue by a robotic apparatus. A guide assembly 120 which may be utilized with either the manual or robotic insertion of anchors into body tissue is illustrated in FIG. 13. The guide assembly 120 is utilized to be certain that the insertion paths along which the anchors are moved into the body tissue have a desired angular orientation relative to each other and to the body tissue.

The guide assembly 120 includes the cylindrical guides 126 and 128 which are supported in a preselected angular relationship relative to each other by the base 124. The guide 128 may be moved toward and away from the guide 126, in the manner indicated by the arrow 136 in FIG. 13, to vary the spacing between the guides.

In the embodiment of the invention illustrated in FIG. 13, the guides 126 and 128 have a construction which corresponds to the tubular construction of the inserters 28 and 38 of FIGS. 2–8. Thus, the guide 126 is provided with a slot 292c through which a portion of the suture 24c extends away from the anchor 18c. Similarly, the guide 128 is provided with a slot 316c through which a portion of the suture 24c extends away from the anchor 20c.

The pusher member 132 has the same cylindrical construction as the pusher member 30 of FIGS. 2–4. However, the pusher member 132 is provided with indicia 360 which cooperates with the guide 126 to indicate the depth to which the anchor 18c has moved into cancellous bone 280c. Thus, as the pusher member is moved downward and toward the right (as viewed in FIG. 13), the indicia 360 moves to a location adjacent to a circular end surface 364 on the guide 126.

When the pusher member 132 has moved into the body tissue 14c to a desired depth, a predetermined mark on the indicia 360 will have moved into alignment with the end surface 364 on the guide 126. This enables a surgeon to visually determine the depth to which the anchor 18c has moved into the body tissue. Once the anchor 18c has moved into the desired depth in the body tissue, movement of the pusher member 132 relative to the guide 126 is interrupted. The anchor 18c is then pivoted under the influence of tension in the suture 24c. During this pivotal movement of the anchor 18c, the pusher member 132 may be moved further into the body tissue 14c through a relatively short predetermined distance to promote the pivoting or toggling action of the anchor.

The pusher member 132 may be utilized to move the anchor 20c into the body tissue 14c. If this is done, the depth to which the anchor 20c is moved into the body tissue 14c will be clearly indicated by movement of the indicia 360 on the pusher member 132 relative to a circular end surface 368 on the guide 128.

It is contemplated that a pair of pusher members, having the same construction as the pusher member 132, could be provided to move the anchors 18c and 20c relative to the guides 126 and 128. If this was done, both anchors 18c and 20c could be simultaneously inserted into the body tissue 14c.

When a robotic apparatus is utilized to move the anchors 18c and 20c into the body tissue 14c, articulate arms of the robotic apparatus could be provided with fiber optic systems. These fiber optic systems would view the pusher members and end surfaces 364 and 366 on the guides 126 and 128 and provide an indication to a suitable control apparatus when the indicia 360 is in a desired position relative to the guides. Alternatively, the articulated arms of the robotic apparatus could be provided with drives, for examples, screw and nut drives, which would indicate the extent of operation of the drives and thereby the extent of movement of the pusher members, corresponding to the pusher member 132, relative to the guides 126 and 128 and the depth of insertion of the anchors 18c and 20c into the body tissue 14c.

In the embodiment of the invention illustrated in FIG. 13, the guides 126 and 128 perform the same functions as the inserters 28 and 38 of FIGS. 2–8. However, it is contemplated that the guides could be constructed so as to receive inserters corresponding to the inserters 28 and 38 and to position the inserters relative to the body tissue.

When the guide assembly 120 is utilized in association with a robotic apparatus, it is contemplated that the guide 126, which is fixedly connected with the base 124 of the guide assembly 120, could be connected with one articulate arm of the robotic apparatus. This would result in the base 124 of the guide assembly being positioned relative to the body tissue 12c and 14c in a patient along with the guide 126. The position of the retainer 140 along the base 124 would be adjusted to position the guide 128 in a desired relationship with the guide 126. It is contemplated that the retainer 140 will be held against movement relative to the base by a suitable set screw which extends through a portion of the retainer into engagement with the base. When the set screw is loosened, the retainer 140 and guide 128 may be moved along the base 124, in the manner indicated schematically by the arrow 136 in FIG. 13. When the set screw is tightened, the retainer 140 and guide 128 are held against movement relative to the base 124.

When the guide 126 and base 124 are connected with one articulate arm of a robotic apparatus, one or more pusher members, corresponding to the pusher member 132, can be moved relative to the guides 126 and 128 by one or more additional articulate arms of the robotic apparatus. For example, if the anchors 18c and 20c are to be sequentially moved into the body tissue 14c, a single robotic arm could be provided to move the pusher member 132 relative to the guide 126 to move the anchor 18c into the body tissue. The same articulate arm could be utilized to move the same pusher member 132 relative to the guide 128 to move the anchor 20c into the body tissue 14c. Alternatively, a pair of pusher members, both of which have the construction of the pusher member 132, could be utilized to simultaneously move both of the anchors 18c and 20c into the body tissue 14c. If this is done, one of the pusher members could be associated with one articulate arm of the robotic apparatus and the second pusher member could be associated with another articulate arm of the robotic apparatus.

In the embodiment of the invention illustrated in FIG. 13, the suture 24c forms a continuous loop which extends between the anchors 18c and 20c in the same manner as is illustrated schematically in FIG. 11. If the anchor 18c is moved into the body tissue 14c before the anchor 20c is moved into the body tissue, the suture 24c would be tensioned between the two anchors 18c and 20c as the anchor 20c moves into the body tissue. As the suture 24c is tightened, it applies force against the body tissue 12c to firmly press the body tissue 12c against the body tissue 14c. If both of the anchors 18c and 20c are simultaneously moved into the body tissue 14c, movement of both anchors relative to the body tissue 14c will be effective to tension the suture.

The tension measuring device 96 of FIG. 12 may be associated with either the guide 126 or the guide 128. If desired, one tension measuring device 96 could be associated with the guide 126 and a second tension measuring device could be associated with the guide 128. Alternatively, a tension measuring device 96 could be mounted on the base 124 in a spaced apart relationship with the guides 126 and 128.

It is contemplated that, rather than being a continuous loop, the suture 24c could have the same construction as the suture 24 of FIGS. 1–10. If this was done, a connector portion of the suture would extend between the two anchors 18c and 20c. Leg portions of the suture would be interconnected with a suitable retainer or crimp, corresponding to the retainer 54 of FIGS. 9 and 10.

Of course, if the suture 24c has the same construction as the suture 24 of FIGS. 1–10, only the connector portion of the suture extending between the two anchors 18c and 20c would be tensioned as the anchors move into the body tissue 14c. The two leg portions of the suture would be tensioned after the anchors 18c and 20c had moved into the body tissue 14c. This could be accomplished manually or by the use of a force application assembly, corresponding to the force application assembly 60 of FIG. 10. In this situation, a force application member, corresponding to the force application member 66 of FIG. 10 may be utilized to press the retainer against the body tissue. While the suture 24c is being tensioned with a predetermined force and while the retainer is being pressed against the body tissue with a predetermined force, force application members, corresponding to force application members 76 and 78 of FIG. 10, would be utilized to effect deformation of the retainer.

Embodiment of FIGS. 14 and 15

In the embodiments of the invention illustrated in FIGS. 1–13, leading end portions of the anchors have been utilized to initiate the formation of openings in the soft body tissue and the hard body tissue. It is contemplated that it may be desired to initiate the formation of openings in either the soft body tissue or the hard body tissue or both with a tool other than the anchors. In the embodiment of the invention illustrated in FIGS. 14 and 15, thin elongated members 146 and 160 are utilized to initiate the formation of the openings in both soft body tissue 12d and hard body tissue 14d.

In addition to initiating formation of openings in the soft body tissue 12d and hard body tissue 14d, the thin elongated members 146 and 160 function as guides along which the anchors 18d and 20d are moved into the body tissues 12d and 14d. Thus, the thin elongated members 146 and 160 are first positioned at desired angles relative to each other and to the body tissues 12d and 14d. The thin elongated members 146 and 160 are forced axially through the soft body tissue 12d into the hard body tissue 14d.

Movement of the thin elongated members 146 and 160 into the hard body tissue 14d is interrupted after the thin elongated members have moved to a depth which is greater than the depth to which it is intended to subsequently move the anchors 18d and 20d into the hard body tissue 14d. The thin elongated members 146 and 160 are moved deeper into the hard body tissue 14d than the intended depth of the anchors 18d and 20d in the hard body tissue 14d to enable the thin elongated members to guide movement of the anchors to their intended depth in the hard body tissue. The thin elongated members 146 and 160 may be simultaneously or sequentially moved through the body tissue 12d into the body tissue 14d.

Anchors 18d and 20d are moved along the stationary thin elongated members 146 and 160 (FIG. 15) into the body tissue 12d and 14d. The anchors 18d and 20d have the same construction as the anchors 18 and 20 of FIGS. 110. However, the anchors 18d and 20d have axially extending cylindrical passages 152 and 166 which receive the thin elongated members 146 and 160. Like the anchors 18 and 20 of FIGS. 1–10, the anchors 18d and 20d (FIGS. 14 and 15) are formed of bone. However, the anchors 18d and 20d could be formed of any of the materials previously mentioned in association with the anchors 18 and 20 of FIGS. 1–10.

When the anchor 18d (FIG. 14) is to be moved along the thin elongated member 146, the anchor 18d is telescopically positioned on the stationary thin elongated member 146. The anchor 18d is moved along the thin elongated member 146 until the leading end portion 34d of the anchor 18d engages the soft body tissue 12d. At this time, the cylindrical thin elongated member 146 extends through the cylindrical passage 152 in the anchor 18d and positions the anchor 18d relative to the body tissues 12d and 14d.

The cylindrical pusher member 30d is then telescopically positioned on the stationary thin elongated member 146 (FIG. 14). The pusher member 30d is moved along the thin elongated member 146 until a circular leading end surface 370 on the pusher member 30d engages a trailing end of the anchor 18d. At this time the cylindrical thin elongated member 146 extends through both the cylindrical passage 152 in the anchor 18d and the cylindrical passage 156 in the pusher member 30d. This enables the stationary thin elongated member 146 to position both the anchor 18d and pusher member 30d relative to the body tissues 12d and 14d.

After the pusher member 30d and anchor 18d have been positioned on the thin elongated member 146, the cylindrical inserter 28d is positioned in a telescopic relationship with the anchor 18d and pusher member 30d. An axial force is applied to the inserter 28d to slide the inserter along the stationary pusher member 30d and anchor 18d through the body tissue 12d into engagement with the body tissue 14d, as shown in FIG. 14. At this time, the leading end portion of the pusher member 30d and anchor 18d are fully enclosed by the inserter 28d. The leading end portion 34d of the anchor 18d is disposed in engagement with the surface 300d on the body tissue 12d.

Movement of the inserter 28d through the body tissue 12d into engagement with the body tissue 14d is guided by the stationary pusher member 30d and stationary anchor 18d. The pusher member 30d and anchor 18d are held in the desired orientation relative to the body tissue by the thin elongated member 146. When the inserter 28d is moved to the position shown in FIG. 14 in engagement with the body tissue 14d, the leading end portion 34d of the anchor 18d is in engagement with the surface 300d of the body tissue 12d and is fully enclosed by the inserter 28d.

An axial force is then applied to the pusher member 30d to move the anchor 18d through the body tissue 12d into the body tissue 14d. During this movement of the pusher member 30d and anchor 18d, both the inserter 28d and thin elongated member 146 are stationary relative to the body tissues 12d and 14d. When the anchor 18d has moved to the desired depth in the body tissue 14d, movement of the pusher member 30d and anchor along the thin elongated member 146 is interrupted.

When the anchor 18d has been moved to the desired depth in the body tissue 14d, the anchor is in the position illustrated in FIG. 14 relative to the thin elongated member 146 and the inserter 28d. Indicia corresponding to the indicia 360 (FIG. 13) is provided on the pusher member 30d (FIG. 14) to indicate when the anchor 18d has moved to the desired position relative to the body tissues 12d and 14d.

The anchor 20d (FIG. 15) is positioned relative to the body tissues 12d and 14d in the same manner as previously explained in conjunction with the anchor 18d. The thin elongated member 160 is utilized to guide movement of the anchor 20d and pusher member relative to the body tissue 12d in the same manner as previously explained in conjunction with the anchor 18d. The thin elongated member 160 may be positioned relative to the body tissue 12d and 14d (FIG. 15) simultaneously with the thin elongated member 146 or after the thin elongated member 146 has been positioned relative to the body tissue 12d and 14d.

The anchor 20d and pusher member 40d are positioned in a telescopic relationship with the thin elongated member 160. The anchor 20d is moved along the stationary thin elongated member 160 into engagement with the surface 300d on the body tissue 12d. The pusher member 40d is moved along the stationary thin elongated member 160 to a position in which a circular leading end surface 374 on the pusher member 40d engages the trailing end of the anchor 20d.

The inserter 38d is then positioned in a telescopic relationship with the stationary pusher member 40d, anchor 20d, and elongated member 160. The cylindrical inserter 38d is moved through the body tissue 12d into engagement with the surface 304d of the body tissue 14d. This movement of the inserter 38d is guided by the stationary pusher member 40d and anchor 20d.

Once the inserter 38d has been moved to the position illustrated in FIG. 15 relative to the body tissue 12d and 14d, the pusher member 40d is moved axially along the stationary thin elongated member 160. Force transmitted from the pusher member 38d to the anchor 20d moves the anchor through the body tissue 12d. Further movement of the pusher member 40d along the stationary thin elongated member 160 moves the anchor 20d to the position illustrated in FIG. 15. Indicia on the pusher member 40d cooperates with the inserter 38d to indicate when the anchor 20d has moved to a desired depth in the body tissue 14d.

Embodiment of FIGS. 14 and 15-Alternate Method

The foregoing description has related to a process in which the thin elongated members 146 and 160 are moved into the body tissue 14d prior to movement of the anchors 18d and 20d into the body tissue 12d and 14d. An alternative method for moving the anchors 18d and 20d into the body tissue 14d involves movement of the thin elongated members 146 and 160 together with the anchors into the body tissues 12d and 14d.

When the anchor 18d is to be moved through the body tissue 12d into the body tissue 14d in accordance with the aforementioned alternative method, the thin elongated member 146 is inserted through the passage 156 in the pusher member 30d (FIG. 14). The thin elongated member 146 is moved to a position in which the pointed end portion 148 of the thin elongated member extends past a circular end surface 370 on the pusher member 30d. The portion of the thin elongated member 146 extending past the end surface 370 on the pusher member 30d is then telescopically inserted through the passage 152 in the anchor 18d.

At this time during the alternative method, the pointed end portion 148 on the thin elongated member 146 extends a short distance past a conical leading end portion 34d of the anchor 18d. This results in the pointed end portion 148 on the thin elongated member forming a point for the leading end portion 34d of the anchor 18d at the location where the passage 152 ends at the leading end portion 34d of the anchor 18d.

The pusher member 30d, thin elongated member 146, and anchor 18d are then telescopically inserted into the inserter 28d. The anchor 18d and pusher member 30d are then moved to a position in which the anchor extends from the inserter 28d. Thus, the anchor is moved to a position corresponding to the position of the anchor 18 in FIG. 2. The portion of the suture 24d adjacent to the anchor 18d is tensioned to press a trailing end portion 32d of the anchor firmly against the end surface 370 on the pusher member 30d.

At this time during the alternative method, the pointed end portion 148 of the thin elongated member 146 extends from the leading end portion 34d of the anchor 18d. Therefore, the pointed end portion 148 of the thin elongated member 146 forms a point at a location where the passage 152 intersects the end portion 34d of the anchor 18d. While the pusher member 30d and thin elongated member 146 are held against movement relative to the inserter 28d, the inserter, pusher member, thin elongated member, and anchor are moved as a unit relative to the body tissue 12d. As this occurs, the pointed end portion 148 of the thin elongated member 146 initiates the formation of an opening at an imperforate area on a surface 300d of the body tissue 12d.

As the thin elongated member 146, pusher member 30d, anchor 18d and inserter 28d are moved together relative to the body tissue 12d, the leading end portion 34d of the anchor 18d moves into the opening in the body tissue 12d which was initiated by the pointed end portion 148 of the thin elongated member. The anchor 18d is pressed into the body tissue 12d under the influence of force applied against the trailing end portion 32d of the anchor by the end surface 370 on the pusher member 30d. At this time, there is no relative movement between the thin elongated member 146, pusher member 30d, anchor 18d, and inserter 28d. During movement of the anchor 18d into the body tissue 12d, the anchor 18d remains in a position relative to the inserter 28d corresponding to the position of the anchor 18 to the inserter 28 in FIGS. 2 and 3.

As the thin elongated member, pusher member 30d, anchor 18d, and inserter 28d are moved together into the body tissue 12d during the alternative method, the pointed end portion 148 on the thin elongated member engages an imperforate area on an outer surface 304d of the bone 14d. Continued movement of the thin elongated member 146, pusher member 30d, anchor 18d and inserter 28d together in a direction toward the bone 14d results in initiation of the formation of an opening in the outer surface 304d of the hard outer layer 278d of the bone 14d by the pointed end portion of the thin elongated member 146. Continued axial movement of the thin elongated member 146, pusher member 30d, anchor 18d and inserter 28d together relative to the bone 14d moves the leading end portion 34d of the anchor 18d into the hard outer layer 278d in the same manner as is illustrated in FIG. 3 for the anchor 18.

As this occurs, the inserter 28d moves into abutting engagement with the outer surface 304d on the hard outer layer 278d of the bone 14d (FIG. 14). At this time during the alternative method, the end surface 370 on the pusher member 30d is disposed within the inserter 28d. This, the pusher member 30d and inserter 28d are in the same relationship as is illustrated in FIG. 3 for the pusher member 30 and inserter 28. At this time, the trailing end portion 32d of the anchor 18d is enclosed by the inserter 28d in the same manner as in which the trailing end portion 32 of the anchor 18 is enclosed by the inserter 28 in FIG. 3.

The thin elongated member 146 is then moved through the hard outer layer 278d of the bone 14d into the cancellous bone 280d (FIG. 14). As the thin elongated member 146 moves into the cancellous bone 280d, the inserter 28d, pusher member 30d and anchor 18d remain stationary relative to the bone 14d. Thus, as the thin elongated member 146 is axially advanced into the cancellous bone 280d, the inserter 28d, pusher member 30d and anchor 18d remain in the same relationship with the bone 14d as is illustrated for the inserter 28, pusher member 30 and anchor 18 in FIG. 3.

When the pointed end portion 148 of the thin elongated member 146 has moved to a desired depth in the cancellous bone 280d, the pusher member 30d is moved axially along the thin elongated member 146. As this occurs, the leading end surface 370 (FIG. 14) on the pusher member 30d applies force against the trailing end portion 32d of the anchor 18d. This force causes the anchor 18d to slide along the thin elongated member 146. As the pusher member 30d moves the anchor 18d along the thin elongated member 146, the inserter 28d and thin elongated member remain stationary in the position illustrated in FIG. 14 relative to the hard outer layer 278d of bone.

Thus during performance of the alternative method, the anchor 18d, inserter 28d, pusher member 30d and thin elongated member 146 are all moved together from a position corresponding to a position illustrated in FIG. 2 for the anchor 18 to a position corresponding to the position illustrated in FIG. 3 for the anchor 18. The thin elongated member 146 is then telescopically extended from the anchor 18*d* (FIG. 14) through the hard outer layer 278*d* of bone into the cancellous bone 280*d* while the anchor 18*d* and pusher member 30*d* remain stationary relative to the bone 14*d*.

The thin elongated member 146 is supported by the anchor 18*d* and pusher member 30*d* during the initial formation of an opening in the hard outer layer 278*d* of the bone 14*d*. After the thin elongated member 146 has initiated the formation of an opening in the hard outer layer 278 of the bone 14*d*, the leading end portion 34*d* of the anchor 18*d* enlarges the opening. This positions the anchor in the desired orientation relative to the opening initiated by the elongated member 146.

After the thin elongated member 146 has been moved to the desired depth in the bone 14*d* during performance of the alternative method, the anchor 18*d* is moved axially along the thin elongated member 146. As the anchor 18*d* moves through the hard outer layer 278*d* of bone and moves into the cancellous bone 280*d*, the thin elongated member 146 cooperates with the passage 152 in the anchor 18*d* to guide movement of the anchor along an insertion path having a longitudinal central axis which is coincident with a longitudinal central axis of the thin elongated member 146.

Movement of the pusher member 30*d* and anchor 18*d* along the stationary thin elongated member is interrupted when the anchor 18*d* has moved to a desired depth in the cancellous bone 280*d*. Indicia, corresponding to the indicia 360 of FIG. 13, is provided on the pusher member 30*d*. This indicia cooperates with the inserter 28*d* to indicate when the anchor 18*d* has been moved to a desired position in the cancellous bone 280. If the anchor 18*d* is being positioned in the cancellous bone 280*d* by a robotic apparatus, in the manner previously discussed, the position of the pusher member 30*d* relative to the inserter 28*d* may be indicated by the position of a movable element in a drive assembly on an articulate arm of the robotic apparatus.

In the foregoing description of the alternative method, the thin elongated member 146 and the leading end portion 34*d* of the anchor 18*d* are moved together through a short distance into the hard outer layer 278*d* of bone, that is, to a position corresponding to the position of the anchor 18 in FIG. 3. The thin elongated member 146 is then moved relative to the anchor 14*d* (FIG. 14). However, the thin elongated member 156 could be moved through the soft body tissue 12*d* to a desired depth in the bone 14*d* before the anchor 18*d* is moved into engagement with the soft body tissue. However, if desired, the thin elongated member 146 and anchor 18*d* could be moved together through the soft body tissue 12*d* to the desired depth in the bone 14*d* without any relative movement between the anchor and thin elongated member.

The anchor 20*d* may be moved through the soft body tissue 12*d* into the hard body tissue 14*d* simultaneously with movement of the anchor 18*d* through the soft body tissue into the hard body tissue. However, if desired, the anchor 20*d* may be moved through the soft body tissue 12*d* and into the hard body tissue 14*d* after the anchor 18*d* has been moved into the hard body tissue.

When the anchor 20*d* is to be positioned relative to the body tissue 12*d* and 14*d* in accordance with the alternative method, the thin elongated member 160 (FIG. 15) is moved through the pusher member 40*d* while the pusher member 40*d*, inserter 38*d*, and anchor 20*d* are spaced from the body tissue 12*d* and 14*d*. The portion of the thin elongated member 160 extending past the end surface 374 on the pusher member 40*d* is inserted through the passage 166 in the anchor 20*d*. When this has been done, the pointed end portion 162 of the thin elongated member 160 will extend a short distance past the pointed leading end portion 44*d* of the anchor 20*d*. This will result in the pointed end portion 162 of the thin elongated member 160 forming a continuation of the pointed leading end portion 44*d* of the anchor 20*d*.

The portion of the suture 24*d* adjacent to the anchor 20*d* is tensioned to press the anchor 20*d* against the end surface 374 on the pusher member 40*d*. While the pusher member 40*d*, thin elongated member 160 and anchor 20*d* are held against movement relative to each other, the thin elongated member, pusher member and anchor are telescopically inserted into the inserter 38*d*. The thin elongated member 160, pusher member 40*d* and anchor 20*d* are moved to a position in which the end surface 374 of the pusher member 40*d* is enclosed by the inserter 38*d*. At this time, the anchor 20*d* will be in the same position relative to the inserter 38*d* as is the anchor 20 relative to the inserter 38 of FIG. 6. However, the thin elongated member 160, pusher member 40*d*, inserter 38*d*, and anchor 20*d* (FIG. 15) will all be spaced from the body tissue 12*d* and 14*d*.

While the thin elongated member 160, pusher member 40*d* and anchor 20*d* are held against movement relative to the inserter 38*d* and only the pointed end 162 of the thin elongated member extends from the anchor, the inserter is moved to a desired position relative to the body tissue 12*d* and 14*d*. In the embodiment of the invention illustrated in FIG. 15, the inserter 28*d* is moved to a position offset from the position in which the inserter 28*d* and pusher member 30*d* have been used to move the anchor 18*d* along the thin elongated member 146 into the bone 14. Thus, as viewed in FIG. 15, the thin elongated member 160, pusher member 40*d*, inserter 38*d*, and anchor 20*d* are offset in a direction which is out of the sheet of drawings on which FIG. 15 is disposed from the location of the anchor 18*d* relative to the sheet of drawings.

While the anchor 20*d* is in the same orientation relative to the inserter 38*d* as is the anchor 20 relative to the inserter 38 of FIG. 6, the pointed end portion 162 of the thin elongated member 160 is moved into engagement with an imperforate area on the outer surface 300*d* of the body tissue 12*d*. At this time, the trailing end portion 42*d* of the anchor 20*d* is disposed within the inserter 38*d* and is engaged by the pusher member 40*d*, in the same manner as is illustrated in FIG. 6 for the anchor 20 and pusher member 40. The thin elongated member (FIG. 15) extends through the pusher member 40*d* and through the passage 166 in the anchor 20*d*. The pointed end portion 162 of the thin elongated member is disposed adjacent to and forms a continuation of the pointed leading end portion 44*d* of the anchor 20*d*.

The pointed end portion 162 of the thin elongated member 160 engages the imperforate outer surface 300*d* of the body tissue 12*d* at the location where the anchor 20*d* is to be inserted into the body tissue 12*d* and 14*d*. While the thin elongated member 160, pusher member 40*d*, inserter 38*d* and anchor 20*d* are held against movement relative to each other, they are pressed into the body tissue 12*d*. As this occurs, the pointed end portion 162 of the thin elongated member initiates the formation of an opening in the surface 300*d* of the body tissue 12*d*. Continued movement of the thin elongated member 160, inserter 38*d*, pusher member 40*d* and anchor 20*d* together into the body tissue 12*d* results in the opening which was initially formed by the pointed end portion 162 of the thin elongated member 160 being enlarged by the pointed leading end portion 44*d* of the anchor 20*d*.

As the thin elongated member 160, pusher member 40d, inserter 38d and anchor 20d continue to be moved together toward the bone 14d, the pointed end portion 162 of the thin elongated member 160 moves into engagement with an imperforate area on the surface 304d of the bone 14d. At this time, the pointed leading end portion of the anchor 20d will have moved into the body tissue 12d. The right (as viewed in FIG. 15) side of the inserter 38d will have just begun moving into the body tissue 12d while the left (as viewed in FIG. 15) side of the inserter 38d will be disposed adjacent to and outside of the body tissue 12d. Of course, the position of the left side of the inserter 38d relative to the body tissue 12d will depend upon the thickness of the body tissue. At this time, the trailing end portion 42d of the anchor 20d is enclosed by the inserter 38d.

Continued axial movement of the thin elongated member 160, pusher member 40, inserter 38d and anchor 20d together, that is without relative movement between them, along the insertion path results in the pointed end portion 162 of the thin elongated member initiating the formation of an opening in the outer surface 304d of the hard layer 278d of bone. Continued movement of the thin elongated member 160, pusher member 40d, inserter 38d, and anchor 20d along the insertion path results in the opening which was initiated by the pointed leading end portion 162d of the thin elongated member 160 being expanded by the pointed leading end portion 44d of the anchor 20d.

The thin elongated member 160, pusher member 40d, inserter 38d and anchor 20d are held against movement relative to each other until the inserter 38d engages the outer surface 304d on the hard outer layer 278d of bone. At this time, the pusher member 40d, inserter 38d and anchor 20d will be in the same position relative to each as is illustrated in FIG. 6 for the inserter 38, pusher member 40 and anchor 20. At this time, the pointed end portion 162 of the thin elongated member 160 is disposed adjacent to and forms a continuation of the leading end portion 44d of the anchor 20d.

While the anchor 20d, inserter 38d, and pusher member 40d are stationary relative to the hard outer layer 278d of the bone 14d, the thin elongated member 160 is moved along the path of insertion into the bone 14d. As this occurs, the thin elongated member 160 moves through the hard outer layer 278d into the cancellous bone 280d. When the thin elongated member has been moved to a desired depth into the soft cancellous bone 280d, that is, to the position illustrated in FIG. 15, movement of the thin elongated member into the cancellous bone is interrupted.

The pusher member 40d is then moved axially along the thin elongated member 160 to push the anchor 20d through the hard outer layer 278d into the cancellous bone 280d. As this occurs, the thin elongated member 160 and inserter 38d are stationary relative to the hard outer layer 278d of the bone 14d. The passage 166 in the anchor 20d slides along the thin elongated member 160 under the influence of force applied against the trailing end portion 42d of the anchor by the end surface 374 on the pusher member 40d.

When the pusher member 40d has moved the anchor 20d to the desired depth into the cancellous bone 280d, movement of the pusher member 40d and anchor 20d along the thin elongated member is interrupted. The pusher member 40d may advantageously be provided with indicia, corresponding to the indicia 360 of FIG. 13, which cooperates with the inserter 38d to indicate the position of the pusher member and the anchor 20d relative to the body tissue 14d. It is contemplated that indicia may be provided on the thin elongated members 146 and 160. The indicia on the thin elongated members 146 and 160 would cooperate with the inserters 28d and 30d to indicate the depth of insertion of the thin elongated members into the body tissue 14d.

In the foregoing description of the alternative method, the thin elongated member 160 and the leading end portion 44d of the anchor 20d are moved together through a short distance into the hard outer layer 278d of bone, that is, to a position corresponding to the position of the anchor 20 in FIG. 6. The thin elongated member 160 is then moved relative to the anchor 20d (FIG. 15). However, the thin elongated member 160 could be moved through the soft body tissue to a desired depth in the bone 14d before the anchor 20d is moved into engagement with the soft body tissue. However, if desired, the thin elongated member 160 and anchor 20d could be moved together through the soft body tissue 12d to the desired depth into the bone 14d without any relative movement between the anchor and the thin elongated member.

As the anchor 20d is moved into the cancellous bone 280d with any of the foregoing methods related to FIGS. 14 and 15, the suture 24d is tensioned. In the embodiment of the Invention illustrated in FIG. 15, the suture 24d forms a continuous closed loop which extends through the anchors 18d and 20d in the manner illustrated schematically in FIG. 11 for the suture 24a. Therefore, as the anchor 20d is moved into the cancellous bone 280d, connector portions 48d and 90d of the suture 24d are tensioned between the anchors 18d and 20d. A tension measuring device, corresponding to the tension measuring device 96 of FIG. 12, may be provided to measure the tension in the suture 24d. If a tension measuring device, corresponding to the tension measuring device 96 of FIG. 12, is utilized to measure the tension in the suture 24d (FIG. 15), the movement of the anchor 20d into the cancellous bone 280d is interrupted when there is a desired tension in the connector portions 48d and 90d of the suture 24d.

It should be understood that the suture 24d could have a pair of leg portions, corresponding to the leg portions 50 and 52 of the suture 24 of FIG. 9, which are interconnected by a suture retainer or crimp, corresponding to the suture retainer or crimp 54 of FIG. 9. If this was done, a force application assembly, corresponding to the force application assembly 60 of FIG. 10, could be utilized to determine when the desired tension force was present in the suture 24d (FIG. 15).

If the anchor 18d is moved into the cancellous bone 280d prior to movement of the anchor 20d into the cancellous bone, the suture 24d will be tightened with a desired tension force during insertion of the anchor 20d into the cancellous bone 280d. However, if both anchors 18d and 20d are inserted at the same time into the cancellous bone 280d, the suture 24d will be tightened to the desired tension during movement of both anchors into the cancellous bone 280d.

If desired, the step of measuring the tension in the suture 24d could be omitted. If this was done, the anchors 18d and 20d would merely be moved to a desired depth into the cancellous bone 280d. By properly sizing the loop formed by the suture 24d and selecting the locations of the insertion paths for the anchors 18d and 20d, a desired tension would be obtained in the suture 24d when the anchors 18d and 20d have been moved to a desired depth into the cancellous bone 280d. However, it is believed that it may be desired to actually measure the tension in the suture 24d to be certain that a desired tension is obtained when the anchors 18d and 20d have been moved into the cancellous bone 280d.

If desired, the anchors 18d and 20d may be left in the orientation illustrated in FIG. 15 relative to the cancellous bone 280d and the hard outer layer 278d. Alternatively, the anchors 18*d* and 20*d* may be toggled or pivoted relative to the cancellous bone 280*d*. In either situation, the anchors 18*d* and 20*d* would be supported in the cancellous bone 280*d* in a spaced apart relationship with the hard outer layer 278*d*.

When the anchor 18*d* is to be pivoted relative to the cancellous bone 280, the thin elongated member 146 is first completely withdrawn from the anchor 18*d*. While the pusher member 30*d* is pressed against the trailing end portion of the anchor 18*d*, the suture 24*d* is tensioned to cause a pivoting movement of the anchor 18*d* relative to the pusher member 30*d* in the manner illustrated schematically in FIGS. 4 and 5 of the anchor 18.

Similarly, if the orientation of the anchor 20*d* is to be changed relative to the cancellous bone 280*d*, the thin elongated member 160 is completely withdrawn from the anchor 20*d*. While the pusher member 40*d* is pressed against the trailing end portion of the anchor 20*d*, the tension in the suture 24*d* causes the anchor to pivot from the orientation shown in FIG. 7 for the anchor 20 to the orientation shown in FIG. 8 for the anchor 20.

In the embodiment of the invention illustrated in FIG. 15, the suture 24*d* extends in a continuous closed loop between the two anchors 18*d* and 20*d*. The suture 24*d* is not tensioned until both anchors 18*d* and 20*d* have been moved into the body tissue 14*d*. Therefore, if the orientation of the anchors 18*d* and 20*d* is to be changed from the orientation illustrated in FIG. 15 to the orientation illustrated in FIG. 9 of the anchors 18 and 20, both anchors may be pivoted at the same time in the cancellous bone 280*d*.

To effect simultaneous pivotal movement of the anchors 18*d* and 20*d* in the cancellous bone 280*d*, the thin elongated member 146 is withdrawn from the anchor 18*d* and the thin elongated member 160 is withdrawn from the anchor 20*d* while the anchors are disposed in the orientation illustrated in FIG. 15 in the body tissue 280*d*. Both pusher members 30*d* and 40*d* are then simultaneously pressed against the trailing end portions of the anchors 18*d* and 20*d*. The resulting tension in the suture 24*d* causes the anchor 18*d* to pivot in a counterclockwise direction about the end portion of the pusher member 30*d*. At the same time, the tension in the suture 24*d* causes the anchor 20*d* to pivot in a clockwise direction about the end portion of the pusher member 40*d*. Of course, the anchors 18*d* and 20*d* could be sequentially pivoted in the cancellous bone 280*d* if desired.

In the specific embodiment of the invention illustrated in FIGS. 14 and 15, the anchors 18*d* and 20*d* are moved along linear insertion paths into the body tissues 12*d* and 14*d*. Therefore, the thin elongated members 146 and 160 have linear configurations. However, it is contemplated that it may be desired to move the anchors 18*d* and 20*d* into body tissues along nonlinear insertion paths.

When the anchors 18*d* and 20*d* are to be moved into body tissues along nonlinear insertion paths, the elongated members 146 and 160 have a nonlinear configuration. For example, if the anchors 18*d* and 20*d* are to be moved along arcuate insertion paths relative to the body tissues 12*d* and 14*d*, the thin elongated members 146 and 160 would have portions with an arcuate configuration. The portions of the thin elongated members having an arcuate configuration would have an arcuate configuration which is the same as the arcuate configuration of the desired insertion paths. The anchors 18*d* and 20*d* would be moved along the arcuate portions of the thin elongated members into the body tissues 12*d* and 14*d*.

It is contemplated that the desired anchor insertion paths into the body tissues 12*d* and 14*d* could have arcuate configurations corresponding to the arcuate configurations of a portion of a circle. In this situation, at least a portion of the thin elongated members 146 and 160 would have arcuate configurations corresponding to the configuration of a portion of a circle. For example, the thin elongated members 146 and 160 could have portions with a circular arcuate extent of 135°.

After the arcuate thin elongated members 146 and 160 have been positioned relative to the body tissues 12*d* and 14*d*, the anchors 18*d* and 20*d* would be moved along the arcuate extent of the thin elongated members. The anchors 18*d* and 20*d* may have passages 152 and 166 with arcuate configurations corresponding to the arcuate configurations of the thin elongated members 146 and 160. The pusher members 30*d* and 40*d* would also have arcuate configurations corresponding to the arcuate configurations of the thin elongated members 146 and 160. The arcuate configurations of the anchor passages 152 and 166 and the arcuate configurations of the pusher members 30*d* and 40*d* would facilitate movement of the anchors along the arcuate portions of the thin elongated members under the influence of force transmitted to the anchors from the pusher members.

If desired, the pusher members 30*d* and 40*d* could have flexible constructions to enable the pusher members to bend as they move along the arcuate portions of the thin elongated members 146 and 160. For example, the pusher members 30*d* and 40*d* could be formed of a polymeric material and be resiliently deflected by the arcuate portion of the thin elongated members 146 and 160. Alternatively, the pusher members 30*d* and 40*d* could be formed of tightly coiled spring wire.

It is contemplated that it may be desired to move the anchors 18*d* and 20*d* along helical insertion paths into the body tissues 12*d* and 14*d*. The thin elongated members 146 and 160 would be formed with helical configurations corresponding to the helical configurations of the anchor insertion paths. The thin elongated members 146 and 160 would be moved into the body tissues 12*d* and 14*d* with a screwing action by rotating the thin elongated members about a straight central axis of the helix. The anchors 18*d* and 20*d* would be moved along the helical portions of the thin elongated members 146 and 160 by pusher members 30*d* and 40*d* having a helical configuration. Alternatively, the pusher members 30*d* and 40*d* could have a flexible construction to enable the pusher members to conform to turns in the helical portions of each of the thin elongated members 146 and 160.

In the embodiment of the invention illustrated in FIGS. 14 and 15, the thin elongated members are offset from each other in the direction of the sheet on which FIG. 15 of the drawings is disposed. However, it is contemplated that the thin elongated members 146 and 160 could be positioned relative to each other with their central axes in a common plane. If this is done, the pointed end portion 148 (FIG. 14) of the thin elongated member 146 and the pointed end portion 162 of the thin elongated member 160 would be disposed in engagement when the thin elongated members have been inserted into the body tissue 12*d* and the body tissue 14*d*. This would facilitate positioning of the anchors 18*d* and 20*d* in engagement with each other, in a manner similar to that illustrated in FIG. 20 for the anchors 18*g* and 20*g*.

Embodiment of FIG. 16

A guide assembly 120*e* for guiding movement of suture anchors into body tissue is illustrated schematically in FIG. 16. The guide assembly 120*e* has the same general construction and mode of operation as the guide assembly 120 of FIG. 13. The guide assembly 120*e* is illustrated in FIG. 16 in association with soft body tissue 12e and 14e. The soft body tissue 12e is formed as a relatively thin layer. The body tissue 14e is formed as a relatively thick mass.

The guide assembly 120e is utilized to guide movement of suture anchors corresponding to the suture anchors 18 and 20 of FIG. 1 along insertion paths into the body tissue 14d with a suture, corresponding to the suture 24 of FIG. 1 extending between the suture anchors. However, the guide assembly 120e could be used in association with a suture which extends in a continuous loop between a pair of suture anchors. The continuous suture loop would be utilized in the same manner as described in conjunction with FIG. 11.

The guide assembly 120e includes a linear base 124e which is positioned in abutting engagement with an outer surface 300e of the layer 12e of body tissue. At this time, the guides 126e and 128e are withdrawn from openings in slide blocks 380 and 382 in the guide assembly 120e. The slide blocks are then moved along slots 384 and 386 in the base 124e until cylindrical openings which extend through the guide blocks are aligned with desired insertion locations for the anchors.

The guide 126e is then positioned in the opening in the slide block 380. The guide 126e is pressed axially into the body tissue 12e and the body tissue 14e to the position illustrated schematically in FIG. 16. The guide 128e is then pressed axially into the body tissue 124e and 114e to the position illustrated schematically in FIG. 16.

Once the guides 126e and 128e have both penetrated the soft body tissue 12e and 14e, anchors, corresponding to the anchors 18 and 20 of FIG. 1, are positioned in cylindrical passages 392 and 394 formed in the guides 126e and 128e. Pusher members, corresponding to the pusher members 30 and 40 of FIGS. 2–8, are then utilized to move the anchors 18 and 20 along the guides 126e and 128e through the layer 124e of soft body tissue into the mass 14e of soft body tissue. As this occurs, the suture extending between the anchors moves along slots 292e and 316e in the side walls of the tubular guides 126e and 128e. If the suture has the construction of the suture 24 of FIG. 1, the leg portions of the suture are tensioned after the anchors have been moved into the mass 14e of soft body tissue. However, if the suture has the loop construction illustrated in FIG. 11, the suture is tensioned as the anchors are moved into the soft body tissue 14e.

The slotted guides 126e and 128e are positioned with their longitudinal central axes extending transverse to each other. This results in the anchor which is moved along the guide 126e, that is the anchor corresponding to the anchor 18 in FIG. 1, moving toward the guide 128e as the anchor is moved into the body tissue. Similarly, the anchor which is moved along the guide 128e, that is, the anchor 20 in FIG. 1, moves toward the guide 126e as the anchor is moved into the body tissue 14e. The anchors may be left in the body tissue 14e with their longitudinal central axes extending parallel to longitudinal central axes of the guides 126e and 128e. Alternatively, the anchors may be pivoted or toggled to positions and orientations corresponding to the orientations of the anchors 18 and 20 in FIG. 10.

Once the anchors have been positioned in the body tissue with the suture extending between the anchors, the guides 126e and 128e are withdrawn from the body tissue 12d and 14d. Tension in the suture which extends between the anchors, is effective to press the layer 124e of body tissue firmly against the relatively large mass 14e of body tissue.

Embodiment of FIG. 17

In the embodiment of FIG. 17, the anchors 18f and 20f and the suture 24f are utilized to press bone 12f on one side of a fracture 178 against bone 14f on the other side of the fracture. The anchors 18f and 20f and the suture 24f have the same construction as the anchors 18 and 20 and suture 24 of FIGS. 1–10. To secure the body tissue or portion 12f of the bone 174 to the body tissue or portion 14f of the bone, the two portions of the bone are firmly pressed together at the fracture 178.

When the anchor 18f is to be positioned relative to the bone 174, the anchor is positioned in an inserter, corresponding to the inserter 28 of FIG. 2. A pusher member, corresponding to the pusher member 30 of FIG. 2, is positioned in the inserter and engages a trailing end portion of the anchor 18f. The anchor 24f is held in the inserter with a leading end portion 34f (FIG. 17) of the anchor extending from the inserter in the same manner as is illustrated in FIG. 2. At this time, the suture 18f extends along a slot in the inserter. Thus, the suture 24f extends along a slot corresponding to the slot 292 in the inserter 28 of FIG. 2.

The longitudinal central axis of the inserter is then positioned in a desired orientation relative to the portion 12f and the portion 14f of the bone 174. The orientation of the inserter corresponds to the path along which the anchor 18f is to be moved into and through the portion 12f of the bone 174 and into and through the portion 14f of the bone. If the anchor 18f is to be moved straight downward (as viewed in FIG. 17) through the portions 12f and 14f of the bone 174, the inserter would be positioned with its longitudinal central axis extending generally perpendicular to the outer surface 300f of the portion 14f of the bone 174. However, in the embodiment of the invention illustrated in FIG. 17 it is preferred to move the anchor along a path which is skewed relative to the outer surface 300f of the bone 174. The inserter may be positioned with its longitudinal axis extending at an angle of between 30° and 90° to the outer surface 300f of the bone.

With the inserter in the desired orientation relative to the surface 300f of the bone 174, the pointed leading end portion 34f of the anchor 18f is pressed against an imperforate area on the outer surface 300f of the bone 174. The pointed leading end portion 34f of the anchor 18f then initiates formation of an opening in the portion 12f of the bone 174. However, if desired, a drill or similar tool could be utilized to form a passage extending through the portion 12f and the portion 14f of the bone at the desired angle relative to the surface 300f of the bone. This passage could have a diameter which is either slightly smaller or slightly greater than the outside diameter of the anchor 18f. If the diameter of the passage which is drilled through the bone 174 is less than the outside diameter of the anchor, the anchor would be effective to expand the passage as the anchor moves into the portion 12f of the bone.

Assuming that the anchor 18f is utilized to form a passage in the bone 174, the pointed leading end portion of the anchor penetrates a hard outer layer 278f of the bone 174 and moves into cancellous bone 280f which is enclosed by the hard outer layer 278f. As this occurs, the pusher member, corresponding to the pusher member 30 is telescopically extended from the inserter, in the manner illustrated schematically in FIG. 4 for the pusher member 30 and inserter 28. This moves the anchor 18f through the portion 12f of the bone 174 and through the portion 14f of the bone.

Immediately after the anchor 18f emerges from the lower (as viewed in FIG. 17) side of the bone 174, the suture 24f is tensioned and the anchor is pivoted or toggled to the position illustrated in FIG. 17. After the anchor 18f has been toggled to the position illustrated in FIG. 17, the pusher member is withdrawn from the bone.

The anchor 20f is moved through the portion 12f of the bone 174 into the portion 14f of the bone 174, in the manner indicated schematically in solid lines in FIG. 17.

The anchor 20f is moved through the portion 14f of the bone 174 and toggled to the position illustrated in dashed lines in FIG. 17.

When the anchor 20f is to be moved through the bone 174, the anchor is positioned in the inserter 38f which has the same construction as the inserters 28 and 38 of FIGS. 28. The pusher member 40f is telescopically moved along the inserter 38f into engagement with the trailing end portion of the anchor 20f. The suture 24f has the same construction as the suture 24 of FIG. 1. Therefore, a leg portion 52f and a connector portion 48f may be received in a slot in the inserter 38f in the same manner as previously described in conjunction with the embodiment of the invention illustrated in FIGS. 2–8.

The inserter 38f and pusher member 40f are positioned in an angular orientation relative to the surface 300f of the bone 174 corresponding to the angle of the desired path of insertion of the anchor 20f into the body tissue 12 and 14. In this specific embodiment of the invention illustrated in FIG. 17, the path of insertion of the anchor 20f into the bone 174 is skewed at an angle of between 55° and 60° relative to the surface 30f. It is contemplated that the path of insertion of the anchor 20f into the bone 174 may be located at an angle between 30° and 90° relative to the surface 300 of the bone 174. As was previously mentioned in conjunction with the anchor 18f, a passage extending through the bone 174 may be preformed by a drill or other tool.

Assuming that the anchor 20f is to be utilized to form its own passage through the bone 174, when a leading end portion 44f of the anchor 20f engages an imperforate surface on the outer surface 300f of the portion 12f of the bone 174, the leading end portion of the anchor initiates formation of an opening in the outer surface of the portion 12f of the bone 174. Continued movement of the pusher member 40f along the path of insertion of the anchor into the bone 174 results in the anchor moving into the hard outer layer 278f of the bone. Continued movement of the pusher member 40f relative to the inserter 38f results in the anchor moving into the cancellous bone 280f in the portion 12f of the bone 174. As the pusher member 40f continues to move the anchor 20f into the bone 174, the anchor moves across the fracture 178 in the manner illustrated schematically in FIG. 17, as the anchor 20f moves through the cancellous bone 280f.

The anchor 20f then moves through the hard outer layer 278f of the portion 14 of the bone 174. Once the anchor has moved out of the bone 14f at the lowest (as viewed in FIG. 17) side of the bone, the suture 24 is tensioned and the anchor is toggled to the position illustrated in dashed lines in FIG. 17.

Once the anchor 18f has been moved to the position illustrated in solid lines in FIG. 17 and the anchor 20f has been moved to the position illustrated in dashed lines in FIG. 17, ends of leg portions 50f and 52f of the suture 24f are tensioned. As this occurs, the suture 24f slides into passages formed in the anchors 18f and 20f. As the leg portions 50f and 52f of the suture 24f are tensioned, the connector portion 48f of the suture is tensioned. Any excess material in the connector portion 48f of the suture 24f is pulled from the connector portion 48f into either one or both of the leg portions 50f and 52f of the suture 24f. A retainer, corresponding to the retainer 54 of FIG. 9, may be utilized to interconnect the leg portions 50f and 52f of the suture 24f. Alternatively, a knot may be utilized to interconnect the leg portions 50f and 52f if desired.

A force application assembly, corresponding to the force application assembly 60 of FIG. 10 may be utilized to apply a predetermined tension force to the leg portions 50f and 52f of the suture 24f. In addition, a force application member, similar to the force application member 66 of FIG. 10, may be utilized to press a crimp against the bone 174 as the suture 24f is tensioned. While the desired tension force is being applied to the suture and while the crimp is being pressed against the bone with the desired force, force application members, corresponding to force application members 76 and 78 of FIG. 10, may be utilized to plastically deform the suture retainer.

It is believed that a guide assembly, similar to the guide assembly 120 of FIG. 13, may advantageously be utilized when the anchors 18f and 20f are being moved into the bone 174f. The guide assembly may have guides, corresponding to the guides 126 and 128 of FIG. 13, which engage the anchors 18f and 20f and the associated pusher members corresponding to the pusher members 30 and 40 of FIGS. 1–8. Alternatively, the guides could be utilized to position inserters, corresponding to the inserters 28 and 38 of FIGS. 2–8.

When the anchors 18f and 20f of FIG. 17 are being moved into the bone 174, it is believed that the use of thin elongated members, corresponding to the thin elongated members 146 and 160 of FIG. 15, may advantageously be utilized to guide movement of the anchors 18f and 20f along preselected paths. Thus, the thin elongated members would be moved through the bone 174. One of the thin elongated members would be moved through the bone 174 along an insertion path to be followed by the anchor 18f. The other thin elongated member would be moved through the bone 174 through an insertion path to be followed by the anchor 20f.

Small passages may be predrilled in the bone 174 to receive the thin elongated members. The predrilled holes for the thin elongated members may have a diameter which is slightly less than the diameter of the thin elongated members. Once the thin elongated members have been moved through the bone 174, the anchors 18f and 20f are moved along the thin elongated members through the bone 174.

Embodiment of FIGS. 18 and 19 he anchors of FIGS. 1–17 all have the same general construction. However, it is contemplated that the anchors could have a different construction if desired. For example, the anchors could be constructed in the manner generally similar to the construction of the anchor 186 of FIG. 18. The anchor 186 has a plurality of barbs, that is barbs 192, 194 and 196. The barbs 192, 194 and 196 engage body tissue to hold the anchor 186 against movement relative to the body tissue. Of course, the anchor could be provided with barbs or projections having a construction which is different than the construction of the barbs or projections 192, 194 and 196 if desired.

The anchor 186 has a known construction. The construction of the anchor 186 is the same as is disclosed in U.S. Pat. No. 5,725,557. However, it should be understood that the anchor 186 is typical of many different known anchor constructions having projections or barbs which engage either soft or hard body tissue to retain the anchor against movement relative to the body tissue. Any one of these known anchors could be utilized in place of the anchor 186 if desired. The anchor 204 of FIG. 19 has a threaded portion 206 which engages body tissue to hold the anchor against movement relative to the body tissue. Although it is believed that the threaded portion 206 may be most effective to hold the anchor 204 against movement relative to bone, the anchor could be utilized in association with soft body tissue if desired.

The anchor 204 has a known construction. The construction of the anchor 204 is the same as is disclosed in U.S. Pat. No. 5,443,482. However, it should be understood that the anchor 204 could have a different construction if desired.

Embodiment of FIGS. 20 and 21

In the embodiment of the invention illustrated in FIGS. 20 and 21, the anchors 18 and 20 are moved into body tissue 12g and 14g along insertion paths which intersect in the body tissue 14g. In FIG. 20, the longitudinal central axes of the insertion paths along which the anchors 18g and 20g are moved into the body tissue 12g and 14g are disposed in a single flat plane.

The anchors 18g and 20g are advantageously interconnected at the location where the paths of insertion of the anchors into the body tissue 12g and 14g intersect. It is believed that movement of the anchors 18g and 20g along intersecting insertion paths into the body tissue 12g and 14g may be facilitated by the utilization of a guide assembly, corresponding to the guide assembly 120 of FIG. 13. In addition, thin elongated members, corresponding to the thin elongated members 146 and 160 of FIG. 15, may be utilized to further guide movement of the anchors 18g and 20g.

Although the anchors 18g and 20g have been illustrated in FIG. 20 in association with soft body tissue 12g having an arcuate outer surface 300g and hard body tissue or bone 14g having an arcuate outer surface 304g, it is contemplated that the anchors 18g and 20g could be moved into body tissue having outer surfaces with many different configurations, including an irregular or flat configuration. It should also be understood that the anchors 18g and 20g may be utilized in association with just soft body tissue. For example, the anchors 18g and 20g could be utilized to connect one piece of soft body tissue, corresponding to the body tissue 12g of FIG. 20, with another piece of soft body tissue, corresponding to the body tissue 14g of FIG. 20.

The anchors 18g and 20g may be sequentially moved through the body tissue 12g and into the body tissue 14g or may be simultaneously moved through the body tissue 12g into the body tissue 14g. Assuming that the anchors 18g and 20g are sequentially moved through the body tissue 12g and into the body tissue 14g, the anchor 18g is first moved through the body tissue 12g into the body tissue 14g. An inserter member and a pusher member, corresponding to the inserter 28 and pusher member 30 of FIG. 2, are utilized to move the anchor 18g into the body tissue 14g. If a guide assembly, similar to the guide assembly 120 of FIG. 13, is utilized to facilitate movement of the anchor 18g along a desired insertion path, the inserter, corresponding to the inserter 28 of FIG. 1, may be omitted and the anchor moved along a guide, corresponding to the guide 126 of FIG. 13.

The pusher member which is utilized to move the anchor 18g through the body tissue 12g and into the body tissue 14g may advantageously be provided with indicia, corresponding to the indicia 360 on the pusher member 132 of FIG. 13. When the indicia 360 on the pusher member indicates that the anchor 18g has been moved to the desired depth in the body tissue 14g, movement of the anchor into the body tissue is interrupted.

The anchor 20g is then moved through the body tissue 12g into the body tissue 14g. The path of movement of the anchor 20g through the body tissue 12g into the body tissue 14g intersects the path of movement of the anchor 18g. It is contemplated that the use of a guide assembly, corresponding to the guide assembly 120 of FIG. 13, will facilitate movement of the anchor 20g along an insertion path which intersects the insertion path of the anchor 18g. However, if desired, the anchor 20g could be moved along its insertion path without the benefit of a guide assembly corresponding to the guide assembly 120 of FIG. 13.

It is believed that it may be desired to utilize thin elongated members, corresponding to the thin elongated members 146 and 160 of FIG. 15, to position the anchors 18g and 20g relative to the body tissue 12g and 14g. Of course, if this was done, passages, corresponding to the passages 152 and 166 in the anchors 18d and 20d of FIG. 15, would be provided in the anchors 18g and 20g.

In the embodiment of the invention illustrated in FIG. 20, the anchors 18g and 20g each have a portion of a suture 24g extending from the anchors. Thus, a leg portion 50g of suture material is secured to the anchor 18g and extends from the anchor to the retainer 54g. Similarly, a leg portion 52g of the suture material is fixedly connected to the anchor 20g and extends to the retainer 54g. In the embodiment of the invention illustrated in FIG. 20, there is no connector portion, corresponding to the connector portion 48 of FIGS. 1 and 9, of the suture 24g extending between the two anchors 18g and 20g. Thus, the leg portions 50g and 52g of the suture 24g are formed as separate segments. Of course, the suture 24g could be provided with a connector portion, corresponding to the connector portion 48 of FIGS. 1 and 9 if desired.

The anchors 18g and 20g are interconnected at the location where the paths along which they move through the body tissue 12g into the body tissue 14g intersect. The manner in which the anchors 18g and 20g are interconnected is illustrated schematically in FIG. 21.

The anchor 18g has a leading end portion 34g which engages a leading end portion 44g of the anchor 20g. Although the leading end portions 34g and 44g of the anchors 18g and 20g have a generally conical configuration, corresponding to the conical configuration of the leading portions 34 and 44 of the anchors 18 and 20 (FIG. 1). It is contemplated that the leading end portions 34g and 44g of the anchors 18g and 20g could have a different configuration if desired. For example, the leading end portions 34g and 44g of the anchors 18g and 20g could have generally wedge-shaped configurations. Alternatively, the leading end portions 34g and 44g of the anchors could be formed with hooks and/or loops.

In the illustrated embodiment of the invention, the leading end portion 34g of the anchor 18g is formed with annular projections 212 (FIG. 21) which engage annular projections 214 on the leading end portion 44g of the anchor 20g. The annular projections 212 on the anchor 18g extend around the end portion 34g of the anchor. Similarly, the annular projections 214 on the anchor 20g extend around the end portion 44g of the anchor.

The projections 212 and 214 on the anchors 18g and 20g engage each other as the anchor 20g moves along its insertion path into engagement with the anchor 18g. The projections 212 and 214 become interconnected in such a manner as to interconnect the anchors 18g and 20g. Thus, the projections 212 and 214 become intermeshed to prevent separation of the anchors 18g and 20g.

It is contemplated that the leading end portions 34g and 44g of the anchors 18g and 20g could be interconnected in a different manner other than by the use of projections corresponding to the projections 212 and 214. Thus, one of the anchors, for example, the anchor 18g, could be provided with a plurality of hooks which would engage a plurality of loops on the other anchor, that is, the anchor 20g. If desired, the anchors 18g and 20g could be formed of materials having magnetic poles such that the leading end portions 34g and 44g of the anchors 18g and 20g are attracted to each other. It is contemplated that magnetic force may be utilized to promote engagement of the leading end portions 34g and 44g of the anchors 18g and 20g with any one of many different types of interconnections between the anchors 18g and 20g. If this was done, the magnetic forces between the anchors 18g and 20g would be utilized to promote engagement of one portion of a mechanical interconnection on the anchor 18g with another portion of a mechanical connection on the anchor 20g.

If desired, fiberoptics could be positioned along the paths of movement of the anchors 18g and 20g into the body tissue 14g. One of more guide members could be inserted through one or more cannulas into engagement with the leading end portion of either the anchor 18g or 20g or both of the anchors to apply force to the anchors to promote engagement of the leading end portions 34g and 44g of the anchors. If this was done, one of the guide members could be utilized to actuate an interconnection device between the anchors 18g and 20g. For example, the guide member could be utilized to actuate a latch so that the latch would lock the leading end portions 34g and 44g of the anchors 18g and 20g together.

Embodiment of FIG. 22

The embodiment of the invention illustrated in FIG. 22 is similar to the embodiment of the invention illustrated in FIGS. 20 and 21. However, in the embodiment of the invention illustrated in FIG. 22, the anchors 18h and 20h are interconnected at the location where their insertion paths into the body tissue 14h intersect by having one anchor move into an opening in the other anchor.

In the embodiment of the invention illustrated in FIG. 22, the anchor 18h is provided with an opening 220 into which the anchor 20h moves. The anchor 20h has a plurality of retainers 224 which engage the portion of the anchor 18h forming the opening 220 to interconnect the two anchors.

If desired, the anchor 18h could be provided with a flexible mesh, a series of hooks, and/or a series of loops which are engaged by the anchor 20h to interconnect the anchors 18h and 20h. Thus, a multiplicity of retainers or hooks, corresponding to the retainers 224, could be provided at axially spaced apart locations along the body of the anchor 20h to engage openings formed by loops or a mesh connected with the anchor 18h. It should be understood that the openings or mesh provided by the anchor 18h could be formed by one or more extensions from the anchor 18h.

It is believed that accurate movement of the anchors 18h and 20h along insertion paths which intersect in the body tissue 14h may be promoted by the use of a robotic assembly to position the anchors. Thus, an inserter assembly connected to one articulate arm of a robotic assembly could be utilized to position the anchor 18h in the body tissue 14h and a second articulate arm of the robotic apparatus could be utilized to position the anchor 20h in the body tissue 14h. If desired, a guide assembly, corresponding to the guide assembly 120 of FIG. 13, could be utilized in association with the robotic arms. If this was done, the guide assembly could be connected with one of the robotic arms for movement therewith relative to the other robotic arm. Accurate placement of the anchors 18h and 20h at the desired depth in the body tissue would be facilitated by pusher member drive assemblies on the robotic arms.

Having described the invention, the following is claimed:

1. A method of securing first body tissue with second body tissue, said method comprising the steps of providing a plurality of anchors with a suture extending between the anchors, moving a first anchor of the plurality of anchors along a first path into the second body tissue, moving a second anchor of the plurality of anchors along a second path into the second body tissue, tensioning at least a portion of the suture extending between the first and second anchors by moving the second anchor along at least a portion of the second path which extends transverse to the first path, and transmitting force through the suture to the first body tissue.

2. A method as set forth in claim 1 wherein said step of moving a first anchor along a first path into the second body tissue includes piercing the first body tissue with a leading end portion of the first anchor.

3. A method as set forth in claim 2 wherein said step of moving a first anchor along a first path into the second body tissue includes piercing the second body tissue with the leading end portion of the first anchor.

4. A method as set forth in claim 3 wherein said step of moving a second anchor along a second path into the second body tissue includes piercing the first body tissue with a leading end portion of the second anchor.

5. A method as set forth in claim 4 wherein said step of moving a second anchor along a second path into the second body tissue includes piercing the second body tissue with the leading end portion of the second anchor.

6. A method as set forth in claim 1 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

7. A method as set forth in claim 6 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

8. A method as set forth in claim 1 further including the steps of sliding a suture retainer along a first portion of the suture which extends from the first anchor, sliding the suture retainer along a second portion of the suture which extends from the second anchor, and gripping the first and second portions of the suture with the suture retainer.

9. A method as set forth in claim 1 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

10. A method as set forth in claim 1 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

11. A method as set forth in claim 1 wherein said step of moving the first anchor along the first path includes moving the first anchor along a first path having a nonlinear central axis, said step of moving the second anchor along the second path includes moving the second anchor along a second path having a nonlinear central axis.

12. A method as set forth in claim 1 wherein said steps of moving the first anchor along a first path and moving the second anchor along a second path include interconnecting the first and second anchors while the first and second anchors are disposed in the second body tissue.

13. A method as set forth in claim 12 wherein said step of interconnecting the first and second anchors includes moving one of the first and second anchors into engagement with the other of the first and second anchors.

14. A method as set forth in claim 12 wherein said step of interconnecting the first an d second anchors includes moving one of the first and second anchors into an opening in the other of the first and second anchors.

15. A method as set forth in claim 1 wherein said step of moving the first anchor of the plurality of anchors along a first path into the second body tissue includes moving the first anchor through a predetermined distance into the second body tissue.

16. A method as set forth in claim 15 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

17. A method as set forth in claim 1 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

18. A method as set forth in claim 1 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

19. A method as set forth in claim 1 further including the steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the-second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

20. A method as set forth in claim 1 wherein said step of moving a first anchor along a first path includes transmitting force from a robotic assembly to the first anchor, said step of moving a second anchor along a second path includes transmitting force from the robotic assembly to the second anchor.

21. A method of securing first body tissue with second body tissue, said method comprising the steps of moving a first anchor along a first path through the first body tissue into the second body tissue with a first suture portion extending from the first anchor, moving a second anchor along a second path through the first body tissue into the second body tissue with a second suture portion extending from the second anchor, tensioning the first and second suture portions with a predetermined force, and gripping the first and second suture portions with a suture retainer while tensioning the first and second suture portions with the predetermined force.

22. A method as set forth in claim 21 wherein said step of gripping the first and second suture portions with the suture retainer includes pressing force transmitting members against the suture retainer, and transmitting ultrasonic vibratory energy to a location where one of the force transmitting members presses against the suture retainer.

23. A method as set forth in claim 21 further including the steps of wrapping the first suture portion around the suture retainer, wrapping the second suture portion around the suture retainer, and moving the suture retainer along the first and second suture portions toward the first body tissue while the first and second suture portions are wrapped around the suture retainer.

24. A method as set forth in claim 23 further including the step of gripping the first and second suture portions with the suture retainer while the first and second suture portions are wrapped around the suture retainer by plastically deforming material of the suture retainer.

25. A method as set forth in claim 21 further including the step of selecting first and second suture portions of a known size and strength, said step of tensioning the first and second suture portions with a predetermined force includes tensioning the first and second suture portions with a force which is a known function of the known size and strength of the first and second suture portions.

26. A method as set forth in claim 21 wherein the first body tissue is a first layer of soft tissue and the second body tissue is a second layer of soft tissue, said method further includes approximating the first and second layers of body tissue, and pressing the first layer of body tissue against the second layer of body tissue.

27. A method as set forth in claim 21 wherein said step of moving the second anchor along the second path through the first body tissue into the second body tissue includes moving the second anchor along a portion of the second path which extends transverse to the first path.

28. A method as set forth in claim 21 wherein a third suture portion extends between the first and second anchors, said step of moving the second anchor along the second path includes moving the second anchor along a portion of the second path which extends transverse to the first path to tension the third suture portion.

29. A method as set forth in claim 21 wherein said step of moving a first anchor along a first path through the first body tissue into the second body tissue includes piercing the first body tissue with a leading end portion of the first anchor.

30. A method as set forth in claim 29 wherein said step of moving a first anchor along a first path through the first body tissue into the second body tissue includes piercing the second body tissue with the leading end portion of the first anchor.

31. A method as set forth in claim 30 wherein said step of moving a second anchor along a second path into the second body tissue includes piercing the first body tissue with a leading end portion of the second anchor.

32. A method as set forth in claim 31 wherein said step of moving a second anchor along a second path into the second body tissue includes piercing the second body tissue with the leading end portion of the second anchor.

33. A method as set forth in claim 21 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

34. A method as set forth in claim 33 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

35. A method as set forth in claim 21 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

36. A method as set forth in claim 21 wherein said step of moving the first anchor along the first path includes moving the first anchor along a first path having a nonlinear central axis, said step of moving the second anchor along the second path includes moving the second anchor along a second path having a nonlinear central axis.

37. A method as set forth in claim 21 wherein said steps of moving the first anchor along a first path and moving the second anchor along a second path include interconnecting the first and second anchors while the first and second anchors are disposed in the second body tissue.

38. A method as set forth in claim 37 wherein said step of interconnecting the first and second anchors includes moving one of the first and second anchors into engagement with the other of the first and second anchors.

39. A method as set forth in claim 37 wherein said step of interconnecting the first and second anchors includes moving of the first and second anchors into an opening in the other of the first and second anchors.

40. A method as set forth in claim 21 wherein said step of moving the first anchor along a first path through the first body tissue into the second body tissue includes moving the first anchor through a predetermined distance into the second body tissue, said step of moving the second anchor along a second path through the first body tissue into the second body tissue includes moving the second anchor through a predetermined distance into the second body tissue.

41. A method as set forth in claim 40 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue, said step of moving the second anchor through a predetermined distance into the second body tissue includes applying force against a trailing end portion of the second anchor with a pusher member having indicia thereon, and detecting when the indicia on the pusher member indicates that the second anchor has been moved through a predetermined distance relative to the second body tissue.

42. A method as set forth in claim 21 further including the step of positioning a guide assembly having first and second guide surfaces relative to at least one of the first and second body tissues, engaging the first anchor with the first guide surface during movement of the first anchor along the first path, and engaging the second anchor with the second guide surface during movement of the second anchor along the second path.

43. A method as set forth in claim 21 further including the steps of moving a thin elongated member along the first path through the first body tissue into the second body tissue, said step of moving a first anchor along the first path through the first body tissue into the second body tissue is at least partially performed with the thin elongated member extending through the first anchor, and moving a thin elongated member along the second path through the first body tissue into the second body tissue, said step of moving a second anchor along the second path through the first body tissue into the second body tissue is at least partially performed with the thin elongated member extending through the second anchor.

44. A method as set forth in claim 21 wherein said steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

45. A method as set forth in claim 21 wherein said step of moving a first anchor along a first path includes transmitting force from a robotic assembly to the first anchor, said step of moving a second anchor along a second path includes transmitting force from the robotic assembly to the second anchor.

46. A method of securing first body tissue with second body tissue, said method comprises the steps of moving a first anchor into first body tissue at a first location, moving the first anchor into the second body tissue, moving a second anchor into the first body tissue at a second location, moving the second anchor into the second body tissue, moving the first anchor in the second body tissue in a direction away from the first location where the first anchor moved into the first body tissue and in a direction toward the second location where the second anchor moved into the first body tissue, pulling a first suture portion into the second body tissue under the influence of force transmitted from the first anchor to the first suture portion as the first anchor moves in the second body tissue in a direction away from the first location where the first anchor moved into the first body tissue and toward the second location where the second anchor moved into the first body tissue, moving the second anchor in the second body tissue in a direction away from the second location where the second anchor moved into the first body tissue and in a direction toward the first location where the first anchor moved into the first body tissue, and pulling a second suture portion into the second body tissue under the influence of force transmitted from the second anchor to the second suture portion as the second anchor moves in the second body tissue in a direction away from the second location where the second anchor moved into the first body tissue and toward the first location where the first anchor moved into the first body tissue.

47. A method as set forth in claim 46 wherein said step of moving the first anchor into the second body tissue in a direction away from the first location where the first anchor moved into the first body tissue and toward the second location where the second anchor moved into the first body tissue includes moving the first anchor along a linear path which extends through the first location where the first anchor moved into the first body tissue, and said step of moving the second anchor in the second body tissue in a direction away from the second location where the second anchor moved into the first body tissue and toward the first location where the first anchor moved into the first body tissue includes moving the second anchor along a linear path which extends through the second location where the second anchor moved into the first body tissue.

48. A method as set forth in claim 46 wherein said step of moving the first anchor in the second body tissue in a direction away from the first location where the first anchor moved into the first body tissue and toward the second location where the second anchor moved into the first body tissue includes moving the first anchor along a nonlinear path which extends through the first location where the first anchor moved into the first body tissue and said step of moving the second anchor in the second body tissue in a direction away from the second location where the second anchor moved into the first body tissue and toward the first location where the first anchor moved into the first body tissue includes moving the second anchor along a nonlinear path which extends through the second location where the second anchor moved into the first body tissue.

49. A method as set forth in claim 46 further including the step of tensioning the first and second suture portions during movement of at least one of said first and second anchors in the second body tissue.

50. A method as set forth in claim 49 wherein said step of tensioning the first and second suture portions includes increasing the tension in the first and second suture portions, said method further includes interrupting said step of increasing the tension in the first and second suture portions when a predetermined tension is present in the first and second suture portions.

51. A method as set forth in claim 46 further including the step of interconnecting the first and second suture portions after performing said steps of moving the first anchor into the second body tissue and moving the second anchor into the second body tissue.

52. A method as set forth in claim 46 wherein said step of moving a first anchor into the first body tissue includes piercing the first body tissue with a leading end portion of the first anchor.

53. A method as set forth in claim 52 wherein said step of moving a first anchor into the second body tissue includes piercing the second body tissue with the leading end portion of the first anchor.

54. A method as set forth in claim 53 wherein said step of moving a second anchor into the first body tissue includes piercing the first body tissue with a leading end portion of the second anchor.

55. A method as set forth in claim 54 wherein said step of moving a second anchor into the second body tissue includes piercing the second body tissue with the leading end portion of the second anchor.

56. A method as set forth in claim 52 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

57. A method as set forth in claim 56 further including the steps of retaining the first anchor against movement relative to the hard outer layer of the bone while tensioning the first suture portion by transmitting force between the first anchor and the cancellous bone while the first anchor is spaced from the hard outer layer of the bone and retaining the second anchor against movement relative to the hard outer layer of the bone while tensioning the second suture portion by transmitting force between the second anchor and the cancellous bone while the second anchor is spaced from the hard outer layer of the bone.

58. A method as set forth in claim 46 further including the steps of sliding a suture retainer along the first suture portion, sliding the suture retainer along the second suture portion, and gripping the first and second suture portions with the suture retainer.

59. A method as set forth in claim 46 further including the step of changing the orientation of the first anchor relative to the second body tissue, said step of changing the orientation of the first anchor relative to the second body tissue includes rotating the first anchor about an axis which extends transverse to a straight line between the first and second locations, said method further includes the step of tensioning at least one of the first and second suture portions by moving a portion of the second anchor in the second body tissue after performing said step of changing the orientation of the first anchor relative to the second body tissue.

60. A method as set forth in claim 46 further including the steps of changing the orientation of the first anchor relative to the second body tissue, said step of changing the orientation of the first anchor relative to the second body tissue includes rotating the first anchor about an axis which extends transverse to a straight line between the first and second locations, and changing the orientation of the second anchor relative to the second body tissue, said step of changing the orientation of the second anchor relative to the second body tissue includes rotating the second anchor about an axis which extends transverse to the straight line between the first and second locations.

61. A method as set forth in claim 60 further including the step of tensioning the first and second suture portions after performance of said step of changing the orientation of the first anchor relative to the second body tissue.

62. A method as set forth in claim 46 further including the step of interconnecting the first and second anchors while the first and second anchors are disposed in the second body tissue.

63. A method as set forth in claim 62 wherein said step of interconnecting the first and second anchors includes moving one of the first and second anchors into engagement with the other of the first and second anchors.

64. A method as set forth in claim 46 wherein said step of interconnecting the first and second anchors includes moving one of the first and second anchors into an opening in the other of the first and second anchors.

65. A method as set forth in claim 46 wherein said step of moving the first anchor into the second body tissue includes moving the first anchor through a predetermined distance into the second body tissue.

66. A method as set forth in claim 65 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

67. A method as set forth in claim 46 further including the step of positioning a guide assembly having first and second guide surfaces relative to at least one of the first and second body tissues, engaging the first anchor with the first guide surface during movement of the first anchor relative to the first and second body tissues, and engaging the second anchor with the second guide surface during movement of the second anchor relative to the first and second body tissues.

68. A method as set forth in claim 46 further including moving a first thin elongated member into the second body tissue, said step of moving a first anchor into the second body tissue is at least partially performed with the first thin elongated member extending through the first anchor, and moving a second thin elongated member into the second body tissue, said step of moving a second anchor into the second body tissue is at least partially performed with the second thin elongated member extending through the second anchor.

69. A method as set forth in claim 46 wherein said steps of providing a guide assembly having a base and first and second tubular guides, moving the first tubular guide through the first body tissue into engagement with the second body tissue, moving the second tubular guide through the first body tissue into engagement with the second body tissue, said step of moving the first anchor into the second body tissue includes moving the first anchor through the first tubular guide into the second body tissue, said step of moving the second anchor into the second body tissue includes moving the second anchor through the second tubular guide into the second body tissue.

70. A method as set forth in claim 46 wherein said step of moving a first anchor into the second body tissue includes transmitting force from a robotic assembly to the first anchor, said step of moving a second anchor into the second body tissue includes transmitting force from the robotic assembly to the second anchor.

71. A method of securing first body tissue with second body tissue, said method comprising the steps of providing first and second anchors with a suture extending between the first and second anchors, moving the first anchor along a first path into the second body tissue, moving the second anchor along a second path into the second body tissue, detecting when a predetermined tension is present in the suture during movement of at least one of the first and second anchors along at least one of the first and second paths, and interrupting movement of at least the one of the first and second anchors along the one of the first and second paths upon detection of the predetermined tension in the suture.

72. A method as set forth in claim 71 wherein said step of moving the first anchor along the first path is performed prior to performance of said step of moving the second anchor along the second path, and said step of detecting when a predetermined tension is present in the suture is performed during movement of the second anchor along the second path.

73. A method as set forth in claim 71 wherein said steps of moving the first and second anchors along the first and second paths are at least partially performed simultaneously, and said step of detecting when a predetermined tension is present in the suture is performed during movement of the first and second anchors along the first and second paths.

74. A method as set forth in claim 71 wherein said step of moving the second anchor along the second path includes moving the second anchor along a portion of the second path which extends transverse to the first path, said step of detecting when a predetermined tension is present in the suture is performed during movement of the second anchor along the portion of the second path which extends transverse to the first path.

75. A method as set forth in claim 71 wherein said step of moving the first anchor along the first path includes initiating formation of a first opening in the second body tissue at a first location with a leading end portion of the first anchor, said step of moving the second anchor along the second path includes initiating formation of a second opening in the second body tissue at a second location with a leading end portion of the second anchor, said step of detecting when a predetermined tension is present in the suture is performed with a portion of the suture extending between the first and second locations.

76. A method as set forth in claim 71 wherein said step of moving the first anchor along the first path includes moving the first anchor along the first path in a direction toward the second path, said step of moving the second anchor along the second path includes moving the second anchor along the second path in a direction toward the first path.

77. A method as set forth in claim 71 wherein said step of moving a first anchor along a first path includes piercing body tissue with a leading end portion of the first anchor.

78. A method as set forth in claim 77 wherein said step of moving a second anchor along a second path includes piercing body tissue with the leading end portion of the second anchor.

79. A method as set forth in claim 71 wherein the second by tissue is bone having a hard outer layer disposed over cancellous bone, said step of moving the first anchor into the second body tissue includes moving the first anchor through the hard outer layer of the bone into the cancellous bone, said step of moving the second anchor in the second body tissue includes moving the second anchor through the hard outer layer of bone into the cancellous bone.

80. A method as set forth in claim 79 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

81. A method as set forth in claim 71 further including the steps of sliding a suture retainer along a first portion of the suture which extends from the first anchor, sliding the suture retainer along a second portion of the suture which extends from the second anchor, and gripping the first and second portions of the suture with the suture retainer while the predetermined tension is present in the suture.

82. A method as set forth in claim 71 further including the step of changing the orientation of the first anchor relative to the second body tissue, said step of changing the orientation of the first anchor relative to the second body tissue includes rotating the first anchor about an axis which extends transverse to the first path, said step of moving the second anchor along at least a portion of the second path is performed after performing said step of changing the orientation of the first anchor relative to the second body tissue.

83. A method as set forth in claim 71 further including the steps of changing the orientation of the first anchor relative to the second body tissue, said step of changing the orientation of the first anchor relative to the second body tissue includes rotating the first anchor relative to the second body tissue about an axis which extends transverse to the first path, and changing the orientation of the second anchor relative to the second body tissue, said step of changing the orientation of the second anchor relative to the second body tissue includes rotating the second anchor relative to the second body tissue about an axis which extends transverse to the second path.

84. A method as set forth in claim 71 wherein said step of moving the first anchor along the first path includes moving the first anchor along a first path having a nonlinear central axis, said step of moving the second anchor along the second path includes moving the second anchor along a second path having a nonlinear central axis.

85. A method as set forth in claim 71 wherein said steps of moving the first anchor along a first path and moving the second anchor along a second path include interconnecting the first and second anchors while the first and second anchors are disposed in the second body tissue.

86. A method as set forth in claim 85 wherein said step of interconnecting the first and second anchors includes moving one of the first and second anchors into engagement with the other of the first and second anchors.

87. A method as set forth in claim 85 wherein said step of interconnecting the first and second anchors includes moving one of the first and second anchors into an opening in the other of the first and second anchors.

88. A method as set forth in claim 71 wherein said step of moving the first anchor of the plurality of anchors along a first path into the second body tissue includes moving the first anchor through a predetermined distance into the second body tissue.

89. A method as set forth in claim 88 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

90. A method as set forth in claim 71 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

91. A method as set forth in claim 71 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

92. A method as set forth in claim 71 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

93. A method as set forth in claim 71 wherein said step of moving a first anchor along a first path includes transmitting force from a robotic assembly to the first anchor, said step of moving a second anchor along a second path includes transmitting force from the robotic assembly to the second anchor.

94. A method of securing first body tissue with second body tissue, said method comprising the steps of providing first and second anchors with a suture extending between the first and second anchors, moving the first anchor along a first path through the first body tissue into the second body tissue, moving the second anchor along a second path through the first body tissue into the second body tissue, and pressing the first body tissue against the second body tissue under the influence of force transmitted to the first body tissue from a portion of the suture extending between a location where the first path enters the first body tissue and a location where the second path enters the first body tissue.

95. A method as set forth in claim 94 wherein said step of moving the second anchor along the second path includes moving the second anchor along a portion of the second path which extends transverse to the first path.

96. A method as set forth in claim 94 wherein said step of moving the second anchor along the second path includes moving the second anchor in the second body tissue while first anchor is stationary in the second body tissue.

97. A method as set forth in claim 94 further including the step of engaging the first body tissue with the portion of the suture extending between the location where the first path enters the first body tissue and the location where the second path enters the first body tissue.

98. A method as set forth in claim 94 wherein said step of moving the first anchor along the first path includes moving the first anchor along a nonlinear portion of the first path, said step of moving the second anchor along the second path includes moving the second anchor along a nonlinear portion of the second path.

99. A method as set forth in claim 94 wherein said steps of moving the first and second anchors along the first and second paths are at least partially performed simultaneously, and said step of pressing the first body tissue against the second body tissue under the influence of force transmitted to the first body tissue from a portion of the suture extending between the location where the first path enters the first body tissue and the location where the second path enters the first body tissue is initiated during movement of the first and second anchors along the first and second paths.

100. A method as set forth in claim 94 wherein said step of moving the second anchor along the second path includes moving the second anchor along a portion of the second path which extends transverse to the first path, said step of pressing the first body tissue against the second body tissue under the influence of force transmitted to the first body tissue from a portion of the suture extending between the location where the first path enters the first body tissue and the location where the second path enters the first body tissue is initiated during movement of the second anchor along the portion of the second path which extends transverse to the first path.

101. A method as set forth in claim 94 further including the steps of detecting when a predetermined tension is present in the portion of the suture extending between the location where the first path enters the first body tissue and the location where the second path enters the first body tissue, and interrupting movement of at least one of the first and second anchors along at least one of the first and second paths upon detection of the predetermined tension in the portion of the suture extending between the location where the first path enters the first body tissue and the location where the second path enters the first body tissue.

102. A method as set forth in claim 94 wherein said step of moving the first anchor along the first path includes initiating formation of the first opening in the second body tissue with a leading end portion of the first anchor, said step of moving the second anchor along the second path includes initiating formation of a second opening in the second body tissue with a leading end portion of the second anchor.

103. A method as set forth in claim 94 wherein said step of moving a first anchor along a first path includes piercing body tissue with a leading end portion of the first anchor.

104. A method as set forth in claim 103 wherein said step of moving a second anchor along a second path includes piercing body tissue with the leading end portion of the second anchor.

105. A method as set forth in claim 94 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

106. A method as set forth in claim 105 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

107. A method as set forth in claim 94 further including the steps of sliding a suture retainer along a first portion of the suture which extends from the first anchor, sliding the suture retainer along a second portion of the suture which extends from the second anchor, and gripping the first and second portions of the suture with the suture retainer.

108. A method as set forth in claim 94 further including the step of changing the orientation of the first anchor relative to the second body tissue, said step of changing the orientation of the first anchor relative to the second body tissue includes rotating the first anchor about an axis which extends transverse to the first path, said step of moving the second anchor along at least a portion of the second path is performed after performing said step of changing the orientation of the first anchor relative to the second body tissue.

109. A method as set forth in claim 94 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

110. A method as set forth in claim 94 wherein said step of moving the first anchor along the first path includes moving the first anchor along a first path having a nonlinear central axis, said step of moving the second anchor along the second path includes moving the second anchor along a second path having a nonlinear central axis.

111. A method as set forth in claim 94 wherein said steps of moving the first anchor along a first path and moving the second anchor along a second path include interconnecting the first and second anchors while the first and second anchors are disposed in the second body tissue.

112. A method as set forth in claim 111 wherein said step of interconnecting the first and second anchors includes moving one of the first and second anchors into engagement with the other of the first and second anchors.

113. A method as set forth in claim 111 wherein said step of interconnecting the first and second anchors includes moving one of the first and second anchors into an opening in the other of the first and second anchors.

114. A method as set forth in claim 94 wherein said step of moving the first anchor of the plurality of anchors along a first path into the second body tissue includes moving the first anchor through a predetermined distance into the second body tissue.

115. A method as set forth in claim 114 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

116. A method as set forth in claim 94 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

117. A method as set forth in claim 94 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

118. A method as set forth in claim 94 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

119. A method as set forth in claim 94 wherein said step of moving a first anchor along a first path includes transmitting force from a robotic assembly to the first anchor, said step of moving a second anchor along a second path includes transmitting force from the robotic assembly to the second anchor.

120. A method of securing first body tissue with second body tissue, said method comprising the steps of providing first and second anchors with a suture extending between the first and second anchors, moving the first anchor along a first path through the first body tissue into the second body tissue, said step of moving the first anchor along the first path includes initiating formation of an opening in the first body tissue with a leading end portion of the first anchor and initiating the formation of an opening in the second body tissue with the leading end portion of the first anchor, moving the second anchor along a second path through the first body tissue into the second body tissue, said step of moving the second anchor along the second path includes initiating formation of an opening in the first body tissue with a leading end portion of the second anchor and initiating formation of an opening in the second body tissue with the leading end portion of the second anchor, and tensioning at least a portion of the suture extending between the first and second paths when the first and second anchors are disposed in engagement with the second body tissue.

121. A method as set forth in claim 120 wherein the second body tissue is bone having a hard outer layer disposed over cancellous bone, said step of moving the first anchor along the first path into the second body tissue includes moving the first anchor through the hard outer layer of the bone into the cancellous bone, said step of moving the second anchor along the second path into the second body tissue includes moving the second anchor through the hard outer layer of bone into the cancellous bone.

122. A method as set forth in claim 121 further including the steps of retaining the first anchor against movement relative to the hard outer layer of the bone by transmitting force between the first anchor and the cancellous bone while the first anchor is spaced from the hard outer layer of the bone and retaining the second anchor against movement relative to the hard outer layer of the bone by transmitting force between the second anchor and the cancellous bone while the second anchor is spaced from the hard outer layer of the bone.

123. A method as set forth in claim 120 further including the steps of sliding a suture retainer along a first portion of the suture which extends between the first and second anchors, sliding the suture retainer along a second portion of the suture which extends between the first and second anchors, and gripping the first and second portions of the suture with the suture retainer.

124. A method as set forth in claim 120 further including the step of changing the orientation of the first anchor relative to the second body tissue, said step of changing the orientation of the first anchor relative to the second body tissue includes rotating the first anchor about an axis which extends transverse to the first path, said step of moving the second anchor along the second path is performed after performing said step of changing the orientation of the first anchor relative to the second body tissue.

125. A method as set forth in claim 120 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

126. A method as set forth in claim 120 wherein the first and second body tissues are soft body tissues, said method further includes the step of placing the first and second body tissues in a side-by-side relationship.

127. A method as set forth in claim 120 wherein said steps of moving the first anchor along a first path and moving the second anchor along a second path include interconnecting the first and second anchors while the first and second anchors are disposed in the second body tissue.

128. A method as set forth in claim 127 wherein said step of interconnecting the first and second anchors includes moving one of the first and second anchors into engagement with the other of the first and second anchors.

129. A method as set forth in claim 127 wherein said step of interconnecting the first and second anchors includes moving of the first and second anchors into an opening in the other of the first and second anchors.

130. A method as set forth in claim 127 wherein said step of moving the first anchor along a first path through the first body tissue into the second body tissue includes moving the first anchor through a predetermined distance into the second body tissue.

131. A method as set forth in claim 130 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

132. A method as set forth in claim 120 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

133. A method as set forth in claim 120 wherein said step of moving a first anchor along a first path includes transmitting force from a robotic assembly to the first anchor, said step of moving a second anchor along a second path includes transmitting force from the robotic assembly to the second anchor.

134. A method as set forth in claim 120 further including the step of detecting when there is a predetermined tension in the suture and interrupting movement of the second anchor along the second path upon detecting the predetermined tension in the suture.

135. A method as set forth in claim 120 wherein said step of moving the second anchor along the second path includes moving the second anchor along a portion of the second path which extends toward the first path.

136. A method as set forth in claim 120 wherein said step of moving the second anchor along the second path includes moving the second anchor in the second body tissue while the first anchor is stationary in the first body tissue.

137. A method as set forth in claim 120 wherein said steps of moving the first and second anchors along the first and second paths are at least partially performed simultaneously.

138. A method of securing first body tissue with second body tissue, said method comprising the steps of providing first and second anchors with a suture disposed in a continuous loop extending between the first and second anchors, moving the first anchor along a first path into the second body tissue with the continuous loop extending through a passage in the first anchor, moving the second anchor along a second path into the second body tissue with the continuous loop extending through a passage in the second anchor, and moving a portion of the suture in the continuous loop along the passage in the second anchor, and tensioning suture in the continuous loop as the second anchor moves in to the second body tissue.

139. A method as set forth in claim 138 wherein said step of moving a portion of the suture along the passage in the second anchor is at least partially performed during movement of the second anchor into the second body tissue.

140. A method as set forth in claim 138 wherein first and second lengths of the suture extend between the passages in the first and second anchors and form portions of the continuous loop, said step of moving a portion of the suture in the continuous loop along the passage in the second anchor includes increasing an extent of one of the first and second lengths of the suture and decreasing an extent of another of the first and second lengths of the suture.

141. A method as set forth in claim 138 further including the step of connecting a first portion of the suture with a second portion of the suture to form the continuous loop, said step of connecting a first portion of the suture with a second portion of the suture includes tying a knot between the first and second portions of the suture.

142. A method as set forth in claim 138 further including the step of gripping first and second portions of the suture with a suture retainer to form the continuous loop.

143. A method as set forth in claim 138 wherein said step of moving the second anchor along the second path includes moving the second anchor along a portion of the second path which extends transverse to the first path while the second anchor is disposed in the second body tissue.

144. A method as set forth in claim 138 further including the step of determining when a predetermined tension is present in the continuous loop.

145. A method as set forth in claim 138 further including the step of interrupting movement of the second anchor along the second path in response to determining that a predetermined tension is present in the continuous loop.

146. A method as set forth in claim 138 wherein said step of moving a first anchor along a first path into the second body tissue includes piercing the first body tissue with a leading end portion of the first anchor.

147. A method as set forth in claim 146 wherein said step of moving a first anchor along a first path into the second body tissue includes piercing the second body tissue with the leading end portion of the first anchor.

148. A method as set forth in claim 147 wherein said step of moving a second anchor along a second path into the second body tissue includes piercing the first body tissue with a leading end portion of the second anchor.

149. A method as set forth in claim 148 wherein said step of moving a second anchor along a second path into the second body tissue includes piercing the second body tissue with the leading end portion of the second anchor.

150. A method as set forth in claim 138 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

151. A method as set forth in claim 150 further including the steps of retaining the first anchor against movement relative to the hard outer layer of the bone while maintaining tension in the continuous loop by transmitting force between the first anchor and the cancellous bone while the first anchor is spaced from the hard outer layer of the bone and retaining the second anchor against movement relative to the hard outer layer of the bone while maintaining tension in the continuous loop by transmitting force between the second anchor and the cancellous bone while the second anchor is spaced from the hard outer layer of the bone.

152. A method as set forth in claim 138 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

153. A method as set forth in claim 138 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

154. A method as set forth in claim 138 wherein said step of moving the first anchor along a first path into the second body tissue includes moving the first anchor through a predetermined distance into the second body tissue.

155. A method as set forth in claim 154 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

156. A method as set forth in claim 138 further including the step of positioning a guide assembly having first and second guide surfaces relative to at least one of the first and second body tissues, engaging the first anchor with the first guide surface during movement of the first anchor along the first path, and engaging the second anchor with the second guide surface during movement of the second anchor along the second path.

157. A method as set forth in claim 138 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

158. A method as set forth in claim 138 wherein said steps of providing a guide assembly having a base and first and second tubular guides, positioning the first tubular guide in alignment with the first path, moving the first tubular guide along the first path into engagement with the second body tissue, positioning the second tubular guide in alignment with the second path, moving the second tubular guide along the second path into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

159. A method as set forth in claim 138 wherein said step of moving a first anchor along a first path includes transmitting force from a robotic assembly to the first anchor, said step of moving a second anchor along a second path includes transmitting force from the robotic assembly to the second anchor.

160. A method of securing first body tissue with second body tissue, said method comprising the steps of providing first and second anchors with a suture extending through passages in the first and second anchors, moving the first anchor along a first path into the second body tissue with the suture extending through the passages in the first and second anchors, moving the second anchor along a second path into the second body tissue with the suture extending through the passages in the first and second anchors, moving a portion of the suture along the passage in the second anchor during movement of the second anchor into the second body tissue, said step of moving a portion of the suture along the passage in the second anchor includes increasing the extent of a portion of the suture extending between the first and second anchors during movement of the second anchor into the second body tissue, and transmitting force through the suture to the first body tissue.

161. A method as set forth in claim 160 wherein the suture extends in a continuous loop between the first and second anchors, said step of moving the second anchor into the second body tissue includes tensioning the continuous loop.

162. A method as set forth in claim 160 further including the step of connecting a first portion of the suture with a second portion of the suture by tying a knot between the first and second portions of the suture after performing said step of moving the second anchor into the second body tissue.

163. A method as set forth in claim 160 further including the step of gripping first and second portions of the suture with a suture retainer after performing said step of moving the second anchor into the second body tissue.

164. A method as set forth in claim 160 wherein said step of moving the second anchor along the second path includes moving the second anchor along a portion of the second path which extends transverse to the first path while the second anchor is disposed in the second body tissue.

165. A method as set forth in claim 160 further including the step of connecting a first portion of the suture with a second portion of the suture at a location disposed between the first and second paths after performing said steps of moving the first anchor along the first path into the second body tissue and moving the second anchor along the second path into the second body tissue.

166. A method as set forth in claim 160 wherein said step of moving a first anchor along a first path includes piercing body tissue with a leading end portion of the first anchor.

167. A method as set forth in claim 166 wherein said step of moving a second anchor along a second path includes piercing body tissue with the leading end portion of the second anchor.

168. A method as set forth in claim 160 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

169. A method as set forth in claim 168 further including the steps of retaining the first anchor against movement relative to the hard outer layer of the bone while transmitting force through the suture by transmitting force between the first anchor and the cancellous bone while the first anchor is spaced from the hard outer layer of the bone and retaining the second anchor against movement relative to the hard outer layer of the bone while transmitting force through the suture by transmitting force between the second anchor and the cancellous bone while the second anchor is spaced from the hard outer layer of the bone.

170. A method as set forth in claim 160 further including the step of changing the orientation of the first anchor relative to the second body tissue, said step of changing the orientation of the first anchor relative to the second body tissue includes rotating the first anchor about an axis which extends transverse to the first path, said step of moving a portion of the suture along the passage in the second anchor is performed after performing said step of changing the orientation of the first anchor relative to the second body tissue.

171. A method as set forth in claim 160 further including the step of changing the orientation of the first anchor relative to the second body tissue, said step of changing the orientation of the first anchor relative to the second body tissue includes rotating the first anchor about an axis which extends transverse to the first path, said step of moving a portion of the suture along the passage in the second anchor is performed after performing said step of changing the orientation of the first anchor relative to the second body tissue.

172. A method as set forth in claim 160 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

173. A method as set forth in claim 160 wherein said step of moving the first anchor along the first path includes moving the first anchor along a first path having a nonlinear central axis, said step of moving the second anchor along the second path includes moving the second anchor along a second path having a nonlinear central axis.

174. A method as set forth in claim 160 wherein said steps of moving the first anchor along a first path and moving the second anchor along a second path include interconnecting the first and second anchors while the first and second anchors are disposed in the second body tissue.

175. A method as set forth in claim 174 wherein said step of interconnecting the first and second anchors includes moving one of the first and second anchors into engagement with the other of the first and second anchors.

176. A method as set forth in claim 174 wherein said step of interconnecting the first and second anchors includes moving one of the first and second anchors into an opening in the other of the first and second anchors.

177. A method as set forth in claim 160 wherein said step of moving the first anchor of the plurality of anchors along a first path into the second body tissue includes moving the first anchor through a predetermined distance into the second body tissue.

178. A method as set forth in claim 177 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

179. A method as set forth in claim 160 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

180. A method as set forth in claim 160 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

181. A method as set forth in claim 160 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

182. A method as set forth in claim 160 wherein said step of moving a first anchor along a first path includes transmitting force from a robotic assembly to the first anchor, said step of moving a second anchor along a second path includes transmitting force from the robotic assembly to the second anchor.

183. A method of securing first body tissue with second body tissue, said method comprising the steps of providing first and second anchors with a suture extending between the first and second anchors, moving the first anchor along a first path into the second body tissue with the suture extending between the first and second anchors, moving the second anchor along a second path into the second body tissue with the suture extending between the first and second anchors, said step of moving the first anchor along the first path into the second body tissue includes decreasing a distance between the first anchor and the second path, said step of moving the second anchor along the second path into the second body tissue includes decreasing a distance between the second anchor and the first path, and transmitting force through the suture to the first body tissue.

184. A method as set forth in claim 183 further including the step of interrupting movement of at least one of the first and second anchors along one of the first and second paths when a predetermined tension is present in the suture.

185. A method as set forth in claim 183 wherein said steps of moving the first and second anchors along the first and second paths are at least partially performed simultaneously.

186. A method as set forth in claim 183 wherein said step of moving the second anchor along the second path into the second body tissue includes moving the second anchor along a portion of the second path which extends transverse to the first path.

187. A method as set forth in claim 183 wherein said step of moving a first anchor along a first path into the second body tissue includes piercing the first body tissue with a leading end portion of the first anchor.

188. A method as set forth in claim 187 wherein said step of moving a first anchor along a first path into the second body tissue includes piercing the second body tissue with the leading end portion of the first anchor.

189. A method as set forth in claim 188 wherein said step of moving a second anchor along a second path into the second body tissue includes piercing the first body tissue with a leading end portion of the second anchor.

190. A method as set forth in claim 189 wherein said step of moving a second anchor along a second path into the second body tissue includes piercing the second body tissue with the leading end portion of the second anchor.

191. A method as set forth in claim 185 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

192. A method as set forth in claim 191 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

193. A method as set forth in claim 183 further including the steps of sliding a suture retainer along a first portion of the suture which extends from the first anchor, sliding the suture retainer along a second portion of the suture which extends from the second anchor, and gripping the first and second portions of the suture with the suture retainer.

194. A method as set forth in claim 183 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

195. A method as set forth in claim 184 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

196. A method as set forth in claim 195 further including the step of tensioning the suture after performance of said step of changing the orientation of the first anchor relative to the second body tissue.

197. A method as set forth in claim 183 wherein said steps of moving the first anchor along a first path and moving the second anchor along a second path include interconnecting the first and second anchors while the first and second anchors are disposed in the second body tissue.

198. A method as set forth in claim 197 wherein said step of interconnecting the first and second anchors includes moving one of the first and second anchors into engagement with the other of the first and second anchors.

199. A method as set forth in claim 197 wherein said step of interconnecting the first and second anchors includes moving one of the first and second anchors into an opening in the other of the first and second anchors.

200. A method as set forth in claim 183 wherein said step of moving the first anchor of the plurality of anchors along a first path into the second body tissue includes moving the first anchor through a predetermined distance into the second body tissue.

201. A method as set forth in claim 200 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

202. A method as set forth in claim 183 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

203. A method as set forth in claim 183 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the anchor.

204. A method as set forth in claim 183 further including the steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

205. A method as set forth in claim 183 wherein said step of moving a first anchor along a first path includes transmitting force from a robotic assembly to the first anchor, said step of moving a second anchor along a second path includes transmitting force from the robotic assembly to the second anchor.

206. A method as set forth in claim 183 wherein said step of moving the first anchor along the first path includes initiating formation of a first opening in the second body tissue with a leading end portion of the first anchor, said step of moving the second anchor along a second path includes initiating formation of a second opening in the second body tissue with a leading end portion of the second anchor.

207. A method as set forth in claim 183 wherein said step of transmitting force through the suture to the first body tissue includes pressing the first body tissue against the second body tissue under the influence of force transmitted to the first body tissue through a portion of the suture disposed between the first and second paths.

208. A method as set forth in claim 183 wherein said step of moving the second anchor along the second path into the second body tissue includes moving the second anchor in the second body tissue while the first anchor is stationary in the second body tissue.

* * * * *

UNITED STATES PATENT AND TRADEMARK OFFICE
CERTIFICATE OF CORRECTION

PATENT NO. : 6,635,073 B2
APPLICATION NO. : 09/789621
DATED : October 21, 2003
INVENTOR(S) : Bonutti Page 1 of 43

It is certified that error appears in the above-identified patent and that said Letters Patent is hereby corrected as shown below:

PLEASE DELETE COLUMNS 1 LINE 1 THRU COLUMNS 80 LINE 47 AND
INSERT COLUMNS 1 LINE 1 THRU COLUMNS 84 LINE 7 AS ATTACHED

Signed and Sealed this

Twenty-fifth Day of March, 2008

JON W. DUDAS
*Director of the United States Patent and Trademark Office*

METHOD OF SECURING BODY TISSUE

RELATED APPLICATION

This application is a continuation-in-part of U.S. patent application Ser. No. 09/556,458, filed May 3, 2000 by Peter M. Bonutti and entitled "Method and Apparatus for Securing Tissue". The benefit of the earlier filing date of the aforementioned application Ser. No. 09/556,458 is hereby claimed for all subject matter common to this application and the aforementioned application.

BACKGROUND OF THE INVENTION

The present invention relates to a method of securing tissue in a body of a patient. The method may be utilized to secure soft body tissues, hard body tissues, or to secure both soft and hard body tissues.

Many different devices have previously been utilized to secure body tissues. Many of these devices have utilized anchors which engage either soft body tissue or hard body tissue to hold a suture in a desired location relative to the body tissue. Various methods and devices for use in positioning anchors relative to either soft or hard body tissues are disclosed in U.S. Pat. Nos. 5,403,348; 5,464,426; 5,534,012; 5,593,425; 5,718,717; and 5,948,002. The devices and methods disclosed in these patents have been generally satisfactory in securing either soft, hard, or hard and soft body tissues. Other devices and methods for securing body tissues are disclosed in U.S. Pat. Nos. 4,235,238; 4,448,194; 4,669,473; 5,085,661; and 5,372,146.

SUMMARY OF THE INVENTION

The present invention relates to a new and improved method of securing a first body tissue with a second body tissue. The first body tissue may be a soft body tissue and the second body may be a hard body tissue. Alternatively, the first and second body tissues may both be soft body tissues. It is also contemplated that both the first and second body tissues could be hard body tissues.

When the first and second body tissues are to be interconnected, a first anchor is moved into the second body tissue. If desired, the first anchor could be moved into and through the second body tissue. A second anchor is also moved into the second body tissue. If desired, the second anchor could be moved into and through the second body tissue. The first body tissue may be pressed against or otherwise secured with the second body tissue under the influence of force transmitted from the suture to the first body tissue.

The suture which extends between the anchors may be tensioned by moving at least one of the anchors into the body tissue along a path which extends transverse to a path along which the other anchor is moved into the body tissue. The paths along which the anchors move into the body tissue may extend toward each other. The transverse paths of movement of the anchors into the body tissue promotes gripping of body tissue with the anchors and suture and promotes tensioning of the suture as the anchors move into the body tissue. Although it is believed that it may be desired to move the anchors into the body tissue along transverse paths, it is contemplated that the anchors could be moved into the body tissue along parallel paths if desired.

A desired tension may be established in the suture by moving the anchors into the body tissue. Alternatively, a desired tension may be established in the suture by applying force to portions of the suture and then interconnecting the portions of the suture. A retainer or a knot may be utilized to interconnect portions of the suture.

Regardless of how the tension is established in the suture, it may be desired to establish a predetermined tension in the suture. This may be done by determining the tension in the suture as the anchors are moved into the body tissue. Alternatively, the tension in the suture may be determined during movement of a retainer relative to portions of the suture prior to gripping of the suture with the retainer.

The suture may be a continuous loop which extends between the two anchors. The tension in the loop may be determined as one or more of the anchors are moved into the body tissue. Alternatively, the suture may be formed by a pair of separate portions which are tensioned after the anchors are moved into the body tissue.

One or more guides may be utilized to facilitate positioning of the anchors for movement along paths disposed in a desired spatial relationship with the body tissue. The guides may have tubular guide surfaces with central axes which extend transverse to each other.

Leading end portions of the anchors may be utilized to initiate the formation of openings in the first and/or second body tissue. The leading end portion of each of the anchors may be utilized to pierce soft body tissue, a hard outer layers of bone, and/or cancellous bone as the anchor is moved into the body tissue. If either or both of the anchors are associated with body tissue which is bone, one or more of the anchors may be supported in a spaced apart relationship with a hard outer layer of bone by cancellous bone which is enclosed by the hard outer layer of bone. If desired, passages for the anchors may be formed with a drill or similar tool.

The anchors may advantageously be interconnected while they are disposed in the body tissue. When this is done, the anchors may be moved along transverse paths which intersect in the body tissue. The anchors may be interconnected at the intersection between the two paths.

There are a plurality of embodiments of the invention. Each embodiment of the invention has one or more features which may be advantageously utilized with one or more of the other embodiments of the invention. It is contemplated that the various features of the embodiments of the invention may be utilized separately or combined in any one of many different combinations.

BRIEF DESCRIPTION OF THE DRAWINGS

The foregoing and other features of the invention will become more apparent upon a consideration of the following description taken in connection with the accompanying drawings wherein:

FIG. 1 is a fragmentary schematic illustration depicting the relationship between a plurality of anchors and body tissue prior to movement of the anchors into the body tissue;

FIG. 2 is a fragmentary schematic illustration depicting the manner in which one of the anchors of FIG. 1 is positioned relative to body tissue prior to initiation of formation of an opening in body tissue with a leading end portion of the anchor;

FIG. 3 is a fragmentary schematic view illustrating the manner in which the anchor of FIG. 2 is moved through first body tissue into second body tissue;

FIG. 4 is a fragmentary schematic illustration illustrating the manner in which the anchor of FIG. 3 is moved deeper into the second body tissue;

FIG. 5 is a fragmentary schematic illustration depicting the manner in which the orientation of the anchor of FIG. 4 is changed relative to the body tissue after the anchor has been moved to a desired depth in the body tissue;

FIG. 6 is a schematic fragmentary illustration, generally similar to FIG. 3, illustrating the manner in which a second one of the anchors of FIG. 1 is moved through first body tissue into second body tissue;

FIG. 7 is a fragmentary schematic illustration, generally similar to FIG. 4, depicting the manner in which the anchor of FIG. 6 is moved deeper into the body tissue;

FIG. 8 is fragmentary schematic illustration, generally similar to FIG. 5, depicting the manner in which the orientation of the anchor of FIG. 7 is changed after the anchor has been moved to a desired depth in the body tissue;

FIG. 9 is a fragmentary schematic illustration depicting the relationship between the anchors of FIG. 1 and a suture extending between the anchors after the anchors have been moved into the body tissue;

FIG. 10 is schematic illustration, generally similar to FIG. 9, depicting the manner in which the suture extending between the anchors is tensioned with a predetermined force and in which a retainer is deformed to grip portions of the suture;

FIG. 11 is a fragmentary schematic illustration, generally similar to FIGS. 1 and 9, depicting the manner in which a pair of anchors interconnected by a continuous loop of suture are positioned relative to body tissue and the loop is tensioned during positioning of the anchors relative to the body tissue;

FIG. 12 is a fragmentary schematic illustration, generally similar to FIG. 6, illustrating the relationship between an anchor of FIG. 11 and an apparatus which is utilized to effect movement of the anchor into body tissue and to measure tension in the continuous loop of suture extending between the anchors of FIG. 11;

FIG. 13 is a schematic illustration, generally similar to FIG. 11, illustrating the manner in which a guide assembly is utilized to position anchors relative to body tissue;

FIG. 14 is a schematic illustration depicting the manner in which a thin elongated member is utilized to guide movement of an anchor into body tissue;

FIG. 15 is a fragmentary schematic illustration depicting the manner in which a second thin elongated member is utilized to guide movement of a second one of the anchors of FIG. 14 into the body tissue;

FIG. 16 is a fragmentary schematic illustration, similar to FIG. 13, of another embodiment of a guide assembly which is utilized to position anchors relative to body tissue and depicting the manner in which tubular guide members extend through first body tissue into second body tissue;

FIG. 17 is a fragmentary schematic illustration depicting the manner in which anchors are utilized to repair a fracture in a bone;

FIG. 18 is a schematic illustration of another embodiment of the anchor;

FIG. 19 is an illustration of still another embodiment of the anchor;

FIG. 20 is a fragmentary schematic illustration, generally similar to FIG. 9, illustrating the manner in which anchors are interconnected at an intersection between transverse paths along which the anchors are moved into body tissue;

FIG. 21 is an enlarged fragmentary view of a portion of FIG. 20 and illustrating how the anchors are interconnected at the intersection of the paths along which the anchors are moved into in the body tissue;

FIG. 22 is a fragmentary schematic illustration, generally similar to FIG. 21, illustrating the manner in which another embodiment of the anchors are interconnected at the intersection between the paths along which the anchors are moved into the body tissue; and FIG. 23 is a fragmentary sectional view, generally similar to FIG. 12, illustrating the manner in which another embodiment of the anchors may be utilized to secure body tissues.

DESCRIPTION OF SPECIFIC PREFERRED EMBODIMENTS OF THE INVENTION

General Description

An apparatus 10 (FIG. 1) is used to secure first human body tissue 12 with second human body tissue 14. In the illustration of FIG. 1, the first body tissue 12 is soft body tissue and the second body tissue 14 is hard body tissue. However, it should be understood that both the first body tissue 12 and the second body tissue 14 could be soft body tissue if desired. Alternatively, both the first body tissue 12 and the second body tissue 14 could be hard body tissue.

The apparatus 10 includes a plurality of suture anchors 18 and 20. Although only two suture anchors 18 and 20 have been illustrated in FIG. 1, it should be understood that a greater number of suture anchors could be provided if desired. For example, it is contemplated that three anchors could be provided if desired.

The apparatus 10 also includes a suture 24 which extends between the suture anchors 18 and 20. Although the illustrated suture 24 is integrally formed as one piece and extends between the anchors 18 and 20, it is contemplated that the suture 24 could be formed by a plurality of separate portions each of which is connected with one of the anchors. Thus, a first segment of a suture could be connected with the left suture anchor 18 and a second segment of a suture could be connected with the right suture anchor 20.

When the first and second body tissues 12 and 14 are to be interconnected, the suture anchors 18 and 20 are moved through the first body tissue 12 into the second body tissue 14. If desired, the suture anchors 18 and 20 could be moved into and through the second body tissue 14.

When the anchor 18 is to be moved into the body tissue 12, the anchor may be positioned in an inserter 28 and pressed against the body tissue 12 by a pusher member 30 (FIG. 2). A trailing end portion 32 of the anchor 18 is positioned in the inserter 28 and is engaged by the pusher member 30. A pointed leading end portion 34 of the anchor 18 extends from the inserter 28.

In the embodiment illustrated in FIG. 2, the inserter 28 has a tubular configuration and the pusher member 30 is telescopically inserted into the inserter. However, if desired, the inserter 28 could have a different configuration and could be constructed in such a manner as to perform the function of the pusher member 30. For example, the inserter 28 could be constructed could be a solid rod with a gripper at one end of the rod. This inserter would grip and apply axial force against a trailing end portion 32 of the anchor 18.

When the anchor 18 is to be moved into the body tissue 12, the leading end portion 34 of the anchor 18 initiates the formation of an opening in the body tissue 12. Force applied against the trailing end portion 32 of the anchor 18 by the pusher member 30 causes the anchor to pierce the body tissue 12. As the anchor 18 moves through the body tissue 12, the leading end portion 34 of the anchor moves into engagement with the body tissue 14.

The leading end portion 34 of the anchor 18 initiates the formation of an opening in the body tissue 14. Force applied against the trailing end portion 32 of the anchor 18 by the pusher member 30 moves the leading end portion of the anchor into the body tissue 14 (FIG. 3). Continued axial movement of the pusher member 30 relative to the inserter 28 moves the anchor 18 deeper into the body tissue 14 (FIG. 4). As the anchor 18 moves into the body tissue 14, the leading end portion 34 of the anchor pierces the body tissue. The anchor 18 may be moved along a linear or nonlinear path in the body tissues 12 and 14.

In the embodiment of the invention illustrated in FIGS. 1-10, the anchor 18 is utilized to form its own passage in the body tissues 12 and 14. However, a drill or other tool could be utilized to form a passage for the anchor 18 in either the body tissue 12 or 14 or in both of the body tissues.

Once the anchor 18 has moved into the body tissue 14, the anchor may be toggled from the orientation shown in FIG. 4 to the orientation shown in FIG. 5 relative to the body tissue 14. Changing the orientation of the anchor 18 relative to the body tissue 14 increases the ability of the anchor to withstand pull out force applied against the anchor by the suture 24.

The anchor 20 (FIG. 1) is inserted into the body tissue in the same manner as previously described in conjunction with the anchor 18. Thus, the anchor 20 is positioned in an inserter 38 (FIG. 6) and is engaged by a pusher member 40. The pusher member 40 engages a trailing end portion 42 of the anchor 20.

The pusher member 40 presses a pointed leading end portion 44 of the anchor 20 against the body tissue 12 to initiate the formation of an opening in the body tissue. The anchor 20 then moves through the body tissue 12 and moves into engagement with the body tissue 14. The continued application of force against the trailing end portion 42 of the anchor 20 by the pusher member 40 causes the leading end portion 44 of the anchor to initiate the formation of an opening in the body tissue 14.

As the anchor 20 moves deeper into the body tissue 14, the anchor pierces the body tissue in the manner illustrated in FIG. 7. The anchor 20 may be moved along a linear or nonlinear path in the body tissue 14.

Once the anchor 20 has moved into the body tissue 14, the orientation of the anchor relative to the body tissue is changed with a toggling action. Thus, the orientation of the anchor 20 is changed from the orientation illustrated in FIG. 7 to the orientation illustrated in FIG. 8. Changing the orientation of the anchor 20 relative to the body tissue increases the ability of the anchor to withstand pull out forces transmitted through the suture 24.

Once both anchors 18 and 20 have moved through the body tissue 12 into the body tissue 14, the pusher members 30 and 40 (FIGS. 4, 5, 7, and 8) are withdrawn from the body tissue. It is contemplated that the anchors 18 and 20 may be either sequentially moved into the body tissue 12 and 14 or simultaneously moved into the body tissue 12 and 14. If the anchors 18 and 20 are sequentially moved into the body tissue 12 and 14, the same inserter and pusher member may be utilized to move both of the anchors into the body tissue. If the anchors 18 and 20 are simultaneously moved into the body tissue 12 and 14, separate inserters 28 and 38 and pusher members 30 and 40 may be used to move the anchors into the body tissue. If desired, the inserters 28 and 38 and pusher members 30 and 40 may be interconnected and form portions of an inserter assembly.

Although it is believed that it will be desired to pivot the anchors 18 and 20 from the orientations illustrated in FIGS. 4 and 7 to the orientations shown in FIGS. 5 and 8, the anchors 18 and 20 may be left in the orientations shown in FIGS. 4 and 7 if desired. It is believed that pivoting the anchors 18 and 20 to the orientations shown in FIGS. 5 and 8 will enable the anchors to remain stationary relative to the body tissue 14 when relatively large tension forces are transmitted to the anchors through the suture 24.

The suture 24 (FIG. 9) is integrally formed as one piece and includes a connector portion 48 which extends between the two anchors 18 and 20. In addition, the suture 24 includes a leg portion 50 which extends from the anchor 18. The suture 24 also includes a leg portion 52 which extends from the anchor 20. A suture retainer (crimp) 54 is utilized to interconnect the leg portions 50 and 52 of the suture 24. Alternatively, the leg portions 50 and 52 may be tied together in a knot to interconnect the leg portions. If desired, the leg portions 50 and 52 could be bonded together by the application of ultrasonic vibratory energy directly to the leg portions.

When the leg portions 50 and 52 of the suture 24 are to be interconnected with the retainer 54, the suture 24 may be tensioned with a force application assembly 60 (FIG. 10). The force application assembly 60 applies a predetermined force, indicated schematically by an arrow 62 in FIG. 10, to the leg portions 50 and 52 of the suture 24. The predetermined force 62 has a magnitude which is a function of the size and strength of the suture 24.

The suture retainer 54 is pressed against the body tissue 12 by a force application member 66. Forces, indicated schematically at 70 and 72 in FIG. 10, are transmitted through the force application member 66 to the suture retainer 54 to press the suture retainer against the body tissue 12. The magnitude of the forces indicated by the arrows 70 and 72 and applied to the suture retainer 54 by the force application member 66, are a function of the size and strength of the suture 24.

While the suture 24 is being tensioned under the influence of force 62 and while the suture retainer 54 is being pressed against the body tissue 12 under the influence of forces 70 and 72, the suture retainer 54 is plastically deformed to firmly grip the suture 24. To plastically deform the suture retainer 54, a pair of force application members 76 and 78 are pressed against opposite sides of the suture retainer 54. The force with which the force application members 76 and 78 are pressed against the suture retainer 54 is indicated schematically by arrows 80 and 82 in FIG. 10. The force applied against the suture retainer 54 by the force application members 76 and 78 plastically deforms the material of the suture retainer while the suture retainer is being pressed against the body tissue 12 by the force application member 66 and while the suture is being tensioned by the force application assembly 60.

In the embodiment of the invention illustrated in FIGS. 1-10, the anchors 18 and 20 are embedded in the body tissue 14 (FIG. 10). However, the anchors 18 and 20 could be moved through the body tissue 14 if desired. This would result in the anchors 18 and 20 engaging an outer surface of the body tissue 14.

When the body tissue 12 and 14 are both soft body tissues, it is contemplated that the body tissues could be placed in apposition. Once the soft body tissues 12 and 14 have been approximated, the anchors 18 and 20 would be moved through the body tissue 12 into the body tissue 14. If desired, the anchors 18 and 20 could be moved through the body tissue 14.

In the embodiment of the invention illustrated in FIGS. 1-10, the body tissue 12 is secured with the body tissue 14 by the suture 24. In this embodiment, the suture 24 extends through the body tissue 12 and presses the body tissue 12 against the body tissue 14. However, the body tissue 12 could be secured with the body tissue 14 in a different manner. For example, the suture 24 could extend around the body tissue 12 without extending through the body tissue 12. The body tissue 12 could be spaced from the body tissue 14 and secured with the body tissue 14 by a portion of the suture extending between the body tissue 12 and the body tissue 14.

In the embodiment of the invention illustrated in FIGS. 1-10, the suture 24 has leg portions 50 and 52 which extend from the suture anchors 18 and 20 and a connector portion 48 which extends between the suture anchors. In the embodiment of the invention illustrated in FIG. 11, the suture is formed as a continuous loop which extends between the two anchors. Since the embodiment of the invention illustrated in FIG. 11 is generally similar to the embodiment of the invention illustrated in FIGS. 1-10, similar numerals will be utilized to designate similar components, the suffix letter "a" being associated with the numerals of FIG. 11 to avoid confusion.

An apparatus 10a (FIG. 11) for use in securing first body tissue 12a with second body tissue 14a includes a plurality of suture anchors 18a and 20a. A suture 24a extends between the anchors 18a and 20a. Although the suture 24a has been illustrated in FIG. 11 as extending between only two anchors 18a and 20a, a greater number of anchors could be provided if desired.

The suture 24a is forms a continuous flexible loop. Thus, the suture 24a includes a first connector portion 48a which extends between the suture anchors 18a and 20a and a second connector portion 90 which extends between the suture anchors. The connector portions 48a and 90 are interconnected by bonding their ends together under the influence of ultrasonic vibratory energy. However, the connector portions 48a and 90 could be integrally formed as one piece. The connector portions 48a and 90 do not have free ends. The connector portions 48a and 90 may be interconnected by a device, such as the retainer 54 of FIG. 9, or a knot.

Since the suture 24a is a continuous closed loop without free ends, the suture 24a is tensioned whenever the anchors 18a and 20a are moved into the body tissue 14a. The anchor 18a is moved through the body tissue 12a into the body tissue 14a in the same manner as previously described in conjunction with the embodiment of the invention illustrated in FIGS. 1-10. The anchor 20a is then moved through the body tissue 12a into the body tissue 14a.

As the anchor 20a moves into the body tissue 14a, the anchor 20a moves from the position illustrated in solid lines in FIG. 11 to the position illustrated in dashed lines in FIG. 11. As the anchor 20a moves into the body tissue 14a, the connector portions 48a and 90 of the suture 24a are both tensioned. The magnitude of the tension force in the continuous loop which is formed by the suture 24a will be a function of magnitude of the force which is utilized to move the suture anchors 18a and 20a into the body tissue 14a.

The anchors 18a and 20a may be moved either sequentially or simultaneously into the body tissue 14a. Thus, the anchor 18a may be moved through the body tissue 12a into the body tissue 14a in the manner illustrated in solid lines in FIG. 11. The anchor 20a may then be moved through the tissue 12a into the tissue 14a to the position illustrated in dashed lines in FIG. 11. Alternatively, the anchors 18a and 20a may both be simultaneously moved through the body tissue 12a and into the body tissue 14a. The anchors 18a and 20a may be moved along either linear or nonlinear paths in the body tissues 12a and 14a.

It is contemplated that an inserter, corresponding to the inserter 18 of FIGS. 2-5, and a pusher member, corresponding to the pusher member 30 of FIGS. 2-5, will be utilized to position the anchor 18a in the body tissue 14a (FIG. 11). Similarly, an inserter, corresponding to the inserter 38 of FIGS. 6-8, and a pusher member, corresponding to the pusher member 40 of FIGS. 6-8, will be utilized to position the anchor 20a in the body tissue 14a (FIG. 11).

In the embodiment of the invention illustrated in FIG. 11, only two anchors 18a and 20a are connected with the continuous loop formed by the suture 24a. However, a greater number of anchors, for example three, could be connected with the loop formed by the suture 24a. Upon insertion of the last anchor of the plurality of anchors, the loop formed by the suture 24a would probably slide in passages in at least one of the other anchors and the suture would be tensioned.

In the embodiment of the invention illustrated in FIG. 12, an apparatus is provided to measure tension in a suture which forms a continuous closed loop. Since the embodiment of the invention illustrated in FIG. 12 is generally similar to the embodiment of the invention illustrated in FIGS. 1-11, similar numerals will be utilized to designate similar components, the suffix letter "b" being associated with the numerals of FIG. 12 to avoid confusion.

An anchor 20b is positioned in an inserter 28b and moved into body tissue under the influence of force applied against a trailing end portion 42b of the anchor 20b by a pusher member 40b. A tension measuring assembly 96 is provided in association with the inserter 38b. The tension measuring assembly 96 includes a force transmitting member 100 having an end portion 102 which engages connector portions 48b and 90b of a suture 24b. Although only a single anchor 20b is illustrated in FIG. 12, it should be understood that the suture 24b forms a continuous loop connected with a second anchor, corresponding to the anchor 18a of FIG. 11.

As the anchor 20b moves into the body tissue 14b, the suture 24b applies force against the end portion 102 of the force transmitting member 100. A force measuring device 112 is connected with the force transmitting member 100. The force measuring device 112 measures the tension force in the continuous closed loop formed by the suture 24b. The force measuring device 112 may be a load cell or other transducer.

During movement of the anchor 20b into the body tissue 14b, the inserter 38b is pressed against the body tissue 14b by a remote inserter drive assembly 110 (FIG. 12). While the inserter 38b is held stationary and pressed against the body tissue 14b, a pusher member drive assembly 114 moves the pusher member 40b and anchor 20b into the body tissue 14b in the manner previously described in conjunction with the embodiment of the invention illustrated in FIGS. 1-10. The anchor 20b may be moved along either a linear path or a nonlinear path into the body tissue 14b.

The force measuring assembly 96 is illustrated in FIG. 12 in association with a suture 24b which is formed as a continuous loop. However, the force measuring assembly 96 could be utilized with a suture having free end portions. Thus, the force measuring assembly 96 could be used with the suture 24 of FIGS. 1-10 if desired. If this was done, the connector portion 48 of the suture 24 would engage the end portion 102 of the force transmitting member 100. If desired, the leg portion 52 of the suture 24 could also engage the end portion 102 of the force transmitting member 100.

If desired, the force measuring device 112, pusher member drive assembly 114, and inserter drive assembly 110 may be formed as part of a robotic tool which is associated with a console that gives a three dimensional view of an operating table in an operating room of a hospital. Controls at the console provide tactile feedback to a surgeon operating the controls. The controls effect operation of the drive assemblies 110 and 114 to move the anchor 20b into the body tissue 14b.

The robotic tool may include apparatus to move an anchor corresponding to the anchors 18 or 18a of FIGS. 1 and 11 into the body tissue 12b and 14b. Thus, the robotic tool also includes a second inserter drive assembly, having the same construction as the inserter drive assembly 110 of FIG. 12, to position an inserter, corresponding to the inserter 28 of FIG. 2, relative to the body tissue 12b and 14b. The robotic tool also includes a second pusher member drive assembly, having the same construction as the pusher member drive assembly 114 of FIG. 12, to position a pusher member, corresponding to the pusher member 40 of FIG. 2, relative to the body tissue 12b and 14b.

The robotic tool may be operated to effect simultaneous movement of two anchors, that is, an anchor corresponding to the anchor 18 (FIG. 1) and an anchor corresponding to the anchor 20b (FIG. 12), into the body tissues 12b and 14b. As the anchors 18 and 20b moves into the body tissue 14b, the continuous loop formed by the suture 24b is tensioned. The force transmitting member 100 transmits a force which is a function of the tension in the suture 24b to the force measuring device 112. When the force measuring device 112 detects that the desired tension is present in the suture 24b, operation of the pusher member drive assemblies is interrupted with the anchors 18 and 20b in a desired position relative to the body tissue 14b.

In the embodiment of the invention illustrated in FIG. 13, a guide assembly is utilized to position a suture anchor relative to the body tissue. Since the embodiment of the invention illustrated in FIG. 13 is generally similar to the embodiments of the invention illustrated in FIGS. 1-12, similar numerals will be utilized to designate similar components, the suffix letter "c" being associated with the numerals of FIG. 13 to avoid confusion.

A guide assembly 120 is utilized in association with an apparatus 10c. The apparatus 10c includes a plurality of suture anchors 18c and 20c. Although only two anchors 18c and 20c have been illustrated, a greater number of anchors could be utilized if desired.

A suture 24c extends from the suture anchors 18c and 20c. In the embodiment of the invention illustrated in FIG. 13, the suture 24c is a continuous loop, in the same manner as the suture 24a of FIG. 11. However, the suture 24c could have free ends and leg portions corresponding to the leg portions 50 and 52 of the suture 24 of FIG. 1.

The guide assembly 120 includes a base 124 which positions guides 126 and 128 relative to body tissue 12c and 14c. The guides 126 and 128 have a tubular configuration. Although only two guides 126 and 128 have been provided for only two anchors 18c and 20c, a greater number of guides could be provided for a greater number of anchors.

The anchors 18c and 20c are positioned in the guides 126 and 128 in the same manner as in which they are positioned in the inserters 28 and 38 of the embodiment of the invention illustrated in FIGS. 2-8. A pusher member 132 is utilized to apply force against the anchors 18c and 20c to move the anchors relative to the guides 126 and 128 and into the body tissue 12c and 14c.

The guide 128 is movable along the base 124 to enable the distance between locations where the anchors 18c and 20c move into the body tissue 12c and 14c to be adjusted. The manner in which the guide 128 is moved along the base 124 is indicated schematically by arrows 136 in FIG. 13. A suitable retainer 140 is provided to connect the guide 128 with the base 124 in a desired position relative to the guide 126.

If the anchors 18c and 20c are to be moved along nonlinear paths in the body tissue 14c, the guides 126 and 128 could have a nonlinear configuration. For example, the guides 126 and 128 could be formed with an arcuate configuration. If this was done, the pusher member 132 would be formed with an arcuate configuration corresponding to the arcuate configuration of the guides 126 and 128.

In the embodiments of the invention illustrated in FIGS. 1-13, the anchors have pointed leading end portions which initiate the formation of openings in the body tissue. In the embodiment of the invention illustrated in FIGS. 14 and 15, thin elongated members are provided to initiate the formation of openings in the body tissue. The thin elongated members are also be utilized to guide movement of the anchors into the body tissue. Since the embodiment of the invention illustrated in FIGS. 14 and 15 is generally similar to the embodiments of the invention illustrated in FIGS. 1-13, similar numerals will be utilized to designate similar components, the suffix letter "d" being associated with the numerals of FIGS. 14 and 15 to avoid confusion.

An apparatus 10d includes a plurality of anchors 18d and 20d which are interconnected by a suture 24d. The suture 24d is formed as a continuous flexible loop, in the same manner as is illustrated in FIG. 11. However, the suture 24d could have legs with free end portions, in the manner illustrated in FIG. 1.

A tubular inserter 28d (FIG. 14) cooperates with a pusher member 30d during movement of the anchor 18d into body tissue. Similarly, a tubular inserter 38d (FIG. 15) cooperates with a pusher member 40d during movement of the anchor into body tissue.

When the anchor 18d (FIG. 14) is to be positioned relative to body tissue, a thin elongated member 146 is utilized to initiate formation of an opening in the body tissue 12d and 14d. The thin elongated member 146 may be a cylindrical rod similar to a K-wire. The thin elongated member 146 has a pointed end portion 148.

When the anchor 18d is to be moved along a linear path in the body tissue 14b, the thin elongated member 146 will have the linear configuration illustrated in FIG. 14. When the anchor 18d is to be moved along an arcuate path, the thin elongated member 146 will have an arcuate configuration.

When the thin elongated member 146 (FIG. 14) is to be moved into the body tissue 12d and 14d, the thin elongated member 146 is positioned in a desired orientation relative to the body tissue. The thin elongated member is then forced axially into the body tissue 12d and 14d. As the thin elongated member 146 moves into the body tissue 12d, the pointed end portion 148 of the thin elongated member initiates the formation of an opening in the body tissue 12d. As the thin elongated member 146 moves through the body tissue 12d, the pointed end portion 148 engages the body tissue 14d and initiates the formation of an opening the body tissue 14d.

Once the thin elongated member 146 has initiated the formation of an opening in the body tissue 14d, the thin elongated member is moved through the hard outer layer 278d of bone into the cancellous bone 280d. The thin elongated member 146 is moved to a desired depth in the cancellous bone 280d. The depth to which the elongated member 146 is moved into the cancellous bone 280d is somewhat greater than a depth to which the anchor 18d is to be moved into the cancellous bone.

Once the thin elongated member 146 has been moved to the desired depth in the cancellous bone 280d, the anchor 18d is telescopically positioned relative to the stationary thin elongated member 146. When this is done, the thin elongated member 146 will extend through a cylindrical passage 152 in the anchor 18d. The pusher member 30d is then positioned in a telescopic relationship with the stationary thin elongated member 146. When this is done, the thin elongated member 146 will extend through a cylindrical passage 156 in the pusher member 30d and the through passage 152 in the anchor 18d. The cylindrical inserter 28d extends around the pusher member 30d and a trailing end portion 32d of the anchor 18d.

The pusher member 30d (FIG. 14) is pressed axially against the trailing end portion of the anchor 18d to slide the pusher member and the anchor along the stationary thin elongated member 146. As the anchor 18d slides along the stationary thin elongated member 146, a pointed leading end portion 34d of the anchor 18d pierces the body tissue 12d and the body tissue 14d. When the anchor 18d has been moved to a desired position relative to the body tissue 14d, movement of the anchor along the thin elongated member is interrupted (FIG. 14).

The anchor 20d (FIG. 15) is positioned relative to the body tissue in the same manner as the anchor 18d. When the anchor 20d is to be positioned relative to the body tissue 12d and 14d, a second thin elongated member 160 (FIG. 15) is positioned in a desired orientation relative to the body tissue 12d and 14d. A pointed end portion 162 of the thin elongated member 160 is then forced into the body tissue. The thin elongated member 160 may have a linear configuration or nonlinear configuration.

The anchor 20d is then telescopically positioned on the stationary thin elongated member 160. When this is done, the thin elongated member 160 will extend through a cylindrical passage 166 (FIG. 15) in the anchor 20d. The anchor 20d is moved along the thin elongated member 160 until a pointed leading end portion 44d of the anchor 20d engages the body tissue 12d. A pusher member 40d is then telescopically moved along the thin elongated member into engagement with a trailing end portion 42d of the anchor 20d. The pusher member 40d then applies force against the trailing end portion 42d of the anchor 20d to move the anchor into the body tissue to the position shown in FIG. 15.

Once the anchors 18d and 20d have been positioned in the body tissue 14d, the thin elongated members 146 and 160 are withdrawn from the anchors and from the body tissue. The anchors 18d and 20d may then be pivoted or toggled relative to each other to change their orientation relative to the body tissue. Alternatively, the anchors 18d and 20d may be left in the orientation illustrated in FIG. 15.

In the embodiment of the invention illustrated in FIG. 13, a guide assembly 120 is utilized to position the guides 126 and 128 relative to the body tissue. A second embodiment of the guide assembly is illustrated in FIG. 16. Since the embodiment of the guide assembly illustrated in FIG. 16 is generally similar to the embodiment of the guide assembly illustrated in FIG. 13, similar numerals will be utilized to designate similar components, the suffix letter "e" being associated with the numerals FIG. 16 to avoid confusion.

A guide assembly 120e includes a base 124e. Tubular cylindrical guides 126e and 128e are provided on the base 124e. The guides 126e and 128e are utilized to guide movement of anchors, corresponding to the anchors 18c and 20c of FIG. 13. The guides 126e and 128e may have either a linear or a nonlinear configuration depending upon the configuration of the paths along which the anchors are to be moved in the boy tissue 12d and 14d. When more than two anchors are to be positioned relative to the body tissues 12e and 14e, a corresponding number of guides would be provided.

In the embodiment of the invention illustrated in FIG. 16, the guides 126e and 128e penetrate both the body tissue 12e and the body tissue 14e. The body tissue 14e is soft body tissue which is easily penetrated by the guides 126e and 128e. Alternatively, the body tissue 14e could be hard body tissue which requires the application of a relatively large force against the guides 126e and 128e to cause them to penetrate the body tissue. The guides 126e and 128e have slots 292e and 316e to receive portions of a suture.

In the embodiment of the invention illustrated in FIGS. 1-10, the suture anchors 18 and 20 are utilized to connect soft body tissue 12 with hard body tissue 14. In the embodiment of the invention illustrated in FIG. 17, the anchors are utilized to connect hard body tissue with hard body tissue. Since the embodiment of the guide assembly illustrated in FIG. 17 is generally similar to the embodiment of the invention illustrated in FIGS. 1-16, similar numerals will be utilized to designate similar components, the suffix letter "f" being associated with the numerals of FIG. 17 to avoid confusion.

First body tissue 12f (FIG. 17) is connected with second body tissue 14f with anchors 18f and 20f. A suture 24f extends between the anchors 18f and 20f. The body tissue 12f and 14f are portions of a bone 174. A fracture 178 extends across the bone 174.

The anchors 18f and 20f (FIG. 17) are moved from one side of the bone 174 to the opposite side of the bone to interconnect the body tissue 12f and 14f with the suture 24f. An inserter 38f and pusher member 40f may be utilized to move the anchors 18f and 20f through the bone 12f and 14f. The pusher member 40f is effective to apply sufficient force against the anchors 18f and 20f to enable them to initiate the formation of openings in the body tissue 12f and 14f and to enable them to be moved from one side of the bone 174 to the opposite side of the bone.

If desired, passages could be drilled through the bone 174 prior to movement of the anchors 18f and 20f through the bone. If thin elongated members, corresponding to the thin elongated members 146 and 160 (FIG. 15) are to be used to guide the anchors 18f and 20f (FIG. 17), the drilled passages would have a relatively small diameter. If the anchors 18f and 20f are to be moved through the bone 174 without thin elongated members, the drilled passages would have a larger diameter.

In the embodiment of the invention illustrated in FIGS. 1-17, the anchors 18 and 20 all have the same general construction. However, it is contemplated that the anchors could have a construction similar to the construction of an anchor 186 illustrated in FIG. 18. The anchor 186 includes a body 190 from which a plurality of barbs 192, 194 and 196 extend. The anchor 186 is connected with a portion of a suture 200. The anchor 186 has a known construction and is merely illustrative of any one of many different types of anchors which may have projections, corresponding to barbs 192, 194 and 196, which engage body tissue. The projections may have a configuration which is substantially different than the configurations of the barbs 192, 194 and 196.

It should be understood that the anchor could have a construction which is different than the construction of the anchors 18, 20 and 186. For example, the anchor could have a construction similar to the construction of an anchor 204 (FIG. 19). The anchor 204 has a threaded portion 206 which engages body tissue.

In the embodiments of the invention illustrated in FIGS. 1-19, the various anchors are connected with the body tissue in a spaced apart relationship. In the embodiment of the invention illustrated in FIGS. 20 and 21, the anchors are interconnected while they are in the body tissue. Since the embodiment of the invention illustrated in FIGS. 20 and 21 is generally similar to the embodiments of the invention illustrated in FIGS. 1-19, similar numerals will be utilized to designate similar components, the suffix letter "g" being associated with the numerals of FIG. 20 to avoid confusion.

An apparatus 10g (FIG. 20) is utilized to secure body tissue 12g to body tissue 14g. The apparatus 10g includes an anchor 18g and an anchor 20g. A suture 24g extends between the anchors 18g and 20g.

The suture 24g includes a first leg portion 50g which extends from the suture 18g and a second leg portion 52g which extends from the anchor 20g. The two leg portions 50g and 52g of the suture 24g are interconnected by a retainer 54g. In the embodiment of the invention illustrated in FIG. 20, the leg portions 50g and 52g of the suture 24g are two separate pieces of suture. However, the leg portions 50g and 52g may be formed as one piece.

The anchor 18g and the anchor 20g engage each other in the body tissue 14g. Portions of the anchors 18g and 20g cooperate to interconnect the anchors and hold them against movement relative to each other. Thus, the anchor 18g has projections 212 (FIG. 21) which engage projections 214 on the anchor 20g.

The projections 212 and 214 (FIG. 21) on the anchors 18g and 20g intermesh in such a manner as to prevent the anchors from being moved relative to each other under the influence of tension in the leg portions 50g and 52g of the suture 24g. Although specific projections 212 and 214 have been illustrated in FIG. 21, it is contemplated that the projections 212 and 214 could have a different configuration if desired.

In the embodiment of the invention illustrated in FIGS. 20 and 21, the anchors 18g and 20g are interconnected by engagement of projections 212 and 214 on the anchors. In the embodiment of the invention illustrated in FIG. 22, the anchors are interconnected by moving a portion of one anchor into an opening in the other anchor. Since the embodiment of the invention illustrated in FIG. 22 is generally similar to the embodiment of the invention illustrated in FIGS. 20 and 21, similar numerals will be utilized to designate similar components, the suffix letter "h" being associated with the numerals of FIG. 22 to avoid confusion.

An anchor 18h and an anchor 20h are connected with a suture 24h. The suture 24h includes a leg portion 50h which is connected to and extends from the anchor 18h. The suture 24h also includes a leg portion 52h which is connected to and extends from the anchor 20h. The leg portions 50h and 52h may be interconnected by a retainer, corresponding to the retainer 54g of FIG. 20. Alternatively, the leg portions 50h and 52h may be integrally formed as one piece.

In accordance with a feature of this embodiment of the invention, the anchor 18h is provided with an opening 220 (FIG. 22) through which a portion of the anchor 20h extends. The anchor 20h has retainers 224 which move through the opening 220 and engage the anchor 18h when the anchors 18h and 20h are disposed in body tissue 14h. Engagement of the retainers 224 with the anchor 18h interconnects the anchors 18h and 20h.

In the embodiments of the invention illustrated in FIGS. 1-15, the anchors are enclosed by the body tissue 14. In the embodiment of the invention illustrated in FIG. 23, the anchor is partially disposed outside of body tissue 12 and 14. Since the embodiment of the invention illustrated in FIG. 23 is generally similar to the embodiments of the invention illustrated in FIGS. 1-22, similar numerals will be utilized to designate similar components, the suffix letter "j" being associated with the numerals of FIG. 23 to avoid confusion.

An apparatus 10j (FIG. 23) includes a plurality of anchors. The plurality of anchors includes the anchor 18j and an anchor 20j. A suture 24j extends between the anchors 18j and 20j. A greater number of anchors could be provided if desired.

The anchor 18j has a shank portion 230 which extends through body tissue 12j into body tissue 14j. If desired, the shank portion 230 of the anchor 18j could extend through the body tissue 14j. A head end portion 234 of the anchor 230 is pressed against the body tissue 12j and presses the body tissue 12j against the body tissue 14j.

Similarly, the anchor 20j includes a shank portion 238 which extends through the body tissue 12j into the body tissue 14j. If desired, the shank portion 238 of the anchor 20j could extend through the body tissue 14j. The anchor 20j has a head end portion 242 which is pressed against the body tissue 12j.

The suture 24j extends around the shank portions 230 and 238 of the anchors 18j and 20j. The suture 24j engages the shank portions 230 and 238 of the anchors 18j and 20j at a location immediately beneath (as viewed in FIG. 23) the head end portions 234 and 242 of the anchors 18j and 20j.

The suture 24j is formed as a continuous loop. The loop extends around the shank portions 230 and 238 of the anchors 18j and 20j. The continuous loop formed by the suture 24j is generally similar to the loop formed by the suture 24a of FIG. 11. However, if desired, the suture 24j (FIG. 23) could be a single strand which extends between the two anchors 18j and 20j. Alternatively, the suture 24j could be formed with two leg portions, corresponding to the leg portions 50 and 52 (FIG. 9) of the suture 24. If the suture 24j (FIG. 23) is formed with a pair of leg portions, the leg portions could be interconnected with a retainer, similar to the retainer 54 of FIG. 9.

Embodiment of FIGS. 1-10

In the embodiment of the invention illustrated in FIGS. 1-10, the apparatus 10 (FIG. 1) includes a plurality of anchors which are interconnected by a suture 24. Although only two anchors 18 and 20 have been illustrated in FIG. 1, it should be understood that a greater number of anchors could be connected with the suture 24. In the embodiment of the invention illustrated in FIG. 1, the anchors 18 and 20 both have the same construction. However, it is contemplated that the anchor 18 could have a construction which is different than a construction of the anchor 20.

The anchor 18 includes a body portion 250 from which the pointed leading end portion 34 extends. The specific anchor 18 illustrated in FIG. 1 has a cylindrical body portion 250 and a generally conical pointed leading end portion 34 which are disposed in a coaxial relationship.

Although the pointed leading end portion 34 of the anchor 18 (FIG. 1) has a conical configuration, the pointed leading end portion could have a different configuration if desired. For example the pointed leading end portion 34 could be wedge-shaped. Alternatively, the pointed leading end portion 34 could have a pyramidal configuration and be formed by the intersection three, four, or more surfaces. The surfaces could be flat or concave in configuration.

The anchor 18 is provided with a pair of passages 254 and 256 through which the suture 24 extends. The passages 254 and 256 have a cylindrical configuration and extend diametrically through the cylindrical body portion 250. Central axes of the passages 254 and 256 extend parallel to each other and intersect a central axis 260 of the anchor. The central axes of the passages 254 and 256 extend perpendicular to the central axis 260 of the anchor 18.

In the illustrated embodiment of the anchor 18, two passages 254 and 256 extend diametrically through the body portion 250 of the anchor. However, it is contemplated that only a single passage may be provided through the anchor. This single passage could be skewed at an acute angle to the central axis 260 of the anchor 18. Alternatively, the passage could extend axially through the anchor.

The anchor 20 (FIG. 1) is identical to the anchor 18. The anchor 20 has a cylindrical body portion 264 through which passages 266 and 268 extend. The anchor 20 has a conical end portion 44 which is coaxial with the cylindrical body portion 264.

The anchors 18 and 20 maybe formed of many different materials. However, the anchors 18 and 20 are formed of bone, specifically, hard compact bone (cortical bone). The bone from which the anchors 18 and 20 are formed may be autogenic bone or allogenic bone. Alternatively, the anchors may be formed of xenogenic bone.

The anchors 18 and 20 may be formed of bone obtained from many different sources. However, it is believed that it may be preferred to form the anchors 18 and 20 of freeze dried bone which has been obtained from a human cadaver. The bone may be harvested under clean conditions and treated to achieve sterility. Of course, the bone forming the anchors 18 and 20 could be obtained in any one of many different ways under any one of many different conditions.

Although the anchors 18 and 20 are formed of bone, the anchors 18 and 20 may be formed of other materials if desired. The anchors 18 and 20 may be formed of biodegradable or non-biodegradable materials. For example, the anchors 18 and 20 may be formed of polycaperlactone. Alternatively, the anchors 18 and 20 may be formed of metal, such as titanium or stainless steel. If desired, the anchors 18 and 20 could be formed of biodegradable or bioerodible copolymers. It is believed that it may be desired to form the anchors 18 and 20 of bone or polymeric materials in order to minimize any possibility of interference with imaging systems such as magnetic resonance imaging systems.

The anchors 18 and 20 have the same construction as disclosed in co-pending U.S. patent application Ser. No. 09/556,458 filed May 3, 2000 by Peter M. Bonutti and entitled "Method and Apparatus for Securing Tissue". However, it should be understood that the anchors 18 and 20 may be constructed with a different configuration if desired. For example, the anchors 18 and 20 may have a construction of any one of the anchors disclosed in U.S. Pat. Nos. 5,527,343 or 5,534,012. The disclosure in the aforementioned U.S. patent application Ser. No. 09/556,458 and the aforementioned U.S. Pat. Nos. 5,527,343 and 5,534,012 are hereby incorporated herein in their entirety by this reference thereto.

It is contemplated that the anchors 18 and 20 will be used in situations where the anchors are exposed to body fluids. In such a situation, the anchors 18 and 20 may be formed of a material which absorbs body fluids and expands. The anchors 18 and 20 may be formed of a polymeric material which absorbs body liquid. The polymeric material may be hydrophilic. The polymeric material may be cellulose, petroylglutamic acid, high purity carboxymethylcellulose, a collagen, or polylactide. Of course, the anchors 18 and 20 could be formed of other materials which absorb body liquid.

When the anchors 18 and 20 are to absorb body liquid and expand, it is contemplated that the anchors may be constructed in accordance with the disclosure in U.S. Pat. No. 5,718,717 issued Feb. 17, 1998 to Peter M. Bonutti and entitled "Suture Anchor". The disclosure in the aforementioned U.S. Pat. No. 5,718,717 is hereby incorporated herein in its entirety by this reference thereto.

The suture 24 (FIG. 1) extends from the anchors 18 and 20. The suture 24 extends through the passages 254 and 256 in the anchor 18. Similarly, the suture 24 extends through the passages 266 and 268 in the anchor 20.

The suture 24 is freely movable relative to the anchors 18 and 20. By being freely movable relative to the anchor passages 254, 256, 266 and 268, the length of the suture between the anchors 18 and 20 can be varied to accommodate positioning of the anchors at different locations in a patient's body. Thus, by pulling on the leg portions 50 and 52 of the suture 24, the length of the connector portion 48 (FIG. 1) of the suture 24 extending between the anchors can be shortened to accommodate positioning of the anchors in the body tissue 14 at the locations which are relatively close together. Similarly, the anchors 18 and 20 can be pulled apart to lengthen the connector portion 48 of the suture 24 to accommodate positioning of the anchors 18 and 20 in the body tissue 14 at locations which are spaced a substantial distance apart.

Once the anchors 18 and 20 have been positioned in body tissue, in the manner illustrated in FIG. 9, force applied to the leg portions 50 and 52 is effective to tension the connector portion 48 of the suture 24. Any excess material in the connector portion 48 of the suture 24 will be pulled into the leg portions 50 and 52 as the leg portions and connector portion are tensioned. This results in the leg portions 50 and 52 and connector portion 48 of the suture 24 being tensioned with substantially the same force by the force application assembly 60 (FIG. 10) prior to gripping of the leg portions 50 and 52 of the suture 24 with the suture retainer 54.

Since the suture 24 is movable relative to the anchors 18 and 20, the tension in the connector portion 48 (FIG. 9) of the suture 24 can be increased after the anchors 18 and 20 have been positioned in the body tissue 14. Thus, once the anchors 18 and 20 have been moved to the positions illustrated in FIG. 9, pulling on the leg portions 50 and 52 of the suture 24 causes the suture to slide in the passages 254 and 256 in the anchor 18 and to slide in the passages 266 and 268 in the anchor 20. As the suture 24 moves in the passages 254, 256, 266 and 268 in the anchors 18 and 20, the length of the connector portion 48 of the suture 24 decreases. At the same time the length of the leg portions 50 and 52 increase.

Pulling on the leg portions 50 and 52 of the flexible suture 24 increases the tension in the leg portions. This increase in tension is transmitted from the leg portions 50 and 52 of the suture 24 through the passages 254, 256, 266 and 268 in the anchors 18 and 20 to the connector portion 48 of the suture. Therefore, pulling on the leg portions 50 and 52 of the suture 24 eliminates any extra length in the connector portion 48 of the suture and effects a corresponding increase in the combined lengths of the leg portions of the suture. As this occurs, tension in the connector portion 48 of the suture 24 increases to equal tension in the leg portions 50 and 52 of the suture.

The suture 24 may be formed of a plastic material which is a biopolymer. Thus, the suture 24 may be formed of polyglycolide which is commercially available under the trademark DEXON. Polyglycolide is a crystalline material that melts about 225° Celsius. Although the suture 24 is a monofilament suture having a continuous outer side surface, it is contemplated that the suture could be formed in a different manner. For example, the suture 24 could be a cable having an interlaced structure formed by a plurality of filaments or strands which have been twisted, braided, twined, and/or threaded together. If desired, the suture 24 and anchors 18 and 20 could be formed of the same polymeric material.

It is contemplated that the suture 24 may be formed of a polyglycolide-based copolymer which is commercially available under the trademark VICRYL. The suture 24 may have a multifilament construction which is similar to the construction of the suture disclosed in U.S. Pat. No. 5,928,267. The disclosure in the aforementioned U.S. Pat. No. 5,928,267 is hereby incorporated herein by this reference thereto.

The strength of the suture 24 will vary as a function of the size of the suture. It is contemplated that the specific strength of a particular suture size will vary depending upon the material from which the suture is constructed and whether the suture has a monofilament or multifilament construction. By consulting a chart, a surgeon can select a suture 24 of a size and strength suitable for a particular use. Thus, a relatively large size suture 24 having substantial strength may be selected when body tissue is to be connected with a bone or when portions of a bone are to be interconnected by the suture. On the other hand, a relatively small size suture 24 having a relatively small strength may be selected when delicate body tissue, such as stomach tissue or intestinal tissue, and/or mucosa are to be interconnected with the suture.

Once a suture of a size and strength suitable for retaining specific body tissue has been selected, the suture is threaded through the passages 254 and 256 in the anchor 18 through the passages 266 and 268 in the anchor 20. By moving the anchors 18 and 20 away from each other, the length of the connector section 48 can be increased. Alternatively, by tensioning the leg portions 50 and 52 (FIG. 1) of the suture 24, the length of the connector portion 48 can be decreased.

In the embodiment of the invention illustrated in FIGS. 1-10, the suture 24 and anchors 18 and 20 are formed of different materials. Thus, the anchors 18 and 20 are formed of bone while the suture 24 is a monofilament of polymeric material. However, it is contemplated that both the suture 24 and the anchors 18 and 20 could be formed of similar materials. For example, the suture 24 and anchors 18 and 20 could both be formed of polymers or copolymers which are biodegradable or bioerodible. Even when the anchors 18 and 20 are formed of metal, it may be desirable to form the suture 24 of a biodegradable polymeric material.

The anchors 18 and 20 could have many different constructions. For example, the anchors 18 and 20 could be constructed in the manner illustrated in FIGS. 18-23 herein. Alternatively, the anchors 18 and 20 have any of the constructions disclosed in U.S. Pat. Nos. 5,403,348 and 5,989,282. If desired, the anchors 18 and 20 could have different constructions. The disclosures in the aforementioned U.S. Pat. Nos. 5,403,348 and 5,989,282 are hereby incorporated herein in their entirety by this reference thereto.

After the anchors 18 and 20 have been connected with the suture 24, in the manner illustrated in FIG. 1, the anchors and suture are used to connect body tissue 12 with the body tissue 14. In the specific embodiment of the invention illustrated in FIGS. 1-10, the body tissue 12 is soft body tissue and the body tissue 14 is hard body tissue. The soft body tissue 12 may be a tendon or a ligament. The body tissue 14 is a bone having a hard (cortical) outer layer 278 and relatively soft cancellous bone 280 which is enclosed by the relatively hard outer layer 278.

It should be understood that many different kinds of soft tissue can be connected with bone at many different locations in a patient's body. For example, the anchors 18 and 20 and suture 24 could be used to secure a meniscus to a bone in a knee joint of a patient. Alternatively, the suture 24 and anchors 18 and 20 could be used to secure the rotator cuff in a shoulder of a patient. The soft tissue 12 may be mucosa. The soft tissue 12 may be musculofascial tissue. It should be understood that the foregoing specific locations for use of the apparatus 10 in the body of a patient have been set forth herein merely as examples and it is contemplated that the apparatus 10 may be used at any desired location in the body of a patient.

In the embodiment of the invention illustrated in FIGS. 1-10, the body tissue 12 is pressed against the body tissue 14 by force transmitted from the suture 24 to the body tissue 12. However, the body tissue 12 could be spaced from the body tissue 14. For example, the suture 24 could extend at least part way around the body tissue 12 with the body tissue 12 spaced from the body tissue 14. The body tissue 12 could be soft body tissue which has a range of movement, relative to the body tissue 14, limited by the suture 24. The body tissue 14 could be either hard body tissue (bone) or soft body tissue. Alternatively, the anchor 18 could be disposed in one bone and the anchor 20 disposed in another bone. If this was done, the suture 24 could be utilized to limit the range of movement between the bones or to hold the bones in engagement with each other.

It is contemplated that the suture 24 and anchors 18 and 20 may be used in vascular tissue. For example, the anchors 18 and 20 could be used to connect the suture 24 with body tissue which forms a portion of a blood vessel. Body tissue forming two sections of a blood vessel may be placed in a side-by-side relationship and interconnected with the anchors 18 and 20 and the suture 24.

When the body tissue 12 is to be secured to the body tissue 14 with the apparatus 10, the anchor 18 is positioned in the inserter 28 (FIG. 2). The illustrated inserter 28 includes a cylindrical tubular outer member 284 which is connected with a suitable handle (not shown). The pusher member 30 has a generally cylindrical configuration and is received in a cylindrical passage 286 in the tubular outer member 284.

The cylindrical passage 286 extends between an entrance opening adjacent to the handle and a circular exit opening 288. The pusher member 30 extends along the passage 286 through the opening adjacent to the handle of the outer member 284. Although the illustrated inserter 28 and pusher member 30 have linear central axes, they could have nonlinear central axes if desired. For example, the inserter 28 and pusher member 30 could have arcuate central axes.

A slot 292 extends between the entrance opening adjacent to the handle of the inserter 28 and the exit opening 288. The slot 292 facilitates positioning the anchor 18 in the passage 286. This is because the anchor 18 is visible through the slot 292. In addition, the connector portion 48 and leg portion 50 of the suture 24 can be readily positioned in the slot 292.

The slot 292 has a straight longitudinal central axis which extends parallel to the longitudinal central axis of the passage 286 and to the longitudinal central axis of the tubular outer member 284. The connector portion 48 and leg portion 50 of the suture 24 extend along the slot 292 away from the opening 288 toward the opposite end portion of the tubular outer member 284. The slot 292 encloses the connector portion 48 and leg portion 50 of the suture 24 and protects the connector portion 48 and leg portion of the suture 24 against being snagged by objects in the environment around the inserter 28.

The passage 286 has a circular cross sectional configuration with a diameter which is slightly greater than the diameter of the body portion 250 of the anchor 18. Immediately adjacent to the exit opening 288, the passage 286 tapers inwardly to a cross sectional size which is somewhat smaller than the cross sectional size of the body portion 250 of the anchor 18. This enables the outer member 284 to firmly grip the trailing end portion 32 of the anchor 18.

The slot 292 has a uniform width throughout the length of the slot until the slot approaches the exit opening 288. Immediately ahead of the exit opening 288, the width of the slot 292 decreases to reduce the cross sectional size of the passage 286.

When the anchor 18 is to be positioned in the inserter 28, the anchor is inserted through the opening to the passage 286 adjacent to the handle with the end portion 34 of the anchor leading. The pusher member 30 is moved into the passage 286 and applies force against the trailing end portion 32 of the anchor 18 to move the anchor along the passage 286. At this time, the connector portion 48 and leg portion 50 of the suture 24 are disposed in the slot 292.

When the anchor 18 approaches the exit opening 288, the tapered leading end portion 34 of the anchor applies force against the outer member 284 to resiliently deflect the end portion of the outer member and expand the exit opening 288. At this time, the portion of the outer member 284 adjacent to the exit opening 288 resiliently grips the body portion 250 of the anchor to hold the anchor in the position illustrated in FIG. 2.

Although the inserter 28 may have many different constructions, the specific inserter 28 illustrated in FIG. 2 has the same construction as is disclosed in U.S. Pat. No. 5,948,002 issued Sep. 7, 1999 for "Apparatus and Method for Use in Positioning a Suture Anchor". It should be understood that the inserter 28 may have a construction which is similar to any one of the constructions illustrated in the aforementioned U.S. Pat. No. 5,948,002. It is also contemplated that the inserter 28 could have a construction which is similar to the construction of any one of many other known inserters. However, it is believed that it may be desired to use an inserter having the construction disclosure in the aforementioned U.S. Pat. No. 5,948,002 to facilitate handling and positioning of the anchor 18 relative to the body tissue 12 and 14. The disclosure in U.S. Pat. No. 5,948,002 is hereby incorporated herein by this reference thereto.

The anchor 18 is held in the inserter 28 with the leading end portion 34 of the anchor extending from the inserter. The pusher member 30 engages the trailing end portion 32 of the anchor 18 to block movement of the anchor along the passage 286 in a direction away from the exit opening 288.

The longitudinal central axis of the inserter 28 is then positioned in an orientation relative to the body tissue 12 corresponding to the orientation of a path along which the anchor is to be moved into the body tissue. Thus, if the anchor 18 is to be moved straight downward (as viewed in FIG. 2) into the body tissue 12 and into the body tissue 14, the inserter 28 would be positioned with its longitudinal central axis extending generally perpendicular to an outer surface 300 of the body tissue 12. However, in the embodiment of the invention illustrated in FIGS. 1-10, it is desired to move the anchor 18 into the body tissue 12 and 14 along a path which is skewed at an acute angle to the outer surface 30 of the body tissue 12.

In the specific instance illustrated in FIG. 2, the inserter 28 is positioned with its longitudinal axis extending at an angle of approximately 40° to the outer surface 300 of the body tissue 12. However, it is contemplated that the inserter 28 could be positioned with its longitudinal axis extending at an angle of between 30° and 90° to the outer surface 300 of the body tissue 12. The specific angle which is selected between the outer surface 300 of the body tissue 12 and the longitudinal central axis of the inserter 28 will depend upon the desired path of movement of the anchor 18 into the body tissue. It is believed that it may be desired to have the path of movement of the anchor 18 into the body tissue 12 and 14 at an angle of between 30° and 70° to the outer surface 300 of the body tissue.

It is believed that it will be desired to move the anchor 18 for a predetermined distance into the body tissue 14. It is also believed that it may be desired to limit the depth of movement of the anchor into the body tissue 14. In order to enable the anchor to be moved through a substantial distance into the body tissue 14 while minimizing the depth to which the anchor is moved into the body tissue, the path of movement of the anchor into the body tissue is skewed at an acute angle to the outer surface 300 of the body tissue 12. When the anchor 18 is to be moved along a path which is skewed relative to the outer surface 300, it is believed that it may be desired to move the anchor into the body tissue 12 and 14 at an angle of between 30° and 70° to the outer surface 300 of the body tissue.

Once a desired angle for the path of movement of the anchor 18 through the body tissue 12 and into the body tissue 14 has been selected, the inserter 28 and pusher member 30 are moved toward the outer surface 300 of the body tissue 12 with the anchor extending from the inserter, in the manner illustrated in FIG. 2. The pointed leading end portion 34 of the anchor 18 is moved into engagement with an imperforate area on the outer surface 300 of the body tissue 12. As the inserter 28 and pusher member 300 continue to move along their longitudinal central axes toward the body tissue 12, the pointed leading end portion 34 of the anchor 18 initiates the formation of an opening in the outer surface 300 of the body tissue 12.

Continued movement of the inserter 28 and pusher member 30 toward the body tissue 12 causes the anchor 18 to pierce body tissue 12. As the anchor 18 moves through the body tissue 12, the pointed leading end portion of the anchor moves into engagement with an imperforate area on an outer surface 304 of the hard outer layer 278 of the bone 14. It should be understood that the body tissue 12 could have a thickness which is greater than the thickness illustrated schematically in FIG. 2. It is contemplated that the body tissue 12 could have a thickness which is substantially greater than the axial extent of the anchor 18.

The pointed leading end portion 34 of the anchor 18 then initiates the formation of an opening in an imperforate area on the surface 304 on the hard outer layer 278 of the bone. Continued movement of the inserter 28 along its path of movement moves the leading end portion 34 of the anchor into the hard outer layer 278 of the bone, in the manner illustrated schematically in FIG. 3. As this occurs, the inserter 28 moves through the soft tissue 12 into abutting engagement with the outer surface 304 on the hard outer layer 278 of the bone 14.

The axial force applied against the inserter 28 is insufficient to cause the inserter to penetrate the hard outer layer 278 of the bone 14. Therefore, movement of the inserter 28 along its longitudinal central axis relative to the body tissue 12 and 14 is interrupted when the leading end portion of the inserter engages the outer surface 304 of the hard outer layer 278 of the bone 14. At this time, the leading end portion 34 of the anchor 18 will have initiated penetration of the outer layer 278 of the bone 14 (FIG. 3).

The movement of the inserter along the path of insertion of the anchor 18 into the body tissue 12 and 14 has been illustrated in FIG. 3 as being interrupted when the inserter engages outer surface 304 of the bone 14. However, it is contemplated that movement of the inserter 28 along the path of insertion of the anchor 18 could be interrupted when the inserter engages the outer surface 300 on the body tissue 12. If this was done, the inserter would be moved from the position illustrated in FIG. 2 along the path of movement of the anchor 18 into the body tissue 12 and 14 until the leading of the inserter engaged the outer surface 300 of the body tissue 12. At this time, the leading end portion 34 of the anchor 18 may or may not have moved into engagement with the bone 14. Whether or not the anchor has moved into engagement with the bone 14 when the inserter 28 engages the outer surface 300 of the body tissue 12 will depend upon the thickness of the body tissue 12, the angle of the path of movement of the anchor relative to the body tissue 12, and the distance which the anchor 18 extends from the inserter 28.

When the tissue 12 is soft tissue and the tissue 14 is bone or other hard body tissue, it is believed that it will be desirable to have the inserter move with the anchor 18 during initiation of penetration of the anchor into the hard body tissue. However, when the body tissue 14 is soft body tissue, it may not be desired to have the inserter hold the trailing end portion 32 of the anchor during initiation of penetration of the anchor into the body tissue 14.

It is contemplated that it may be desired to move the inserter 28 into the bone 14. Thus, the inserter 28 could be moved through the hard outer layer 278 of the bone 14 into the cancellous bone 280. This would have the advantage of enabling the inserter 28 to at least partially support the anchor 18 as the anchor moves through the hard outer layer 278 of the bone 14.

In the embodiment of the invention illustrated in FIGS. 1-10, the body tissue 14 is hard body tissue, that is, bone. It is believed that initiation of penetration of the anchor into the hard outer layer 278 of the bone 14 will be facilitated by having the anchor held in the inserter 28 as the pointed leading end portion 34 begins to move through the imperforate outer surface 304 of the outer layer 278. Therefore, it is believed that it may be desired to move the inserter 28 through the soft body tissue 12 into engagement with the outer surface 304 of the bone 14 during at least the initiation of formation of an opening in the hard outer layer 278 of the bone 14.

Once the inserter 28 has moved into engagement with the outer surface 304 of the bone 14 and movement of the inserter relative to the bone 14 is interrupted, the pusher member 30 is moved relative to the inserter 28 to apply force against the trailing end portion 32 of the anchor and to move the anchor further into the bone 14, in the manner illustrated in FIG. 4. Thus, the inserter 28 is held stationary relative to the body tissue 12 and 14 while the pusher member 30 is moved axially along the longitudinal central axis of the inserter 28. The pusher member is telescopically extended from the inserter 28 and moves the anchor 18 through the hard outer layer 278 of the bone 14 into the relatively soft cancellous bone 280 (FIG. 4).

As this occurs, the suture 24 moves along the slot 292 in the inserter 28. As the anchor 18 moves into the bone 14, the anchor pulls the suture 24 into the bone. This results in movement of the suture 24 along the slot 292 in the inserter 28. As the anchor 18 moves into the cancellous bone 280, the leading end portion 34 of the anchor pierces the cancellous bone.

The anchor 18 is moved into the body tissue 12 and 14 along an insertion path which is skewed at an acute angle to the outer surface 300 of the body tissue 12 and the outer surface 304 of the body tissue 14. Therefore, the distance which the anchor 18 is moved into the bone 14 tends to be maximized while the depth, as measured perpendicular to the outer surfaces 300 and 304 of the body tissue 12 and 14, of insertion of the anchor is minimized.

If the inserter 28 was positioned in engagement with the outer surface 304 of the bone 14 with the longitudinal central axis of the inserter extending perpendicular to the outer surface of the bone, and if the pusher member 300 was moved through the same distance relative to the inserter 28 from the retracted condition shown in FIG. 3 to the extended condition shown in FIG. 4, the anchor 18 would be moved further into the bone 14 as measured along a path extending perpendicular to the outer surface 304 of the bone. It is believed that in at least some locations in a patient's body, it will be desired to have the distance which the anchor is moved into the bone 14 maximized while at the same time minimizing the depth of penetration of the anchor. This may be due to the bone 14 being relatively thin, the particular configuration of the bone 14, or other causes.

In order to increase the resistance of the anchor to pull out under the influence of tension forces in the suture 24, the anchor is toggled or pivoted from the orientation illustrated in FIG. 4 to the orientation illustrated in FIG. 5. This results in the anchor being moved from a position in which a longitudinal central axis of the anchor is aligned with the longitudinal central axis of a path of movement of the anchor into the bone 14 (FIG. 4) to a position in which the longitudinal central axis of the anchor is skewed relative to the path of movement of the anchor into the bone 14 (FIG. 5).

Once the anchor 18 has been moved to the desired depth in the bone 14 (FIG. 4), toggling movement of the anchor is initiated by tensioning the connector portion 48 and leg portion 50 of the suture 24. A sloping or bevel surface 310 is provided on the leading end portion of the pusher member 30 to facilitate initiation of the pivotal movement of the anchor 18 relative to the pusher member 30. The force applied against the anchor 18 by the suture 24 pulls the anchor back or upward (as viewed in FIG. 4) toward the surface 310 on the pusher member 30. Therefore, the tension in the suture 24 tends to rotate the anchor 18 in a counterclockwise direction from the position illustrated in FIG. 4 to the position illustrated in FIG. 5 relative to the soft cancellous bone 280.

As the anchor 18 is pivoted, the upper (as viewed in FIG. 5) portion of the anchor deflects the soft cancellous bone tissue 280. The viscoelastic nature of the soft cancellous bone tissue 280 causes the tissue to tend to close behind the anchor as it is pivoted upward to the position shown in FIG. 5. The manner in which the anchor 18 is pivoted relative to the body tissue is similar to that disclosed in U.S. Pat. Nos. 5,948,002; 5,941,900; and 5,403,348.

Once the anchor 18 has been moved to the position illustrated in FIG. 5, the pusher member 30 is withdrawn from the body tissue 12 and 14. This results in the anchor 18 being supported in the body tissue 12 and 14 by the cancellous bone 280. The anchor 18 is spaced from the hard outer layer 278 of the bone 14. Therefore, tension forces in the suture 24 are transmitted from outer side surfaces of the anchor to the cancellous bone 280 while the anchor is maintained in a spaced apart relationship with the hard outer layer 278 of bone. The manner in which the anchor 18 is supported in the cancellous bone 280 in a spaced apart relationship with the hard outer layer 278 of bone is the same as is disclosed in U.S. Pat. No. 6,077,292.

Rotating the anchor 18 relative to the path of movement of the anchor into the body tissue 12 and 14 increases the resistance of the anchor to pull out forces transmitted through the suture 24 to the anchor. The anchor 18 could remain in the bone 14 in the orientation shown in FIG. 4 in which the longitudinal central axis of the anchor is coincident with the longitudinal central axis of the path along which the anchor moves into the bone. However, by toggling or pivoting the anchor from the position shown in FIG. 4 to the position shown in FIG. 5 the resistance of the anchor to pull out forces tends to be increased. Of course, if the anchor is to be subjected to only relatively small pull out forces, the anchor could be left in the position shown in FIG. 4 relative to the bone 14 without being pivoted to the orientation illustrated in FIG. 5.

In the embodiment of the invention illustrated in FIGS. 1-10, the anchor 18 is moved into the body tissue 12 and 14 from the initial position of FIG. 2 to the intermediate position of FIG. 4 along a linear path. However, the anchor 18 could be moved from the initial position (FIG. 2) to the intermediate position (FIG. 4) along a nonlinear path if desired. For example, the anchor 18 could be moved along an arcuate path from the initial position to the intermediate position.

When the anchor 18 is to be moved along an arcuate path from the initial position (FIG. 2) to the intermediate position (FIG. 4), the inserter 28 and pusher member 30 may be formed with an arcuate configuration. The arcuate configuration of the inserter 28 and pusher member 30 would be the same as the arcuate configuration of the path along which the anchor 18 is to be moved into the body tissue 12 and 14.

When the inserter 28 and pusher member 30 have a rigid construction, it is believed that it may be desired to form the passage 286 in the inserter and to form the pusher member 30 to have the same arc of curvature. This is done to facilitate movement of the pusher member 30 along the passage 286 in the inserter 28. However, it is contemplated that the inserter 28 and/or pusher member 30 could have a flexible construction if desired. For example, the inserter 28 and pusher member 30 could have a construction similar to the construction disclosed in U.S. Pat. No. 5,897,574. The disclosure in U.S. Pat. No. 5,897,574 is hereby included herein in its entirety by this reference thereto.

The anchor 20 is moved through the soft body tissue 12 into the hard body tissue 14 in the same manner as in which the anchor 18 is moved through the soft body tissue into the hard body tissue. Thus, the anchor 20 is positioned in an inserter 38 (FIG. 6) having the same construction as the inserter 28 of FIG. 3. A pusher member 40 (FIG. 6) is telescopically moved along the inserter 38 into engagement with the trailing end portion 42 of the anchor 20 in the same manner as previously described in conjunction with the anchor 18, pusher member 30 and inserter 28 of FIG. 3.

The leg portion 52 of the suture 24 and the connector portion 48 of the suture are at least partially received in a slot 316 in the inserter 38 in the same manner as in which the suture is received in the slot 292 in the inserter 28 of FIG. 3. The inserter 38 and pusher member 40 have the same construction and cooperate in the same manner as is disclosed in U.S. Pat. No. 5,948,002 and have the same construction and mode of operation as the inserter 28 and pusher member 30 of FIGS. 2-4.

When the anchor 20 is to be used in securing the body tissue 12 to the body tissue 14, the anchor 20 is positioned in the inserter 38 and the pusher member 40 is moved into engagement with the trailing end portion of the anchor. The leading end portion 44 of the anchor is then moved from a position spaced from the body tissue 12 to a position in which the leading end portion engages an imperforate area on the outer surface 300 of the body tissue 12. At this time, the inserter 38 and pusher member 40 are positioned in an angular orientation relative to the surface 300 of the body tissue 12 corresponding to the angle of the desired path of insertion of the anchor 20 into the body tissue 12 and 14.

In the specific situation illustrated in FIG. 6, the path of insertion of the anchor 20 into the body tissue 12 and 14 is skewed at an acute angle of approximately 40° relative to the surface 300 of the body tissue 12. It is contemplated that the path of insertion of the anchor 20 into the body tissue 12 and 14 may be located an at angle between 30° and 90° relative to the surface 300 of the body tissue 12. In order to reduce the depth of insertion of the anchor 20 into the bone 14, it is believed that it may be desired to have the path of movement of the anchor 20 into the body tissue 12 and 14 skewed at an acute angle of between 30° and 70° relative to the surface 300 of the body tissue 12.

When the inserter 38 and pusher member 40 have been positioned with their longitudinal central axes coincident with the longitudinal central axis of the desired path of movement of the anchor 20 into the body tissue 12 and 14, the pusher member 40 and inserter 38 are moved together toward the surface 300 of the body tissue 12. As this occurs, the pointed leading end portion 44 of the anchor 20 initiates the formation of an opening in the surface 300 of the body tissue 12.

The inserter 38, pusher member 40, and anchor 20 continue to move together relative to the body tissue 12 and 14 as the anchor pierces the body tissue 12. When the pointed leading end portion 44 of the anchor 20 engages an imperforate portion of the outer surface 304 of the bone 14, the leading end portion 44 of the anchor initiates formation of an opening in the outer surface 304 of the bone 14.

Continued movement of the inserter 38, pusher member 40 and anchor 20 together along the path of insertion of the anchor into the body tissue 12 and 14 results in the leading end portion 44 of the anchor moving into the hard outer layer 278 of the bone 14 in the manner illustrated in FIG. 6. As this occurs, the inserter 38 moves into engagement with the outer surface 304 of the bone 14. Movement of the inserter 38 relative to the bone 14 is interrupted with the inserter in engagement with the outer surface 304 of the bone, in the manner illustrated schematically in FIG. 6.

It may be desired to move the inserter 38 through the body tissue 12 into engagement with the bone 14, in the manner illustrated in FIG. 6. This results in the anchor 20 being supported by the inserter 38 as the anchor initially penetrates the hard outer layer 278 of the bone 14. The anchor 20, inserter 38 and pusher member 40 are moved together along the path of movement of the anchor into the body tissue 12 and 14 until the inserter 38 engages the surface 304 on the hard outer layer 278 of the bone. By the time the inserter 38 engages the surface 304 on the hard outer layer 278 of the bone 14, the leading end portion of the anchor has moved into the hard outer layer of the bone (FIG. 6).

When the inserter 38 moves into engagement with the outer surface 304 of the bone 14, movement of the inserter relative to the bone is interrupted. The pusher member 40 is then moved relative to inserter 38. Movement of the pusher member 40 relative to the inserter 38 applies force against the trailing end portion 42 of the anchor 20 and moves the anchor 20 into the bone 14. The anchor 20 is moved into the bone 14 through the hard outer layer 278 and into the cancellous bone 280 as the pusher member 40 is telescopically extended from the inserter 38 (FIG. 7). As the anchor 20 moves into the bone 14, the suture 24 moves along the slot 316 in the inserter 38.

Once the anchor 20 has been moved to the desired depth in the cancellous bone 280, the pusher member 40 and inserter 38 may be withdrawn from the body tissue 12 and 14 and the anchor left in the orientation illustrated in FIG. 7 relative to the body tissue. Thus, the anchor may remain in the cancellous bone 280 with a longitudinal central axis 320 of the anchor aligned with the central axis of the path of movement of the anchor into the body tissue 12 and 14. Alternatively, the orientation of the anchor relative to the path of movement of the anchor into the body tissue 12 and 14 may be changed to increase the resistance to the anchor to pull out forces transmitted through the suture 24.

When the orientation of the anchor 20 is to be changed relative to the bone 14 from the orientation illustrated in FIG. 7 to the orientation illustrated in FIG. 8, the suture 24 is tensioned. Tensioning the suture 24 tends to pivot the anchor 20 in a clockwise direction (as viewed in FIGS. 7 and 8) about a location where the trailing end portion 42 of the anchor engages the pusher member 40. The pusher member 40 has a bevel surface 324 which extends transversely to a longitudinal central axis of the pusher member 40. The bevel surface 324 facilitates pivotal movement of the anchor 20 relative to the pusher member 40.

When the anchor 20 has been pivoted to the orientation illustrated in FIG. 8, the pusher member 40 is telescopically moved back into the inserter 38. The inserter 38 and pusher member 40 are then withdrawn from the body tissue 12. When the anchor 20 is in the orientation shown in FIG. 8, the central axis 320 of the anchor extends transverse to the path of movement of the anchor into the bone 14. This increases the pull out force which is required to remove the anchor from the bone.

After the anchors 18 and 20 have been moved into the bone and toggled to the orientations illustrated in FIGS. 5 and 8, the anchors are pointed toward each other (FIG. 9). Thus, the leading end portion 34 of the anchor 18 points toward the anchor 20 and the leading end portion 44 of the anchor 20 points toward the anchor 18. At this time, the longitudinal central axis 260 of the anchor 18 extends generally parallel to the outer surface 300 of the body tissue 12 and to the outer surface 304 of the bone 14. Similarly, the central axis 320 of the anchor 20 extends parallel to the outer surface 300 of the body tissue 12 and to the outer surface 304 of the bone 14. At this time, both the anchors 18 and 20 are supported by the cancellous bone 280 in a spaced apart relationship with the hard outer layer 278 of the bone 14.

In FIG. 9, the central axes 260 and 320 of the anchors 18 and 20 are disposed in a plane which extends perpendicular to the outer surface 300 of the body tissue 12 and the outer surface 304 of the body tissue 14. However, it is contemplated that the axes 260 and 320 of the anchors 18 and 20 could be offset relative to each other. For example, one of the axes 260 or 320 could be offset from the other axis in a direction extending into the sheet on which the drawing of FIG. 9 is disposed. In addition, rather than being generally parallel to the outer surfaces 300 and 304 of the body tissue 12 and 14, the axes 260 and 320 of the anchors 18 and 20 could be skewed at a greater angle relative to the outer surfaces of the body tissue.

The paths of movement of the anchors 18 and 20 into the body tissue 12 and 14 have central axes disposed in a plane which extends perpendicular to the outer surfaces 300 and 304 of the body tissue 12 and 14. However, the path of movement of one of the anchors, for example, the anchor 18, into the body tissue 12 and 14 could have a central axis which is offset from the central axis of the path of movement of the other anchor into the body tissue.

Regardless of whether or not the central axes of the paths along which the anchors 18 and 20 move into the body tissue 12 and 14 are disposed in the same plane, it is believed that it may be desired to have the paths extend toward each other. Thus, the path along which the anchor 18 moves into the body tissue 12 and 14 extends toward the path along which the anchor 20 moves into the body tissue. Even though the central axes of the paths along which the anchors move into the body tissue are not disposed in a common plane, the anchor 18 moves toward the location where the anchor 20 enters the body tissue 12 and 14 as the anchor 18 is moved into the body tissue. Similarly, the anchor 20 moves toward locations where the anchor 18 moved into the body tissue 12 and 14 as the anchor 20 is moved into the body tissue.

By having the anchors 18 and 20 move along insertion paths which extend toward each other, even though central axes of the insertion paths may not be disposed in a common plane, the anchors approach each other as they move in the cancellous material of the bone 14. This results in the suture 24 being effective to press the body tissue 12 against the body tissue 14 with a clinching action. The clinching action with which the suture 24 presses the body tissue 12 against the bone 14 is similar to the clinching action which is obtained by the legs of a staple. This clinching action increases the force which is transmitted from the suture 24 to the body tissue 12 and increases the resistance of the anchors 18 and 20 to pull out under the influence of tension forces in the suture.

Although it is believed that it may be desired to move the anchors 18 and 20 toward each other along their insertion paths to decrease the distance between the anchors as they move into the body tissue 14, the anchors could be moved along insertion paths which are either parallel or diverge. For example, the insertion path of the anchor 18 into the body tissue 12 and 14 could extend parallel to the insertion path of the anchor 20 into the body tissue. If this was done, the insertion paths of the anchors 18 and 20 would have parallel central axes disposed in a plane extending perpendicular to the outer surfaces 300 and 304 of the body tissue 12 and 14.

Alternatively, it is contemplated that the anchors 18 and 20 could be moved into the body tissue 12 and 14 along diverging insertion paths. Thus, the anchor 18 could be moved along an insertion path which extends parallel to the illustrated insertion path of the anchor 20 in FIG. 7. Similarly, the anchor 20 could be moved along an insertion path which extends parallel to the insertion path of the anchor 18 in FIG. 4. It should be understood that the angular orientation of the insertion paths for the anchors 18 and 20 relative to each other will depend upon the specific environment in which the anchors are utilized.

In the embodiment of the invention illustrated in FIGS. 1–10, the anchor 20 is moved into the body tissue 12 and 14 from an initial position to the intermediate position of FIG. 7 along a linear path. However, the anchor 20 could be moved from the initial position to the intermediate position (FIG. 7) along a nonlinear path if desired. For example, the anchor 20 could be moved along an arcuate path from the initial position to the intermediate position.

When the anchor 20 is to be moved along an arcuate path from the initial position to the intermediate position, the inserter 38 and pusher member 40 may be formed with an arcuate configuration. The arcuate configuration of the inserter 38 and pusher member 40 would be the same as the arcuate configuration of the path along which the anchor 20 is to be moved into the body tissue 12 and 14.

When the inserter 38 and pusher member 40 have a rigid construction, it is believed that it may be desired to form the passage in the inserter and to form the pusher member 40 to have the same arc of curvature. This is done to facilitate movement of the pusher member 40 along the passage in the inserter 38. However, it is contemplated that the inserter 38 and/or pusher member 40 could have a flexible construction if desired. For example, the inserter 38 and pusher member 40 could have a construction similar to the construction disclosed in U.S. Pat. No. 5,897,574.

Once the anchors 18 and 20 have been moved to the position illustrated in FIG. 9, ends of the leg portions 50 and 52 of the suture are positioned in an opening in the retainer or crimp 54. While the leg portions 50 and 52 of the suture are tensioned at a location above the retainer 54, as viewed in FIG. 9, the retainer is moved downward toward the body tissue 12. As the retainer 54 is moved downward toward the body tissue 12, the tension in the connector portion 48, leg portion 50 and leg portion 52 of the suture is increased.

By initially providing the connector portion 48 of the suture with a length which is slightly less than the length illustrated in FIG. 9, the connector portion 48 of the suture 24 is tensioned as the anchor 20 is moved into the bone 14. This is because as the anchor 20 moves into the bone 14, the anchor pulls the suture 24 into the bone. If the connector portion of the suture 48 is shorter than is required when the anchors 18 and 20 have been moved to the positions illustrated in FIG. 9, the connector portion of the suture 48 is tensioned as the anchor 20 moves into the bone 14. This tensioning of the connector portion 48 of the suture 24 causes the suture to move relative to the anchor 20 in the passages 266 and 268. As this occurs, the length of the leg portion 52 of the suture 24 is decreased and the length of the connector portion 48 of the suture is increased.

After the anchors 18 and 20 have been positioned in the body tissue 14, the surgeon pulls on the free end of the leg portions 50 and 52 and moves the retainer 54 toward the body tissue 12. As this occurs, the leg portions 50 and 52 of the suture 24 are tensioned. Any excess material in the connector portion 48 of the suture 24 is pulled from the connector portion 48 by movement of the suture relative to the anchors 18 and 20 and a resulting increasing of the overall length of the leg portions 50 and 52. Since the suture 24 is movable in the passages 254, 256, 266 and 268 in the anchors 18 and 20, the same tension is present in the connector portion 48 and leg portions 50 and 52 of the suture 24.

When the retainer 54 has been moved downward into engagement with the outer surface 300 of the body tissue 12 and the desired tension is present in the connector portion 48 and leg portions 50 and 52 of the suture 24, the crimp is plastically deformed to grip the leg portions of the suture. Plastic deformation of the suture retainer results in cold flowing of the material of the suture retainer. If desired, energy, such as heat or vibrational energy, may be transmitted to the retainer 54 to facilitate plastic deformation of the material of the retainer under the influence of force applied against opposite sides of the retainer.

The retainer 54 may be plastically deformed in the same manner as disclosed in U.S. patent application Ser. No. 09/685,795 filed Oct. 10, 2000 by Peter M. Bonutti et al. and entitled "Method and Apparatus for Securing a Suture". The disclosure in the aforementioned application Ser. No. 09/685,795 is hereby incorporated herein in its entirety by this reference thereto.

It is contemplated that the suture retainer 54 could be plastically deformed in other ways if desired. For example, ultrasonic vibratory energy may be transmitted to the material of the suture retainer 54 to effect heating of at least some of the material of the suture retainer. The ultrasonic vibratory energy may be applied while the suture 54 is being tensioned with a predetermined force and while a predetermined force is being transmitted from the connector portion 48 and leg portions 50 and 52 of the suture 24 to the body tissue 12. It is contemplated that the suture retainer 54 may be deformed by the use of ultrasonic vibratory energy in the manner disclosed in U.S. patent application Ser. No. 09/524,397 filed Mar. 13, 2000 by Peter M. Bonutti et al. and entitled "Method of Using Ultrasonic Vibration to Secure Body Tissue". The disclosure in the aforementioned application Ser. No. 09/524,397 is hereby incorporated herein in its entirety by this reference thereto.

In the embodiment of the invention illustrated in FIG. 9, the connector portion 48 and leg portions 50 and 52 of the suture 24 are pressed against the body tissue 12 by tension in the suture. If desired, a protective member, such as a pledget, may be positioned between the suture 24 and the body tissue 12. The protective member may be provided with openings through which the suture 24 extends into the body tissue 12. During tensioning of the suture 24, the retainer 54 may be moved into engagement with the protective member. The protective member may have the same construction as any of the protective members disclosed in U.S. Pat. No. 4,823,794.

It is believed that it may be desired to tension the suture 24 with a predetermined tension. It is also believed that it will be desired to transmit a predetermined force from the retainer 54 to the body tissue 12 during tensioning of the suture 24. This may be accomplished by utilizing the apparatus which is illustrated schematically in FIG. 10.

The apparatus includes of FIG. 10 the force application assembly 60 which applies an upwardly (as viewed in FIG. 10) directed force 62 to the leg portions 50 and 52 of the suture 24. Contemporaneously with the application of the predetermined tension force 62 to the leg portions 50 and 52 of the suture 24, the force application member 66 presses the suture retainer 54 downward toward the body tissue 12 with a predetermined force indicated by the arrows 70 and 72 in FIG. 10. While the predetermined tension force 62 is applied to the suture 24 and the predetermined forces 70 and 72 are applied to the retainer 54 by the force application member 66, the retainer is plastically deformed under the influence of forces 80 and 82 applied against opposite sides of the retainer by the force application members 76 and 78.

Although the leg portions 50 and 52 of the suture 24 could extend straight through the suture retainer 54, it is preferred to form a plurality of bends in the leg portions 50 and 52 of the suture 24. In the illustrated embodiment of the suture retainer 54, two bends are formed in the leg portion 50 of the suture 24 as it is wrapped around the suture retainer 54. Similarly, two bends are formed in the leg portion 52 of the suture 24 as it is wrapped around the suture retainer 54.

The suture retainer 54 has a spherical configuration. A cylindrical passage 340 extends through the center of the spherical suture retainer 54. If desired, the suture retainer 54 could have a different configuration. For example, the suture retainer 54 could have an oval or elliptical configuration. Although the passage 340 has a linear central axis, the passage could have a nonlinear central axis. If desired, a plurality of passages having the same or different configurations could be provided in the suture retainer 54. The suture retainer 54 could have any one of the constructions disclosed in the aforementioned U.S. patent application Ser. Nos. 09/685,795 and 09/524,397.

After the leg portions 50 and 52 of the suture 24 have been inserted through the suture retainer 54, in the manner indicated schematically in FIG. 10, the suture retainer is moved along the leg sections 50 and 52 to tension the leg sections of the suture 24. The downward forces 70 and 72 are then applied against the suture retainer 54 by the force application member 66. This downward force results in the transmission of a predetermined force from the suture retainer to the body tissue 12 as the leg portions 50 and 52 of the suture 24 are tensioned with a predetermined tension force.

While the predetermined tension is maintained in the leg portions 50 and 52 and the connector portion 48 of the suture 24 and while the suture retainer 54 is being pressed downward against the body tissue 12 with a predetermined force, the force application members 76 and 78 are pressed against opposite sides of the suture retainer 54. The force applied against the suture retainer member 54 by the force application members 76 and 78 plastically deforms the material of the suture retainer. If desired, ultrasonic vibratory energy could be applied to the suture retainer 54 by either or both of the force application members 76 and 78.

The force applied against the material of the suture retainer 54 results in a collapsing of the passage 340. In addition, cold flowing of the material of the suture retainer results in a flow of the material around the leg portions 50 and 52 of the suture 24.

A transducer or load cell 344 is provided to measure the amount of force, indicated by the arrow 62, which is utilized to tension the leg portions 50 and 52 of the suture. While the predetermined tension force is applied to the leg portions 50 and 52 of the suture, the force application members 76 and 78 are applying clamping forces against opposite sides of the suture retainer. Upon disengagement of the force application members 76 and 78 from the suture retainer 54, the application of downward (as viewed in FIG. 10) force against the suture retainer 54 is also interrupted. The upward tensioning of the leg portions 50 and 52 of the suture 24 is also interrupted.

The suture retainer 54 may be formed of many different materials. However, it is believed that it will be preferred to form the suture retainer 54 of a biodegradable polymer. One biodegradable polymer which may be utilized is polycaperlactone. Alternatively, the suture retainer could be formed of polyethylene oxide terephthalate or polybutylene terephthalate. It is also contemplated that other biodegradable or bioerodible copolymers could be utilized if desired.

Although it is preferred to form the suture retainer 54 of a biodegradable material, the suture retainer could be formed of a material which is not biodegradable. For example, the suture retainer 54 could be formed of an acetyl resin such as "Delrin" (trademark). Alternatively, the suture retainer 54 could be formed of a para-dimethylamino-benzenediazo sodium sulfonated, such as "Dexon" (trademark). If desired, the suture retainer 54 may be formed of the same material as the suture 24. However, the suture retainer 54 could be formed of a material which is different than the material of the suture 24. The manner in which the suture retainer 54 cooperates with the suture 24 is the same as is disclosed in the aforementioned U.S. patent application Ser. No. 09/685, 795 filed Oct. 10, 2000 by Peter M. Bonutti et al. and entitled "Method and Apparatus for Securing a Suture.

In the embodiment of the invention illustrated in FIGS. 1-10, the suture 24 is tightened with a desired tension by pulling on the leg portions 50 and 52 of the suture. The tension is maintained in the suture 24 by the retainer 54. However, if desired, the suture 24 could be further tensioned by the application of heat to the suture. The application of heat to the polymeric material of the suture 24 causes the suture to shrink and increase the tension in the suture.

Rather than using the suture retainer 54 to interconnect the leg portions 50 and 52, the leg portions could be bonded to each other. This could be accomplished by the application of heat and/or ultrasonic vibratory energy to the leg portions. The application of heat and/or ultrasonic vibratory energy to the leg portions 50 and 52 causes them to weld together in the manner disclosed in the aforementioned U.S. patent application Ser. No. 09/524,397 filed Mar. 13, 2000 by Peter M. Bonutti et al. and entitled "Method of Using Ultrasonic Vibration to Secure Body Tissue".

Embodiment of FIG. 11

In the embodiment of FIG. 11, the anchors 18a and 20a are interconnected by a suture 24a which forms a continuous loop. By forming a continuous closed loop with the suture 24a, anchors 18a and 20a are interconnected when the anchors are moved into the body tissue 12a and 14a.

In the illustrated embodiment of the invention, the suture 24a is formed into a continuous flexible ring by the application of ultrasonic energy to end portions of the suture. This may be accomplished in the manner disclosed in the aforementioned U.S. patent application Ser. No. 09/524,397 filed Mar. 13, 2000. The continuous loop of the suture 24a may be closed to form a flexible ring by knotting together opposite ends of a length of suture. Alternatively, opposite ends of a length of suture material may be spliced or bonded together to form a continuous closed loop. If desired, a connector member formed of polymeric material could be utilized to interconnect opposite ends of a length of suture material to form the continuous closed loop.

The loop of the suture 24a forms a continuous flexible ring which extends through passages 254a and 256a in the suture anchor 18a. The continuous flexible ring formed by the suture 24a extends through passages 266a and 268a in the anchor 20a. The continuous loop or flexible ring formed by the suture 24a is freely movable in the passages 254a and 256a in the anchor 18a and in the passages 266a and 268a in the anchor 20a. This enables the length of the connector portion 48a and the connector portion 90 of the suture 24a to be varied as the suture anchors 18a and 20a are positioned relative to the body tissue 12a and 14a.

The anchor 18a has the same construction as the suture anchor 18 of FIGS. 1-10. Similarly, the anchor 20a has the same construction as the suture anchor 20 of FIGS. 1-10. Although the suture 24a forms a continuous closed loop between the suture anchors 18a and 20a, the suture 24a is formed of the same material as the suture 24 of FIGS. 1-10.

It should be understood that the anchors 18a and 20a may be formed with any of many known configurations, including the configurations illustrated in FIGS. 18 and 19 herein. It should also be understood that the anchors 18a and 20a maybe formed of any of many known materials, including the anchor materials mentioned herein in association with the embodiment of FIGS. 1-10. The suture 24a may be formed with any known suture constructions mentioned herein in association with the embodiment of FIGS. 1-10. The suture 24a may be formed of many known materials, including the suture materials mentioned herein in association with the embodiment of FIGS. 1-10.

The apparatus 10a of FIG. 11 is associated with body tissue 12a and 14a having arcuate outer surfaces 300a and 304a. In the illustration of FIG. 11, the body tissue 14a is hard body tissue, that is bone, while the body tissue 12a is soft body tissue, such as a tendon or ligament. However, it should be understood that both the body tissue 12a and the body tissue 14a could be soft body tissue.

If the body tissue 12a and 14a are both soft body tissue, the apparatus 10a would be utilized to connect the soft body tissue 12a with the soft body tissue 14a in a manner similar to the disclosure in U.S. Pat. No. 5,464,426 to Peter M. Bonutti for "Method of Closing Discontinuity in Tissue". In the event that both of the body tissues 12a and 14a are soft body tissue, the anchors 18a and 20a may be embedded in the soft tissue forming the soft tissue 14a in much the same manner as is illustrated in FIG. 11. However, it is also contemplated that the anchors 18a and 20a could be moved into and through the soft body tissue 12a and into and through the soft body tissue 14a.

In the illustration of FIG. 11, the body tissue 14a is bone having a hard outer layer 278a which encloses a relatively soft cancellous bone 280a. The body tissue 12a and 14a may be many different tissues in a patient's body. For example, the tissue 12a could be a meniscus and the tissue 14a could be a bone in a patient's leg. Alternatively, the tissue 12a could be a rotor (musculotendinous) cuff and the tissue 14a could be a bone in an upper portion of a patient's body. The body tissues 12a and 14a could be vascular tissue.

An inserter and pusher member corresponding to the inserter 28 and pusher member 30 of FIG. 2 are utilized to move the anchor 18a into and through the body tissue 12a and into the body tissue 14a. As the anchor 18a moves into the body tissue 12a, a pointed leading end portion 34a of the anchor 18a initiates the formation of an opening in an imperforate surface on the outer surface 300a of the body tissue 12a. As the anchor 18a moves into and through the soft body tissue 12a, the leading end portion 34a is utilized to pierce the body tissue 12a.

As the anchor 18a moves through the body tissue 12a, the leading end portion 34a of the anchor 12a moves into engagement with the outer surface 304a on the hard outer layer 278a of the bone 14a. The force applied against the anchor 18a by the pusher member causes the leading end portion 34a of the anchor 18a to initiate the formation of an opening at an imperforate area on the outer surface 304a of the hard outer layer 278a. As the anchor 18a is moved into the hard outer layer 278a, the leading end portion 34a of the anchor pierces the outer layer ahead of the pusher member. As the anchor 18a moves through the outer layer 278a, the leading end portion 34a of the anchor initiates the formation of an opening in the soft cancellous bone 280a. As the anchor 18a is pushed into the soft cancellous bone 280a by the pusher member, the leading end portion 34a of the anchor 18a deforms the soft cancellous bone.

The anchor 18a moves through the soft body tissue 12a and the hard outer layer 278a of the bone 14a into the soft cancellous bone 280a along an insertion path having a straight longitudinal central axis 350. However, the anchor 18a could be moved along a nonlinear path if desired. As the suture anchor 18a moves through the body tissue 12a into the body tissue 14a, a longitudinal central axis 260a of the anchor 18a is coincident with the longitudinal central axis 350 of the path along which the anchor moves into the body tissue.

Once the anchor 18a has been moved to a desired depth in the body tissue 14a, the pusher member 30 (FIG. 4) may be moved from the extended condition back to the retracted condition of FIG. 3. The inserter, corresponding to the inserter 28 of FIGS. 3 and 4, may then be withdrawn from the body tissue 12a.

Alternatively, the orientation of the anchor 18a may be changed from an orientation in which the longitudinal central axis 360a of the anchor 18a is aligned with the longitudinal central axis 350 of the path along which the anchor is inserted into the body tissue 12a and 14a to an orientation in which the central axis 260a of the anchor extends transverse to the longitudinal central axis 350 of the insertion path. It is believed that it may be desired to change the orientation of the anchor 18a relative to the insertion path in order to increase the resistance of the anchor to tension forces transmitted through the suture 24a to the anchor 18a.

In order to move the anchor 18a from an orientation in which the longitudinal central axis 260a of the anchor is aligned with the longitudinal central axis 350 of the insertion path to the orientation illustrated in FIG. 11, the suture 24a is tensioned. The tension forces initiate a toggling or pivoting action about the end portion of the pusher member which engages the anchor 18a. This toggling action occurs in the same manner as was previously discussed in conjunction with the embodiment of the invention illustrated in FIGS. 4 and 5.

Once the anchor 18a has been pivoted to the desired orientation relative to the body tissue 14a, the pusher member is telescopically withdrawn into the inserter and the inserter is removed from the soft body tissue 12. The viscoelastic nature of the body tissues 12a and 14a cause the passages formed by the anchor 18a to constrict as the pusher member and inserter are withdrawn from the body tissues 12a and 14a.

Once the anchor 18a has been positioned in the body tissue 14a, in the manner illustrated schematically in solid lines in FIG. 11, the anchor 20a is positioned in the body tissue 14a. To position the anchor 20a in the body tissue 14a, the anchor is moved from the position illustrated in solid lines in FIG. 11 along an insertion path having a central axis 354. The insertion path along which the anchor 20a is moved into the body tissue 12a and 14a may be either linear or nonlinear.

An inserter and pusher member, corresponding to the inserter 38 and pusher member 40 of FIGS. 6 and 7, are utilized to move the suture anchor 20a through the body tissue 12a and into the body tissue 14a in the same manner as previously described in conjunction with the embodiment of the invention illustrated in FIGS. 1-10. As the anchor 20a is moved along the insertion path by the pusher member, the longitudinal central axis 320a of the anchor is aligned with the longitudinal central axis 354 of the insertion path.

In the embodiment of the invention illustrated in FIG. 11, the anchors 18a and 20a are formed with pointed leading end portions 34a and 44a. The pointed end portions 34a and 44a enable the anchors 18a and 20a to form their own passages through the body tissues 12a and 14a. However, it is contemplated that the anchors 12a and 14a could be provided with blunt leading end portions. If this was done, passages for the anchors 12a and 14a could be formed in the body tissues by a suitable tool, such as a drill.

As the anchor 20a moves along the insertion path, the suture 24a is tensioned by movement of the anchor 20a. Thus, as the anchor 20a moves along the insertion path, the connector sections 48a and 90 of the suture are tensioned and pressed against the outer surface 300a of the body tissue 12a. The flexible suture 24a conforms to any irregularities in the outer surface 300a of the body tissue 12a and is effective to firmly press the body tissue 12a against the outer surface 304a on the bone 14a.

As the suture 24a moves from the initial loose condition, indicated schematically in solid lines in FIG. 11, to the tensioned condition, indicated schematically in dashed lines in FIG. 11, the suture may move in the passages 266a and 268a in the anchor 20a to enable the length of the connector sections 48a and 90 of the suture 24a to be adjusted. This shifting movement of the suture 24a relative to the anchor 20a results in the same tension forces being present in both connector sections 48a and 90 of the suture 24a.

As the anchor 20a is moved along the insertion path 354, the tension forces in both connector sections 48a and 90a of the suture increase. When a desired tension is present in both of the connector sections 48a and 90 of the suture 24a, movement of the suture anchor 20a along the insertion path is interrupted. Thus, as the anchor 20a is moved into the cancellous bone 280a, the suture 24a is pulled taut between the two anchors 18a and 20a. As the anchor 20a moves along the insertion path, the tension in the suture 24a increases and the force which is transmitted from the suture to the body tissue 12a increases. The increase in force transmitted to the body tissue 12a firmly presses the body tissue against the bone 14a.

In order to enhance the resistance of the anchor 20a to pull out forces applied to the anchor by the suture 24a, the anchor may be pivoted from an orientation in which the longitudinal central axis 320a of the anchor is aligned with the central axis 354 of the insertion path to an orientation in which the central axis of the anchor 20a extends transverse to the central axis of the insertion path. This toggling or pivotal movement of the anchor 20a is initiated by tension in the suture 24a as the anchor is moved along the insertion path by the pusher member. A bevel surface on the leading end portion of the pusher member promotes pivoting or toggling of the anchor relative to the pusher member.

During movement of the anchor 20a along the insertion path 354 by the pusher member, the suture 24a is pulled against the anchor 18a which was initially inserted into the body tissue 14a. As the suture 24a is pulled against the anchor 18a and the anchor 20a moves into the body tissue 14a, a toggling action is automatically initiated by the resulting tension in the suture 24a. This toggling action results in pivotal movement of the anchor 20a about a leading end portion of the pusher member. As the anchor 20a pivots relative to the leading end portion of the pusher member, the anchor moves from an orientation in which the longitudinal central axis 320a of the anchor is coincident with the longitudinal central axis 354 of the insertion path to the orientation illustrated schematically in dashed lines in FIG. 11. As the anchor 20a moves toward the position illustrated in dashed lines in FIG. 11, the central axis 320a of the anchor moves out of alignment with the central axis 354 of the insertion path.

In the embodiment of the invention illustrated in FIG. 11, the central axes 350 and 354 of the insertion paths for the anchors 18a and 20a are disposed in a plane which extends through a center of curvature of the outer surface 300a of the body tissue 12a and a center of curvature of the outer surface 304a of the body tissue 14a. The central axes 350 and 354 of the insertion paths along which the anchors 18a and 20a are moved into the body tissue 12a and 14a intersect at the center of curvature of the outer surface 300a of the body tissue 12a and the outer surface 304a of the body tissue 14a.

Although the central axes 350 and 354 of the insertion paths along which the anchors 18a and 20a are moved into the body tissue 12a and 14a are disposed in a single plane, it is contemplated that the central axes 350 and 354 of the insertion paths could be offset relative to each other. Thus, the central axis 354 could be offset from the central axis 350 in a direction extending into the sheet of the drawing of FIG. 11. Although the central axes 350 and 354 of the insertion paths intersect at the center of curvature of the outer surface 300a of the body tissue 12a and the outer surface 304a of the body tissue 14a, the angle of the axes 350 and 354 relative to the outer surfaces 300a and 304a of the body tissue 12a and 14a could be such that the axes 350 and 354 do not extend through the center of curvature of the surfaces 300a and 304a of the body tissue 12a and 14a.

In the embodiment of the invention illustrated schematically in FIG. 11, the central axes 350 and 354 of the insertion paths of the anchors 18a and 20a extend generally perpendicular to a tangent to the arcuate outer surface 300a of the body tissue 12a. It is contemplated that the central axes 350 and 354 of the insertion paths along which the anchors 18a and 20a are moved into the body tissue 12a and 14a could be skewed at an angle of between 30° and 90° relative to a tangent to the outer surface 300a of the body tissue 12a.

In the embodiment of the invention illustrated in FIG. 11, the anchor 18a is disposed deeper in the body tissue 14a than is the anchor 20a. Thus, the distance which the anchor 18a was moved along its insertion path from the outer surface 304a of the body tissue 14a was greater than the distance which the anchor 20a was moved along its insertion path from the outer surface of the body tissue 14a. It is contemplated that the anchors 18a and 20a could be moved to substantially the same depth in the body tissue 14a if desired. It is also contemplated that the anchor 20a could be moved deeper into the body tissue 14a than the anchor 18a.

The anchors 18a and 20a have been illustrated in FIG. 11 with their longitudinal central axes 260a and 320a extending transverse to each other. It is contemplated that the anchors 18a and 20a could be positioned in the body tissue 14a with their longitudinal central axes 260a and 320a disposed in a parallel relationship. In FIG. 11, the outer side surfaces 300a and 304a of the body tissue 12a and 14a have been illustrated as having an arcuate configuration. However, it is contemplated that the body tissues 12a and 14a could have outer surfaces which have an irregular arcuate configuration, or an irregular generally flat configuration, or a combination of irregular, arcuate and flat configurations. For example, the surface 304a could be disposed on the end of a bone and the central axes 350 and 354 of the insertion paths for the anchors 18a and 20a could be offset so as to extend through the sides of the bone.

It is contemplated that the apparatus 10a will be utilized in many different environments to secure body tissue. Thus, the apparatus 10a may be used to connect a meniscus with a bone in a knee joint of a patient. It is also contemplated that the apparatus 10a may be utilized to connect a rotator cuff with the bone in a shoulder of a patient. The apparatus 10a may be used to interconnect sections of blood vessels. The apparatus 10a may be used to secure mucosa. It should be understood that these are only specific examples of many different locations in a patient's body in which the apparatus 10a may be utilized to secure body tissues.

Although the apparatus 10a has been described in FIG. 11 in conjunction with the connection of soft body tissue 12a with bone 14a, it is contemplated that the apparatus 10a may be utilized to connect one portion of soft body tissue in a patient's body with another portion of the soft body tissue in a patient's body. For example, layers of soft tissue may be positioned in a side-by-side relationship and interconnected using the apparatus 10a. When relatively thin layers of soft tissue are placed in apposition, the anchors 18a and 20a may be moved through the both layers of tissue and disposed adjacent to a side of the tissue in a manner similar to that disclosed in the aforementioned U.S. Pat. No. 5,464,426. Alternatively, the anchors 18a and 20a may be moved through a relatively thin layer of soft body tissue into a relatively thick mass of soft body tissue. When this is done, it is believed that it may be desired to have the anchors embedded in the soft body tissue in the same manner as is illustrated schematically in FIG. 11.

In the foregoing description, the anchor 18a has been inserted into the body tissue 14a before the anchor 20a is inserted into the body tissue 14a. It should be understood that both anchors 18a and 20a could be inserted into the body tissue at the same time. Thus, a first pusher member and inserter, corresponding to the pusher member 30 and inserter 28 of FIG. 2 could be used to move the anchor 18a along a first insertion path into the body tissue 14a at the same time that a second inserter and pusher member, corresponding to the inserter and pusher member 38 and 40 of FIG. 6, are utilized to move the anchor 20a into the body tissue 14a. As this occurs, the rate of insertion of the anchors 18a and 20a could be coordinated so that they would be at the same depth in the body tissue 14a at the same time.

As the anchors 18a and 20a are moved together into the body tissue 14a, the suture 24a is pulled into the body tissue 14a by both of the anchors. This results in the suture 24a being tensioned between the two anchors as both of the anchors move relative to the body tissue 14a. Since both anchors 18a and 20a are being moved at the same time relative to the body tissue 14a, there will be relative movement between the suture 24a and both of the anchors to obtain the required length of suture in the connector portion 48a and 90. Adjusting of the lengths of the connector portions 48a and 90 of the suture 24a is accommodated by the fact that the suture can move in the passages 254a and 256a in the anchor 18a and in the passages 266a and 268a in the anchor 20a.

If desired, both anchors could be left in the body tissue 14a with their longitudinal central axes coincident with the longitudinal central axes of their paths of insertion. Thus, the anchor 18a could be left in the body tissue 14a with its central axis 260a coincident with the central axis 350 of the insertion path of the anchor 18a. Similarly, the anchor 20a could be left in the body tissue 14a with its central axis 320a coincident with the central axis 354 of the insertion path of the anchor 20a into the body tissue 14a. If it is desired to leave the anchors in the body tissue 14a with their central axes 260a and 320a coincident with the central axes 350 and 354 of their insertion paths, the beveled surfaces, corresponding to the surface 310 of FIG. 4 and the surface 324 of FIG. 7 on the pusher members could be omitted.

Since the central axes 350 and 354 of the insertion paths of the anchors 18a and 20a into the body tissue 14a extend transverse to each other, the anchors 18a and 20a move toward each other as they move along their insertion paths. Thus, as the anchor 18a is moved along the longitudinal central axis 350 of its insertion path into the body tissue 14a, the anchor 18a moves toward the axis 354 of the insertion path for the anchor 20a. Similarly, as the anchor 20a moves along the central axis 354 of its insertion path, the anchor 20a moves toward the insertion path for the anchor 18a. By moving the anchors 18a and 20a toward each other along their insertion paths, the suture 24a grips the body tissues 12a and 14a with a clinching action. This clinching action firmly presses the body tissue 12a against the body tissue 14a. If the anchors 18a and 20a are toggled or pivoted to the orientation indicated in solid lines for the anchor 18a and dashed lines for the anchor 20a in FIG. 11, the clinching action of the suture 24a against the body tissues 12a and 14a is increased. This clinching action tends to maximize the tension forces which can be transmitted through the suture 24a without pulling the anchors 18a and 20a out of the body tissue 14a.

The anchors 18a and 20a are supported in the cancellous bone 280a in a spaced apart relationship with the hard outer layer 278a of the bone 14a. Thus, the tension forces transmitted through the suture 24a are transmitted from the anchors 18a and 20a to the cancellous bone 280a.

In the embodiment of the invention illustrated in FIG. 8, the suture 24a extends through both the body tissue 12a and the body tissue 14a. Tension in the suture 24a presses the body tissue 12a against the body tissue 14a. However, the suture 24a could extend across the body tissue 12a and the anchors 18a and 20a moved into the body tissue 14a without passing through the body tissue. If this was done, the suture 24a would extend into the body tissue 14a at locations offset from opposite edges of the body tissue 12a. Alternatively, the body tissue 12a could be spaced from the body tissue 14a and an extension could extend from the continuous loop formed by the suture 24a to the body tissue 12a.

It is contemplated that it may be desired to increase the tension in the suture 24a after the anchors 18a and 20a have been positioned relative to the body tissues 12a and 14a. This may be done by contracting the suture 24a under the influence of heat. If the suture 24a is to be heated, it may be desired to position a protective member between the suture and the tissue 12a. The protective member may have any desired construction, including any of the constructions disclosed in U.S. Pat. No. 4,823,794.

Embodiment of FIG. 12

In the embodiment of the invention illustrated in FIG. 11, a force application assembly 60 is effective to apply tension force to the suture 24 and to determine when a predetermined tension force is present in the suture 24. In the embodiment of the invention illustrated in FIG. 12, a tension measuring device 106 is associated with the inserter 38b and pushrod 40b for a suture anchor 20b. The suture anchor 20b is connected with a second suture anchor (not shown) corresponding to the suture anchor 18a in FIG. 11, by a suture 24b. The suture 24b is formed as a continuous closed loop which extends between the suture anchor 20b and another suture anchor, corresponding to the suture anchor 18a of FIG. 11.

The suture anchor corresponding to the suture anchor 18a of FIG. 11 is moved into the body tissue 14b, to a position corresponding to the position illustrated in solid lines in FIG. 11. The suture anchor 20b is then moved through the body tissue 12b and into the body tissue 14b with an inserter 38b and pusher member 40b (FIG. 12). The suture anchor 20b is moved through the hard outer layer 278b of the bone forming the body tissue 14b into the relatively soft cancellous bone 280b. The anchor 20b is then pivoted or toggled to a position corresponding to the position illustrated in dashed lines in FIG. 11 for the suture anchor 20a.

As the anchor 20b is moved into the body tissue 14b, tension in the connector portions 48b and 90b of the suture 24b is measured by the force measuring device 106. When a predetermined tension is present in the connector portion 48b and 90b of the suture 24b, the output from the force measuring device 106 causes the pusher member drive assembly 114 to interrupt movement of the pusher member into the body tissue 14b. When this occurs, a longitudinal central axis 320b of the anchor 20b is coincident with a longitudinal central axis 354b of the path along which the anchor 20b is moved into the body tissues 12b and 14b. The connector portions 48b and 90b of the suture 24b extend through the slot 316b in the inserter 38b.

In the illustrated embodiment of the invention, the force transmitting member 100 of the tension measuring device 96 is disposed in the slot 316b in the side wall of the tubular inserter 38b. The connector portions 48b and 90b of the suture 24b extend across the end portion 102 of the force transmitting member 100. Although the force transmitting member 100 has been illustrated in FIG. 12 as being disposed in the slot 316b, it is contemplated that the force transmitting member 100 could be disposed outside of the slot adjacent to an outer side surface of the inserter 38b.

As the pusher member drive assembly 114 is operated to move the pusher member 40b axially relative to the stationary inserter 38b, the anchor 20b is moved from the position illustrated in FIG. 12 into the body tissue 14b. As the suture anchor 20b moves into the body tissue 14b, the suture 24b is pulled into the body tissue along with the suture anchor. As this occurs, a tension force is established in the connector portions 48b and 90b of the suture 24b.

The tension force in the connector portions 48b and 90b of the suture 24b results in the application of a downward (as viewed in FIG. 12) force against the end portion 102 of the force transmitting member 100 by the connector portions 48b and 90b of the suture 24b. This force is transmitted through the force transmitting member 100 to the force measuring device 112. The force measuring device 112 includes a piezoelectric cell. When the force measuring device 112 detects that a predetermined tension force is present in the connector portions 48b and 90b of the suture 24b, an output signal from the force measuring device is transmitted to a control apparatus, that is, a microprocessor, which interrupts operation of the pusher drive assembly 114.

At the time when operation of the pusher drive assembly 114 is interrupted, the tension force in the connector portions 48b and 90b of the suture 24b have initiated toggling or pivoting movement of the suture anchor 20b in the cancellous bone 280b. This toggling or pivotal action moves the central axis of the anchor 20b from an orientation in which it is aligned with the central axis 354b of the path along which the suture anchor 20b is moved into the body tissue 14b to an orientation in which the central axis 320b of the suture anchor 20b extends transverse to the central axis 354b of the path along which the suture anchor moves into the body tissue 14b. When the operation of the pusher drive assembly 114 is interrupted, the anchor 20b will have pivoted to a position corresponding to the position illustrated in dashed lines in FIG. 11 for the anchor 20a.

Although it is believed that it will be preferred to utilize a tension measuring device, corresponding to the tension measuring device 96, which is connected with the inserter 38b, it is contemplated that the tension measuring device could be separate from the inserter 38b. For example, the tension measuring device 96 could engage the connector portions 48b and 90b of the suture 24b at a location which is approximately midway between the anchor 20b and the another anchor connected with the suture 24b and corresponding to the anchor 18a of FIG. 11. If desired, a tension measuring device could be substituted for the force application assembly of FIG. 10.

It is contemplated that a protective member, such as a pledget, could be provided between the suture 24b and the body tissue 12b. The protective member provided between the suture 24b and the body tissue 12b may be formed of a biodegradable or bioerodible polymer or copolymer if desired. The protective member may have any one of the constructions disclosed in U.S. Pat. No. 4,823,794.

It is contemplated that a robotic apparatus may be utilized to position suture anchors corresponding to the suture anchors 18 and 20 of FIGS. 1-10, the suture anchors 18a and 20a of FIG. 11, and the suture anchor 20b of FIG. 12 relative to body tissue. The inserters 28 (FIGS. 2-4), 38 (FIGS. 6 and 7), and 38b (FIG. 12) along with the pusher members 30 (FIGS. 2-4), 40 (FIGS. 6 and 7), and 40b (FIG. 12) are connected with articulate arms of the robotic apparatus. Devices for effecting relative movement between the inserter members and the pusher members, similar to the pusher member drive assembly 114 and inserter drive assembly 110 of FIG. 12, are connected with the articulate arms of the robotic apparatus.

Operation of the pusher member drive assembly 114 and the inserter drive assembly 110 is controlled by one or more computers in the robotic apparatus. The tension measuring device 96 is also be associated with an articulate arm of the robotic apparatus. The tension measuring device 96 is mounted on the articulate arm of the robotic apparatus in association with a slot, corresponding to the slot 316b of FIG. 12, in the inserter 38b. Alternatively, the tension measuring device 96 could be mounted on the articulate arm of the robotic apparatus in a spaced apart relationship with the inserter.

It is contemplated that the robotic apparatus will be utilized to position anchors, corresponding to the anchors 18 and 20 of FIGS. 1-10, the anchors 18a and 20a of FIG. 11, and the anchor 18b of FIG. 12 relative to body tissue at many different locations in a patient's body. The body tissue may be hard body tissue, soft body tissue, or a combination of hard and soft body tissue. If desired, a drill or similar tool could be associated with an articulate arm of the robotic apparatus to assist in the formation of an opening in the body tissue. The drill would form an opening extending through the hard outer layer 278b into the cancellous bone 280b. The opening formed by the drill could have a cross sectional area which is smaller than the cross sectional area of the anchor 20b.

The robotic apparatus may have any one of many different constructions. It is contemplated that the robotic apparatus may have a construction similar to the construction illustrated in U.S. Pat. Nos. 6,063,095 and 6,102,850. The disclosures in the aforementioned U.S. Pat. Nos. 6,063,095 and 6,102,850 are hereby incorporated herein in their entirety by this reference thereto.

Embodiment of FIG. 13

In the embodiments of the invention illustrated in FIGS. 1-12, the suture anchors 18, 20, 18a, 20a, and 20b are either positioned manually relative to body tissue or positioned relative to the body tissue by a robotic apparatus. A guide assembly 120 which may be utilized with either the manual or robotic insertion of anchors into body tissue is illustrated in FIG. 13. The guide assembly 120 is utilized to be certain that the insertion paths along which the anchors are moved into the body tissue have a desired angular orientation relative to each other and to the body tissue.

The guide assembly 120 includes the cylindrical guides 126 and 128 which are supported in a preselected angular relationship relative to each other by the base 124. The guide 128 may be moved toward and away from the guide 126, in the manner indicated by the arrow 136 in FIG. 13, to vary the spacing between the guides.

In the embodiment of the invention illustrated in FIG. 13, the guides 126 and 128 have a construction which corresponds to the tubular construction of the inserters 28 and 38 of FIGS. 2-8. Thus, the guide 126 is provided with a slot 292c through which a portion of the suture 24c extends away from the anchor 18c. Similarly, the guide 128 is provided with a slot 316c through which a portion of the suture 24c extends away from the anchor 20c.

The pusher member 132 has the same cylindrical construction as the pusher member 30 of FIGS. 2-4. However, the pusher member 132 is provided with indicia 360 which cooperates with the guide 126 to indicate the depth to which the anchor 18c has moved into cancellous bone 280c. Thus, as the pusher member is moved downward and toward the right (as viewed in FIG. 13), the indicia 360 moves to a location adjacent to a circular end surface 364 on the guide 126.

When the pusher member 132 has moved into the body tissue 14c to a desired depth, a predetermined mark on the indicia 360 will have moved into alignment with the end surface 364 on the guide 126. This enables a surgeon to visually determine the depth to which the anchor 18c has moved into the body tissue. Once the anchor 18c has moved into the desired depth in the body tissue, movement of the pusher member 132 relative to the guide 126 is interrupted. The anchor 18c is then pivoted under the influence of tension in the suture 24c. During this pivotal movement of the anchor 18c, the pusher member 132 may be moved further into the body tissue 14c through a relatively short predetermined distance to promote the pivoting or toggling action of the anchor.

The pusher member 132 may be utilized to move the anchor 20c into the body tissue 14c. If this is done, the depth to which the anchor 20c is moved into the body tissue 14c will be clearly indicated by movement of the indicia 360 on the pusher member 132 relative to a circular end surface 368 on the guide 128.

It is contemplated that a pair of pusher members, having the same construction as the pusher member 132, could be provided to move the anchors 18c and 20c relative to the guides 126 and 128. If this was done, both anchors 18c and 20c could be simultaneously inserted into the body tissue 14c.

When a robotic apparatus is utilized to move the anchors 18c and 20c into the body tissue 14c, articulate arms of the robotic apparatus could be provided with fiber optic systems. These fiber optic systems would view the pusher members and end surfaces 364 and 366 on the guides 126 and 128 and provide an indication to a suitable control apparatus when the indicia 360 is in a desired position relative to the guides. Alternatively, the articulated arms of the robotic apparatus could be provided with drives, for examples, screw and nut drives, which would indicate the extent of operation of the drives and thereby the extent of movement of the pusher members, corresponding to the pusher member 132, relative to the guides 126 and 128 and the depth of insertion of the anchors 18c and 20c into the body tissue 14c.

In the embodiment of the invention illustrated in FIG. 13, the guides 126 and 128 perform the same functions as the inserters 28 and 38 of FIGS. 2-8. However, it is contemplated that the guides could be constructed so as to receive inserters corresponding to the inserters 28 and 38 and to position the inserters relative to the body tissue.

When the guide assembly 120 is utilized in association with a robotic apparatus, it is contemplated that the guide 126, which is fixedly connected with the base 124 of the guide assembly 120, could be connected with one articulate arm of the robotic apparatus. This would result in the base 124 of the guide assembly being positioned relative to the body tissue 12c and 14c in a patient along with the guide 126. The position of the retainer 140 along the base 124 would be adjusted to position the guide 128 in a desired relationship with the guide 126. It is contemplated that the retainer 140 will be held against movement relative to the base by a suitable set screw which extends through a portion of the retainer into engagement with the base. When the set screw is loosened, the retainer 140 and guide 128 may be moved along the base 124, in the manner indicated schematically by the arrow 136 in FIG. 13. When the set screw is tightened, the retainer 140 and guide 128 are held against movement relative to the base 124.

When the guide 126 and base 124 are connected with one articulate arm of a robotic apparatus, one or more pusher members, corresponding to the pusher member 132, can be moved relative to the guides 126 and 128 by one or more additional articulate arms of the robotic apparatus. For example, if the anchors 18c and 20c are to be sequentially moved into the body tissue 14c, a single robotic arm could be provided to move the pusher member 132 relative to the guide 126 to move the anchor 18c into the body tissue. The same articulate arm could be utilized to move the same pusher member 132 relative to the guide 128 to move the anchor 20c into the body tissue 14c. Alternatively, a pair of pusher members, both of which have the construction of the pusher member 132, could be utilized to simultaneously move both of the anchors 18c and 20c into the body tissue 14c. If this is done, one of the pusher members could be associated with one articulate arm of the robotic apparatus and the second pusher member could be associated with another articulate arm of the robotic apparatus.

In the embodiment of the invention illustrated in FIG. 13, the suture 24c forms a continuous loop which extends between the anchors 18c and 20c in the same manner as is illustrated schematically in FIG. 11. If the anchor 18c is moved into the body tissue 14c before the anchor 20c is moved into the body tissue, the suture 24c would be tensioned between the two anchors 18c and 20c as the anchor 20c moves into the body tissue. As the suture 24c is tightened, it applies force against the body tissue 12c to firmly press the body tissue 12c against the body tissue 14c. If both of the anchors 18c and 20c are simultaneously moved into the body tissue 14c, movement of both anchors relative to the body tissue 14c will be effective to tension the suture.

The tension measuring device 96 of FIG. 12 may be associated with either the guide 126 or the guide 128. If desired, one tension measuring device 96 could be associated with the guide 126 and a second tension measuring device could be associated with the guide 128. Alternatively, a tension measuring device 96 could be mounted on the base 124 in a spaced apart relationship with the guides 126 and 128.

It is contemplated that, rather than being a continuous loop, the suture 24c could have the same construction as the suture 24 of FIGS. 1-10. If this was done, a connector portion of the suture would extend between the two anchors 18c and 20c. Leg portions of the suture would be interconnected with a suitable retainer or crimp, corresponding to the retainer 54 of FIGS. 9 and 10.

Of course, if the suture 24c has the same construction as the suture 24 of FIGS. 1-10, only the connector portion of the suture extending between the two anchors 18c and 20c would be tensioned as the anchors move into the body tissue 14c. The two leg portions of the suture would be tensioned after the anchors 18c and 20c had moved into the body tissue 14c. This could be accomplished manually or by the use of a force application assembly, corresponding to the force application assembly 60 of FIG. 10. In this situation, a force application member, corresponding to the force application member 66 of FIG. 10 may be utilized to press the retainer against the body tissue. While the suture 24c is being tensioned with a predetermined force and while the retainer is being pressed against the body tissue with a predetermined force, force application members, corresponding to force application members 76 and 78 of FIG. 10, would be utilized to effect deformation of the retainer.

Embodiment of FIGS. 14 and 15

In the embodiments of the invention illustrated in FIGS. 1-13, leading end portions of the anchors have been utilized to initiate the formation of openings in the soft body tissue and the hard body tissue. It is contemplated that it may be desired to initiate the formation of openings in either the soft body tissue or the hard body tissue or both with a tool other than the anchors. In the embodiment of the invention illustrated in FIGS. 14 and 15, thin elongated members 146 and 160 are utilized to initiate the formation of the openings in both soft body tissue 12d and hard body tissue 14d.

In addition to initiating formation of openings in the soft body tissue 12d and hard body tissue 14d, the thin elongated members 146 and 160 function as guides along which the anchors 18d and 20d are moved into the body tissues 12d and 14d. Thus, the thin elongated members 146 and 160 are first positioned at desired angles relative to each other and to the body tissues 12d and 14d. The thin elongated members 146 and 160 are forced axially through the soft body tissue 12d into the hard body tissue 14d.

Movement of the thin elongated members 146 and 160 into the hard body tissue 14d is interrupted after the thin elongated members have moved to a depth which is greater than the depth to which it is intended to subsequently move the anchors 18d and 20d into the hard body tissue 14d. The thin elongated members 146 and 160 are moved deeper into the hard body tissue 14d than the intended depth of the anchors 18d and 20d in the hard body tissue 14d to enable the thin elongated members to guide movement of the anchors to their intended depth in the hard body tissue. The thin elongated members 146 and 160 may be simultaneously or sequentially moved through the body tissue 12d into the body tissue 14d.

Anchors 18d and 20d are moved along the stationary thin elongated members 146 and 160 (FIG. 15) into the body tissue 12d and 14d. The anchors 18d and 20d have the same construction as the anchors 18 and 20 of FIGS. 1-10. However, the anchors 18d and 20d have axially extending cylindrical passages 152 and 166 which receive the thin elongated members 146 and 160. Like the anchors 18 and 20 of FIGS. 1-10, the anchors 18d and 20d (FIGS. 14 and 15) are formed of bone. However, the anchors 18d and 20d could be formed of any of the materials previously mentioned in association with the anchors 18 and 20 of FIGS. 1-10.

When the anchor 18d (FIG. 14) is to be moved along the thin elongated member 146, the anchor 18d is telescopically positioned on the stationary thin elongated member 146. The anchor 18d is moved along the thin elongated member 146 until the leading end portion 34d of the anchor 18d engages the soft body tissue 12d. At this time, the cylindrical thin elongated member 146 extends through the cylindrical passage 152 in the anchor 18d and positions the anchor 18d relative to the body tissues 12d and 14d.

The cylindrical pusher member 30d is then telescopically positioned on the stationary thin elongated member 146 (FIG. 14). The pusher member 30d is moved along the thin elongated member 146 until a circular leading end surface 370 on the pusher member 30d engages a trailing end of the anchor 18d. At this time the cylindrical thin elongated member 146 extends through both the cylindrical passage 152 in the anchor 18d and the cylindrical passage 156 in the pusher member 30d. This enables the stationary thin elongated member 146 to position both the anchor 18d and pusher member 30d relative to the body tissues 12d and 14d.

After the pusher member 30d and anchor 18d have been positioned on the thin elongated member 146, the cylindrical inserter 28d is positioned in a telescopic relationship with the anchor 18d and pusher member 30d. An axial force is applied to the inserter 28d to slide the inserter along the stationary pusher member 30d and anchor 18d through the body tissue 12d into engagement with the body tissue 14d, as shown in FIG. 14. At this time, the leading end portion of the pusher member 30d and anchor 18d are fully enclosed by the inserter 28d. The leading end portion 34d of the anchor 18d is disposed in engagement with the surface 300d on the body tissue 12d.

Movement of the inserter 28d through the body tissue 12d into engagement with the body tissue 14d is guided by the stationary pusher member 30d and stationary anchor 18d. The pusher member 30d and anchor 18d are held in the desired orientation relative to the body tissue by the thin elongated member 146. When the inserter 28d is moved to the position shown in FIG. 14 in engagement with the body tissue 14d, the leading end portion 34d of the anchor 18d is in engagement with the surface 300d of the body tissue 12d and is fully enclosed by the inserter 28d.

An axial force is then applied to the pusher member 30d to move the anchor 18d through the body tissue 12d into the body tissue 14d. During this movement of the pusher member 30d and anchor 18d, both the inserter 28d and thin elongated member 146 are stationary relative to the body tissues 12d and 14d. When the anchor 18d has moved to the desired depth in the body tissue 14d, movement of the pusher member 30d and anchor along the thin elongated member 146 is interrupted.

When the anchor 18d has been moved to the desired depth in the body tissue 14d, the anchor is in the position illustrated in FIG. 14 relative to the thin elongated member 146 and the inserter 28d. Indicia corresponding to the indicia 360 (FIG. 13) is provided on the pusher member 30d (FIG. 14) to indicate when the anchor 18d has moved to the desired position relative to the body tissues 12d and 14d.

The anchor 20d (FIG. 15) is positioned relative to the body tissues 12d and 14d in the same manner as previously explained in conjunction with the anchor 18d. The thin elongated member 160 is utilized to guide movement of the anchor 20d and pusher member relative to the body tissue 12d in the same manner as previously explained in conjunction with the anchor 18d. The thin elongated member 160 may be positioned relative to the body tissue 12d and 14d (FIG. 15) simultaneously with the thin elongated member 146 or after the thin elongated member 146 has been positioned relative to the body tissue 12d and 14d.

The anchor 20d and pusher member 40d are positioned in a telescopic relationship with the thin elongated member 160. The anchor 20d is moved along the stationary thin elongated member 160 into engagement with the surface 300d on the body tissue 12d. The pusher member 40d is moved along the stationary thin elongated member 160 to a position in which a circular leading end surface 374 on the pusher member 40d engages the trailing end of the anchor 20d.

The inserter 38d is then positioned in a telescopic relationship with the stationary pusher member 40d, anchor 20d, and elongated member 160. The cylindrical inserter 38d is moved through the body tissue 12d into engagement with the surface 304d of the body tissue 14d. This movement of the inserter 38d is guided by the stationary pusher member 40d and anchor 20d.

Once the inserter 38d has been moved to the position illustrated in FIG. 15 relative to the body tissue 12d and 14d, the pusher member 40d is moved axially along the stationary thin elongated member 160. Force transmitted from the pusher member 38d to the anchor 20d moves the anchor through the body tissue 12d. Further movement of the pusher member 40d along the stationary thin elongated member 160 moves the anchor 20d to the position illustrated in FIG. 15. Indicia on the pusher member 40d cooperates with the inserter 38d to indicate when the anchor 20d has moved to a desired depth in the body tissue 14d.

Embodiment of FIGS. 14 and 15-Alternate Method

The foregoing description has related to a process in which the thin elongated members 146 and 160 are moved into the body tissue 14d prior to movement of the anchors 18d and 20d into the body tissue 12d and 14d. An alternative method for moving the anchors 18d and 20d into the body tissue 14d involves movement of the thin elongated members 146 and 160 together with the anchors into the body tissues 12d and 14d.

When the anchor 18d is to be moved through the body tissue 12d into the body tissue 14d in accordance with the aforementioned alternative method, the thin elongated member 146 is inserted through the passage 156 in the pusher member 30d (FIG. 14). The thin elongated member 146 is moved to a position in which the pointed end portion 148 of the thin elongated member extends past a circular end surface 370 on the pusher member 30d. The portion of the thin elongated member 146 extending past the end surface 370 on the pusher member 30d is then telescopically inserted through the passage 152 in the anchor 18d.

At this time during the alternative method, the pointed end portion 148 on the thin elongated member 146 extends a short distance past a conical leading end portion 34d of the anchor 18d. This results in the pointed end portion 148 on the thin elongated member forming a point for the leading end portion 34d of the anchor 18d at the location where the passage 152 ends at the leading end portion 34d of the anchor 18d.

The pusher member 30d, thin elongated member 146, and anchor 18d are then telescopically inserted into the inserter 28d. The anchor 18d and pusher member 30d are then moved to a position in which the anchor extends from the inserter 28d. Thus, the anchor is moved to a position corresponding to the position of the anchor 18 in FIG. 2. The portion of the suture 24d adjacent to the anchor 18d is tensioned to press a trailing end portion 32d of the anchor firmly against the end surface 370 on the pusher member 30d.

At this time during the alternative method, the pointed end portion 148 of the thin elongated member 146 extends from the leading end portion 34d of the anchor 18d. Therefore, the pointed end portion 148 of the thin elongated member 146 forms a point at a location where the passage 152 intersects the end portion 34d of the anchor 18d. While the pusher member 30d and thin elongated member 146 are held against movement relative to the inserter 28d, the inserter, pusher member, thin elongated member, and anchor are moved as a unit relative to the body tissue 12d. As this occurs, the pointed end portion 148 of the thin elongated member 146 initiates the formation of an opening at an imperforate area on a surface 300d of the body tissue 12d.

As the thin elongated member 146, pusher member 30d, anchor 18d and inserter 28d are moved together relative to the body tissue 12d, the leading end portion 34d of the anchor 18d moves into the opening in the body tissue 12d which was initiated by the pointed end portion 148 of the thin elongated member. The anchor 18d is pressed into the body tissue 12d under the influence of force applied against the trailing end portion 32d of the anchor by the end surface 370 on the pusher member 30d. At this time, there is no relative movement between the thin elongated member 146, pusher member 30d, anchor 18d, and inserter 28d. During movement of the anchor 18d into the body tissue 12d, the anchor 18d remains in a position relative to the inserter 28d corresponding to the position of the anchor 18 to the inserter 28 in FIGS. 2 and 3.

As the thin elongated member, pusher member 30d, anchor 18d, and inserter 28d are moved together into the body tissue 12d during the alternative method, the pointed end portion 148 on the thin elongated member engages an imperforate area on an outer surface 304d of the bone 14d. Continued movement of the thin elongated member 146, pusher member 30d, anchor 18d and inserter 28d together in a direction toward the bone 14d results in initiation of the formation of an opening in the outer surface 304d of the hard outer layer 278d of the bone 14d by the pointed end portion of the thin elongated member 146. Continued axial movement of the thin elongated member 146, pusher member 30d, anchor 18d and inserter 28d together relative to the bone 14d moves the leading end portion 34d of the anchor 18d into the hard outer layer 278d in the same manner as is illustrated in FIG. 3 for the anchor 18.

As this occurs, the inserter 28d moves into abutting engagement with the outer surface 304d on the hard outer layer 278d of the bone 14d (FIG. 14). At this time during the alternative method, the end surface 370 on the pusher member 30d is disposed within the inserter 28d. Thus, the pusher member 30d and inserter 28d are in the same relationship as is illustrated in FIG. 3 for the pusher member 30 and inserter 28. At this time, the trailing end portion 32d of the anchor 18d is enclosed by the inserter 28d in the same manner as in which the trailing end portion 32 of the anchor 18 is enclosed by the inserter 28 in FIG. 3.

The thin elongated member 146 is then moved through the hard outer layer 278d of the bone 14d into the cancellous bone 280d (FIG. 14). As the thin elongated member 146 moves into the cancellous bone 280d, the inserter 28d, pusher member 30d and anchor 18d remain stationary relative to the bone 14d. Thus, as the thin elongated member 146 is axially advanced into the cancellous bone 280d, the inserter 28d, pusher member 30d and anchor 18d remain in the same relationship with the bone 14d as is illustrated for the inserter 28, pusher member 30 and anchor 18 in FIG. 3.

When the pointed end portion 148 of the thin elongated member 146 has moved to a desired depth in the cancellous bone 280d, the pusher member 30d is moved axially along the thin elongated member 146. As this occurs, the leading end surface 370 (FIG. 14) on the pusher member 30d applies force against the trailing end portion 32d of the anchor 18d. This force causes the anchor 18d to slide along the thin elongated member 146. As the pusher member 30d moves the anchor 18d along the thin elongated member 146, the inserter 28d and thin elongated member remain stationary in the position illustrated in FIG. 14 relative to the hard outer layer 278d of bone.

Thus during performance of the alternative method, the anchor 18d, inserter 28d, pusher member 30d and thin elongated member 146 are all moved together from a position corresponding to a position illustrated in FIG. 2 for the anchor 18 to a position corresponding to the position illustrated in FIG. 3 for the anchor 18. The thin elongated member 146 is then telescopically extended from the anchor 18d (FIG. 14) through the hard outer layer 278d of bone into the cancellous bone 280d while the anchor 18d and pusher member 30d remain stationary relative to the bone 14d.

The thin elongated member 146 is supported by the anchor 18d and pusher member 30d during the initial formation of an opening in the hard outer layer 278d of the bone 14d. After the thin elongated member 146 has initiated the formation of an opening in the hard outer layer 278 of the bone 14d, the leading end portion 34d of the anchor 18d enlarges the opening. This positions the anchor in the desired orientation relative to the opening initiated by the elongated member 146.

After the thin elongated member 146 has been moved to the desired depth in the bone 14d during performance of the alternative method, the anchor 18d is moved axially along the thin elongated member 146. As the anchor 18d moves through the hard outer layer 278d of bone and moves into the cancellous bone 280d, the thin elongated member 146 cooperates with the passage 152 in the anchor 18d to guide movement of the anchor along an insertion path having a longitudinal central axis which is coincident with a longitudinal central axis of the thin elongated member 146.

Movement of the pusher member 30d and anchor 18d along the stationary thin elongated member is interrupted when the anchor 18d has moved to a desired depth in the cancellous bone 280d. Indicia, corresponding to the indicia 360 of FIG. 13, is provided on the pusher member 30d. This indicia cooperates with the inserter 28d to indicate when the anchor 18d has been moved to a desired position in the cancellous bone 280. If the anchor 18d is being positioned in the cancellous bone 280d by a robotic apparatus, in the manner previously discussed, the position of the pusher member 30d relative to the inserter 28d may be indicated by the position of a movable element in a drive assembly on an articulate arm of the robotic apparatus.

In the foregoing description of the alternative method, the thin elongated member 146 and the leading end portion 34d of the anchor 18d are moved together through a short distance into the hard outer layer 278d of bone, that is, to a position corresponding to the position of the anchor 18 in FIG. 3. The thin elongated member 146 is then moved relative to the anchor 14d (FIG. 14). However, the thin elongated member 156 could be moved through the soft body tissue 12d to a desired depth in the bone 14d before the anchor 18d is moved into engagement with the soft body tissue. However, if desired, the thin elongated member 146 and anchor 18d could be moved together through the soft body tissue 12d to the desired depth in the bone 14d without any relative movement between the anchor and thin elongated member.

The anchor 20d may be moved through the soft body tissue 12d into the hard body tissue 14d simultaneously with movement of the anchor 18d through the soft body tissue into the hard body tissue. However, if desired, the anchor 20d may be moved through the soft body tissue 12d and into the hard body tissue 14d after the anchor 18d has been moved into the hard body tissue.

When the anchor 20d is to be positioned relative to the body tissue 12d and 14d in accordance with the alternative method, the thin elongated member 160 (FIG. 15) is moved through the pusher member 40d while the pusher member 40d, inserter 38d, and anchor 20d are spaced from the body tissue 12d and 14d. The portion of the thin elongated member 160 extending past the end surface 374 on the pusher member 40d is inserted through the passage 166 in the anchor 20d. When this has been done, the pointed end portion 162 of the thin elongated member 160 will extend a short distance past the pointed leading end portion 44d of the anchor 20d. This will result in the pointed end portion 162 of the thin elongated member 160 forming a continuation of the pointed leading end portion 44d of the anchor 20d.

The portion of the suture 24d adjacent to the anchor 20d is tensioned to press the anchor 20d against the end surface 374 on the pusher member 40d. While the pusher member 40d, thin elongated member 160 and anchor 20d are held against movement relative to each other, the thin elongated member, pusher member and anchor are telescopically inserted into the inserter 38d. The thin elongated member 160, pusher member 40d and anchor 20d are moved to a position in which the end surface 374 of the pusher member 40d is enclosed by the inserter 38d. At this time, the anchor 20d will be in the same position relative to the inserter 38d as is the anchor 20 relative to the inserter 38 of FIG. 6. However, the thin elongated member 160, pusher member 40d, inserter 38d, and anchor 20d (FIG. 15) will all be spaced from the body tissue 12d and 14d.

While the thin elongated member 160, pusher member 40d and anchor 20d are held against movement relative to the inserter 38d and only the pointed end 162 of the thin elongated member extends from the anchor, the inserter is moved to a desired position relative to the body tissue 12d and 14d. In the embodiment of the invention illustrated in FIG. 15, the inserter 28d is moved to a position offset from the position in which the inserter 28d and pusher member 30d have been used to move the anchor 18d along the thin elongated member 146 into the bone 14. Thus, as viewed in FIG. 15, the thin elongated member 160, pusher member 40d, inserter 38d, and anchor 20d are offset in a direction which is out of the sheet of drawings on which FIG. 15 is disposed from the location of the anchor 18d relative to the sheet of drawings.

While the anchor 20d is in the same orientation relative to the inserter 38d as is the anchor 20 relative to the inserter 38 of FIG. 6, the pointed end portion 162 of the thin elongated member 160 is moved into engagement with an imperforate area on the outer surface 300d of the body tissue 12d. At this time, the trailing end portion 42d of the anchor 20d is disposed within the inserter 38d and is engaged by the pusher member 40d, in the same manner as is illustrated in FIG. 6 for the anchor 20 and pusher member 40. The thin elongated member (FIG. 15) extends through the pusher member 40d and through the passage 166 in the anchor 20d. The pointed end portion 162 of the thin elongated member is disposed adjacent to and forms a continuation of the pointed leading end portion 44d of the anchor 20d.

The pointed end portion 162 of the thin elongated member 160 engages the imperforate outer surface 300d of the body tissue 12d at the location where the anchor 20d is to be inserted into the body tissue 12d and 14d. While the thin elongated member 160, pusher member 40d, inserter 38d and anchor 20d are held against movement relative to each other, they are pressed into the body tissue 12d. As this occurs, the pointed end portion 162 of the thin elongated member initiates the formation of an opening in the surface 300d of the body tissue 12d. Continued movement of the thin elongated member 160, inserter 38d, pusher member 40d and anchor 20d together into the body tissue 12d results in the opening which was initially formed by the pointed end portion 162 of the thin elongated member 160 being enlarged by the pointed leading end portion 44d of the anchor 20d.

As the thin elongated member 160, pusher member 40d, inserter 38d and anchor 20d continue to be moved together toward the bone 14d, the pointed end portion 162 of the thin elongated member 160 moves into engagement with an imperforate area on the surface 304d of the bone 14d. At this time, the pointed leading end portion of the anchor 20d will have moved into the body tissue 12d. The right (as viewed in FIG. 15) side of the inserter 38d will have just begun moving into the body tissue 12d while the left (as viewed in FIG. 15) side of the inserter 38d will be disposed adjacent to and outside of the body tissue 12d. Of course, the position of the left side of the inserter 38d relative to the body tissue 12d will depend upon the thickness of the body tissue. At this time, the trailing end portion 42d of the anchor 20d is enclosed by the inserter 38d.

Continued axial movement of the thin elongated member 160, pusher member 40, inserter 38d and anchor 20d together, that is without relative movement between them, along the insertion path results in the pointed end portion 162 of the thin elongated member initiating the formation of an opening in the outer surface 304d of the hard layer 278d of bone. Continued movement of the thin elongated member 160, pusher member 40d, inserter 38d, and anchor 20d along the insertion path results in the opening which was initiated by the pointed leading end portion 162d of the thin elongated member 160 being expanded by the pointed leading end portion 44d of the anchor 20d.

The thin elongated member 160, pusher member 40d, inserter 38d and anchor 20d are held against movement relative to each other until the inserter 38d engages the outer surface 304d on the hard outer layer 278d of bone. At this time, the pusher member 40d, inserter 38d and anchor 20d will be in the same position relative to each as is illustrated in FIG. 6 for the inserter 38, pusher member 40 and anchor 20. At this time, the pointed end portion 162 of the thin elongated member 160 is disposed adjacent to and forms a continuation of the leading end portion 44d of the anchor 20d.

While the anchor 20d, inserter 38d, and pusher member 40d are stationary relative to the hard outer layer 278d of the bone 14d, the thin elongated member 160 is moved along the path of insertion into the bone 14d. As this occurs, the thin elongated member 160 moves through the hard outer layer 278d into the cancellous bone 280d. When the thin elongated member has been moved to a desired depth into the soft cancellous bone 280d, that is, to the position illustrated in FIG. 15, movement of the thin elongated member into the cancellous bone is interrupted.

The pusher member 40d is then moved axially along the thin elongated member 160 to push the anchor 20d through the hard outer layer 278d into the cancellous bone 280d. As this occurs, the thin elongated member 160 and inserter 38d are stationary relative to the hard outer layer 278d of the bone 14d. The passage 166 in the anchor 20d slides along the thin elongated member 160 under the influence of force applied against the trailing end portion 42d of the anchor by the end surface 374 on the pusher member 40d.

When the pusher member 40d has moved the anchor 20d to the desired depth into the cancellous bone 280d, movement of the pusher member 40d and anchor 20d along the thin elongated member is interrupted. The pusher member 40d may advantageously be provided with indicia, corresponding to the indicia 360 of FIG. 13, which cooperates with the inserter 38d to indicate the position of the pusher member and the anchor 20d relative to the body tissue 14d. It is contemplated that indicia may be provided on the thin elongated members 146 and 160. The indicia on the thin elongated members 146 and 160 would cooperate with the inserters 28d and 30d to indicate the depth of insertion of the thin elongated members into the body tissue 14d.

In the foregoing description of the alternative method, the thin elongated member 160 and the leading end portion 44d of the anchor 20d are moved together through a short distance into the hard outer layer 278d of bone, that is, to a position corresponding to the position of the anchor 20 in FIG. 6. The thin elongated member 160 is then moved relative to the anchor 20d (FIG. 15). However, the thin elongated member 160 could be moved through the soft body tissue to a desired depth in the bone 14d before the anchor 20d is moved into engagement with the soft body tissue. However, if desired, the thin elongated member 160 and anchor 20d could be moved together through the soft body tissue 12d to the desired depth into the bone 14d without any relative movement between the anchor and the thin elongated member.

As the anchor 20d is moved into the cancellous bone 280d with any of the foregoing methods related to FIGS. 14 and 15, the suture 24d is tensioned. In the embodiment of the invention illustrated in FIG. 15, the suture 24d forms a continuous closed loop which extends through the anchors 18d and 20d in the manner illustrated schematically in FIG. 11 for the suture 24a. Therefore, as the anchor 20d is moved into the cancellous bone 280d, connector portions 48d and 90d of the suture 24d are tensioned between the anchors 18d and 20d. A tension measuring device, corresponding to the tension measuring device 96 of FIG. 12, may be provided to measure the tension in the suture 24d. If a tension measuring device, corresponding to the tension measuring device 96 of FIG. 12, is utilized to measure the tension in the suture 24d (FIG. 15), the movement of the anchor 20d into the cancellous bone 280d is interrupted when there is a desired tension in the connector portions 48d and 90d of the suture 24d.

It should be understood that the suture 24d could have a pair of leg portions, corresponding to the leg portions 50 and 52 of the suture 24 of FIG. 9, which are interconnected by a suture retainer or crimp, corresponding to the suture retainer or crimp 54 of FIG. 9. If this was done, a force application assembly, corresponding to the force application assembly 60 of FIG. 10, could be utilized to determine when the desired tension force was present in the suture 24d (FIG. 15).

If the anchor 18d is moved into the cancellous bone 280d prior to movement of the anchor 20d into the cancellous bone, the suture 24d will be tightened with a desired tension force during insertion of the anchor 20d into the cancellous bone 280d. However, if both anchors 18d and 20d are inserted at the same time into the cancellous bone 280d, the suture 24d will be tightened to the desired tension during movement of both anchors into the cancellous bone 280d.

If desired, the step of measuring the tension in the suture 24d could be omitted. If this was done, the anchors 18d and 20d would merely be moved to a desired depth into the cancellous bone 280d. By properly sizing the loop formed by the suture 24d and selecting the locations of the insertion paths for the anchors 18d and 20d, a desired tension would be obtained in the suture 24d when the anchors 18d and 20d have been moved to a desired depth into the cancellous bone 280d. However, it is believed that it may be desired to actually measure the tension in the suture 24d to be certain that a desired tension is obtained when the anchors 18d and 20d have been moved into the cancellous bone 280d.

If desired, the anchors 18d and 20d may be left in the orientation illustrated in FIG. 15 relative to the cancellous bone 280d and the hard outer layer 278d. Alternatively, the anchors 18d and 20d may be toggled or pivoted relative to the cancellous bone 280d. In either situation, the anchors 18d and 20d would be supported in the cancellous bone 280d in a spaced apart relationship with the hard outer layer 278d.

When the anchor 18d is to be pivoted relative to the cancellous bone 280, the thin elongated member 146 is first completely withdrawn from the anchor 18d. While the pusher member 30d is pressed against the trailing end portion of the anchor 18d, the suture 24d is tensioned to cause a pivoting movement of the anchor 18d relative to the pusher member 30d in the manner illustrated schematically in FIGS. 4 and 5 of the anchor 18.

Similarly, if the orientation of the anchor 20d is to be changed relative to the cancellous bone 280d, the thin elongated member 160 is completely withdrawn from the anchor 20d. While the pusher member 40d is pressed against the trailing end portion of the anchor 20d, the tension in the suture 24d causes the anchor to pivot from the orientation shown in FIG. 7 for the anchor 20 to the orientation shown in FIG. 8 for the anchor 20.

In the embodiment of the invention illustrated in FIG. 15, the suture 24d extends in a continuous closed loop between the two anchors 18d and 20d. The suture 24d is not tensioned until both anchors 18d and 20d have been moved into the body tissue 14d. Therefore, if the orientation of the anchors 18d and 20d is to be changed from the orientation illustrated in FIG. 15 to the orientation illustrated in FIG. 9 of the anchors 18 and 20, both anchors may be pivoted at the same time in the cancellous bone 280d.

To effect simultaneous pivotal movement of the anchors 18d and 20d in the cancellous bone 280d, the thin elongated member 146 is withdrawn from the anchor 18d and the thin elongated member 160 is withdrawn from the anchor 20d while the anchors are disposed in the orientation illustrated in FIG. 15 in the body tissue 280d. Both pusher members 30d and 40d are then simultaneously pressed against the trailing end portions of the anchors 18d and 20d. The resulting tension in the suture 24d causes the anchor 18d to pivot in a counterclockwise direction about the end portion of the pusher member 30d. At the same time, the tension in the suture 24d causes the anchor 20d to pivot in a clockwise direction about the end portion of the pusher member 40d. Of course, the anchors 18d and 20d could be sequentially pivoted in the cancellous bone 280d if desired.

In the specific embodiment of the invention illustrated in FIGS. 14 and 15, the anchors 18d and 20d are moved along linear insertion paths into the body tissues 12d and 14d. Therefore, the thin elongated members 146 and 160 have linear configurations. However, it is contemplated that it may be desired to move the anchors 18d and 20d into body tissues along nonlinear insertion paths.

When the anchors 18d and 20d are to be moved into body tissues along nonlinear insertion paths, the elongated members 146 and 160 have a nonlinear configuration. For example, if the anchors 18d and 20d are to be moved along arcuate insertion paths relative to the body tissues 12d and 14d, the thin elongated members 146 and 160 would have portions with an arcuate configuration. The portions of the thin elongated members having an arcuate configuration would have an arcuate configuration which is the same as the arcuate configuration of the desired insertion paths. The anchors 18d and 20d would be moved along the arcuate portions of the thin elongated members into the body tissues 12d and 14d.

It is contemplated that the desired anchor insertion paths into the body tissues 12d and 14d could have arcuate configurations corresponding to the arcuate configurations of a portion of a circle. In this situation, at least a portion of the thin elongated members 146 and 160 would have arcuate configurations corresponding to the configuration of a portion of a circle. For example, the thin elongated members 146 and 160 could have portions with a circular arcuate extent of 135°.

After the arcuate thin elongated members 146 and 160 have been positioned relative to the body tissues 12d and 14d, the anchors 18d and 20d would be moved along the arcuate extent of the thin elongated members. The anchors 18d and 20d may have passages 152 and 166 with arcuate configurations corresponding to the arcuate configurations of the thin elongated members 146 and 160. The pusher members 30d and 40d would also have arcuate configurations corresponding to the arcuate configurations of the thin elongated members 146 and 160. The arcuate configurations of the anchor passages 152 and 166 and the arcuate configurations of the pusher members 30d and 40d would facilitate movement of the anchors along the arcuate portions of the thin elongated members under the influence of force transmitted to the anchors from the pusher members.

If desired, the pusher members 30d and 40d could have flexible constructions to enable the pusher members to bend as they move along the arcuate portions of the thin elongated members 146 and 160. For example, the pusher members 30d and 40d could be formed of a polymeric material and be resiliently deflected by the arcuate portion of the thin elongated members 146 and 160. Alternatively, the pusher members 30d and 40d could be formed of tightly coiled spring wire.

It is contemplated that it may be desired to move the anchors 18d and 20d along helical insertion paths into the body tissues 12d and 14d. The thin elongated members 146 and 160 would be formed with helical configurations corresponding to the helical configurations of the anchor insertion paths. The thin elongated members 146 and 160 would be moved into the body tissues 12d and 14d with a screwing action by rotating the thin elongated members about a straight central axis of the helix. The anchors 18d and 20d would be moved along the helical portions of the thin elongated members 146 and 160 by pusher members 30d and 40d having a helical configuration. Alternatively, the pusher members 30d and 40d could have a flexible construction to enable the pusher members to conform to turns in the helical portions of each of the thin elongated members 146 and 160.

In the embodiment of the invention illustrated in FIGS. 14 and 15, the thin elongated members are offset from each other in the direction of the sheet on which FIG. 15 of the drawings is disposed. However, it is contemplated that the thin elongated members 146 and 160 could be positioned relative to each other with their central axes in a common plane. If this is done, the pointed end portion 148 (FIG. 14) of the thin elongated member 146 and the pointed end portion 162 of the thin elongated member 160 would be disposed in engagement when the thin elongated members have been inserted into the body tissue 12d and the body tissue 14d. This would facilitate positioning of the anchors 18d and 20d in engagement with each other, in a manner similar to that illustrated in FIG. 20 for the anchors 18g and 20g.

Embodiment of FIG. 16

A guide assembly 120e for guiding movement of suture anchors into body tissue is illustrated schematically in FIG. 16. The guide assembly 120e has the same general construction and mode of operation as the guide assembly 120 of FIG. 13. The guide assembly 120e is illustrated in FIG. 16 in association with soft body tissue 12e and 14e. The soft body tissue 12e is formed as a relatively thin layer. The body tissue 14e is formed as a relatively thick mass.

The guide assembly 120e is utilized to guide movement of suture anchors corresponding to the suture anchors 18 and 20 of FIG. 1 along insertion paths into the body tissue 14d with a suture, corresponding to the suture 24 of FIG. 1 extending between the suture anchors. However, the guide assembly 120e could be used in association with a suture which extends in a continuous loop between a pair of suture anchors. The continuous suture loop would be utilized in the same manner as described in conjunction with FIG. 11.

The guide assembly 120e includes a linear base 124e which is positioned in abutting engagement with an outer surface 300e of the layer 12e of body tissue. At this time, the guides 126e and 128e are withdrawn from openings in slide blocks 380 and 382 in the guide assembly 120e. The slide blocks are then moved along slots 384 and 386 in the base 124e until cylindrical openings which extend through the guide blocks are aligned with desired insertion locations for the anchors.

The guide 126e is then positioned in the opening in the slide block 380. The guide 126e is pressed axially into the body tissue 12e and the body tissue 14e to the position illustrated schematically in FIG. 16. The guide 128e is then pressed axially into the body tissue 124e and 114e to the position illustrated schematically in FIG. 16.

Once the guides 126e and 128e have both penetrated the soft body tissue 12e and 14e, anchors, corresponding to the anchors 18 and 20 of FIG. 1, are positioned in cylindrical passages 392 and 394 formed in the guides 126e and 128e. Pusher members, corresponding to the pusher members 30 and 40 of FIGS. 2-8, are then utilized to move the anchors 18 and 20 along the guides 126e and 128e through the layer 124e of soft body tissue into the mass 14e of soft body tissue. As this occurs, the suture extending between the anchors moves along slots 292e and 316e in the side walls of the tubular guides 126e and 128e. If the suture has the construction of the suture 24 of FIG. 1, the leg portions of the suture are tensioned after the anchors have been moved into the mass 14e of soft body tissue. However, if the suture has the loop construction illustrated in FIG. 11, the suture is tensioned as the anchors are moved into the soft body tissue 14e.

The slotted guides 126e and 128e are positioned with their longitudinal central axes extending transverse to each other. This results in the anchor which is moved along the guide 126e, that is the anchor corresponding to the anchor 18 in FIG. 1, moving toward the guide 128e as the anchor is moved into the body tissue. Similarly, the anchor which is moved along the guide 128e, that is, the anchor 20 in FIG. 1, moves toward the guide 126e as the anchor is moved into the body tissue 14e. The anchors may be left in the body tissue 14e with their longitudinal central axes extending parallel to longitudinal central axes of the guides 126e and 128e. Alternatively, the anchors may be pivoted or toggled to positions and orientations corresponding to the orientations of the anchors 18 and 20 in FIG. 10.

Once the anchors have been positioned in the body tissue with the suture extending between the anchors, the guides 126e and 128e are withdrawn from the body tissue 12d and 14d. Tension in the suture which extends between the anchors, is effective to press the layer 124e of body tissue firmly against the relatively large mass 14e of body tissue.

Embodiment of FIG. 17

In the embodiment of FIG. 17, the anchors 18f and 20f and the suture 24f are utilized to press bone 12f on one side of a fracture 178 against bone 14f on the other side of the fracture. The anchors 18f and 20f and the suture 24f have the same construction as the anchors 18 and 20 and suture 24 of FIGS. 1-10. To secure the body tissue or portion 12f of the bone 174 to the body tissue or portion 14f of the bone, the two portions of the bone are firmly pressed together at the fracture 178.

When the anchor 18f is to be positioned relative to the bone 174, the anchor is positioned in an inserter, corresponding to the inserter 28 of FIG. 2. A pusher member, corresponding to the pusher member 30 of FIG. 2, is positioned in the inserter and engages a trailing end portion of the anchor 18f. The anchor 24f is held in the inserter with a leading end portion 34f (FIG. 17) of the anchor extending from the inserter in the same manner as is illustrated in FIG. 2. At this time, the suture 18f extends along a slot in the inserter. Thus, the suture 24f extends along a slot corresponding to the slot 292 in the inserter 28 of FIG. 2.

The longitudinal central axis of the inserter is then positioned in a desired orientation relative to the portion 12f and the portion 14f of the bone 174. The orientation of the inserter corresponds to the path along which the anchor 18f is to be moved into and through the portion 12f of the bone 174 and into and through the portion 14f of the bone. If the anchor 18f is to be moved straight downward (as viewed in FIG. 17) through the portions 12f and 14f of the bone 174, the inserter would be positioned with its longitudinal central axis extending generally perpendicular to the outer surface 300f of the portion 14f of the bone 174. However, in the embodiment of the invention illustrated in FIG. 17 it is preferred to move the anchor along a path which is skewed relative to the outer surface 300f of the bone 174. The inserter may be positioned with its longitudinal axis extending at an angle of between 30° and 90° to the outer surface 300f of the bone.

With the inserter in the desired orientation relative to the surface 300f of the bone 174, the pointed leading end portion 34f of the anchor 18f is pressed against an imperforate area on the outer surface 300f of the bone 174. The pointed leading end portion 34f of the anchor 18f then initiates formation of an opening in the portion 12f of the bone 174. However, if desired, a drill or similar tool could be utilized to form a passage extending through the portion 12f and the portion 14f of the bone at the desired angle relative to the surface 300f of the bone. This passage could have a diameter which is either slightly smaller or slightly greater than the outside diameter of the anchor 18f. If the diameter of the passage which is drilled through the bone 174 is less than the outside diameter of the anchor, the anchor would be effective to expand the passage as the anchor moves into the portion 12f of the bone.

Assuming that the anchor 18f is utilized to form a passage in the bone 174, the pointed leading end portion of the anchor penetrates a hard outer layer 278f of the bone 174 and moves into cancellous bone 280f which is enclosed by the hard outer layer 278f. As this occurs, the pusher member, corresponding to the pusher member 30 is telescopically extended from the inserter, in the manner illustrated schematically in FIG. 4 for the pusher member 30 and inserter 28. This moves the anchor 18f through the portion 12f of the bone 174 and through the portion 14f of the bone.

Immediately after the anchor 18f emerges from the lower (as viewed in FIG. 17) side of the bone 174, the suture 24f is tensioned and the anchor is pivoted or toggled to the position illustrated in FIG. 17. After the anchor 18f has been toggled to the position illustrated in FIG. 17, the pusher member is withdrawn from the bone.

The anchor 20f is moved through the portion 12f of the bone 174 into the portion 14f of the bone 174, in the manner indicated schematically in solid lines in FIG. 17. The anchor 20f is moved through the portion 14f of the bone 174 and toggled to the position illustrated in dashed lines in FIG. 17.

When the anchor 20f is to be moved through the bone 174, the anchor is positioned in the inserter 38f which has the same construction as the inserters 28 and 38 of FIGS. 2-8. The pusher member 40f is telescopically moved along the inserter 38f into engagement with the trailing end portion of the anchor 20f. The suture 24f has the same construction as the suture 24 of FIG. 1. Therefore, a leg portion 52f and a connector portion 48f may be received in a slot in the inserter 38f in the same manner as previously described in conjunction with the embodiment of the invention illustrated in FIGS. 2-8.

The inserter 38f and pusher member 40f are positioned in an angular orientation relative to the surface 300f of the bone 174 corresponding to the angle of the desired path of insertion of the anchor 20f into the body tissue 12 and 14. In this specific embodiment of the invention illustrated in FIG. 17, the path of insertion of the anchor 20f into the bone 174 is skewed at an angle of between 55° and 60° relative to the surface 30f. It is contemplated that the path of insertion of the anchor 20f into the bone 174 may be located at an angle between 30° and 90° relative to the surface 300 of the bone 174. As was previously mentioned in conjunction with the anchor 18f, a passage extending through the bone 174 may be preformed by a drill or other tool.

Assuming that the anchor 20f is to be utilized to form its own passage through the bone 174, when a leading end portion 44f of the anchor 20f engages an imperforate surface on the outer surface 300f of the portion 12f of the bone 174, the leading end portion of the anchor initiates formation of an opening in the outer surface of the portion 12f of the bone 174. Continued movement of the pusher member 40f along the path of insertion of the anchor into the bone 174 results in the anchor moving into the hard outer layer 278f of the bone. Continued movement of the pusher member 40f relative to the inserter 38f results in the anchor moving into the cancellous bone 280f in the portion 12f of the bone 174. As the pusher member 40f continues to move the anchor 20f into the bone 174, the anchor moves across the fracture 178 in the manner illustrated schematically in FIG. 17, as the anchor 20f moves through the cancellous bone 280f.

The anchor 20f then moves through the hard outer layer 278f of the portion 14 of the bone 174. Once the anchor has moved out of the bone 14f at the lowest (as viewed in FIG. 17) side of the bone, the suture 24 is tensioned and the anchor is toggled to the position illustrated in dashed lines in FIG. 17.

Once the anchor 18f has been moved to the position illustrated in solid lines in FIG. 17 and the anchor 20f has been moved to the position illustrated in dashed lines in FIG. 17, ends of leg portions 50f and 52f of the suture 24f are tensioned. As this occurs, the suture 24f slides into passages formed in the anchors 18f and 20f. As the leg portions 50f and 52f of the suture 24f are tensioned, the connector portion 48f of the suture is tensioned. Any excess material in the connector portion 48f of the suture 24f is pulled from the connector portion 48f into either one or both of the leg portions 50f and 52f of the suture 24f. A retainer, corresponding to the retainer 54 of FIG. 9, may be utilized to interconnect the leg portions 50f and 52f of the suture 24f. Alternatively, a knot may be utilized to interconnect the leg portions 50f and 52f if desired.

A force application assembly, corresponding to the force application assembly 60 of FIG. 10 may be utilized to apply a predetermined tension force to the leg portions 50f and 52f of the suture 24f. In addition, a force application member, similar to the force application member 66 of FIG. 10, may be utilized to press a crimp against the bone 174 as the suture 24f is tensioned. While the desired tension force is being applied to the suture and while the crimp is being pressed against the bone with the desired force, force application members, corresponding to force application members 76 and 78 of FIG. 10, may be utilized to plastically deform the suture retainer.

It is believed that a guide assembly, similar to the guide assembly 120 of FIG. 13, may advantageously be utilized when the anchors 18f and 20f are being moved into the bone 174f. The guide assembly may have guides, corresponding to the guides 126 and 128 of FIG. 13, which engage the anchors 18f and 20f and the associated pusher members corresponding to the pusher members 30 and 40 of FIGS. 1-8. Alternatively, the guides could be utilized to position inserters, corresponding to the inserters 28 and 38 of FIGS. 2-8.

When the anchors 18f and 20f of FIG. 17 are being moved into the bone 174, it is believed that the use of thin elongated members, corresponding to the thin elongated members 146 and 160 of FIG. 15, may advantageously be utilized to guide movement of the anchors 18f and 20f along preselected paths. Thus, the thin elongated members would be moved through the bone 174. One of the thin elongated members would be moved through the bone 174 along an insertion path to be followed by the anchor 18f. The other thin elongated member would be moved through the bone 174 through an insertion path to be followed by the anchor 20f.

Small passages may be predrilled in the bone 174 to receive the thin elongated members. The predrilled holes for the thin elongated members may have a diameter which is slightly less than the diameter of the thin elongated members. Once the thin elongated members have been moved through the bone 174, the anchors 18f and 20f are moved along the thin elongated members through the bone 174.

Embodiment of FIGS. 18 and 19

The anchors of FIGS. 1-17 all have the same general construction. However, it is contemplated that the anchors could have a different construction if desired. For example, the anchors could be constructed in the manner generally similar to the construction of the anchor 186 of FIG. 18. The anchor 186 has a plurality of barbs, that is barbs 192, 194 and 196. The barbs 192, 194 and 196 engage body tissue to hold the anchor 186 against movement relative to the body tissue. Of course, the anchor could be provided with barbs or projections having a construction which is different than the construction of the barbs or projections 192, 194 and 196 if desired.

The anchor 186 has a known construction. The construction of the anchor 186 is the same as is disclosed in U.S. Pat. No. 5,725,557. However, it should be understood that the anchor 186 is typical of many different known anchor constructions having projections or barbs which engage either soft or hard body tissue to retain the anchor against movement relative to the body tissue. Any one of these known anchors could be utilized in place of the anchor 186 if desired. The anchor 204 of FIG. 19 has a threaded portion 206 which engages body tissue to hold the anchor against movement relative to the body tissue. Although it is believed that the threaded portion 206 may be most effective to hold the anchor 204 against movement relative to bone, the anchor could be utilized in association with soft body tissue if desired.

The anchor 204 has a known construction. The construction of the anchor 204 is the same as is disclosed in U.S. Pat.

No. 5,443,482. However, it should be understood that the anchor 204 could have a different construction if desired.

Embodiment of FIGS. 20 and 21

In the embodiment of the invention illustrated in FIGS. 20 and 21, the anchors 18 and 20 are moved into body tissue 12g and 14g along insertion paths which intersect in the body tissue 14g. In FIG. 20, the longitudinal central axes of the insertion paths along which the anchors 18g and 20g are moved into the body tissue 12g and 14g are disposed in a single flat plane.

The anchors 18g and 20g are advantageously interconnected at the location where the paths of insertion of the anchors into the body tissue 12g and 14g intersect. It is believed that movement of the anchors 18g and 20g along intersecting insertion paths into the body tissue 12g and 14g may be facilitated by the utilization of a guide assembly, corresponding to the guide assembly 120 of FIG. 13. In addition, thin elongated members, corresponding to the thin elongated members 146 and 160 of FIG. 15, may be utilized to further guide movement of the anchors 18g and 20g.

Although the anchors 18g and 20g have been illustrated in FIG. 20 in association with soft body tissue 12g having an arcuate outer surface 300g and hard body tissue or bone 14g having an arcuate outer surface 304g, it is contemplated that the anchors 18g and 20g could be moved into body tissue having outer surfaces with many different configurations, including an irregular or flat configuration. It should also be understood that the anchors 18g and 20g may be utilized in association with just soft body tissue. For example, the anchors 18g and 20g could be utilized to connect one piece of soft body tissue, corresponding to the body tissue 12g of FIG. 20, with another piece of soft body tissue, corresponding to the body tissue 14g of FIG. 20.

The anchors 18g and 20g may be sequentially moved through the body tissue 12g and into the body tissue 14g or may be simultaneously moved through the body tissue 12g into the body tissue 14g. Assuming that the anchors 18g and 20g are sequentially moved through the body tissue 12g and into the body tissue 14g, the anchor 18g is first moved through the body tissue 12g into the body tissue 14g. An inserter member and a pusher member, corresponding to the inserter 28 and pusher member 30 of FIG. 2, are utilized to move the anchor 18g into the body tissue 14g. If a guide assembly, similar to the guide assembly 120 of FIG. 13, is utilized to facilitate movement of the anchor 18g along a desired insertion path, the inserter, corresponding to the inserter 28 of FIG. 1, may be omitted and the anchor moved along a guide, corresponding to the guide 126 of FIG. 13.

The pusher member which is utilized to move the anchor 18g through the body tissue 12g and into the body tissue 14g may advantageously be provided with indicia, corresponding to the indicia 360 on the pusher member 132 of FIG. 13. When the indicia 360 on the pusher member indicates that the anchor 18g has been moved to the desired depth in the body tissue 14g, movement of the anchor into the body tissue is interrupted.

The anchor 20g is then moved through the body tissue 12g into the body tissue 14g. The path of movement of the anchor 20g through the body tissue 12g into the body tissue 14g intersects the path of movement of the anchor 18g. It is contemplated that the use of a guide assembly, corresponding to the guide assembly 120 of FIG. 13, will facilitate movement of the anchor 20g along an insertion path which intersects the insertion path of the anchor 18g. However, if desired, the anchor 20g could be moved along its insertion path without the benefit of a guide assembly corresponding to the guide assembly 120 of FIG. 13.

It is believed that it may be desired to utilize thin elongated members, corresponding to the thin elongated members 146 and 160 of FIG. 15, to position the anchors 18g and 20g relative to the body tissue 12g and 14g. Of course, if this was done, passages, corresponding to the passages 152 and 166 in the anchors 18d and 20d of FIG. 15, would be provided in the anchors 18g and 20g.

In the embodiment of the invention illustrated in FIG. 20, the anchors 18g and 20g each have a portion of a suture 24g extending from the anchors. Thus, a leg portion 50g of suture material is secured to the anchor 18g and extends from the anchor to the retainer 54g. Similarly, a leg portion 52g of the suture material is fixedly connected to the anchor 20g and extends to the retainer 54g. In the embodiment of the invention illustrated in FIG. 20, there is no connector portion, corresponding to the connector portion 48 of FIGS. 1 and 9, of the suture 24g extending between the two anchors 18g and 20g. Thus, the leg portions 50g and 52g of the suture 24g are formed as separate segments. Of course, the suture 24g could be provided with a connector portion, corresponding to the connector portion 48 of FIGS. 1 and 9 if desired.

The anchors 18g and 20g are interconnected at the location where the paths along which they move through the body tissue 12g into the body tissue 14g intersect. The manner in which the anchors 18g and 20g are interconnected is illustrated schematically in FIG. 21.

The anchor 18g has a leading end portion 34g which engages a leading end portion 44g of the anchor 20g. Although the leading end portions 34g and 44g of the anchors 18g and 20g have a generally conical configuration, corresponding to the conical configuration of the leading portions 34 and 44 of the anchors 18 and 20 (FIG. 1). It is contemplated that the leading end portions 34g and 44g of the anchors 18g and 20g could have a different configuration if desired. For example, the leading end portions 34g and 44g of the anchors 18g and 20g could have generally wedge-shaped configurations. Alternatively, is the leading end portions 34g and 44g of the anchors could be formed with hooks and/or loops.

In the illustrated embodiment of the invention, the leading end portion 34g of the anchor 18g is formed with annular projections 212 (FIG. 21) which engage annular projections 214 on the leading end portion 44g of the anchor 20g. The annular projections 212 on the anchor 18g extend around the end portion 34g of the anchor. Similarly, the annular projections 214 on the anchor 20g extend around the end portion 44g of the anchor.

The projections 212 and 214 on the anchors 18g and 20g engage each other as the anchor 20g moves along its insertion path into engagement with the anchor 18g. The projections 212 and 214 become interconnected in such a manner as to interconnect the anchors 18g and 20g. Thus, the projections 212 and 214 become intermeshed to prevent separation of the anchors 18g and 20g.

It is contemplated that the leading end portions 34g and 44g of the anchors 18g and 20g could be interconnected in a different manner other than by the use of projections corresponding to the projections 212 and 214. Thus, one of the anchors, for example, the anchor 18g, could be provided with a plurality of hooks which would engage a plurality of loops on the other anchor, that is, the anchor 20g. If desired, the anchors 18g and 20g could be formed of materials having magnetic poles such that the leading end portions 34g and 44g of the anchors 18g and 20g are attracted to each other. It is contemplated that magnetic force may be utilized to promote engagement of the leading end portions 34g and 44g of the anchors 18g and 20g with any one of many different types of interconnections between the anchors 18g and 20g. If this was done, the magnetic forces between the anchors 18g and 20g would be utilized to promote engagement of one portion of a mechanical interconnection on the anchor 18g with another portion of a mechanical connection on the anchor 20g.

If desired, fiberoptics could be positioned along the paths of movement of the anchors 18g and 20g into the body tissue 14g. One of more guide members could be inserted through one or more cannulas into engagement with the leading end portion of either the anchor 18g or 20g or both of the anchors to apply force to the anchors to promote engagement of the leading end portions 34g and 44g of the anchors. If this was done, one of the guide members could be utilized to actuate an interconnection device between the anchors 18g and 20g. For example, the guide member could be utilized to actuate a latch so that the latch would lock the leading end portions 34g and 44g of the anchors 18g and 20g together.

Embodiment of FIG. 22

The embodiment of the invention illustrated in FIG. 22 is similar to the embodiment of the invention illustrated in FIGS. 20 and 21. However, in the embodiment of the invention illustrated in FIG. 22, the anchors 18h and 20h are interconnected at the location where their insertion paths into the body tissue 14h intersect by having one anchor move into an opening in the other anchor.

In the embodiment of the invention illustrated in FIG. 22, the anchor 18h is provided with an opening 220 into which the anchor 20h moves. The anchor 20h has a plurality of retainers 224 which engage the portion of the anchor 18h forming the opening 220 to interconnect the two anchors.

If desired, the anchor 18h could be provided with a flexible mesh, a series of hooks, and/or a series of loops which are engaged by the anchor 20h to interconnect the anchors 18h and 20h. Thus, a multiplicity of retainers or hooks, corresponding to the retainers 224, could be provided at axially spaced apart locations along the body of the anchor 20h to engage openings formed by loops or a mesh connected with the anchor 18h. It should be understood that the openings or mesh provided by the anchor 18h could be formed by one or more extensions from the anchor 18h.

It is believed that accurate movement of the anchors 18h and 20h along insertion paths which intersect in the body tissue 14h may be promoted by the use of a robotic assembly to position the anchors. Thus, an inserter assembly connected to one articulate arm of a robotic assembly could be utilized to position the anchor 18h in the body tissue 14h and a second articulate arm of the robotic apparatus could be utilized to position the anchor 20h in the body tissue 14h. If desired, a guide assembly, corresponding to the guide assembly 120 of FIG. 13, could be utilized in association with the robotic arms. If this was done, the guide assembly could be connected with one of the robotic arms for movement therewith relative to the other robotic arm. Accurate placement of the anchors 18h and 20h at the desired depth in the body tissue would be facilitated by pusher member drive assemblies on the robotic arms.

Embodiment of FIG. 23

In the embodiments of the invention illustrated in FIGS. 1-22, anchors have been completely enclosed by the body tissue into which they are inserted. Thus, the anchors 18 and 20 have been completely enclosed by the body tissue 14 (FIG. 9) into which the anchors are inserted. In the embodiment of the invention illustrated in FIG. 23, anchors 18j and 20j are only partially enclosed by the body tissue into which they are inserted. Portions of the anchors 18 and 20 extend from the body tissue.

In the embodiment of the invention illustrated in FIG. 23, a portion of the anchor 18j is inserted through the body tissue 12j into the body tissue 14j. Thus, the shank portion 230 of the anchor 18j is inserted through the body tissue 12j into the body tissue 14j. Similarly, the anchor 20j is provided with a shank portion which is inserted through the body tissue 12j into the body tissue 14j.

In the embodiment of the invention illustrated in FIG. 23, the suture 24j is connected with the shank portions 230 and 238 of the anchors 18j and 20j immediately beneath head end portions 234 and 242 of the anchors. However, the suture 24j could be connected with the shank portions 230 and 238 of the anchors 18j and 20j at a location spaced from the head end portions 234 and 238 of the anchors.

For example, the shank portion 230 of the anchor 18j could be provided by an opening which is engaged by the suture 24j and which moves into the body tissue 14j when the anchor 18j moves into the body tissue. This opening could be formed as a recess which functions as a hook to engage a bend in the suture 24j. The hook in the shank portion 230 of the anchor 18j could be formed adjacent to a pointed leading end portion 34j of the shank portion 230. Alternatively, a hole could extend diametrically through the shank portion 230 of the anchor 18j. The opening through which the suture 24j extends could be formed adjacent to the leading end portion 34j of the anchor 18j or at any desired location along the shank portion 230 of the anchor 18j.

The anchor 20j may be provided with a series of generally hook-shaped recesses in the shank portion 238j of the anchor. These recesses may be provided at axially spaced apart locations along the shank portion 238 of the anchor 20j. The suture 234j may be formed as a loop, in the manner indicated schematically in FIG. 11 for the suture 20a. If this is done, the suture loop could be moved into engagement with a recess in the shank portion 238 of the anchor 20j which would result in a desired amount of tension being removed from the suture 24j as the shank portion 238 of the anchor 20j moves through the body tissue 12j into the body tissue 14j.

For example, if there is a relatively large amount of slack in the suture 24j, the suture would engage a recess adjacent to a pointed leading end portion 44j of the anchor 20j. However, if there was relatively little slack in the suture 24j, the suture would be disposed in engagement with a recess spaced along the shank portion 238 at a distance from the pointed leading end portion 44j of the anchor 20j. It is contemplated that a series of recesses could be provided along the shank portion 238 of the anchor 20j to engage the suture 24j even if the suture is positioned beneath the head end portion 234 of the anchor 18j, in the manner illustrated in FIG. 23, rather than being disposed in engagement with a recess or opening in the shank portion 230 of the anchor 18j.

The head end portions 234 and 242 on the anchors 18j and 20j engage the body tissue 12j to limit the extent of movement of the anchors into the body tissue 14j. In addition, the head end portions 234 and 242 of the anchors 18j and 20j press the suture 24j against the body tissue 12j to facilitate locating the suture 24j in a desired orientation relative to the body tissue. If the suture 24j engages a hole or a recess in a shank portion 230 or 238 of an anchor 18j or 20j, the head end portions 234 and 242 could be omitted. Alternatively, the head end portions could be provided with slots or notches through which the suture would extend. The notches or slots in the head end portions 234 and 242 of the anchors 18j and 20j may be located on sides of the anchors opposite from the other anchor. Thus, the recess or slot in the head end portion 234 of the anchor 18j would be provided on a side of the anchor 18j opposite from the anchor 20j. The suture 24j would extend from an opening or recess in the shank portion 230 of the anchor 18j into the slot. The suture 24j would then extend across the head end portion 234 of the anchor 18j to the anchor 20j. By having the suture 24j extend across the head end portion 234 of the anchor 18j, any tendency for the suture to cut the soft body tissue 12j would be minimized.

The loop forming the suture 24j would then be moved across the head end portion 242 of the anchor 20j into a notch or slot inside of the head end portion 242 of the anchor 20j opposite from the anchor 18j. The suture 24j would then be pulled downward (as viewed in FIG. 23) along the shank portion 238 of the anchor 20j and engaged with a selected recess of a series of recesses in the shank portion 238 of the anchor 20j. Once this has been done, the anchor 20j would be moved through the body tissue 12j into the body tissue 14j. Since the path of movement of the anchor 20j through the body tissue 12j into the body tissue 14j extends transverse to the path of movement of the anchor 18j through the body tissue 12j and into the body tissue 14j, the tension in the suture 24j would be increased as the anchor 20j moves into the body tissue 14j.

CONCLUSION

The present invention relates to a new and improved method of securing a first body tissue 12 with a second body tissue 14. The first body tissue 12 may be a soft body tissue and the second body tissue 14 may be a hard body tissue. Alternatively, the first and second body tissues 12 and 14 may both be soft body tissues. It is also contemplated that both the first and second body tissues 12 and 14 could be hard body tissues.

When the first and second body tissues are to be interconnected, a first anchor 18 is moved into the second body tissue 14. If desired, the first anchor 18 could be moved into and through the second body tissue 14. A second anchor 20 is also moved into the second body tissue 14. If desired, the second anchor 20 could be moved into and through the second body tissue 14. The first body tissue 12 may be pressed against or otherwise secured with the second body tissue 14 under the influence of force transmitted from the suture 24 to the first body tissue 12.

The suture 24 which extends between the anchors 18 and 20 may be tensioned by moving at least one of the anchors 18 and 20 into the body tissue along a path which extends transverse to a path along which the other anchor is moved into the body tissue. The paths along which the anchors 18 and 20 move into the body tissue 14 may extend toward each other. The transverse paths of movement of the anchors 18 and 20 into the body tissue 14 promote gripping of body tissue with the anchors and suture 24 and promotes tensioning of the suture as the anchors move into the body tissue. Although it is believed that it may be desired to move the anchors 18 and 20 into the body tissue along transverse paths, it is contemplated that the anchors could be moved into the body tissue along parallel paths if desired.

A desired tension may be established in the suture 24 by moving the anchors 18 and 20 into the body tissue (FIGS. 11, 13-15, and 23). Alternatively, a desired tension may be established in the suture 24 by applying force to portions of the suture and then interconnecting the portions of the suture (FIGS. 1-10, 12, 17, and 20-22). A retainer 54 or a knot may be utilized to interconnect portions of the suture 24.

Regardless of how the tension is established in the suture 24, it may be desired to establish a predetermined tension in the suture. This may be done by determining the tension in the suture 24 as the anchors are moved into the body tissue (FIG. 12). Alternatively, the tension in the suture 24 may be determined during movement of a retainer relative to portions of the suture prior to gripping of the suture with the retainer (FIG. 10).

The suture 24 may be a continuous loop (FIGS. 11, 13-15, and 23) which extends between the two anchors 18 and 20. The tension in the loop may be determined as one or more of the anchors 18 and 20 are moved into the body tissue 14. Alternatively, the suture 24 may be formed by a pair of separate portions (FIGS. 1-10, 12, 17 and 20-22), which are tensioned after the anchors 18 and 20 are moved into the body tissue.

One or more guides 126 and 128 may be utilized to facilitate positioning of the anchors for movement along paths disposed in a desired spatial relationship with the body tissue. The guides 126 and 128 may have tubular guide surfaces with central axes which extend transverse to each other.

Leading end portions 34 and 44 of the anchors 18 and 20 may be utilized to initiate the formation of openings in the first and/or second body tissue 12 and 14. The leading end portion of each of the anchors 18 and 20 may be utilized to pierce soft body tissue, a hard outer layer of bone, and/or cancellous bone as the anchor is moved into the body tissue. If either or both of the anchors 18 and 20 are associated with body tissue which is bone, one or more of the anchors may be supported in a spaced apart relationship with a hard outer layer 278 of bone by cancellous bone 280 which is enclosed by the hard outer layer of bone. If desired, passages for the anchors may be formed with a drill or similar tool.

The anchors 18 and 20 may advantageously be interconnected while they are disposed in the body tissue (FIGS. 20-22). When this is done, the anchors 18 and 20 may be moved along transverse paths which intersect in the body tissue. The anchors 18 and 20 may be interconnected at the intersection between the two paths.

There are a plurality of embodiments of the invention. Each embodiment of the invention has one or more features which may be advantageously utilized with one or more of the other embodiments of the invention. It is contemplated that the various features of the embodiments of the invention may be utilized separately or combined in any one of many different combinations.

Having described the invention, the following is claimed:

1. A method of securing first body tissue with second body tissue, said method comprising the steps of providing a plurality of anchors with a suture extending between the anchors, moving a first anchor of the plurality of anchors along a first path into the second body tissue, moving a second anchor of the plurality of anchors along a second path into the second body tissue, tensioning at least a portion of the suture extending between the first and second anchors by moving the second anchor along at least a portion of the second path which extends transverse to the first path, and transmitting force through the suture to the first body tissue.

2. A method as set forth in claim 1 wherein said step of moving a first anchor along a first path into the second body tissue includes piercing the first body tissue with a leading end portion of the first anchor.

3. A method as set forth in claim 2 wherein said step of moving a first anchor along a first path into the second body tissue includes piercing the second body tissue with the leading end portion of the first anchor.

4. A method as set forth in claim 3 wherein said step of moving a second anchor along a second path into the second body tissue includes piercing the first body tissue with a leading end portion of the second anchor.

5. A method as set forth in claim 4 wherein said step of moving a second anchor along a second path into the second body tissue includes piercing the second body tissue with the leading end portion of the second anchor.

6. A method as set forth in claim 1 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

7. A method as set forth in claim 6 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

8. A method as set forth in claim 1 further including the steps of sliding a suture retainer along a first portion of the suture which extends from the first anchor, sliding the suture retainer along a second portion of the suture which extends from the second anchor, and gripping the first and second portions of the suture with the suture retainer.

9. A method as set forth in claim 1 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

10. A method as set forth in claim 1 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

11. A method as set forth in claim 1 wherein said step of moving the first anchor along the first path includes moving the first anchor along a first path having a nonlinear central axis, said step of moving the second anchor along the second path includes moving the second anchor along a second path having a nonlinear central axis.

12. A method as set forth in claim 1 wherein said steps of moving the first anchor along a first path and moving the second anchor along a second path include interconnecting the first and second anchors while the first and second anchors are disposed in the second body tissue.

13. A method as set forth in claim 12 wherein said step of interconnecting the first and second anchors includes moving one of the first and second anchors into engagement with the other of the first and second anchors.

14. A method as set forth in claim 12 wherein said step of interconnecting the first and second anchors includes moving one of the first and second anchors into an opening in the other of the first and second anchors.

15. A method as set forth in claim 1 wherein said step of moving the first anchor of the plurality of anchors along a first path into the second body tissue includes moving the first anchor through a predetermined distance into the second body tissue.

16. A method as set forth in claim 15 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

17. A method as set forth in claim 1 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

18. A method as set forth in claim 1 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

19. A method as set forth in claim 1 further including the steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

20. A method as set forth in claim 1 wherein said step of moving a first anchor along a first path includes transmitting force from a robotic assembly to the first anchor, said step of moving a second anchor along a second path includes transmitting force from the robotic assembly to the second anchor.

21. A method of securing first body tissue with second body tissue, said method comprising the steps of moving a first anchor along a first path through the first body tissue into the second body tissue with a first suture portion extending from the first anchor, moving a second anchor along a second path through the first body tissue into the second body tissue with a second suture portion extending from the second anchor, tensioning the first and second suture portions with a predetermined force, and gripping the first and second suture portions with a suture retainer while tensioning the first and second suture portions with the predetermined force.

22. A method as set forth in claim 21 wherein said step of gripping the first and second suture portions with the suture retainer includes pressing force transmitting members against the suture retainer, and transmitting ultrasonic vibratory energy to a location where one of the force transmitting members presses against the suture retainer.

23. A method as set forth in claim 21 further including the steps of wrapping the first suture portion around the suture retainer, wrapping the second suture portion around the suture retainer, and moving the suture retainer along the first and second suture portions toward the first body tissue while the first and second suture portions are wrapped around the suture retainer.

24. A method as set forth in claim 23 further including the step of gripping the first and second suture portions with the suture retainer while the first and second suture portions are wrapped around the suture retainer by plastically deforming material of the suture retainer.

25. A method as set forth in claim 21 further including the step of selecting first and second suture portions of a known size and strength, said step of tensioning the first and second suture portions with a predetermined force includes tensioning the first and second suture portions with a force which is a known function of the known size and strength of the first and second suture portions.

26. A method as set forth in claim 21 wherein the first body tissue is a first layer of soft tissue and the second body tissue is a second layer of soft tissue, said method further includes approximating the first and second layers of body tissue, and pressing the first layer of body tissue against the second layer of body tissue.

27. A method as set forth in claim 21 wherein said step of moving the second anchor along the second path through the first body tissue into the second body tissue includes moving the second anchor along a portion of the second path which extends transverse to the first path.

28. A method as set forth in claim 21 wherein a third suture portion extends between the first and second anchors, said step of moving the second anchor along the second path includes moving the second anchor along a portion of the second path which extends transverse to the first path to tension the third suture portion.

29. A method as set forth in claim 21 wherein said step of moving a first anchor along a first path through the first body tissue into the second body tissue includes piercing the first body tissue with a leading end portion of the first anchor.

30. A method as set forth in claim 29 wherein said step of moving a first anchor along a first path through the first body tissue into the second body tissue includes piercing the second body tissue with the leading end portion of the first anchor.

31. A method as set forth in claim 30 wherein said step of moving a second anchor along a second path into the second body tissue includes piercing the first body tissue with a leading end portion of the second anchor.

32. A method as set forth in claim 31 wherein said step of moving a second anchor along a second path into the second body tissue includes piercing the second body tissue with the leading end portion of the second anchor.

33. A method as set forth in claim 21 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

34. A method as set forth in claim 33 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

35. A method as set forth in claim 21 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

36. A method as set forth in claim 21 wherein said step of moving the first anchor along the first path includes moving the first anchor along a first path having a nonlinear central axis, said step of moving the second anchor along the second path includes moving the second anchor along a second path having a nonlinear central axis.

37. A method as set forth in claim 21 wherein said steps of moving the first anchor along a first path and moving the second anchor along a second path include interconnecting the first and second anchors while the first and second anchors are disposed in the second body tissue.

38. A method as set forth in claim 37 wherein said step of interconnecting the first and second anchors includes moving one of the first and second anchors into engagement with the other of the first and second anchors.

39. A method as set forth in claim 37 wherein said step of interconnecting the first and second anchors includes moving of the first and second anchors into an opening in the other of the first and second anchors.

40. A method as set forth in claim 21 wherein said step of moving the first anchor along a first path through the first body tissue into the second body tissue includes moving the first anchor through a predetermined distance into the second body tissue, said step of moving the second anchor along a second path through the first body tissue into the second body tissue includes moving the second anchor through a predetermined distance into the second body tissue.

41. A method as set forth in claim 40 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue, said step of moving the second anchor through a predetermined distance into the second body tissue includes applying force against a trailing end portion of the second anchor with a pusher member having indicia thereon, and detecting when the indicia on the pusher member indicates that the second anchor has been moved through a predetermined distance relative to the second body tissue.

42. A method as set forth in claim 21 further including the step of positioning a guide assembly having first and second guide surfaces relative to at least one of the first and second body tissues, engaging the first anchor with the first guide surface during movement of the first anchor along the first path, and engaging the second anchor with the second guide surface during movement of the second anchor along the second path.

43. A method as set forth in claim 21 further including the steps of moving a thin elongated member along the first path through the first body tissue into the second body tissue, said step of moving a first anchor along the first path through the first body tissue into the second body tissue is at least partially performed with the thin elongated member extending through the first anchor, and moving a thin elongated member along the second path through the first body tissue into the second body tissue, said step of moving a second anchor along the second path through the first body tissue into the second body tissue is at least partially performed with the thin elongated member extending through the second anchor.

44. A method as set forth in claim 21 wherein said steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

45. A method as set forth in claim 21 wherein said step of moving a first anchor along a first path includes transmitting force from a robotic assembly to the first anchor, said step of moving a second anchor along a second path includes transmitting force from the robotic assembly to the second anchor.

46. A method of securing first body tissue with second body tissue, said method comprises the steps of moving a first anchor into first body tissue at a first location, moving the first anchor into the second body tissue, moving a second anchor into the first body tissue at a second location, moving the second anchor into the second body tissue, moving the first anchor in the second body tissue in a direction away from the first location where the first anchor moved into the first body tissue and in a direction toward the second location where the second anchor moved into the first body tissue, pulling a first suture portion into the second body tissue under the influence of force transmitted from the first anchor to the first suture portion as the first anchor moves in the second body tissue in a direction away from the first location where the first anchor moved into the first body tissue and toward the second location where the second anchor moved into the first body tissue, moving the second anchor in the second body tissue in a direction away from the second location where the second anchor moved into the first body tissue and in a direction toward the first location where the first anchor moved into the first body tissue, and pulling a second suture portion into the second body tissue under the influence of force transmitted from the second anchor to the second suture portion as the second anchor moves in the second body tissue in a direction away from the second location where the second anchor moved into the first body tissue and toward the first location where the first anchor moved into the first body tissue.

47. A method as set forth in claim 46 wherein said step of moving the first anchor into the second body tissue in a direction away from the first location where the first anchor moved into the first body tissue and toward the second location where the second anchor moved into the first body tissue includes moving the first anchor along a linear path which extends through the first location where the first anchor moved into the first body tissue, and said step of moving the second anchor in the second body tissue in a direction away from the second location where the second anchor moved into the first body tissue and toward the first location where the first anchor moved into the first body tissue includes moving the second anchor along a linear path which extends through the second location where the second anchor moved into the first body tissue.

48. A method as set forth in claim 46 wherein said step of moving the first anchor in the second body tissue in a direction away from the first location where the first anchor moved into the first body tissue and toward the second location where the second anchor moved into the first body tissue includes moving the first anchor along a nonlinear path which extends through the first location where the first anchor moved into the first body tissue and said step of moving the second anchor in the second body tissue in a direction away from the second location where the second anchor moved into the first body tissue and toward the first location where the first anchor moved into the first body tissue includes moving the second anchor along a nonlinear path which extends through the second location where the second anchor moved into the first body tissue.

49. A method as set forth in claim 46 further including the step of tensioning the first and second suture portions during movement of at least one of said first and second anchors in the second body tissue.

50. A method as set forth in claim 49 wherein said step of tensioning the first and second suture portions includes increasing the tension in the first and second suture portions, said method further includes interrupting said step of increasing the tension in the first and second suture portions when a predetermined tension is present in the first and second suture portions.

51. A method as set forth in claim 46 further including the step of interconnecting the first and second suture portions after performing said steps of moving the first anchor into the second body tissue and moving the second anchor into the second body tissue.

52. A method as set forth in claim 46 wherein said step of moving a first anchor into the first body tissue includes piercing the first body tissue with a leading end portion of the first anchor.

53. A method as set forth in claim 52 wherein said step of moving a first anchor into the second body tissue includes piercing the second body tissue with the leading end portion of the first anchor.

54. A method as set forth in claim 53 wherein said step of moving a second anchor into the first body tissue includes piercing the first body tissue with a leading end portion of the second anchor.

55. A method as set forth in claim 54 wherein said step of moving a second anchor into the second body tissue includes piercing the second body tissue with the leading end portion of the second anchor.

56. A method as set forth in claim 46 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

57. A method as set forth in claim 56 further including the steps of retaining the first anchor against movement relative to the hard outer layer of the bone while tensioning the first suture portion by transmitting force between the first anchor and the cancellous bone while the first anchor is spaced from the hard outer layer of the bone and retaining the second anchor against movement relative to the hard outer layer of the bone while tensioning the second suture portion by transmitting force between the second anchor and the cancellous bone while the second anchor is spaced from the hard outer layer of the bone.

58. A method as set forth in claim 46 further including the steps of sliding a suture retainer along the first suture portion, sliding the suture retainer along the second suture portion, and gripping the first and second suture portions with the suture retainer.

59. A method as set forth in claim 46 further including the step of changing the orientation of the first anchor relative to the second body tissue, said step of changing the orientation of the first anchor relative to the second body tissue includes rotating the first anchor about an axis which extends transverse to a straight line between the first and second locations, said method further includes the step of tensioning at least one of the first and second suture portions by moving a portion of the second anchor in the second body tissue after performing said step of changing the orientation of the first anchor relative to the second body tissue.

60. A method as set forth in claim 46 further including the steps of changing the orientation of the first anchor relative to the second body tissue, said step of changing the orientation of the first anchor relative to the second body tissue includes rotating the first anchor about an axis which extends transverse to a straight line between the first and second locations, and changing the orientation of the second anchor relative to the second body tissue, said step of changing the orientation of the second anchor relative to the second body tissue includes rotating the second anchor about an axis which extends transverse to the straight line between the first and second locations.

61. A method as set forth in claim 60 further including the step of tensioning the first and second suture portions after performance of said step of changing the orientation of the first anchor relative to the second body tissue.

62. A method as set forth in claim 46 further including the step of interconnecting the first and second anchors while the first and second anchors are disposed in the second body tissue.

63. A method as set forth in claim 62 wherein said step of interconnecting the first and second anchors includes moving one of the first and second anchors into engagement with the other of the first and second anchors.

64. A method as set forth in claim 62 wherein said step of interconnecting the first and second anchors includes moving one of the first and second anchors into an opening in the other of the first and second anchors.

65. A method as set forth in claim 46 wherein said step of moving the first anchor into the second body tissue includes moving the first anchor through a predetermined distance into the second body tissue.

66. A method as set forth in claim 65 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

67. A method as set forth in claim 46 further including the step of positioning a guide assembly having first and second guide surfaces relative to at least one of the first and second body tissues, engaging the first anchor with the first guide surface during movement of the first anchor relative to the first and second body tissues, and engaging the second anchor with the second guide surface during movement of the second anchor relative to the first and second body tissues.

68. A method as set forth in claim 46 further including moving a first thin elongated member into the second body tissue, said step of moving a first anchor into the second body tissue is at least partially performed with the first thin elongated member extending through the first anchor, and moving a second thin elongated member into the second body tissue, said step of moving a second anchor into the second body tissue is at least partially performed with the second thin elongated member extending through the second anchor.

69. A method as set forth in claim 46 wherein said steps of providing a guide assembly having a base and first and second tubular guides, moving the first tubular guide through the first body tissue into engagement with the second body tissue, moving the second tubular guide through the first body tissue into engagement with the second body tissue, said step of moving the first anchor into the second body tissue includes moving the first anchor through the first tubular guide into the second body tissue, said step of moving the second anchor into the second body tissue includes moving the second anchor through the second tubular guide into the second body tissue.

70. A method as set forth in claim 46 wherein said step of moving a first anchor into the second body tissue includes transmitting force from a robotic assembly to the first anchor, said step of moving a second anchor into the second body tissue includes transmitting force from the robotic assembly to the second anchor.

71. A method of securing first body tissue with second body tissue, said method comprising the steps of providing first and second anchors with a suture extending between the first and second anchors, moving the first anchor along a first path into the second body tissue, moving the second anchor along a second path into the second body tissue, detecting when a predetermined tension is present in the suture during movement of at least one of the first and second anchors along at least one of the first and second paths, and interrupting movement of at least the one of the first and second anchors along the one of the first and second paths upon detection of the predetermined tension in the suture.

72. A method as set forth in claim 71 wherein said step of moving the first anchor along the first path is performed prior to performance of said step of moving the second anchor along the second path, and said step of detecting when a predetermined tension is present in the suture is performed during movement of the second anchor along the second path.

73. A method as set forth in claim 71 wherein said steps of moving the first and second anchors along the first and second paths are at least partially performed simultaneously, and said step of detecting when a predetermined tension is present in the suture is performed during movement of the first and second anchors along the first and second paths.

74. A method as set forth in claim 71 wherein said step of moving the second anchor along the second path includes moving the second anchor along a portion of the second path which extends transverse to the first path, said step of detecting when a predetermined tension is present in the suture is performed during movement of the second anchor along the portion of the second path which extends transverse to the first path.

75. A method as set forth in claim 71 wherein said step of moving the first anchor along the first path includes initiating formation of a first opening in the second body tissue at a first location with a leading end portion of the first anchor, said step of moving the second anchor along the second path includes initiating formation of a second opening in the second body tissue at a second location with a leading end portion of the second anchor, said step of detecting when a predetermined tension is present in the suture is performed with a portion of the suture extending between the first and second locations.

76. A method as set forth in claim 71 wherein said step of moving the first anchor along the first path includes moving the first anchor along the first path in a direction toward the second path, said step of moving the second anchor along the second path includes moving the second anchor along the second path in a direction toward the first path.

77. A method as set forth in claim 71 wherein said step of moving a first anchor along a first path includes piercing body tissue with a leading end portion of the first anchor.

78. A method as set forth in claim 77 wherein said step of moving a second anchor along a second path includes piercing body tissue with the leading end portion of the second anchor.

79. A method as set forth in claim 71 wherein the second body tissue is bone having a hard outer layer disposed over cancellous bone, said step of moving the first anchor into the second body tissue includes moving the first anchor through the hard outer layer of the bone into the cancellous bone, said step of moving the second anchor in the second body tissue includes moving the second anchor through the hard outer layer of bone into the cancellous bone.

80. A method as set forth in claim 79 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

81. A method as set forth in claim 71 further including the steps of sliding a suture retainer along a first portion of the suture which extends from the first anchor, sliding the suture retainer along a second portion of the suture which extends from the second anchor, and gripping the first and second portions of the suture with the suture retainer while the predetermined tension is present in the suture.

82. A method as set forth in claim 71 further including the step of changing the orientation of the first anchor relative to the second body tissue, said step of changing the orientation of the first anchor relative to the second body tissue includes rotating the first anchor about an axis which extends transverse to the first path, said step of moving the second anchor along at least a portion of the second path is performed after performing said step of changing the orientation of the first anchor relative to the second body tissue.

83. A method as set forth in claim 71 further including the steps of changing the orientation of the first anchor relative to the second body tissue, said step of changing the orientation of the first anchor relative to the second body tissue includes rotating the first anchor relative to the second body tissue about an axis which extends transverse to the first path, and changing the orientation of the second anchor relative to the second body tissue, said step of changing the orientation of the second anchor relative to the second body tissue includes rotating the second anchor relative to the second body tissue about an axis which extends transverse to the second path.

84. A method as set forth in claim 71 wherein said step of moving the first anchor along the first path includes moving the first anchor along a first path having a nonlinear central axis, said step of moving the second anchor along the second path includes moving the second anchor along a second path having a nonlinear central axis.

85. A method as set forth in claim 71 wherein said steps of moving the first anchor along a first path and moving the second anchor along a second path include interconnecting the first and second anchors while the first and second anchors are disposed in the second body tissue.

86. A method as set forth in claim 85 wherein said step of interconnecting the first and second anchors includes moving one of the first and second anchors into engagement with the other of the first and second anchors.

87. A method as set forth in claim 85 wherein said step of interconnecting the first and second anchors includes moving one of the first and second anchors into an opening in the other of the first and second anchors.

88. A method as set forth in claim 71 wherein said step of moving the first anchor of the plurality of anchors along a first path into the second body tissue includes moving the first anchor through a predetermined distance into the second body tissue.

89. A method as set forth in claim 88 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

90. A method as set forth in claim 71 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

91. A method as set forth in claim 71 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

92. A method as set forth in claim 71 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

93. A method as set forth in claim 71 wherein said step of moving a first anchor along a first path includes transmitting force from a robotic assembly to the first anchor, said step of moving a second anchor along a second path includes transmitting force from the robotic assembly to the second anchor.

94. A method of securing first body tissue with second body tissue, said method comprising the steps of providing first and second anchors with a suture extending between the first and second anchors, moving the first anchor along a first path through the first body tissue into the second body tissue, moving the second anchor along a second path through the first body tissue into the second body tissue, and pressing the first body tissue against the second body tissue under the influence of force transmitted to the first body tissue from a portion of the suture extending between a location where the first path enters the first body tissue and a location where the second path enters the first body tissue.

95. A method as set forth in claim 94 wherein said step of moving the second anchor along the second path includes moving the second anchor along a portion of the second path which extends transverse to the first path.

96. A method as set forth in claim 94 wherein said step of moving the second anchor along the second path includes moving the second anchor in the second body tissue while first anchor is stationary in the second body tissue.

97. A method as set forth in claim 94 further including the step of engaging the first body tissue with the portion of the suture extending between the location where the first path enters the first body tissue and the location where the second path enters the first body tissue.

98. A method as set forth in claim 94 wherein said step of moving the first anchor along the first path includes moving the first anchor along a nonlinear portion of the first path, said step of moving the second anchor along the second path includes moving the second anchor along a nonlinear portion of the second path.

99. A method as set forth in claim 94 wherein said steps of moving the first and second anchors along the first and second paths are at least partially performed simultaneously, and said step of pressing the first body tissue against the second body tissue under the influence of force transmitted to the first body tissue from a portion of the suture extending between the location where the first path enters the first body tissue and the location where the second path enters the first body tissue is initiated during movement of the first and second anchors along the first and second paths.

100. A method as set forth in claim 94 wherein said step of moving the second anchor along the second path includes moving the second anchor along a portion of the second path which extends transverse to the first path, said step of pressing the first body tissue against the second body tissue under the influence of force transmitted to the first body tissue from a portion of the suture extending between the location where the first path enters the first body tissue and the location where the second path enters the first body tissue is initiated during movement of the second anchor along the portion of the second path which extends transverse to the first path.

101. A method as set forth in claim 94 further including the steps of detecting when a predetermined tension is present in the portion of the suture extending between the location where the first path enters the first body tissue and the location where the second path enters the first body tissue, and interrupting movement of at least one of the first and second anchors along at least one of the first and second paths upon detection of the predetermined tension in the portion of the suture extending between the location where the first path enters the first body tissue and the location where the second path enters the first body tissue.

102. A method as set forth in claim 94 wherein said step of moving the first anchor along the first path includes initiating formation of the first opening in the second body tissue with a leading end portion of the first anchor, said step of moving the second anchor along the second path includes initiating formation of a second opening in the second body tissue with a leading end portion of the second anchor.

103. A method as set forth in claim 94 wherein said step of moving a first anchor along a first path includes piercing body tissue with a leading end portion of the first anchor.

104. A method as set forth in claim 103 wherein said step of moving a second anchor along a second path includes piercing body tissue with the leading end portion of the second anchor.

105. A method as set forth in claim 94 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

106. A method as set forth in claim 105 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

107. A method as set forth in claim 94 further including the steps of sliding a suture retainer along a first portion of the suture which extends from the first anchor, sliding the suture retainer along a second portion of the suture which extends from the second anchor, and gripping the first and second portions of the suture with the suture retainer.

108. A method as set forth in claim 94 further including the step of changing the orientation of the first anchor relative to the second body tissue, said step of changing the orientation of the first anchor relative to the second body tissue includes rotating the first anchor about an axis which extends transverse to the first path, said step of moving the second anchor along at least a portion of the second path is performed after performing said step of changing the orientation of the first anchor relative to the second body tissue.

109. A method as set forth in claim 94 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

110. A method as set forth in claim 94 wherein said step of moving the first anchor along the first path includes moving the first anchor along a first path having a nonlinear central axis, said step of moving the second anchor along the second path includes moving the second anchor along a second path having a nonlinear central axis.

111. A method as set forth in claim 94 wherein said steps of moving the first anchor along a first path and moving the second anchor along a second path include interconnecting the first and second anchors while the first and second anchors are disposed in the second body tissue.

112. A method as set forth in claim 111 wherein said step of interconnecting the first and second anchors includes moving one of the first and second anchors into engagement with the other of the first and second anchors.

113. A method as set forth in claim 111 wherein said step of interconnecting the first and second anchors includes moving one of the first and second anchors into an opening in the other of the first and second anchors.

114. A method as set forth in claim 94 wherein said step of moving the first anchor of the plurality of anchors along a first path into the second body tissue includes moving the first anchor through a predetermined distance into the second body tissue.

115. A method as set forth in claim 114 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

116. A method as set forth in claim 94 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

117. A method as set forth in claim 94 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

118. A method as set forth in claim 94 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

119. A method as set forth in claim 94 wherein said step of moving a first anchor along a first path includes transmitting force from a robotic assembly to the first anchor, said step of moving a second anchor along a second path includes transmitting force from the robotic assembly to the second anchor.

120. A method of securing first body tissue with second body tissue, said method comprising the steps of providing first and second anchors with a suture extending between the first and second anchors, moving the first anchor along a first path through the first body tissue into the second body tissue, said step of moving the first anchor along the first path includes initiating formation of an opening in the first body tissue with a leading end portion of the first anchor and initiating the formation of an opening in the second body tissue with the leading end portion of the first anchor, moving the second anchor along a second path through the first body tissue into the second body tissue, said step of moving the second anchor along the second path includes initiating formation of an opening in the first body tissue with a leading end portion of the second anchor and initiating formation of an opening in the second body tissue with the leading end portion of the second anchor, and tensioning at least a portion of the suture extending between the first and second paths when the first and second anchors are disposed in engagement with the second body tissue.

121. A method as set forth in claim 120 wherein the second body tissue is bone having a hard outer layer disposed over cancellous bone, said step of moving the first anchor along the first path into the second body tissue includes moving the first anchor through the hard outer layer of the bone into the cancellous bone, said step of moving the second anchor along the second path into the second body tissue includes moving the second anchor through the hard outer layer of bone into the cancellous bone.

122. A method as set forth in claim 121 further including the steps of retaining the first anchor against movement relative to the hard outer layer of the bone by transmitting force between the first anchor and the cancellous bone while the first anchor is spaced from the hard outer layer of the bone and retaining the second anchor against movement relative to the hard outer layer of the bone by transmitting force between the second anchor and the cancellous bone while the second anchor is spaced from the hard outer layer of the bone.

123. A method as set forth in claim 120 further including the steps of sliding a suture retainer along a first portion of the suture which extends between the first and second anchors, sliding the suture retainer along a second portion of the suture which extends between the first and second anchors, and gripping the first and second portions of the suture with the suture retainer.

124. A method as set forth in claim 120 further including the step of changing the orientation of the first anchor relative to the second body tissue, said step of changing the orientation of the first anchor relative to the second body tissue includes rotating the first anchor about an axis which extends transverse to the first path, said step of moving the second anchor along the second path is performed after performing said step of changing the orientation of the first anchor relative to the second body tissue.

125. A method as set forth in claim 120 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

126. A method as set forth in claim 120 wherein the first and second body tissues are soft body tissues, said method further includes the step of placing the first and second body tissues in a side-by-side relationship.

127. A method as set forth in claim 120 wherein said steps of moving the first anchor along a first path and moving the second anchor along a second path include interconnecting the first and second anchors while the first and second anchors are disposed in the second body tissue.

128. A method as set forth in claim 127 wherein said step of interconnecting the first and second anchors includes moving one of the first and second anchors into engagement with the other of the first and second anchors.

129. A method as set forth in claim 127 wherein said step of interconnecting the first and second anchors includes moving of the first and second anchors into an opening in the other of the first and second anchors.

130. A method as set forth in claim 120 wherein said step of moving the first anchor along a first path through the first body tissue into the second body tissue includes moving the first anchor through a predetermined distance into the second body tissue.

131. A method as set forth in claim 130 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

132. A method as set forth in claim 120 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

133. A method as set forth in claim 120 wherein said step of moving a first anchor along a first path includes transmitting force from a robotic assembly to the first anchor, said step of moving a second anchor along a second path includes transmitting force from the robotic assembly to the second anchor.

134. A method as set forth in claim 120 further including the step of detecting when there is a predetermined tension in the suture and interrupting movement of the second anchor along the second path upon detecting the predetermined tension in the suture.

135. A method as set forth in claim 120 wherein said step of moving the second anchor along the second path includes moving the second anchor along a portion of the second path which extends toward the first path.

136. A method as set forth in claim 120 wherein said step of moving the second anchor along the second path includes moving the second anchor in the second body tissue while the first anchor is stationary in the first body tissue.

137. A method as set forth in claim 120 wherein said steps of moving the first and second anchors along the first and second paths are at least partially performed simultaneously.

138. A method of securing first body tissue with second body tissue, said method comprising the steps of providing first and second anchors with a suture disposed in a continuous loop extending between the first and second anchors, moving the first anchor along a first path into the second body tissue with the continuous loop extending through a passage in the first anchor, moving the second anchor along a second path into the second body tissue with the continuous loop extending through a passage in the second anchor, and moving a portion of the suture in the continuous loop along the passage in the second anchor, and tensioning suture in the continuous loop as the second anchor moves in to the second body tissue.

139. A method as set forth in claim 138 wherein said step of moving a portion of the suture along the passage in the second anchor is at least partially performed during movement of the second anchor into the second body tissue.

140. A method as set forth in claim 138 wherein first and second lengths of the suture extend between the passages in the first and second anchors and form portions of the continuous loop, said step of moving a portion of the suture in the continuous loop along the passage in the second anchor includes increasing an extent of one of the first and second lengths of the suture and decreasing an extent of another of the first and second lengths of the suture.

141. A method as set forth in claim 138 further including the step of connecting a first portion of the suture with a second portion of the suture to form the continuous loop, said step of connecting a first portion of the suture with a second portion of the suture includes tying a knot between the first and second portions of the suture.

142. A method as set forth in claim 138 further including the step of gripping first and second portions of the suture with a suture retainer to form the continuous loop.

143. A method as set forth in claim 138 wherein said step of moving the second anchor along the second path includes moving the second anchor along a portion of the second path which extends transverse to the first path while the second anchor is disposed in the second body tissue.

144. A method as set forth in claim 138 further including the step of determining when a predetermined tension is present in the continuous loop.

145. A method as set forth in claim 138 further including the step of interrupting movement of the second anchor along the second path in response to determining that a predetermined tension is present in the continuous loop.

146. A method as set forth in claim 138 wherein said step of moving a first anchor along a first path into the second body tissue includes piercing the first body tissue with a leading end portion of the first anchor.

147. A method as set forth in claim 146 wherein said step of moving a first anchor along a first path into the second body tissue includes piercing the second body tissue with the leading end portion of the first anchor.

148. A method as set forth in claim 147 wherein said step of moving a second anchor along a second path into the second body tissue includes piercing the first body tissue with a leading end portion of the second anchor.

149. A method as set forth in claim 148 wherein said step of moving a second anchor along a second path into the second body tissue includes piercing the second body tissue with the leading end portion of the second anchor.

150. A method as set forth in claim 138 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

151. A method as set forth in claim 150 further including the steps of retaining the first anchor against movement relative to the hard outer layer of the bone while maintaining tension in the continuous loop by transmitting force between the first anchor and the cancellous bone while the first anchor is spaced from the hard outer layer of the bone and retaining the second anchor against movement relative to the hard outer layer of the bone while maintaining tension in the continuous loop by transmitting force between the second anchor and the cancellous bone while the second anchor is spaced from the hard outer layer of the bone.

152. A method as set forth in claim 138 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

153. A method as set forth in claim 138 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

154. A method as set forth in claim 138 wherein said step of moving the first anchor along a first path into the second body tissue includes moving the first anchor through a predetermined distance into the second body tissue.

155. A method as set forth in claim 154 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

156. A method as set forth in claim 138 further including the step of positioning a guide assembly having first and second guide surfaces relative to at least one of the first and second body tissues, engaging the first anchor with the first guide surface during movement of the first anchor along the first path, and engaging the second anchor with the second guide surface during movement of the second anchor along the second path.

157. A method as set forth in claim 138 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

158. A method as set forth in claim 138 wherein said steps of providing a guide assembly having a base and first and second tubular guides, positioning the first tubular guide in alignment with the first path, moving the first tubular guide along the first path into engagement with the second body tissue, positioning the second tubular guide in alignment with the second path, moving the second tubular guide along the second path into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

159. A method as set forth in claim 138 wherein said step of moving a first anchor along a first path includes transmitting force from a robotic assembly to the first anchor, said step of moving a second anchor along a second path includes transmitting force from the robotic assembly to the second anchor.

160. A method of securing first body tissue with second body tissue, said method comprising the steps of providing first and second anchors with a suture extending through passages in the first and second anchors, moving the first anchor along a first path into the second body tissue with the suture extending through the passages in the first and second anchors, moving the second anchor along a second path into the second body tissue with the suture extending through the passages in the first and second anchors, moving a portion of the suture along the passage in the second anchor during movement of the second anchor into the second body tissue, said step of moving a portion of the suture along the passage in the second anchor includes increasing the extent of a portion of the suture extending between the first and second anchors during movement of the second anchor into the second body tissue, and transmitting force through the suture to the first body tissue.

161. A method as set forth in claim 160 wherein the suture extends in a continuous loop between the first and second anchors, said step of moving the second anchor into the second body tissue includes tensioning the continuous loop.

162. A method as set forth in claim 160 further including the step of connecting a first portion of the suture with a second portion of the suture by tying a knot between the first and second portions of the suture after performing said step of moving the second anchor into the second body tissue.

163. A method as set forth in claim 160 further including the step of gripping first and second portions of the suture with a suture retainer after performing said step of moving the second anchor into the second body tissue.

164. A method as set forth in claim 160 wherein said step of moving the second anchor along the second path includes moving the second anchor along a portion of the second path which extends transverse to the first path while the second anchor is disposed in the second body tissue.

165. A method as set forth in claim 160 further including the step of connecting a first portion of the suture with a second portion of the suture at a location disposed between the first and second paths after performing said steps of moving the first anchor along the first path into the second body tissue and moving the second anchor along the second path into the second body tissue.

166. A method as set forth in claim 160 wherein said step of moving a first anchor along a first path includes piercing body tissue with a leading end portion of the first anchor.

167. A method as set forth in claim 166 wherein said step of moving a second anchor along a second path includes piercing body tissue with the leading end portion of the second anchor.

168. A method as set forth in claim 160 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

169. A method as set forth in claim 168 further including the steps of retaining the first anchor against movement relative to the hard outer layer of the bone while transmitting force through the suture by transmitting force between the first anchor and the cancellous bone while the first anchor is spaced from the hard outer layer of the bone and retaining the second anchor against movement relative to the hard outer layer of the bone while transmitting force through the suture by transmitting force between the second anchor and the cancellous bone while the second anchor is spaced from the hard outer layer of the bone.

170. A method as set forth in claim 160 further including the steps of sliding a suture retainer along a first portion of the suture which extends from the first anchor, sliding the suture retainer along a second portion of the suture which extends from the second anchor, and gripping the first and second portions of the suture with the suture retainer.

171. A method as set forth in claim 160 further including the step of changing the orientation of the first anchor relative to the second body tissue, said step of changing the orientation of the first anchor relative to the second body tissue includes rotating the first anchor about an axis which extends transverse to the first path, said step of moving a portion of the suture along the passage in the second anchor is performed after performing said step of changing the orientation of the first anchor relative to the second body tissue.

172. A method as set forth in claim 160 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

173. A method as set forth in claim 160 wherein said step of moving the first anchor along the first path includes moving the first anchor along a first path having a nonlinear central axis, said step of moving the second anchor along the second path includes moving the second anchor along a second path having a nonlinear central axis.

174. A method as set forth in claim 160 wherein said steps of moving the first anchor along a first path and moving the second anchor along a second path include interconnecting the first and second anchors while the first and second anchors are disposed in the second body tissue.

175. A method as set forth in claim 174 wherein said step of interconnecting the first and second anchors includes moving one of the first and second anchors into engagement with the other of the first and second anchors.

176. A method as set forth in claim 174 wherein said step of interconnecting the first and second anchors includes moving one of the first and second anchors into an opening in the other of the first and second anchors.

177. A method as set forth in claim 160 wherein said step of moving the first anchor of the plurality of anchors along a first path into the second body tissue includes moving the first anchor through a predetermined distance into the second body tissue.

178. A method as set forth in claim 177 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

179. A method as set forth in claim 160 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

180. A method as set forth in claim 160 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the second anchor.

181. A method as set forth in claim 160 further including the steps of providing a guide assembly having a base and first and second tubular guides, positioning the first tubular guide in alignment with the first path, positioning the second tubular guide in alignment with the second path, said step of moving the first anchor along the first path includes moving the first anchor through the first tubular guide into the second body tissue, said step of moving the second anchor along the second path includes moving the second anchor through the second tubular guide into the second body tissue.

182. A method as set forth in claim 160 wherein said step of moving a first anchor along a first path includes transmitting force from a robotic assembly to the first anchor, said step of moving a second anchor along a second path includes transmitting force from the robotic assembly to the second anchor.

183. A method of securing first body tissue with second body tissue, said method comprising the steps of providing first and second anchors with a suture extending between the first and second anchors, moving the first anchor along a first path into the second body tissue with the suture extending between the first and second anchors, moving the second anchor along a second path into the second body tissue with the suture extending between the first and second anchors, said step of moving the first anchor along the first path into the second body tissue includes decreasing a distance between the first anchor and the second path, said step of moving the second anchor along the second path into the second body tissue includes decreasing a distance between the second anchor and the first path, and transmitting force through the suture to the first body tissue.

184. A method as set forth in claim 183 further including the step of interrupting movement of at least one of the first and second anchors along one of the first and second paths when a predetermined tension is present in the suture.

185. A method as set forth in claim 183 wherein said steps of moving the first and second anchors along the first and second paths are at least partially performed simultaneously.

186. A method as set forth in claim 183 wherein said step of moving the second anchor along the second path into the second body tissue includes moving the second anchor along a portion of the second path which extends transverse to the first path.

187. A method as set forth in claim 183 wherein said step of moving a first anchor along a first path into the second body tissue includes piercing the first body tissue with a leading end portion of the first anchor.

188. A method as set forth in claim 187 wherein said step of moving a first anchor along a first path into the second body tissue includes piercing the second body tissue with the leading end portion of the first anchor.

189. A method as set forth in claim 188 wherein said step of moving a second anchor along a second path into the second body tissue includes piercing the first body tissue with a leading end portion of the second anchor.

190. A method as set forth in claim 189 wherein said step of moving a second anchor along a second path into the second body tissue includes piercing the second body tissue with the leading end portion of the second anchor.

191. A method as set forth in claim 183 wherein the second body tissue is bone having a hard outer layer disposed over cancellous bone, said step of moving the first anchor into the second body tissue includes moving the first anchor through the hard outer layer of the bone into the cancellous bone, said step of moving the second anchor into the second body tissue includes moving the second anchor through the hard outer layer of bone into the cancellous bone.

192. A method as set forth in claim 191 further including the steps of retaining the first anchor against movement relative to the hard outer layer of the bone while maintaining tension in the suture by transmitting force between the first anchor and the cancellous bone while the first anchor is spaced from the hard outer layer of the bone and retaining the second anchor against movement relative to the hard outer layer of the bone while maintaining tension in the suture by transmitting force between the second anchor and the cancellous bone while the second anchor is spaced from the hard outer layer of the bone.

193. A method as set forth in claim 183 further including the steps of sliding a suture retainer along a first portion of the suture which extends from the first anchor, sliding the suture retainer along a second portion of the suture which extends from the second anchor, and gripping the first and second portions of the suture with the suture retainer.

194. A method as set forth in claim 183 further including the step of changing the orientation of the first anchor relative to the second body tissue, said step of changing the orientation of the first anchor relative to the second body tissue includes rotating the first anchor about an axis which extends transverse to the first path, said step of tensioning at least a portion of the suture by moving the second anchor along at least a portion of the second path is performed after performing said step of changing the orientation of the first anchor relative to the second body tissue.

195. A method as set forth in claim 183 further including the steps of changing the orientation of the first anchor relative to the second body tissue, said step of changing the orientation of the first anchor relative to the second body tissue includes rotating the first anchor about an axis which extends transverse to the first path, and changing the orientation of the second anchor relative to the second body tissue, said step of changing the orientation of the second anchor relative to the second body tissue includes rotating the second anchor about an axis which extends transverse to the second path.

196. A method as set forth in claim 195 further including the step of tensioning the suture after performance of said step of changing the orientation of the first anchor relative to the second body tissue.

197. A method as set forth in claim 183 wherein said steps of moving the first anchor along a first path and moving the second anchor along a second path include interconnecting the first and second anchors while the first and second anchors are disposed in the second body tissue.

198. A method as set forth in claim 197 wherein said step of interconnecting the first and second anchors includes moving one of the first and second anchors into engagement with the other of the first and second anchors.

199. A method as set forth in claim 197 wherein said step of interconnecting the first and second anchors includes moving one of the first and second anchors into an opening in the other of the first and second anchors.

200. A method as set forth in claim 183 wherein said step of moving the first anchor of the plurality of anchors along a first path into the second body tissue includes moving the first anchor through a predetermined distance into the second body tissue.

201. A method as set forth in claim 200 wherein said step of moving the first anchor through a predetermined distance into the second body tissue includes applying force against a trailing end portion of the first anchor with a pusher member having indicia thereon, and detecting when the indicia on the pusher member indicates that the first anchor has been moved through a predetermined distance relative to the second body tissue.

202. A method as set forth in claim 183 further including the step of positioning a guide assembly having first and second guide surfaces relative to at least one of the first and second body tissues, moving the first anchor along the first guide surface during movement of the first anchor along the first path, and moving the second anchor along the second guide surface during movement of the second anchor along the second path.

203. A method as set forth in claim 183 further including moving a thin elongated member along the first path into the second body tissue, said step of moving a first anchor along a first path into the second body tissue is at least partially performed with the thin elongated member extending through the first anchor, and moving a thin elongated member along the second path into the second body tissue, said step of moving a second anchor along a second path into the second body tissue is at least partially performed with the thin elongated member extending through the anchor.

204. A method as set forth in claim 183 further including the steps of providing a guide assembly having a base and first and second tubular guides, positioning the first tubular guide in alignment with the first path, moving the first tubular guide along the first path through the first body tissue into engagement with the second body tissue, positioning the second tubular guide in alignment with the second path, moving the second tubular guide along the second path through the first body tissue into engagement with the second body tissue, said step of moving the first anchor along the first path includes moving the first anchor through the first tubular guide into the second body tissue, said step of moving the second anchor along the second path includes moving the second anchor through the second tubular guide into the second body tissue.

205. A method as set forth in claim 183 wherein said step of moving a first anchor along a first path includes transmitting force from a robotic assembly to the first anchor, said step of moving a second anchor along a second path includes transmitting force from the robotic assembly to the second anchor.

206. A method as set forth in claim 183 wherein said step of moving the first anchor along the first path includes initiating formation of a first opening in the second body tissue with a leading end portion of the first anchor, said step of moving the second anchor along a second path includes initiating formation of a second opening in the second body tissue with a leading end portion of the second anchor.

207. A method as set forth in claim 183 wherein said step of transmitting force through the suture to the first body tissue includes pressing the first body tissue against the second body tissue under the influence of force transmitted to the first body tissue through a portion of the suture disposed between the first and second paths.

208. A method as set forth in claim 183 wherein said step of moving the second anchor along the second path into the second body tissue includes moving the second anchor in the second body tissue while the first anchor is stationary in the second body tissue.

* * * * *